US012709629B2

(12) United States Patent
Kuniyoshi et al.

(10) Patent No.: US 12,709,629 B2
(45) **Date of Patent: *Aug. 18, 2026**

(54) CYCLOPENTENYL PURINE DERIVATIVE OR SALT THEREOF

(71) Applicant: FUJIFILM Corporation, Tokyo (JP)

(72) Inventors: Hidenobu Kuniyoshi, Ashigarakami-gun (JP); Takehiro Yamane, Ashigarakami-gun (JP); Takayuki Yamakawa, Ashigarakami-gun (JP); Hideyasu Fujiwara, Ashigarakami-gun (JP); Eiichi Kodama, Sendai (JP)

(73) Assignee: FUJIFILM Corporation, Tokyo (JP)

( * ) Notice: Subject to any disclaimer, the term of this patent is extended or adjusted under 35 U.S.C. 154(b) by 1511 days.

This patent is subject to a terminal disclaimer.

(21) Appl. No.: 17/158,547

(22) Filed: Jan. 26, 2021

(65) Prior Publication Data

US 2021/0155644 A1 May 27, 2021

Related U.S. Application Data

(63) Continuation of application No. PCT/JP2019/029447, filed on Jul. 26, 2019.

(30) Foreign Application Priority Data

Jul. 27, 2018 (JP) ................................ 2018-141748

(51) Int. Cl.

| | |
|---|---|
| *C07F 9/6561* | (2006.01) |
| *A61P 31/20* | (2006.01) |
| *C07F 9/6574* | (2006.01) |

(52) U.S. Cl.

CPC .......... *C07F 9/65616* (2013.01); *A61P 31/20* (2018.01); *C07F 9/65744* (2013.01)

(58) Field of Classification Search

None

See application file for complete search history.

(56) References Cited

U.S. PATENT DOCUMENTS 5,034,394 A 7/1991 Daluge
5,324,730 A 6/1994 Ichikawa et al.

(Continued)

FOREIGN PATENT DOCUMENTS

CA 1339896 C 6/1998
CN 1328565 A 12/2001

(Continued)

OTHER PUBLICATIONS

McGuigan et al., J. Med. Chem. 2005, 48, 10, 3504-3515 (Year: 2005).*

(Continued)

*Primary Examiner* — Jeffrey S Lundgren
*Assistant Examiner* — Anthony Joseph Seitz
(74) *Attorney, Agent, or Firm* — Sughrue Mion, PLLC

(57) ABSTRACT

An object of the present invention is to provide a compound exhibiting an excellent drug efficacy as an anti-adenoviral agent, and an anti-adenoviral agent. The present invention provides an anti-adenoviral agent including a compound represented by General Formula [1]

(Continued)

[1]

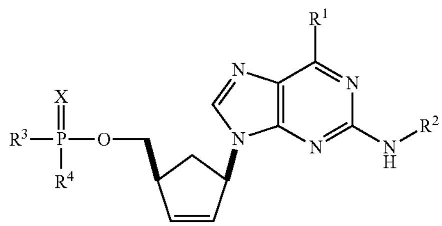

(in the formula, $R^1$ represents a hydrogen atom, a halogen atom, an amino group which may be substituted, a monocyclic nitrogen-containing heterocyclic ring group which may be substituted (provided that a nitrogen atom forming the ring is bonded to a carbon atom to which $R^1$ is bonded), a monocyclic nitrogen- and oxygen-containing heterocyclic ring group which may be substituted (provided that a nitrogen atom forming the ring is bonded to a carbon atom to which $R^1$ is bonded), a $C_{1-6}$ alkoxy group which may be substituted, a hydroxyl group which may be protected, or the like; $R^2$ represents a hydrogen atom or an amino protecting group; $R^3$ represents a $C_{1-20}$ alkoxy group which may be substituted, an aryloxy group which may be substituted, an amino group which may be substituted, or the like; $R^4$ represents a $C_{1-20}$ alkoxy group which may be substituted, an aryloxy group which may be substituted, an amino group which may be substituted, or the like; and X represents an oxygen atom or a sulfur atom) or a salt thereof.

18 Claims, 1 Drawing Sheet

Specification includes a Sequence Listing.

(56) References Cited

U.S. PATENT DOCUMENTS

| | | | | |
|---|---|---|---|---|
| 5,369,098 | A | 11/1994 | Slusarchyk | |
| 2001/0031745 | A1 | 10/2001 | McGuigan et al. | |
| 2004/0167096 | A1 | 8/2004 | Cheng et al. | |
| 2021/0147456 | A1* | 5/2021 | Kuniyoshi | A61K 31/683 |
| 2023/0295202 | A1* | 9/2023 | Kuniyoshi | C07F 9/65616 514/81 |

FOREIGN PATENT DOCUMENTS

| | | | | |
|---|---|---|---|---|
| JP | 2-45486 | A | 2/1990 | |
| JP | H02-131473 | A | 5/1990 | |
| JP | 4-91094 | A | 3/1992 | |
| JP | 4-297463 | A | 10/1992 | |
| JP | 2793825 | B2 | 9/1998 | |
| JP | 2002-525374 | A | 8/2002 | |
| WO | 93/00099 | A2 | 1/1993 | |
| WO | WO-0142256 | A1 * | 6/2001 | C07F 9/65616 |

OTHER PUBLICATIONS

Uchio et al., Graefes Arch Clin Exp Ophthalmol 245, 1319-1325 (2007) (Year: 2007).*

Office Action dated Dec. 7, 2021 from the Japanese Patent Office in Japanese Application No. 2020-532502.

Office Action dated Jun. 28, 2023 in Chinese Application No. 201980050210.2.

Communication dated May 20, 2022, issued in European Application No. 19 840 531.8.

Extended European Search Report dated Aug. 2, 2021 from the European Patent Office in European Application No. 19840531.8.

R. Anthony Vere Hodge, "Meeting report: 29th International Conference on Antiviral Research in La Jolla, CA, USA" Antiviral Research, 2017, vol. 137, pp. 23-40 (18 pages total).

Communication dated Dec. 8, 2023, issued in Chinese Application No. 201980050210.2.

Brown et al., "Pharmacokinetics and Safety of Intravenous Cidofovir for Life-Threatening Viral Infections in Pediatric Hematopoietic Stem Cell Transplant Recipients", Antimicrobial Agents and Chemotherapy, vol. 59, No. 7, Jul. 2015, pp. 3718-3725.

Skevaki et al., "Treatment of Viral Conjunctivitis with Antiviral Drugs", Drugs, vol. 71, No. 3, pp. 331 to 347, 2011.

Lenaerts et al., "Antiviral therapy for adenovirus infections" Antiviral Research, vol. 71, 2006, pp. 172-180.

International Search Report dated Sep. 10, 2019 from the International Searching Authority in International Application No. PCT/JP2019/029447.

Written Opinion dated Sep. 10, 2019 from the International Bureau in International Application No. PCT/JP2019/029447.

International Preliminary Report on Patentability dated Feb. 2, 2021 from the International Bureau in International Application No. PCT/JP2019/029447.

Chrysanthi L. Skevaki et al., "Treatment of Viral Conjunctivitis with Antiviral Drugs", Drugs, 2011, vol. 71, No. 3, pp. 331-347 (17 pages).

Office Action dated Jun. 14, 2022 from the European Patent Office in Application No. 19842018.4, corresponding to U.S. Appl. No. 18/296,151.

Office Action issued Jan. 18, 2022 in Japanese Application No. 2020-532503, corresponding to U.S. Appl. No. 18/296,151.

Peter C Van Der Vliet et al., "Role of DNA polymerase γ in adenovirus DNA replication, Mechanism of inhibition by 2', 3'-Dideoxyucleoside 5'-Triphosphates", 1981, Biochemistry, vol. 20, pp. 2628-2632 (5 pages total).

International Preliminary Report on Patentability dated Feb. 2, 2021, issued by the International Searching Authority in application No. PCT/JP2019/029448, corresponding to U.S. Appl. No. 18/296,151.

International Search Report dated Oct. 1, 2019, issued by the International Searching Authority in application No. PCT/JP2019/029448, corresponding to U.S. Appl. No. 18/296,151.

Toyofumi Yamaguchi et al., "Synthetic Nucleosides and Nucleotides. 43. Inhibition of Vertebrate Telomerases by Carbocyclic Oxetanocin G (C.OXT-G) Triphosphate Analgues and Influence of C.OXT-G Treatment on Telomere Length in Human HL60 Cells", Nucleosides, Nucleotides, and Nucleic Acids, vol. 25, No. 4-6, Jan. 1, 2006, XP055666350, pp. 539-551, (14 pages, total).

Abstract of Toyofumi Yamaguchi et al., "Synthetic Nucleosides and Nucleotides. 43. Inhibition of Vertebrate Telomerases by Carbocyclic Oxetanocin G (C.OXT-G) Triphosphate Analogues and Influence of C.OXT-G Treatment on Telomere Length in Human HL60 Cells", Nucleosides, Nucleotides & Nucleic Acids, vol. 25, No. 4-6, Jan. 1, 2006, pp. 539-551, provided by Reaxys, a trademark of Elsevier Life Sciences IP Limited (2 pages, total).

Written Opinion dated Oct. 1, 2019, issued by the International Searching Authority in application No. PCT/JP2019/029448, corresponding to U.S. Appl. No. 18/296,151.

Mehellou, et al., "Aryloxy Phosphoramidate Triesters: a Technology for Delivering Monophosphorylated Nucleosides and Sugars into Cells", ChemMedChem (2009), 4(11), 1779-1791.

Roman, Cristina Arbelo, "Diastereoselective Synthesis of (Aryloxy)phosphoramidate Prodrugs," European Journal of Organic Chemistry, 2011 (25), 4899-4909.

Mehellou, et al., "The Pro Tide Prodrug Technology: From the Concept to the Clinic," Journal of Medicinal Chemistry (2018), 61(6), 2211-2226.

Sinokrot, "Advanced prodrug strategies in nucleoside and non-nucleoside antiviral agents: a review of the recent five years," Molecules (2017), 22(10), 1736/1-1736/18.

(56) References Cited

OTHER PUBLICATIONS

Wang, et al., "Phosphoramidate prodrugs of (-)-β-D-(2R,4R)-dioxolane-thymine (DOT) as potent anti-HIV agents," Antiviral Chemistry & Chemotherapy, 2012, 22(5), 217-238.
Mcguigan, "The application of phosphoramidate Pro Tide technology to the potent anti-HCV compound 4'-azidocytidine (R1479)," Bioorganic & Medicinal Chemistry Letters, 2009, 19(15), 4250-4254.
Extended European Search Report dated Aug. 19, 2021, from the European Patent Office in European application No. 19842018.4, corresponding to U.S. Appl. No. 18/296,151.
Office Action issued Aug. 25, 2022 in U.S. Appl. No. 17/158,520.
Office Action issued Jan. 5, 2023 in U.S. Appl. No. 17/158,520.
Office Action issued Apr. 19, 2024 in U.S. Appl. No. 18/296,151.
Notice of Allowance issued Sep. 11, 2024 by the United States Patent and Trademark Office in U.S. Appl. No. 18/296,151.

* cited by examiner

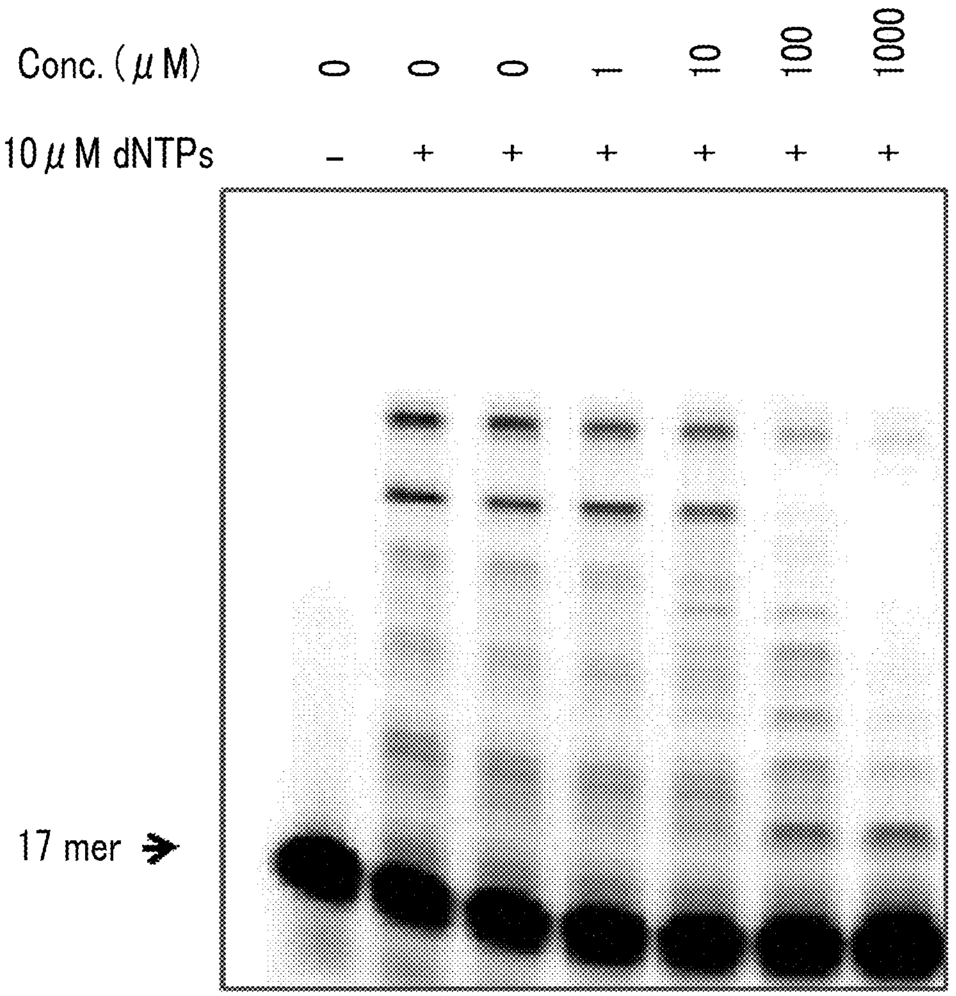
Conc. (μM)
0
0
0
1
10
100
1000
10μM dNTPs
–
+
+
+
+
+
+
17 mer

CYCLOPENTENYL PURINE DERIVATIVE OR SALT THEREOF

CROSS-REFERENCE TO RELATED APPLICATIONS

This application is a Continuation of PCT International Application No. PCT/JP2019/029447 filed on Jul. 26, 2019, which claims priority under 35 U.S.C § 119(a) to Japanese Patent Application No. 2018-141748 filed on Jul. 27, 2018. Each of the above application(s) is hereby expressly incorporated by reference, in its entirety, into the present application.

BACKGROUND OF THE INVENTION

1. Field of the Invention

The present invention relates to a cyclopentenyl purine derivative or a salt thereof, and an anti-adenoviral agent containing the same.

2. Description of the Related Art

Adenovirus is a double-stranded linear DNA virus and is a causative virus that causes various pathological conditions such as respiratory infection, pharyngoconjunctival fever, epidemic keratoconjunctivitis, hepatitis, gastroenteritis, cystitis, and encephalitis.

Although there is no pharmaceutical product approved as an anti-adenoviral agent, for example, cidofovir is known to be clinically effective (Antiviral Research, vol. 71, pp. 172 to 180, 2006). On the other hand, cidofovir is known to be toxic upon systemic administration and ocular instillation administration (Antimicrobial Agents and Chemotherapy, vol. 59(7), pp. 3718 to 3725, 2015, and Drugs, vol. 71(3), pp. 331 to 347, 2011).

On the other hand, cyclopentenyl purine derivatives are expected to be applied to various pharmaceutical products, and for example, compounds having an anti-hepatitis B virus effect and an anti-human immunodeficiency virus activity are known (JP2793825B and WO2001/042256A).

SUMMARY OF THE INVENTION

An object of the present invention is to provide a compound exhibiting an excellent drug efficacy against adenovirus and an excellent anti-adenoviral agent.

As a result of extensive studies, the present inventors have found that a compound represented by General Formula [1] or a salt thereof exhibits an excellent drug efficacy against adenovirus. The present invention has been completed based on these findings.

The present invention provides the following.

(1) An anti-adenoviral agent comprising:

a compound represented by General Formula [1]:

[1]

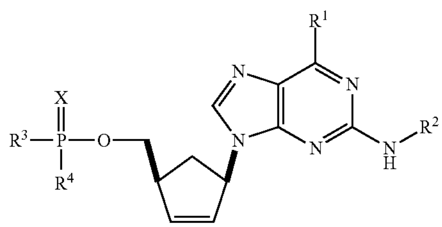

in the formula, $R^1$ represents a hydrogen atom, a halogen atom, an amino group which may be substituted, a monocyclic nitrogen-containing heterocyclic ring group which may be substituted (provided that a nitrogen atom forming the ring is bonded to a carbon atom to which $R^1$ is bonded), a monocyclic nitrogen- and oxygen-containing heterocyclic ring group which may be substituted (provided that a nitrogen atom forming the ring is bonded to a carbon atom to which $R^1$ is bonded), a $C_{1-6}$ alkoxy group which may be substituted, a $C_{3-8}$ cycloalkoxy group which may be substituted, a $C_{1-6}$ alkylthio group which may be substituted, a hydroxyl group which may be protected, or a thiol group which may be protected;

$R^2$ represents a hydrogen atom or an amino protecting group;

$R^3$ represents a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, a hydroxyl group which may be protected, or —O—P(O)(OH)—O—$PO_3H$;

$R^4$ represents a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, or a hydroxyl group which may be protected; or $R^3$ and $R^4$, together with a phosphorus atom to which $R^3$ and $R^4$ are bonded, may be combined to form a 5- to 10-membered nitrogen- and phosphorus-containing heterocyclic ring which may be substituted, a 5- to 10-membered oxygen- and phosphorus-containing heterocyclic ring which may be substituted, or a 5- to 10-membered nitrogen-, oxygen-, and phosphorus-containing heterocyclic ring which may be substituted; and X represents an oxygen atom or a sulfur atom; or a salt thereof.

(2) The anti-adenoviral agent according to (1), in which $R^2$ is a hydrogen atom.

(3) The anti-adenoviral agent according to (1) or (2), in which X is an oxygen atom.

(4) The anti-adenoviral agent according to any one of (1) to (3), in which $R^1$ is a halogen atom, an amino group which may be substituted, a monocyclic nitrogen-containing heterocyclic ring group which may be substituted (provided that a nitrogen atom forming the ring is bonded to a carbon atom to which $R^1$ is bonded), a monocyclic nitrogen- and oxygen-containing heterocyclic ring group which may be substituted (provided that a nitrogen atom forming the ring is bonded to a carbon atom to which $R^1$ is bonded), a $C_{1-6}$ alkoxy group which may be substituted, a $C_{3-8}$ cycloalkoxy group which may be substituted, a $C_{1-6}$ alkylthio group which may be substituted, a hydroxyl group which may be protected, or a thiol group which may be protected.

(5) The anti-adenoviral agent according to (4), in which $R^1$ is a halogen atom, an amino group which may be substituted with one or more substituents selected from Substituent group A, a monocyclic nitrogen-containing heterocyclic ring group which may be substituted with one or more substituents selected from Substituent group A (provided that a nitrogen atom forming the ring is bonded to a carbon atom to which $R^1$ is bonded), a monocyclic nitrogen- and oxygen-containing heterocyclic ring group which may be substituted with one or more substituents selected from Substituent group A (provided that a nitrogen atom forming the ring is bonded to a carbon atom to which $R^1$ is bonded), a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylthio group which may be substituted with one or more substituents selected from Substituent group A, a hydroxyl group which may be protected, or a thiol group which may be protected.

Substituent group A:

a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; an amino group which may be substituted with one or more substituents selected from Substituent group B; a $C_{1-6}$ alkoxycarbonyl group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B.

Substituent group B:

a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an aryloxycarbonyl group; an aryl $C_{1-6}$ alkoxycarbonyl group; an aryl group; an aryloxy group; a heterocyclic oxy group which may be substituted with one or more substituents selected from a hydroxyl group and a hydroxymethyl group; an aryl $C_{1-6}$ alkoxy group; and an acyloxy group.

(6) The anti-adenoviral agent according to (4), in which $R^1$ is a halogen atom, an amino group which may be substituted with one or more substituents selected from Substituent group A, a monocyclic nitrogen-containing heterocyclic ring group which may be substituted with one or more substituents selected from Substituent group A (provided that a nitrogen atom forming the ring is bonded to a carbon atom to which $R^1$ is bonded), a monocyclic nitrogen- and oxygen-containing heterocyclic ring group which may be substituted with one or more substituents selected from Substituent group A (provided that a nitrogen atom forming the ring is bonded to a carbon atom to which $R^1$ is bonded), a $C_{1-6}$ alkoxy group which may be substituted with one or more substituents selected from Substituent group A, a hydroxyl group which may be protected, or a thiol group which may be protected.

(7) The anti-adenoviral agent according to (4), in which $R^1$ is a halogen atom, an amino group which may be substituted with one or more substituents selected from Substituent group A, a monocyclic nitrogen-containing heterocyclic ring group which may be substituted with one or more substituents selected from Substituent group A (provided that a nitrogen atom forming the ring is bonded to a carbon atom to which $R^1$ is bonded), a monocyclic nitrogen- and oxygen-containing heterocyclic ring group which may be substituted with one or more substituents selected from Substituent group A (provided that a nitrogen atom forming the ring is bonded to a carbon atom to which $R^1$ is bonded), a $C_{1-6}$ alkoxy group which may be substituted with one or more substituents selected from Substituent group A, or a hydroxyl group.

(8) The anti-adenoviral agent according to any one of (1) to (7), in which $R^3$ is a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, or $—O—P(O)(OH)—O—PO_3H$.

(9) The anti-adenoviral agent according to (8), in which $R^3$ is a $C_{1-20}$ alkoxy group which may be substituted with one or more substituents selected from Substituent group A, a $C_{3}$_s cycloalkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, an amino group which may be substituted with one or more substituents selected from Substituent group A, or $—O—P(O)(OH)—O—PO_3H$.

Substituent group A:

a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; an amino group which may be substituted with one or more substituents selected from Substituent group B; a $C_{1-6}$ alkoxycarbonyl group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B.

Substituent group B:

a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an aryloxycarbonyl group; an aryl $C_{1-6}$ alkoxycarbonyl group; an aryl group; an aryloxy group; a heterocyclic oxy group which may be substituted with one or more substituents selected from a hydroxyl group and a hydroxymethyl group; an aryl $C_{1-6}$ alkoxy group; and an acyloxy group.

(10) The anti-adenoviral agent according to (8), in which $R^3$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or —O—P(O)(OH)—O—$PO_3$H.

(11) The anti-adenoviral agent according to (8), in which $R^3$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, or —O—P(O)(OH)—O—$PO_3$H.

(12) The anti-adenoviral agent according to any one of (1) to (11), in which $R^4$ is a $C_{1-20}$ alkoxy group which may be substituted with one or more substituents selected from Substituent group A, a $C_{3-8}$ cycloalkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, an amino group which may be substituted with one or more substituents selected from Substituent group A, or a hydroxyl group which may be protected.

Substituent group A:

a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; an amino group which may be substituted with one or more substituents selected from Substituent group B; a $C_{1-6}$ alkoxycarbonyl group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B.

Substituent group B:

a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an aryloxycarbonyl group; an aryl $C_{1-6}$ alkoxycarbonyl group; an aryl group; an aryloxy group; a heterocyclic oxy group which may be substituted with one or more substituents selected from a hydroxyl group and a hydroxymethyl group; an aryl $C_{1-6}$ alkoxy group; and an acyloxy group.

(13) The anti-adenoviral agent according to (12), in which $R^4$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or a hydroxyl group which may be protected.

(14) The anti-adenoviral agent according to (12), in which $R^4$ is a $C_{1-20}$ alkoxy group which may be substituted with one or more substituents selected from Substituent group A, an amino group which may be substituted with one or more substituents selected from Substituent group A, or a hydroxyl group which may be protected.

(15) The anti-adenoviral agent according to any one of (1) to (7), in which a ring formed by combining $R^3$ and $R^4$ together with a phosphorus atom to which $R^3$ and $R^4$ are bonded is a 5- to 10-membered oxygen- and phosphorus-containing heterocyclic ring which may be substituted.

(16) An anti-adenoviral agent comprising:

a compound selected from isopropyl ((((1S,4R)-4-(2-amino-6-chloro-9H-purin-9-yl)cyclopent-2-en-1-yl)methoxy)(phenoxy)phosphoryl)-L-alaninate, S-(2-(((((1S,4R)-4-(2-amino-6-methoxy-9H-purin-9-yl)cyclopent-2-en-1 -yl)methoxy)(phenoxy)phosphoryl)oxy)ethyl) 2,2-dimethylpropanethioate, methyl ((((1S,4R)-4-(2-amino-6-methoxy-9H-purin-9-yl)cyclopent-2-en-1-yl)methoxy)(4-chlorophenoxy)phosphoryl)-L-alaninate, methyl ((((1S,4R)-4-(2-amino-6-methoxy-9H-purin-9-yl)cyclopent-2-en-1-yl)methoxy)(4-bromophenoxy)phosphoryl)-L-alaninate, isopropyl ((((1S,4R)-4-(2-amino-6-methoxy-9H-purin-9-yl)cyclopent-2-en-1-yl)methoxy)(phenoxy)phosphoryl)-L-alaninate, methyl ((((1S,4R)-4-(2-amino-6-chloro-9H-purin-9-yl)cyclopent-2-en-1-yl)methoxy)(4-chlorophenoxy)phosphoryl)-L-alaninate, methyl ((((1S,4R)-4-(2-amino-6-methoxy-9H-purin-9-yl)cyclopent-2-en-1-yl)methoxy)(2-(pivaloylthio)ethoxy)phosphoryl)-L-alaninate, ethyl ((((1S,4R)-4-(2-amino-6-methoxy-9H-purin-9-yl)cyclopent-2-en-1-yl)methoxy)(phenoxy)phosphoryl)-L-alaninate, ((1R,4S)-4-(2-amino-6-methoxy-9H-purin-9-yl)cyclopent-2-en-1-yl)methyl bis(pivaloyloxymethyl)phosphate, cyclopropyl ((((1S,4R)-4-(2-amino-6-methoxy-9H-purin-9-yl)cyclopent-2-en-1-yl)methoxy)(phenoxy)phosphoryl)-L-alaninate, isopropyl ((((1S,4R)-4-(2-amino-6-chloro-9H-purin-9-yl)cyclopent-2-en-1-yl)methoxy)(4-chlorophenoxy)phosphoryl)-L-alaninate, isopropyl ((((1S,4R)-4-(2-amino-6-methoxy-9H-purin-9-yl)cyclopent-2-en-1-yl)methoxy)(4-chlorophenoxy)phosphoryl)-L-alaninate, isopropyl ((((1S,4R)-4-(2-amino-6-chloro-9H-purin-9-yl)cyclopent-2-en-1-yl)methoxy)(2-(pivaloylthio)ethoxy)phosphoryl)-L-alaninate, isopropyl ((((1S,4R)-4-(2-amino-6-methoxy-9H-purin-9-yl)cyclopent-2-en-1-yl)methoxy)(2-(pivaloylthio)ethoxy)phosphoryl)-L-alaninate, isopropyl ((R)-(((1S,4R)-4-(2-amino-6-ethoxy-9H-purin-9-yl)cyclopent-2-en-1-yl)methoxy)(phenoxy)phosphoryl)-L-alaninate, isopropyl ((R)-(((1S,4R)-4-(2-amino-6-isopropoxy-9H-purin-9-yl)cyclopent-2-en-1-yl)methoxy)(phenoxy)phosphoryl)-L-alaninate, isopropyl ((R)-(((1S,4R)-4-(2-amino-6-(2-methoxyethoxy)-9H-purin-9-yl)cyclopent-2-en-1-yl)methoxy)(phenoxy)phosphoryl)-L-alaninate, isopropyl ((R)-(((1S,4R)-4-(2-amino-6-(dimethylamino)-9H-purin-9-yl)cyclopent-2-en-1-yl)methoxy)(phenoxy)phosphoryl)-L-alaninate, isopropyl ((R)-(((1S,4R)-4-(2-amino-6-cyclobutoxy-9H-purin-9-yl)cyclopent-2-en-1-yl)methoxy)(phenoxy)phosphoryl)-L-alaninate, isopropyl ((((1S,4R)-4-(2-amino-6-methoxy-9H-purin-9-yl)cyclopent-2-en-1-yl)methoxy)(3-methoxyphenoxy)phosphoryl)-L-alaninate, isopropyl ((R)-(((1S,4R)-4-(2-amino-6-(azetidin-1-yl)-9H-purin-9-yl)cyclopent-2-en-1-yl)methoxy)(phenoxy)phosphoryl)-L-alaninate, isopropyl 2-(((((1S,4R)-4-(2-amino-6-methoxy-9H-purin-9-yl)cyclopent-2-en-1-yl)methoxy)(phenoxy)phosphoryl)amino)-2-methylpropanoate, isopropyl ((((1S,4R)-4-(2-amino-6-methoxy-9H-purin-9-yl)cyclopent-2-en-1-yl)methoxy)(phenoxy)phosphoryl)-L-leucinate, isopropyl ((((1S,4R)-4-(2-amino-6-methoxy-9H-purin-9-yl)cyclopent-2-en-1 -yl)methoxy)(3-(dimethylamino)phenoxy)phosphoryl)-L-alaninate, isopropyl ((((1S,4R)-4-(2-amino-6-methoxy-9H-purin-9-yl)cyclopent-2-en-1-yl)methoxy)(4-bromophenoxy)phosphoryl)-L-alaninate, isopropyl ((((1S,4R)-4-(2-amino-6-methoxy-9H-purin-9-yl)cyclopent-2-en-1-yl)methoxy)(3,5-dimethoxyphenoxy)phosphoryl)-L-alaninate, isopropyl ((((1S,4R)-4-(2-amino-6-methoxy-9H-purin-9-yl)cyclopent-2-en-1-yl)methoxy)(3,4-dimethoxyphenoxy)phosphoryl)-L-alaninate, isopropyl ((((1S,4R)-4-(2-amino-6-methoxy-9H-purin-9-yl)cyclopent-2-en-1-yl)methoxy)(benzo[d][1,3]dioxolo-5-yloxy)phosphoryl)-L-alaninate, isopropyl ((((1S,4R)-4-(2-amino-6-methoxy-9H-purin-9-yl)cyclopent-2-en-1-yl)methoxy)(3-(2-methoxyethoxy)phenoxy)phosphoryl)-L-alaninate, and isopropyl ((((1 S,4R)-4-(2-amino-6-methoxy)-9H-purin-9-yl)cyclopent-2-en-1-yl)methoxy)(naphthalen-1-yloxy)phosphoryl)-L-alaninate; or a salt thereof.

(17) A compound selected from isopropyl ((((1S,4R)-4-(2-amino-6-chloro-9H-purin-9-yl)cyclopent-2-en-1-yl)methoxy)(phenoxy)phosphoryl)-L-alaninate, S-(2-(((((1S,4R)-4-(2-amino-6-methoxy-9H-purin-9-yl)cyclopent-2-en-1-yl)methoxy)(phenoxy)phosphoryl)oxy)ethyl) 2,2-dimethylpropanethioate, isopropyl ((((1S,4R)-4-(2-amino-6-methoxy-9H-purin-9-yl)cyclopent-2-en-1-yl)methoxy)(phenoxy)phosphoryl)-L-alaninate, methyl ((((1S,4R)-4-(2-amino-6-methoxy-9H-purin-9-yl)cyclopent-2-en-1-yl)methoxy)(2-(pivaloylthio)ethoxy)phosphoryl)-L-alaninate, isopropyl ((((1S,4R)-4-(2-amino-6-methoxy-9H-purin-9-yl)cyclopent-2-en-1-yl)methoxy)(4-chlorophenoxy)phosphoryl)-L-alaninate, isopropyl ((((1S,4R)-4-(2-amino-6-methoxy-9H-purin-9-yl)cyclopent-2-en-1-yl)methoxy)(2-(pivaloylthio)ethoxy)phosphoryl)-L-alaninate, isopropyl ((R)-(((1S,4R)-4-(2-amino-6-ethoxy-9H-purin-9-yl)cyclopent-2-en-1-yl)methoxy)(phenoxy)phosphoryl)-L-alaninate, isopropyl ((R)-(((1S,4R)-4-(2-amino-6-(2-methoxyethoxy)-9H-purin-9-yl)cyclopent-2-en-1-yl)methoxy)(phenoxy)phosphoryl)-L-alaninate, isopropyl ((((1S,4R)-4-(2- amino-6-methoxy-9H-purin-9-yl)cyclopent-2-en-1-yl) methoxy)(3-methoxyphenoxy)phosphoryl)-L-alaninate, isopropyl ((((1S,4R)-4-(2-amino-6-methoxy-9H-purin-9-yl)cyclopent-2-en-1-yl)methoxy)(benzo[d][1,3]dioxolo-5-yloxy)phosphoryl)-L-alaninate, and isopropyl ((((1S,4R)-4-(2-amino-6-methoxy-9H-purin-9-yl)cyclopent-2-en-1-yl)methoxy)(3-(2-methoxy-ethoxy)phenoxy)phosphoryl)-L-alaninate; or a salt thereof.

(18) A compound represented by General Formula [1c]:

[1c]

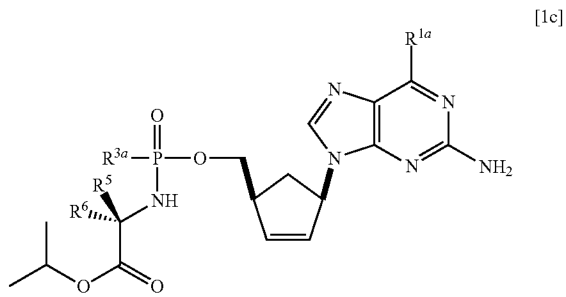

in the formula, $R^{1a}$ represents a halogen atom, a $C_{1-6}$ alkoxy group which may be substituted, or a group represented by General Formula —$NR^7R^8$ where $R^7$ and $R^8$ each represent a $C_{1-6}$ alkyl group which may be identically or differently substituted; or $R^7$ and $R^8$ together with a nitrogen atom to which $R^7$ and $R^8$ are bonded may be combined to form a monocyclic nitrogen-containing heterocyclic ring group which may be substituted;

$R^{3a}$ represents an aryloxy group which may be substituted or a heterocyclic oxy group which may be substituted; and $R^5$ and $R^6$ are the same or different from each other and each represent a hydrogen atom or a $C_{1-6}$ alkyl group which may be substituted; or a salt thereof.

(A) A medicine for treating an adenovirus infection, comprising a compound represented by General Formula [1] or a salt thereof.

(B) A method for suppressing adenovirus, comprising administering a compound represented by General Formula [1] or a salt thereof to a subject (preferably a mammal such as a human).

(C) A method for treating an adenovirus infection, comprising administering a compound represented by General Formula [1] or a salt thereof to a subject (preferably a mammal such as a human).

(D) A compound represented by General Formula [1] or a salt thereof for use in suppressing adenovirus.

(E) A compound represented by General Formula [1] or a salt thereof for use in the treatment of an adenovirus infection.

(F) Use of a compound represented by General Formula [1] or a salt thereof for the production of an anti-adenoviral agent.

(G) Use of a compound represented by General Formula [1] or a salt thereof for the production of a medicine for treating an adenovirus infection.

The compound represented by General Formula [1] or a salt thereof according to an aspect of the present invention is useful as an anti-adenoviral agent. The compound represented by General Formula [1] or a salt thereof according to the aspect of the present invention is useful as an agent for treating adenovirus.

BRIEF DESCRIPTION OF THE DRAWINGS

FIG. 1 shows the results of electrophoresis. An extension reaction of DNA was evaluated by detecting a fluorescently labeled DNA.

DESCRIPTION OF THE PREFERRED EMBODIMENTS

Hereinafter, the present invention will be described in detail.

In the present invention, the individual terms have the following meanings, unless otherwise indicated.

The halogen atom refers to a fluorine atom, a chlorine atom, a bromine atom, or an iodine atom.

The $C_{1-6}$ alkyl group refers to a linear or branched $C_{1-6}$ alkyl group such as a methyl group, an ethyl group, a propyl group, an isopropyl group, a butyl group, a sec-butyl group, an isobutyl group, a tert-butyl group, a pentyl group, an isopentyl group, a 2-methylbutyl group, a 2-pentyl group, a 3-pentyl group, or a hexyl group.

The $C_{1-20}$ alkyl group refers to a linear or branched $C_{1-20}$ alkyl group such as a methyl group, an ethyl group, a propyl group, an isopropyl group, a butyl group, a sec-butyl group, an isobutyl group, a tert-butyl group, a pentyl group, an isopentyl group, a 2-methylbutyl group, a 2-pentyl group, a 3-pentyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, a heptyl group, a 1-methylhexyl group, a 2-methylhexyl group, a 3-methylhexyl group, a 4-methylhexyl group, a 5-methylhexyl group, a 1-propylbutyl group, a 4,4-dimethylpentyl group, an octyl group, a 1-methylheptyl group, a 2-methylheptyl group, a 3-methylheptyl group, a 4-methylheptyl group, a 5-methylheptyl group, a 6-methylheptyl group, a 1-propylpentyl group, a 2-ethylhexyl group, a 5,5-dimethylhexyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, or an eicosanyl group.

The $C_{1-6}$ alkylthio group refers to a linear or branched $C_{1-6}$ alkylthio group such as a methylthio group, an ethylthio group, a propylthio group, an isopropylthio group, a butylthio group, an isobutylthio group, a sec-butylthio group, a tert-butylthio group, a pentylthio group, or a hexylthio group.

The $C_{1-20}$ alkylthio group refers to a linear or branched $C_{1-20}$ alkylthio group such as a methylthio group, an ethylthio group, a propylthio group, an isopropylthio group, a butylthio group, an isobutylthio group, a sec-butylthio group, a tert-butylthio group, a pentylthio group, a hexylthio group, a heptylthio group, an octylthio group, a nonylthio group, a decylthio group, an undecylthio group, a dodecylthio group, a tridecylthio group, a tetradecylthio group, a pentadecylthio group, a hexadecylthio group, a heptadecylthio group, an octadecylthio, a nonadecylthio group, or an eicosanylthio group.

The $C_{1-6}$ alkylsulfonyl group refers to a $C_{1-6}$ alkylsulfonyl group such as a methylsulfonyl group, an ethylsulfonyl group, or a propylsulfonyl group.

The $C_{1-6}$ alkylsulfonyloxy group refers to a $C_{1-6}$ alkylsulfonyloxy group such as a methylsulfonyloxy group or an ethylsulfonyloxy group.

The $C_{1-6}$ alkyldisulfanyl group refers to a linear or branched $C_{1-6}$ alkyldisulfanyl group such as a methyldisulfanyl group, an ethyldisulfanyl group, a propyldisulfanyl group, an isopropyldisulfanyl group, a butyldisulfanyl group, a sec-butyldisulfanyl group, an isobutyldisulfanyl group, a tert-butyldisulfanyl group, a pentyldisulfanyl group, an isopentyldisulfanyl group, a 2-methylbutyldisulfanyl group, a 2-pentyldisulfanyl group, a 3-pentyldisulfanyl group, or a hexyldisulfanyl group.

The $C_{2-6}$ alkenyl group refers to a linear or branched $C_{2-6}$ alkenyl group such as a vinyl group, an allyl group, a propenyl group, an isopropenyl group, a butenyl group, an isobutenyl group, a 1,3-butadienyl group, a pentenyl group, or a hexenyl group.

The $C_{2-6}$ alkynyl group refers to a linear or branched $C_{2-6}$ alkynyl group such as an ethynyl group, a propynyl group, a butynyl group, a pentynyl group, or a hexynyl group.

The $C_{3-8}$ cycloalkyl group refers to a $C_{3-8}$ cycloalkyl group such as a cyclopropyl group, a cyclobutyl group, a cyclopentyl group, a cyclohexyl group, or a cycloheptyl group.

The $C_{3-8}$ cycloalkyldisulfanyl group refers to a $C_{3-8}$ cycloalkyldisulfanyl group such as a cyclopropyldisulfanyl group, a cyclobutyldisulfanyl group, cyclopentyldisulfanyl group, a cyclohexyldisulfanyl group, or a cycloheptyldisulfanyl group.

The $C_{1-6}$ alkoxy group refers to a linear or branched $C_{1-6}$ alkyloxy group such as a methoxy group, an ethoxy group, a propoxy group, an isopropoxy group, a butoxy group, an isobutoxy group, a sec-butoxy group, a tert-butoxy group, a pentyloxy group, or a hexyloxy group.

The $C_{1-20}$ alkoxy group refers to a linear or branched $C_{1-20}$ alkyloxy group such as a methoxy group, an ethoxy group, a propoxy group, an isopropoxy group, a butoxy group, an isobutoxy group, a sec-butoxy group, a tert-butoxy group, a pentyloxy group, a hexyloxy group, a heptyloxy group, an octyloxy group, a nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group, or an eicosanyloxy group.

The $C_{1-6}$ alkoxy $C_{1-6}$ alkyl group refers to a $C_{1-6}$ alkyloxy $C_{1-6}$ alkyl group such as a methoxymethyl group or a 1-ethoxyethyl group.

The $C_{1-6}$ alkoxycarbonyl group refers to a linear or branched $C_{1-6}$ alkyloxycarbonyl group such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, or a hexyloxycarbonyl group.

The $C_{1-20}$ alkoxycarbonyl group refers to a linear or branched $C_{1-20}$ alkyloxycarbonyl group such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, a hexyloxycarbonyl group, a heptyloxycarbonyl group, an octyloxycarbonyl group, a nonyloxycarbonyl group, a decyloxycarbonyl group, an undecyloxycarbonyl group, a dodecyloxycarbonyl group, a tridecyloxycarbonyl group, a tetradecyloxycarbonyl group, a pentadecyloxycarbonyl group, a hexadecyloxycarbonyl group, a heptadecyloxycarbonyl group, an octadecyloxycarbonyl group, a nonadecyloxycarbonyl group, or an eicosanyloxycarbonyl group.

The $C_{1-6}$ alkoxycarbonyloxy group refers to a linear or branched $C_{1-6}$ alkyloxycarbonyloxy group such as a methoxycarbonyloxy group, an ethoxycarbonyloxy group, a propoxycarbonyloxy group, an isopropoxycarbonyloxy group, a butoxycarbonyloxy group, an isobutoxycarbonyloxy group, a sec-butoxycarbonyloxy group, a tert-butoxycarbonyloxy group, a pentyloxycarbonyloxy group, or a hexyloxycarbonyloxy group.

The $C_{3-8}$ cycloalkoxy group refers to a $C_{3-8}$ cycloalkyloxy group such as a cyclopropoxy group, a cyclobutoxy group, a cyclopentyloxy group, a cyclohexyloxy group, or a cycloheptyloxy group.

The $C_{3-8}$ cycloalkoxycarbonyl group refers to a $C_{3-8}$ cycloalkoxycarbonyl group such as a cyclopropoxycarbonyl group, a cyclobutoxycarbonyl group, a cyclopentyloxycarbonyl group, a cyclohexyloxycarbonyl group, a cycloheptyloxycarbonyl group, or a cyclooctyloxycarbonyl group.

The aryl group refers to a phenyl group, a naphthyl group, or the like.

The aryloxy group refers to a phenoxy group, a naphthalen-1-yloxy group, a naphthalen-2-yloxy group, or the like.

The arylsulfonyl group refers to a benzenesulfonyl group, a p-toluenesulfonyl group, a naphthalenesulfonyl group, or the like.

The arylsulfonyloxy group refers to a benzenesulfonyloxy group, a p-toluenesulfonyloxy group, or the like.

The aryldisulfanyl group refers to a phenyldisulfanyl group, a naphthyldisulfanyl group, or the like.

The aryl $C_{1-6}$ alkyl group refers to an aryl $C_{1-6}$ alkyl group such as a benzyl group, a diphenylmethyl group, a trityl group, a phenethyl group, a 2-phenylpropyl group, a 3-phenylpropyl group, or a naphthylmethyl group.

The aryl $C_{1-6}$ alkoxy group refers to an aryl $C_{1-6}$ alkyloxy group such as a benzyloxy group, a diphenylmethoxy group, a trityloxy group, a phenethyloxy group, a 2-phenylpropoxy group, a 3-phenylpropoxy group, or a naphthylmethoxy group.

The aryl $C_{1-6}$ alkoxy $C_{1-6}$ alkyl group refers to an aryl $C_{1-6}$ alkyloxy $C_{1-6}$ alkyl group such as a benzyloxymethyl group or a phenethyloxymethyl group.

The aryl $C_{1-6}$ alkoxycarbonyl group refers to an aryl $C_{1-6}$ alkyloxycarbonyl group such as a benzyloxycarbonyl group or a phenethyloxycarbonyl group.

The aryloxycarbonyl group refers to a phenoxycarbonyl group, a naphthalen-1-yloxycarbonyl group, or a naphthalen-2-yloxycarbonyl group.

The monocyclic nitrogen-containing heterocyclic ring group refers to a monocyclic nitrogen-containing heterocyclic ring group which contains only a nitrogen atom as a heteroatom forming the ring, such as an aziridinyl group, an azetidinyl group, a pyrrolidinyl group, a pyrrolinyl group, a pyrrolyl group, a piperidyl group, a tetrahydropyridyl group, a dihydropyridyl group, a pyridyl group, a homopiperidinyl group, an octahydroazocinyl group, an imidazolidinyl group, an imidazolinyl group, an imidazolyl group, a pyrazolidinyl group, a pyrazolinyl group, a pyrazolyl group, a piperazinyl group, a pyrazinyl group, a pyridazinyl group, a pyrimidinyl group, a homopiperazinyl group, a triazolyl group, or a tetrazolyl group.

The monocyclic oxygen-containing heterocyclic ring group refers to a monocyclic oxygen-containing heterocyclic ring group which contains only an oxygen atom as a heteroatom forming the ring, such as an oxetanyl group, a tetrahydrofuranyl group, a furanyl group, a tetrahydropyranyl group, a pyranyl group, a 1,3-dioxanyl group, or a 1,4-dioxanyl group.

The monocyclic sulfur-containing heterocyclic ring group refers to a thienyl group.

The monocyclic nitrogen- and oxygen-containing heterocyclic ring group refers to a monocyclic nitrogen- and oxygen-containing heterocyclic ring group which contains only a nitrogen atom and an oxygen atom as heteroatoms forming the ring, such as an oxazolyl group, an isoxazolyl group, an oxadiazolyl group, a morpholinyl group, or an oxazepanyl group.

The monocyclic nitrogen- and sulfur-containing heterocyclic ring group refers to a monocyclic nitrogen- and sulfur-containing heterocyclic ring group which contains only a nitrogen atom and a sulfur atom as heteroatoms forming the ring, such as a thiazolyl group, an isothiazolyl group, a thiadiazolyl group, a thiomorpholinyl group, a 1-oxidothiomorpholinyl group, or a 1,1-dioxidothiomorpholinyl group.

The monocyclic heterocyclic ring group refers to a monocyclic nitrogen-containing heterocyclic ring group, a monocyclic oxygen-containing heterocyclic ring group, a monocyclic sulfur-containing heterocyclic ring group, a monocyclic nitrogen- and oxygen-containing heterocyclic ring group, or a monocyclic nitrogen- and sulfur-containing heterocyclic ring group.

The bicyclic nitrogen-containing heterocyclic ring group refers to a bicyclic nitrogen-containing heterocyclic ring group which contains only a nitrogen atom as a heteroatom forming the ring, such as an indolinyl group, an indolyl group, an isoindolinyl group, an isoindolyl group, a benzimidazolyl group, an indazolyl group, a benzotriazolyl group, a pyrazolopyridinyl group, a quinolyl group, a tetrahydroquinolinyl group, a quinolyl group, a tetrahydroisoquinolinyl group, an isoquinolinyl group, a quinolizinyl group, a cinnolinyl group, a phthalazinyl group, a quinazolinyl group, a dihydroquinoxalinyl group, a quinoxalinyl group, a naphthyridinyl group, a purinyl group, a pteridinyl group, or a quinuclidinyl group.

The bicyclic oxygen-containing heterocyclic ring group refers to a bicyclic oxygen-containing heterocyclic ring group which contains only an oxygen atom as a heteroatom forming the ring, such as a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group, or a 1,4-benzodioxanyl group.

The bicyclic sulfur-containing heterocyclic ring group refers to a bicyclic sulfur-containing heterocyclic ring group which contains only a sulfur atom as a heteroatom forming the ring, such as a 2,3-dihydrobenzothienyl group or a benzothienyl group.

The bicyclic nitrogen- and oxygen-containing heterocyclic ring group refers to a bicyclic nitrogen- and oxygen-containing heterocyclic ring group which contains only a nitrogen atom and an oxygen atom as heteroatoms forming the ring, such as a benzoxazolyl group, a benzisoxazolyl group, a benzoxadiazolyl group, a benzomorpholinyl group, a dihydropyranopyridyl group, a dioxolopyridyl group, a furopyridinyl group, a dihydrodioxynopyridyl group, or a dihydropyridooxazinyl group.

The bicyclic nitrogen- and sulfur-containing heterocyclic ring group refers to a bicyclic nitrogen- and sulfur-containing heterocyclic ring group which contains a nitrogen atom and a sulfur atom as heteroatoms forming the ring, such as a benzothiazolyl group, a benzoisothiazolyl group, or a benzothiadiazolyl group.

The bicyclic heterocyclic ring group refers to a bicyclic nitrogen-containing heterocyclic ring group, a bicyclic oxygen-containing heterocyclic ring group, a bicyclic sulfur-containing heterocyclic ring group, a bicyclic nitrogen- and oxygen-containing heterocyclic ring group, or a bicyclic nitrogen- and sulfur-containing heterocyclic ring group.

The spiro heterocyclic ring group refers to a spiro heterocyclic ring group which contains a nitrogen atom, an oxygen atom, or a sulfur atom as a heteroatom forming the ring, such as a 2-oxa-6-azaspiro[3.3]heptyl group, a 1,4-dioxaspiro[4.5]decyl group, a 1-oxa-8-azaspiro[4.5]decyl group, or a 1-thia-8-azaspiro[4.5]decyl group.

The bridged heterocyclic ring group refers to a bridged heterocyclic ring group which contains a nitrogen atom, an oxygen atom, or a sulfur atom as a heteroatom forming the ring, such as a 3-oxa-8-azabicyclo[3.2.1]octyl group, an 8-oxa-3-azabicyclo[3.2.1]octyl group, or a quinuclidinyl group.

The heterocyclic ring group refers to a monocyclic heterocyclic ring group, a bicyclic heterocyclic ring group, a spiro heterocyclic ring group, or a bridged heterocyclic ring group.

The heterocyclic oxy group refers to a substituent in which an oxygen atom is bonded to a heterocyclic ring group, such as a pyrrolidinyloxy group, a piperidinyloxy group, a tetrahydrofuranyloxy group, a tetrahydropyranyloxy group, or a tetrahydrothiopyranyloxy group.

The 5- to 10-membered nitrogen- and phosphorus-containing heterocyclic ring refers to a 5- to 10-membered nitrogen- and phosphorus-containing heterocyclic ring which contains only a nitrogen atom and a phosphorus atom as heteroatoms forming the ring and which may be fused, such as 1,3,2-diazaphospholidine, 1,3,2-diazaphosphinane, 1,3,2-diazaphosphepane, or 1,3,2-diazaphosphocane.

The 5- to 10-membered oxygen- and phosphorus-containing heterocyclic ring refers to a 5- to 10-membered oxygen- and phosphorus-containing heterocyclic ring which contains only an oxygen atom and a phosphorus atom as heteroatoms forming the ring and which may be fused, such as 1,3,2-dioxaphospholane, 1,3,2-dioxaphosphinane, 1,3,2-dioxaphosphepane, 1,3,2-dioxaphosphocane, benzo[d][1,3,2]dioxaphosphor, or 4H-benzo[d][1,3,2]dioxaphosphinine.

The 5- to 10-membered nitrogen-, oxygen-, and phosphorus-containing heterocyclic ring refers to a 5- to 10-membered nitrogen-, oxygen-, and phosphorus-containing heterocyclic ring which contains only a nitrogen atom, an oxygen atom, and a phosphorus atom as heteroatoms forming the ring and which may be fused, such as 1,3,2-oxazaphospholidine, 2,3-dihydrobenzo[d][1,3,2]oxazaphosphor, 1,3,2-oxazaphosphinane, or 3,4-dihydro-4H-benzo[e][1,3,2]oxazaphosphinine.

The 6- to 10-membered oxygen- and phosphorus-containing heterocyclic ring refers to a 6- to 10-membered oxygen- and phosphorus-containing heterocyclic ring which contains only an oxygen atom and a phosphorus atom as heteroatoms forming the ring and which may be fused, such as 1,3,2-dioxaphosphinane, 1,3,2-dioxaphosphepane, or 1,3,2-dioxaphosphocane.

The $C_{2-6}$ alkanoyl group refers to a linear or branched $C_{2-6}$ alkanoyl group such as an acetyl group, a propionyl group, a valeryl group, an isovaleryl group, or a pivaloyl group.

The $C_{3-8}$ cycloalkylcarbonyl group refers to a $C_{3-8}$ cycloalkylcarbonyl group such as a cyclopropylcarbonyl group, a cyclobutylcarbonyl group, a cyclopentylcarbonyl group, a cyclohexylcarbonyl group, or a cycloheptylcarbonyl group.

The aroyl group refers to a benzoyl group, a naphthoyl group, or the like.

The heterocyclic carbonyl group refers to a heterocyclic carbonyl group such as a pyrrolylcarbonyl group, a pyridylcarbonyl group, a furanylcarbonyl group, or a thienylcarbonyl group.

The acyl group refers to a formyl group, a succinyl group, a glutaryl group, a maleoyl group, a phthaloyl group, a $C_{2-6}$ alkanoyl group, a $C_{3-8}$ cycloalkylcarbonyl group, an aroyl group, or a heterocyclic carbonyl group.

The $C_{2-6}$ alkanoyloxy group refers to a linear or branched $C_{2-6}$ alkanoyloxy group such as an acetyloxy group, a propionyloxy group, a valeryloxy group, an isovaleryloxy group, or a pivaloyloxy group.

The $C_{1-6}$ alkylcarbonyloxy group refers to a linear or branched $C_{1-6}$ alkylcarbonyloxy group such as a methylcarbonyloxy group, an ethylcarbonyloxy group, a propylcarbonyloxy group, an isopropylcarbonyloxy group, a butylcarbonyloxy group, a sec-butylcarbonyloxy group, an isobutylcarbonyloxy group, or a tert-butylcarbonyloxy group.

The $C_{3-8}$ cycloalkylcarbonyloxy group refers to a $C_{3-8}$ cycloalkylcarbonyloxy group such as a cyclopropylcarbonyloxy group, a cyclobutylcarbonyloxy group, a cyclopentylcarbonyloxy group, a cyclohexylcarbonyloxy group, or a cycloheptylcarbonyloxy group.

The aroyloxy group refers to a benzoyloxy group, a naphthoyloxy group, or the like.

The heterocyclic carbonyloxy group refers to a heterocyclic carbonyloxy group such as a pyrrolylcarbonyloxy group, a pyridylcarbonyloxy group, a furanylcarbonyloxy group, or a thienylcarbonyloxy group.

The acyloxy group refers to a $C_{2-6}$ alkanoyloxy group, a $C_{3-8}$ cycloalkylcarbonyloxy group, an aroyloxy group, or a heterocyclic carbonyloxy group.

The $C_{2-6}$ alkanoylthio group refers to a linear or branched $C_{2-6}$ alkanoylthio group such as an acetylthio group, a propionylthio group, a valerylthio group, an isovalerylthio group, or a pivaloylthio group.

The $C_{1-6}$ alkylcarbonylthio group refers to a linear or branched $C_{1-6}$ alkylcarbonylthio group such as a methylcarbonylthio group, an ethylcarbonylthio group, a propylcarbonylthio group, an isopropylcarbonylthio group, a butylcarbonylthio group, a sec-butylcarbonylthio group, an isobutylcarbonylthio group, or a tert-butylcarbonylthio group.

The $C_{3-8}$ cycloalkylcarbonylthio group refers to a $C_{3-8}$ cycloalkylcarbonylthio group such as a cyclopropylcarbonylthio group, a cyclobutylcarbonylthio group, a cyclopentylcarbonylthio group, a cyclohexylcarbonylthio group, or a cycloheptylcarbonylthio group.

The aroylthio group refers to a benzoylthio group, a naphthoylthio group, or the like.

The heterocyclic carbonylthio group refers to a heterocyclic carbonylthio group such as a pyrrolylcarbonylthio group, a pyridylcarbonylthio group, a furanylcarbonylthio group, or a thienylcarbonylthio group.

The acylthio group refers to a $C_{2-6}$ alkanoylthio group, a $C_{3-8}$ cycloalkylcarbonylthio group, an aroylthio group, or a heterocyclic carbonylthio group.

The silyl group refers to a trimethylsilyl group, a triethylsilyl group, a tributylsilyl group, or a tert-butyldimethylsilyl group.

The leaving group refers to a halogen atom, a $C_{1-6}$ alkylsulfonyloxy group, an aryloxy group, or an arylsulfonyloxy group. The $C_{1-6}$ alkylsulfonyloxy group, aryloxy group, and arylsulfonyloxy group may be substituted with one or more substituents selected from a halogen atom, a nitro group, a $C_{1-6}$ alkyl group, and a $C_{1-6}$ alkoxy group.

The hydroxyl protecting group is any conventional group which can be used as a protecting group for a hydroxyl group, and examples thereof include the groups described in, for example, T. W. Greene et al., Protective Groups in Organic Synthesis, 4th edition, pp. 16 to 299, 2007, John Wiley & Sons, Inc. Specific examples of the hydroxyl protecting group include a $C_{1-6}$ alkyl group, a $C_{2-6}$ alkenyl group, an aryl $C_{1-6}$ alkyl group, a $C_{1-6}$ alkoxy $C_{1-6}$ alkyl group, an aryl $C_{1-6}$ alkoxy $C_{1-6}$ alkyl group, an acyl group, a $C_{1-6}$ alkoxycarbonyl group, an aryl $C_{1-6}$ alkoxycarbonyl group, a $C_{1-6}$ alkylsulfonyl group, an arylsulfonyl group, a silyl group, a tetrahydrofuranyl group, and a tetrahydropyranyl group.

The thiol protecting group is any conventional group which can be used as a protecting group for a thiol group, and examples thereof include the groups described in, for example, W.

Greene et al., Protective Groups in Organic Synthesis, 4th edition, pp. 647 to 695, 2007, John Wiley & Sons, Inc. Specific examples of the thiol protecting group include a $C_{1-6}$ alkyl group, a $C_{2-6}$ alkenyl group, an aryl $C_{1-6}$ alkyl group, a $C_{1-6}$ alkoxy $C_{1-6}$ alkyl group, an acyl group, and a silyl group.

The amino protecting group is any conventional group which can be used as a protecting group for an amino group, and examples thereof include the groups described in, for example, W. Greene et al., Protective Groups in Organic Synthesis, 4th edition, pp. 696 to 926, 2007, John Wiley & Sons, Inc. Specific examples of the amino protecting group include an aryl $C_{1-6}$ alkyl group, a $C_{1-6}$ alkoxy $C_{1-6}$ alkyl group, an acyl group, a $C_{1-6}$ alkoxycarbonyl group, an aryl $C_1$_6 alkoxycarbonyl group, an aryloxycarbonyl group, a $C_{1-6}$ alkylsulfonyl group, an arylsulfonyl group, and a silyl group.

Aliphatic hydrocarbons refer to pentane, hexane, heptane, cyclohexane, methylcyclohexane, and ethylcyclohexane.

Halogenated hydrocarbons refer to dichloromethane, chloroform, and dichloroethane.

Ethers refer to diethyl ether, diisopropyl ether, dioxane, tetrahydrofuran, anisole, ethylene glycol dimethyl ether, diethylene glycol dimethyl ether, and diethylene glycol diethyl ether.

Ketones refer to acetone, 2-butanone, 4-methyl-2-pentanone, and methyl isobutyl ketone.

Esters refer to methyl acetate, ethyl acetate, propyl acetate, and butyl acetate.

Amides refer to N,N-dimethylformamide, N,N-dimethylacetamide, and N-methylpyrrolidone.

Nitriles refer to acetonitrile and propionitrile.

Sulfoxides refer to dimethyl sulfoxide and sulfolane.

Aromatic hydrocarbons refer to benzene, toluene, and xylene.

The inorganic base refers to sodium hydroxide, potassium hydroxide, sodium methoxide, sodium ethoxide, tert-butoxy sodium, tert-butoxy potassium, sodium hydrogen carbonate, sodium carbonate, potassium carbonate, tripotassium phosphate, potassium acetate, cesium fluoride, cesium carbonate, or tert-butyl magnesium chloride.

The organic base refers to triethylamine, N,N-diisopropylethylamine, 1,8-diazabicyclo(5.4.0)undec-7-ene (DBU), pyridine, 4-dimethylaminopyridine, N-methylmorpholine, or imidazole.

Individual substituent groups have the following meanings.

<Substituent group A> a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a C3_s cycloalkyldisulfanyl group which may be substituted with one or more substituents selected from Substituent group B; a $C_{1-6}$ alkoxy group which may be substituted with one or more substituents selected from Substituent group B; an amino group which may be substituted with one or more substituents selected from Substituent group B; a $C_{1-6}$ alkoxycarbonyl group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B. <Substituent group B> a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an aryloxycarbonyl group; an aryl C1_6 alkoxycarbonyl group; an aryl group; an aryloxy group; a heterocyclic oxy group which may be substituted with one or more substituents selected from a hydroxyl group and a hydroxymethyl group; an aryl $C_{1-6}$ alkoxy group; and an acyloxy group.

<Substituent Group A1>

A halogen atom; a $C_{1-6}$ alkyl group which may be substituted with one or more halogen atoms; a $C_{1-6}$ alkoxy group which may be substituted with one or more $C_{1-6}$ alkoxy groups; and an amino group which may be substituted with one or more $C_{1-6}$ alkyl groups.

Examples of salts of the compound represented by General Formula [1] include salts in basic groups such as an amino group, and salts in acidic groups such as a hydroxyl group and a carboxyl group, which are commonly known.

Examples of salts in basic groups include salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylene sulfonic acid, and naphthalene sulfonic acid.

Examples of salts in acidic groups include salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

Among the salts mentioned above, preferred salts include pharmacologically acceptable salts.

The compound represented by General Formula [1] or a salt thereof according to the embodiment of the present invention can be used for the treatment of adenovirus.

The treatment refers to preventing, treating, or the like of a variety of diseases.

The treatment agent refers to a substance which is provided for the purpose of preventing or treating a variety of diseases.

The preventing refers to inhibition of disease onset, reduction of disease onset risk, delay of disease onset, or the like.

The treating refers to improvement of, inhibition of progression of, or the like of a target disease or condition.

The compound represented by General Formula [1] according to the embodiment of the present invention is a mixture of a compound represented by General Formula [1a] and a compound represented by General Formula [1b]

[1a]

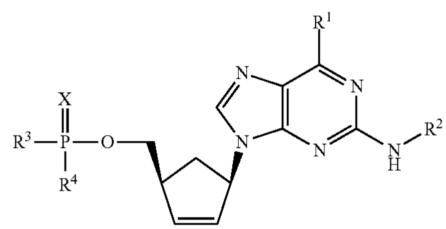

[1b]

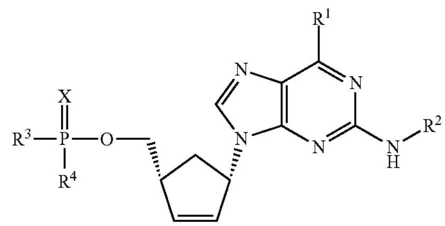

(In the formulae, $R^1$, $R^2$, $R^3$, $R^4$, and X are as defined above).

The compound represented by General Formula [1] according to the embodiment of the present invention is preferably the compound represented by General Formula [1a] or the compound represented by General Formula [1b] and more preferably the compound represented by General Formula [1a].

$R^1$ $R^1$ is a hydrogen atom, a halogen atom, an amino group which may be substituted, a monocyclic nitrogen-containing heterocyclic ring group which may be substituted (provided that a nitrogen atom forming the ring is bonded to a carbon atom to which $R^1$ is bonded), a monocyclic nitrogen- and oxygen-containing heterocyclic ring group which may be substituted (provided that a nitrogen atom forming the ring is bonded to a carbon atom to which $R^1$ is bonded), a $C_{1-6}$ alkoxy group which may be substituted, a $C_{3-8}$ cycloalkoxy group which may be substituted, a $C_{1-6}$ alkylthio group which may be substituted, a hydroxyl group which may be protected, or a thiol group which may be protected.

$R^1$ is preferably a halogen atom, an amino group which may be substituted, a monocyclic nitrogen-containing heterocyclic ring group which may be substituted (provided that a nitrogen atom forming the ring is bonded to a carbon atom to which $R^1$ is bonded), a monocyclic nitrogen- and oxygen-containing heterocyclic ring group which may be substituted (provided that a nitrogen atom forming the ring is bonded to a carbon atom to which $R^1$ is bonded), a $C_{1-6}$ alkoxy group which may be substituted, a $C_{3-8}$ cycloalkoxy group which may be substituted, a $C_{1-6}$ alkylthio group which may be substituted, a hydroxyl group which may be protected, or a thiol group which may be protected.

In another aspect, $R^1$ is preferably a halogen atom, an amino group which may be substituted with one or more substituents selected from Substituent group A, a monocyclic nitrogen-containing heterocyclic ring group which may be substituted with one or more substituents selected from Substituent group A (provided that a nitrogen atom forming the ring is bonded to a carbon atom to which $R^1$ is bonded), a monocyclic nitrogen- and oxygen-containing heterocyclic ring group which may be substituted with one or more substituents selected from Substituent group A (provided that a nitrogen atom forming the ring is bonded to a carbon atom to which $R^1$ is bonded), a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylthio group which may be substituted with one or more substituents selected from Substituent group A, a hydroxyl group which may be protected, or a thiol group which may be protected; more preferably a halogen atom, an amino group which may be substituted with one or more substituents selected from Substituent group A, a $C_{1-6}$ alkoxy group which may be substituted with one or more substituents selected from Substituent group A, a hydroxyl group which may be protected, or a thiol group which may be protected; still more preferably a halogen atom, an amino group which may be substituted with one or more substituents selected from Substituent group A, a $C_{1-6}$ alkoxy group which may be substituted with one or more substituents selected from substituent group A, or a hydroxyl group; and even still more preferably a $C_{1-6}$ alkoxy group which may be substituted with one or more $C_{1-6}$ alkoxy groups or a halogen atom.

The substituent of the amino group which may be substituted with one or more substituents selected from Substituent group A in the definition of $R^1$ is preferably a $C_{1-6}$ alkyl group which may be substituted with one or more substituents selected from Substituent group B or a $C_{3-8}$ cycloalkyl group which may be substituted with one or more substituents selected from Substituent group B, and more preferably a $C_{1-6}$ alkyl group or a $C_{3-8}$ cycloalkyl group.

In another aspect, the substituent of the amino group which may be substituted with one or more substituents selected from Substituent group A in the definition of $R^1$ is preferably a $C_{1-6}$ alkyl group which may be substituted with one or more substituents selected from Substituent group B, more preferably a $C_{1-6}$ alkyl group, and still more preferably a methyl group or an ethyl group.

The substituent of the monocyclic nitrogen-containing heterocyclic ring group which may be substituted with one or more substituents selected from Substituent group A (provided that a nitrogen atom forming the ring is bonded to a carbon atom to which $R^1$ is bonded), in the definition of $R^1$, is preferably a halogen atom, a $C_{1-6}$ alkyl group which may be substituted with one or more substituents selected from Substituent group B, or a $C_{1-6}$ alkoxy group which may be substituted with one or more substituents selected from Substituent group B.

The substituent of the monocyclic nitrogen- and oxygen-containing heterocyclic ring group which may be substituted with one or more substituents selected from Substituent group A (provided that a nitrogen atom forming the ring is bonded to a carbon atom to which $R^1$ is bonded) is preferably a halogen atom, a $C_{1-6}$ alkyl group which may be substituted with one or more substituents selected from Substituent group B, or a $C_{1-6}$ alkoxy group which may be substituted with one or more substituents selected from Substituent group B.

The substituent of the $C_{1-6}$ alkoxy group which may be substituted with one or more substituents selected from Substituent group A in the definition of $R^1$ is preferably a halogen atom or a $C_{1-6}$ alkoxy group which may be substituted with one or more substituents selected from Substituent group B.

The substituent of the $C_{3-8}$ cycloalkoxy group which may be substituted with one or more substituents selected from Substituent group A in the definition of $R^1$ is preferably a halogen atom or a $C_{1-6}$ alkyl group which may be substituted with one or more substituents selected from Substituent group B.

The substituent of the $C_{1-6}$ alkylthio group which may be substituted with one or more substituents selected from Substituent group A in the definition of $R^1$ is preferably a halogen atom or a $C_{1-6}$ alkoxy group which may be substituted with one or more substituents selected from Substituent group B.

$R^2$ $R^2$ is a hydrogen atom or an amino protecting group.

$R^2$ is preferably a hydrogen atom or an acyl group, more preferably a hydrogen atom or a $C_{2-6}$ alkanoyl group, and still more preferably a hydrogen atom.

$R^3$ $R^3$ is a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, or $—O—P(O)(OH)—O—PO_3H$.

$R^3$ is preferably a $C_{1-20}$ alkoxy group which may be substituted with one or more substituents selected from Substituent group A, a $C_{3-8}$ cycloalkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, an amino group which may be substituted with one or more substituents selected from Substituent group A, or —O—P(O)(OH)—O—$PO_3$H; more preferably a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic oxy group which may be substituted with one or more substituents selected from Substituent group A, an amino group which may be substituted with one or more substituents selected from Substituent group A, or —O—P(O)(OH)—O—$PO_3$H; still more preferably a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic oxy group which may be substituted with one or more substituents selected from Substituent group A, or —O—P(O)(OH)—O—$PO_3$H; and even still more preferably a $C_{1-20}$ alkoxy group which may be substituted with one or more substituents selected from Substituent group A, an aryloxy group which may be substituted with one or more substituents selected from Substituent group A, a heterocyclic oxy group which may be substituted with one or more substituents selected from Substituent group A, or —O—P(O)(OH)—O—$PO_3$H.

The substituent of the $C_{1-20}$ alkoxy group which may be substituted with one or more substituents selected from Substituent group A in the definition of $R^3$ is preferably a $C_{1-6}$ alkyldisulfanyl group which may be substituted with one or more substituents selected from Substituent group B, a $C_{1-6}$ alkylcarbonyloxy group which may be substituted with one or more substituents selected from Substituent group B, or a $C_{1-6}$ alkylcarbonylthio group which may be substituted with one or more substituents selected from Substituent group B.

Here, the substituent of the $C_{1-6}$ alkyldisulfanyl group which may be substituted with one or more substituents selected from Substituent group B is preferably a hydroxyl group, a $C_{1-6}$ alkoxy group, an aryl $C_{1-6}$ alkoxy group, or an acyloxy group and more preferably an aryl $C_{1-6}$ alkoxy group.

The substituent of the $C_{1-6}$ alkylcarbonyloxy group which may be substituted with one or more substituents selected from Substituent group B is preferably a hydroxyl group, a $C_{1-6}$ alkoxy group, an aryl $C_{1-6}$ alkoxy group, or an acyloxy group and more preferably a hydroxyl group.

The substituent of the $C_{1-6}$ alkylcarbonylthio group which may be substituted with one or more substituents selected from Substituent group B is preferably a hydroxyl group, a $C_{1-6}$ alkoxy group, an aryl $C_{1-6}$ alkoxy group, or an acyloxy group and more preferably a hydroxyl group.

The substituent of the aryloxy group which may be substituted with one or more substituents selected from Substituent group A in the definition of $R^3$ is preferably a halogen atom, a $C_{1-6}$ alkyl group which may be substituted with one or more substituents selected from Substituent group B, a $C_{1-6}$ alkoxy group which may be substituted with one or more substituents selected from Substituent group B, or an amino group which may be substituted with one or more substituents selected from Substituent group B, and more preferably a halogen atom, a $C_{1-6}$ alkyl group which may be substituted with one or more halogen atoms, a $C_{1-6}$ alkoxy group which may be substituted with one or more $C_{1-6}$ alkoxy groups, or an amino group which may be substituted with one or more $C_{1-6}$ alkyl groups.

The substituent of the heterocyclic oxy group which may be substituted with one or more substituents selected from Substituent group A in the definition of $R^3$ is preferably a halogen atom, a $C_{1-6}$ alkyl group which may be substituted with one or more substituents selected from Substituent group B, a $C_{1-6}$ alkoxy group which may be substituted with one or more substituents selected from Substituent group B, or an amino group which may be substituted with one or more substituents selected from Substituent group B, and more preferably a halogen atom, a $C_{1-6}$ alkyl group which may be substituted with one or more halogen atoms, a $C_{1-6}$ alkoxy group which may be substituted with one or more $C_{1-6}$ alkoxy groups, or an amino group which may be substituted with one or more $C_{1-6}$ alkyl groups.

$R^4$ $R^4$ is a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, or a hydroxyl group which may be protected.

$R^4$ is preferably a $C_{1-20}$ alkoxy group which may be substituted with one or more substituents selected from Substituent group A, a $C_{3-8}$ cycloalkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, an amino group which may be substituted with one or more substituents selected from Substituent group A, or a hydroxyl group which may be protected; more preferably a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or a hydroxyl group which may be protected; and still more preferably a $C_{1-20}$ alkoxy group which may be substituted with one or more substituents selected from Substituent group A, an amino group which may be substituted with one or more substituents selected from Substituent group A, or a hydroxyl group which may be protected.

The substituent of the $C_{1-20}$ alkoxy group which may be substituted with one or more substituents selected from Substituent group A in the definition of $R^4$ is preferably a $C_{1-6}$ alkyldisulfanyl group which may be substituted with one or more substituents selected from Substituent group B, a $C_{1-6}$ alkylcarbonyloxy group which may be substituted with one or more substituents selected from Substituent group B, or a $C_{1-6}$ alkylcarbonylthio group which may be substituted with one or more substituents selected from Substituent group B.

Here, the substituent of the $C_{1-6}$ alkyldisulfanyl group which may be substituted with one or more substituents selected from Substituent group B is preferably a hydroxyl group, a $C_{1-6}$ alkoxy group, an aryl $C_{1-6}$ alkoxy group, or an acyloxy group and more preferably an aryl $C_{1-6}$ alkoxy group.

The substituent of the $C_{1-6}$ alkylcarbonyloxy group which may be substituted with one or more substituents selected from Substituent group B is preferably a hydroxyl group, a $C_{1-6}$ alkoxy group, an aryl $C_{1-6}$ alkoxy group, or an acyloxy group and more preferably a hydroxyl group.

The substituent of the $C_{1-6}$ alkylcarbonylthio group which may be substituted with one or more substituents selected from Substituent group B is preferably a hydroxyl group, a $C_{1-6}$ alkoxy group, an aryl $C_{1-6}$ alkoxy group, or an acyloxy group and more preferably a hydroxyl group.

The substituent of the aryloxy group which may be substituted with one or more substituents selected from Substituent group A in the definition of $R^4$ is preferably a halogen atom, a $C_{1-6}$ alkyl group which may be substituted with one or more substituents selected from Substituent group B, or a $C_{1-6}$ alkoxy group which may be substituted with one or more substituents selected from Substituent group B, and more preferably a halogen atom.

The substituent of the amino group which may be substituted with one or more substituents selected from Substituent group A in the definition of $R^4$ is preferably a $C_{1-6}$ alkyl group which may be substituted with one or more substituents selected from Substituent group B, more preferably a $C_{1-6}$ alkyl group substituted with one or more $C_{1-6}$ alkoxycarbonyl group, and still more preferably an ethyl group substituted with an isopropoxycarbonyl group.

$R^3$ and $R^4$, together with the phosphorus atom to which $R^3$ and $R^4$ are bonded, may be combined to form a 5- to 10-membered nitrogen- and phosphorus-containing heterocyclic ring which may be substituted, a 5- to 10-membered oxygen- and phosphorus-containing heterocyclic ring which may be substituted, or a 5- to 10-membered nitrogen-, oxygen-, and phosphorus-containing heterocyclic ring which may be substituted.

The ring formed by combining $R^3$ and $R^4$ together with the phosphorus atom to which $R^3$ and $R^4$ are bonded is preferably a 5- to 10-membered oxygen- and phosphorus-containing heterocyclic ring which may be substituted and more preferably 1,3,2-dioxaphosphinane or 4H-benzo[d][1,3,2]dioxaphosphinine.

The substituent of the 5- to 10-membered nitrogen- and phosphorus-containing heterocyclic ring which may be substituted, the 5- to 10-membered oxygen- and phosphorus-containing heterocyclic ring which may be substituted, or the 5- to 10-membered nitrogen-, oxygen-, and phosphorus-containing heterocyclic ring which may be substituted, each of which being formed by combining $R^3$ and $R^4$ together with the phosphorus atom to which $R^3$ and $R^4$ are bonded, is preferably a $C_{1-6}$ alkoxy group which may be substituted with one or more substituents selected from Substituent group A or an aryl group which may be substituted with one or more substituents selected from Substituent group A.

Here, the substituent of the aryl group which may be substituted with one or more substituents selected from Substituent group A is preferably a halogen atom.

X

X represents an oxygen atom or a sulfur atom.

X is preferably an oxygen atom.

The compound represented by General Formula [1] is preferably a compound in which $R^1$ is a halogen atom, an amino group which may be substituted with one or more substituents selected from Substituent group A, a monocyclic nitrogen-containing heterocyclic ring group which may be substituted with one or more substituents selected from Substituent group A (provided that a nitrogen atom forming the ring is bonded to a carbon atom to which $R^1$ is bonded), a monocyclic nitrogen- and oxygen-containing heterocyclic ring group which may be substituted with one or more substituents selected from Substituent group A (provided that a nitrogen atom forming the ring is bonded to a carbon atom to which $R^1$ is bonded), a $C_{1-6}$ alkoxy group which may be substituted with one or more substituents selected from Substituent group A, a hydroxyl group which may be protected, or a thiol group which may be protected; $R^2$ is a hydrogen atom; $R^3$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic oxy group which may be substituted with one or more substituents selected from Substituent group A, an amino group which may be substituted with one or more substituents selected from Substituent group A, or —O—P(O)(OH)—O—$PO_3H$; $R^4$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or a hydroxyl group which may be protected; and X is an oxygen atom.

The compound represented by General Formula [1] is more preferably a compound in which $R^1$ is a halogen atom, an amino group which may be substituted with one or more substituents selected from Substituent group A, a monocyclic nitrogen-containing heterocyclic ring group which may be substituted with one or more substituents selected from Substituent group A (provided that a nitrogen atom forming the ring is bonded to a carbon atom to which $R^1$ is bonded), a monocyclic nitrogen- and oxygen-containing heterocyclic ring group which may be substituted with one or more substituents selected from Substituent group A (provided that a nitrogen atom forming the ring is bonded to a carbon atom to which $R^1$ is bonded), a $C_{1-6}$ alkoxy group which may be substituted with one or more substituents selected from Substituent group A, or a hydroxyl group; $R^2$ is a hydrogen atom; $R^3$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic oxy group which may be substituted with one or more substituents selected from Substituent group A, or —O—P(O)(OH)—O—$PO_3H$; $R^4$ is a $C_{1-20}$ alkoxy group which may be substituted with one or more substituents selected from Substituent group A, an amino group which may be substituted with one or more substituents selected from Substituent group A, or a hydroxyl group which may be protected; and X is an oxygen atom.

The compound represented by General Formula [1] is still more preferably a compound in which $R^1$ is a $C_{1-6}$ alkoxy group which may be substituted with one or more $C_{1-6}$ alkoxy groups or a halogen atom; $R^2$ is a hydrogen atom; $R^3$ is a $C_{1-20}$ alkoxy group which may be substituted with one or more substituents selected from Substituent group A, an aryloxy group which may be substituted with one or more substituents selected from Substituent group A, a heterocyclic oxy group which may be substituted with one or more substituents selected from Substituent group A, or —O—P(O)(OH)—O—$PO_3H$; $R^4$ is a $C_{1-20}$ alkoxy group which may be substituted with one or more substituents selected from Substituent group A, an amino group which may be substituted with one or more substituents selected from Substituent group A, or a hydroxyl group which may be protected; and X is an oxygen atom.

The compound represented by General Formula [1] is preferably isopropyl ((((1S,4R)-4-(2-amino-6-chloro-9H-purin-9-yl)cyclopent-2-en-1-yl)methoxy)(phenoxy)phosphoryl)-L-alaninate (Example 2-2-1), S-(2-(((((1S,4R)-4-(2-amino-6-methoxy-9H-purin-9-yl)cyclopent-2-en-1-yl)methoxy)(phenoxy)phosphoryl)oxy)ethyl) 2,2-dimethylpropanethioate (Example 2-1), methyl ((((1S,4R)-4-(2-amino-6-methoxy-9H-purin-9-yl)cyclopent-2-en-1-yl)methoxy)(4-chlorophenoxy)phosphoryl)-L-alaninate (Example 1-2-2), methyl ((((1S,4R)-4-(2-amino-6-methoxy-9H-purin-9-yl)cyclopent-2-en-1-yl)methoxy)(4-bromophenoxy)phosphoryl)-L-alaninate (Example 1-2-3), isopropyl ((((1S,4R)-4-(2-amino-6-methoxy-9H-purin-9-yl)cyclopent-2-en-1-yl)methoxy)(phenoxy)phosphoryl)-L-alaninate (Example 2-2-12), methyl ((((1S,4R)-4-(2-amino-6-chloro-9H-purin-9-yl)cyclopent-2-en-1-yl)methoxy)(4-chlorophenoxy)phosphoryl)-L-alaninate (Example 1-2-4), methyl ((((1S,4R)-4-(2-amino-6-methoxy-9H-purin-9-yl)cyclopent-2-en-1-yl)methoxy)(2-(pivaloylthio)ethoxy)phosphoryl)-L-alaninate (Example 1-2-12), ethyl ((((1S,4R)-4-(2-amino-6-methoxy-9H-purin-9-yl)cyclopent-2-en-1-yl)methoxy)(phenoxy)phosphoryl)-L-alaninate (Example 1-2-34), ((1R,4S)-4-(2-amino-6-methoxy-9H-purin-9-yl)cyclopent-2-en-1-yl)methyl bis(pivaloyloxymethyl) phosphate (Example 3-2-6), cyclopropyl ((((1S,4R)-4-(2-amino-6-methoxy-9H-purin-9-yl)cyclopent-2-en-1-yl)methoxy)(phenoxy)phosphoryl)-L-alaninate (Example 1-2-58), isopropyl ((((1S,4R)-4-(2-amino-6-chloro-9H-purin-9-yl)cyclopent-2-en-1-yl)methoxy)(4-chlorophenoxy)phosphoryl)-L-alaninate (Example 1-2-70), isopropyl ((((1S,4R)-4-(2-amino-6-methoxy-9H-purin-9-yl)cyclopent-2-en-1-yl)methoxy)(4-chlorophenoxy)phosphoryl)-L-alaninate (Example 1-2-72), isopropyl ((((1S,4R)-4-(2-amino-6-chloro-9H-purin-9-yl)cyclopent-2-en-1-yl)methoxy)(2-(pivaloylthio)ethoxy)phosphoryl)-L-alaninate (Example 1-2-73), isopropyl ((((1S,4R)-4-(2-amino-6-methoxy-9H-purin-9-yl)cyclopent-2-en-1-yl)methoxy)(2-(pivaloylthio)ethoxy)phosphoryl)-L-alaninate (Example 1-2-74), isopropyl ((R)-(((1S,4R)-4-(2-amino-6-ethoxy-9H-purin-9-yl)cyclopent-2-en-1-yl)methoxy)(phenoxy)phosphoryl)-L-alaninate (Example 2-2-17), isopropyl ((R)-(((1S,4R)-4-(2-amino-6-isopropoxy-9H-purin-9-yl)cyclopent-2-en-1-yl)methoxy)(phenoxy)phosphoryl)-L-alaninate (Example 2-2-19), isopropyl ((R)-(((1S,4R)-4-(2-amino-6-(2-methoxyethoxy)-9H-purin-9-yl)cyclopent-2-en-1-yl)methoxy)(phenoxy)phosphoryl)-L-alaninate (Example 2-2-21), isopropyl ((R)-(((1S,4R)-4-(2-amino-6-(dimethylamino)-9H-purin-9-yl)cyclopent-2-en-1-yl)methoxy)(phenoxy)phosphoryl)-L-alaninate (Example 2-2-25), isopropyl ((R)-(((1S,4R)-4-(2-amino-6-cyclobutoxy-9H-purin-9-yl)cyclopent-2-en-1-yl)methoxy)(phenoxy)phosphoryl)-L-alaninate (Example 2-2-35), isopropyl ((((1S,4R)-4-(2-amino-6-methoxy-9H-purin-9-yl)cyclopent-2-en-1-yl)methoxy)(3-methoxyphenoxy)phosphoryl)-L-alaninate (Example 6-2-7), isopropyl ((R)-(((1S,4R)-4-(2-amino-6-(azetidin-1-yl)-9H-purin-9-yl)cyclopent-2-en-1-yl)methoxy)(phenoxy)phosphoryl)-L-alaninate (Example 2-2-37), isopropyl 2-(((((1S,4R)-4-(2-amino-6-methoxy-9H-purin-9-yl)cyclopent-2-en-1-yl)methoxy)(phenoxy)phosphoryl)amino)-2-methylpropanoate (Example 7-2-5), isopropyl ((((1S,4R)-4-(2-amino-6-methoxy-9H-purin-9-yl)cyclopent-2-en-1-yl)methoxy)(phenoxy)phosphoryl)-L-leucinate (Example 7-1-1), isopropyl ((((1S,4R)-4-(2 -amino-6-methoxy-9H-purin-9-yl)cyclopent-2-en-1-yl)methoxy)(3-(dimethylamino)phenoxy)phosphoryl)-L-alaninate (Example 6-2-9), isopropyl ((((1S,4R)-4-(2-amino-6-methoxy-9H-purin-9-yl)cyclopent-2-en-1-yl)methoxy)(4-bromophenoxy)phosphoryl)-L-alaninate (Example 6-2-15), isopropyl ((((1S,4R)-4-(2-amino-6-methoxy-9H-purin-9-yl)cyclopent-2-en-1-yl)methoxy)(3,5-dimethoxyphenoxy)phosphoryl)-L-alaninate (Example 6-2-17), isopropyl ((((1S,4R)-4-(2-amino-6-methoxy-9H-purin-9-yl)cyclopent-2-en-1-yl)methoxy)(3,4-dimethoxyphenoxy)phosphoryl)-L-alaninate (Example 6-2-19), isopropyl ((((1S,4R)-4-(2-amino-6-methoxy-9H-purin-9-yl)cyclopent-2-en-1-yl)methoxy)(benzo[d][1,3]dioxolo-5-yloxy)phosphoryl)-L-alaninate (Example 6-2-21), isopropyl ((((1S,4R)-4-(2-amino-6-methoxy-9H-purin-9-yl)cyclopent-2-en-1-yl)methoxy)(3-(2-methoxyethoxy)phenoxy)phosphoryl)-L-alaninate (Example 6-2-23), or isopropyl ((((1S,4R)-4-(2-amino-6-methoxy)-9H-purin-9-yl)cyclopent-2-en-1-yl)methoxy)(naphthalen-1-yloxy)phosphoryl)-L-alaninate (Example 6-2-25).

The compound represented by General Formula [1] is more preferably isopropyl ((((1S,4R)-4-(2-amino-6-chloro-9H-purin-9-yl)cyclopent-2-en-1-yl)methoxy)(phenoxy)phosphoryl)-L-alaninate (Example 2-2-1), S-(2-(((((1S,4R)-4-(2-amino-6-methoxy-9H-purin-9-yl)cyclopent-2-en-1-yl)methoxy)(phenoxy)phosphoryl)oxy)ethyl) 2,2-dimethylpropanethioate (Example 2-1), isopropyl ((((1S,4R)-4-(2-amino-6-methoxy-9H-purin-9-yl)cyclopent-2-en-1-yl)methoxy)(phenoxy)phosphoryl)-L-alaninate (Example 2-2-12), methyl ((((1S,4R)-4-(2-amino-6-methoxy-9H-purin-9-yl)cyclopent-2-en-1-yl)methoxy)(2-(pivaloylthio)ethoxy)phosphoryl)-L-alaninate (Example 1-2-12), isopropyl ((((1S,4R)-4-(2-amino-6-methoxy-9H-purin-9-yl)cyclopent-2-en-1-yl)methoxy)(4-chlorophenoxy)phosphoryl)-L-alaninate (Example 1-2-72), isopropyl ((((1S,4R)-4-(2-amino-6-methoxy-9H-purin-9-yl)cyclopent-2-en-1-yl)methoxy)(2-(pivaloylthio)ethoxy)phosphoryl)-L-alaninate (Example 1-2-74), isopropyl ((R)-(((1S,4R)-4-(2-amino-6-ethoxy-9H-purin-9-yl)cyclopent-2-en-1-yl)methoxy)(phenoxy)phosphoryl)-L-alaninate (Example 2-2-17), isopropyl ((R)-(((1S,4R)-4-(2-amino-6-(2-methoxyethoxy)-9H-purin-9-yl)cyclopent-2-en-1-yl)methoxy)(phenoxy)phosphoryl)-L-alaninate (Example 2-2-21), isopropyl ((((1S,4R)-4-(2-amino-6-methoxy-9H-purin-9-yl)cyclopent-2-en-1-yl)methoxy)(3-methoxyphenoxy)phosphoryl)-L-alaninate (Example 6-2-7), isopropyl ((((1S,4R)-4-(2-amino-6-methoxy-9H-purin-9-yl)cyclopent-2-en-1-yl)methoxy)(benzo[d][1,3]dioxolo-5-yloxy)phosphoryl)-L-alaninate (Example 6-2-21), or isopropyl ((((1S,4R)-4-(2-amino-6-methoxy-9H-purin-9-yl)cyclopent-2-en-1-yl)methoxy)(3-(2 -methoxyethoxy)phenoxy)phosphoryl)-L-alaninate (Example 6-2-23).

In another aspect, the compound represented by General Formula [1] is preferably a compound represented by General Formula [1c],

[1c]

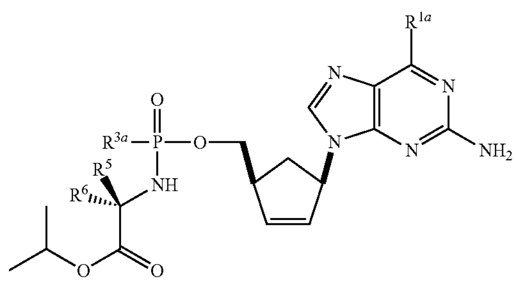

in the formula, $R^{1a}$ represents a halogen atom, a $C_{1-6}$ alkoxy group which may be substituted, or a group represented by General Formula —$NR^7R^8$ where $R^7$ and $R^8$ each represent a $C_{1-6}$ alkyl group which may be identically or differently substituted; or $R^7$ and $R^8$ together with a nitrogen atom to which $R^7$ and $R^8$ are bonded may be combined to form a monocyclic nitrogen-containing heterocyclic ring group which may be substituted;

$R^{3a}$ represents an aryloxy group which may be substituted or a heterocyclic oxy group which may be substituted; and $R^5$ and $R^6$ are the same or different from each other and each represent a hydrogen atom or a $C_{1-6}$ alkyl group which may be substituted.

Examples of the substituent of the $C_{1-6}$ alkoxy group of $R^{1a}$; the substituent of the $C_{1-6}$ alkyl group of $R^7$ and $R^8$; the substituent of the monocyclic nitrogen-containing heterocyclic ring group of $R^7$ and $R^8$; the substituent of the aryloxy group of $R^{3a}$; the substituent of the heterocyclic oxy group of $R^{3a}$; and the substituent of the $C_{1-6}$ alkyl group of $R^5$ and $R^6$ include one or more substituents selected from Substituent group A.

The compound represented by General Formula [1c] is preferably a compound in which $R^{1a}$ is a $C_{1-6}$ alkoxy group which may be substituted with one or more $C_{1-6}$ alkoxy groups or a halogen atom; $R^{3a}$ is an aryloxy group which may be substituted with one or more substituents selected from Substituent group A1 or a heterocyclic oxy group which may be substituted with one or more substituents selected from Substituent group A1; and $R^5$ and $R^6$ are the same or different from each other and each are a hydrogen atom or a $C_{1-6}$ alkyl group.

The compound represented by General Formula [1c] is more preferably a compound in which $R^{1a}$ is a $C_{1-6}$ alkoxy group which may be substituted with one or more $C_{1-6}$ alkoxy groups or a halogen atom; $R^{3a}$ is an aryloxy group which may be substituted with one or more substituents selected from Substituent group A1; $R^5$ is a hydrogen atom or a $C_{1-6}$ alkyl group; and $R^6$ is a $C_{1-6}$ alkyl group.

The compound represented by General Formula [1c] is still more preferably a compound in which $R^{1a}$ is a $C_{1-6}$ alkoxy group which may be substituted with one or more $C_{1-6}$ alkoxy groups; $R^{3a}$ is a phenoxy group which may be substituted with one or more substituents selected from Substituent group A1; $R^5$ is a hydrogen atom; and $R^6$ is a methyl group.

In a case where isomers (for example, a tautomer, an optical isomer, and a geometric isomer) are present for the compound represented by General Formula [1] or a salt thereof, the present invention also includes those isomers and further includes solvates, hydrates, and various forms of crystals.

Next, a method for producing the compound represented by General Formula [1] will be described.

The compound represented by General Formula [1] is produced by combining methods known per se, and can be produced, for example, according to the following production methods.

[Production Method 1]

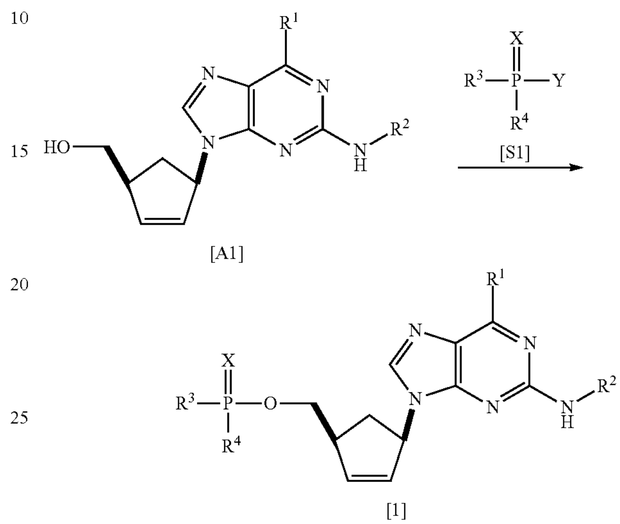

[A1]

[1]

(In the formulae, Y represents a leaving group, and $R^1$, $R^2$, $R^3$, $R^4$, and X are as defined above).

As a compound of General Formula [A1], for example, 2-amino-9-(cis-3-(hydroxymethyl)cyclobutyl)-1,9-dihydro-6H-purin-6-one is known.

As a compound of General Formula [S1], for example, ((chlorophosphoryl)bis(oxy))bis(methylene)bis(2,2-dimethylpropanoate) or 2-chloro-4H-benzo[d][1,3,2]dioxaphosphinine 2-oxide and methyl (chloro(phenoxy)phosphorothioyl)-L-alaninate are known.

The compound of General Formula [1] can be produced by reacting the compound of General Formula [A1] with the compound of General Formula [S1] in the presence of a base.

The solvent used in this reaction is not particularly limited as long as it does not affect the reaction and examples thereof include ethers and amides. These solvents may be used as a mixture thereof.

Preferred examples of the solvent include ethers, with tetrahydrofuran being more preferred.

The amount of the solvent to be used is not particularly limited, but may be 1 to 200-fold amount (v/w) with respect to the compound of General Formula [A1].

The amount of the compound of General Formula [S1] to be used may be a 0.1 to 20-fold molar amount and preferably a 1 to 10-fold molar amount with respect to the compound of General Formula [A1].

The base used in this reaction may be, for example, tert-butyl magnesium chloride. The amount of the base to be used may be a 0.1 to 5-fold molar amount and preferably a 1 to 2-fold molar amount with respect to the compound of General Formula [A1].

This reaction may be carried out at −78° C. to 100° C., preferably −78° C. to 40° C. for 30 minutes to 48 hours.

The compound of General Formula [A1] and the compound of General Formula [S1] can be derived into other compounds of General Formula [A1] and other compounds of General Formula [S1], for example, by subjecting them to a reaction known per se such as condensation, addition, oxidation, reduction, rearrangement, substitution, halogenation, dehydration, or hydrolysis, or an appropriate combination of these reactions.

In a case where an amino group, a hydroxyl group, or a carboxyl group is present in the compounds of General Formula [A1] and intermediates thereof, the protecting group for such a group can be appropriately rearranged to carry out the reaction. In addition, in a case where two or more protecting groups are present, a reaction known per se can be carried out to make selective deprotection.

Among the compounds used in the above-mentioned production method, a compound that can take the form of a salt can also be used as a salt. Examples of such a salt include the same salts as the salts of the compound represented by General Formula [1] according to the embodiment of the present invention described above.

In a case where isomers (for example, a tautomer, an optical isomer, and a geometric isomer) are present for the compounds used in the above-mentioned production method, these isomers can also be used. In addition, in a case where solvates, hydrates, and various forms of crystals are present, these solvates, hydrates, and various forms of crystals can also be used.

The compound represented by General Formula [1] or a salt thereof can be used as an anti-adenoviral agent or as a medicine for treating an adenovirus infection. Examples of the adenovirus infection include respiratory infection, pharyngoconjunctival fever, epidemic keratoconjunctivitis, hepatitis, gastroenteritis, cystitis, and encephalitis. The anti-adenoviral agent according to the embodiment of the present invention and the medicine for treating an adenovirus infection according to the embodiment of the present invention can be provided as a pharmaceutical composition.

In a pharmaceutical composition containing the compound represented by General Formula [1] or a salt thereof according to the embodiment of the present invention, an additive commonly used in formulation may be appropriately mixed.

Examples of the additive include an excipient, a disintegrating agent, a binding agent, a lubricant, a taste masking agent, a colorant, a flavoring agent, a surfactant, a coating agent, and a plasticizer.

Examples of the excipient include sugar alcohols such as erythritol, mannitol, xylitol, and sorbitol; sugars such as white sugar, powdered sugar, lactose, and glucose; cyclodextrins such as α-cyclodextrin, β-cyclodextrin, γ-cyclodextrin, hydroxypropyl β-cyclodextrin, and sodium sulfobutylether β-cyclodextrin; celluloses such as crystalline cellulose and microcrystalline cellulose; and starches such as corn starch, potato starch, and pregelatinized starch.

Examples of the disintegrating agent include carmellose, carmellose calcium, croscarmellose sodium, sodium carboxymethyl starch, crospovidone, low-substituted hydroxypropyl cellulose, and a partially pregelatinized starch.

Examples of the binding agent include hydroxypropyl cellulose, carmellose sodium, and methylcellulose.

Examples of the lubricant include stearic acid, magnesium stearate, calcium stearate, talc, hydrated silicon dioxide, light anhydrous silicic acid, and sucrose fatty acid ester.

Examples of the taste masking agent include aspartame, saccharin, *stevia*, thaumatin, and acesulfame potassium.

Examples of the colorant include titanium dioxide, iron sesquioxide, yellow ferric oxide, black iron oxide, Food Red No. 102, Food Yellow No. 4, and Food Yellow No. 5.

Examples of the flavoring agent include an essential oil such as an orange oil, a lemon oil, a peppermint oil, or a pine oil; an essence such as an orange essence or a peppermint essence; a flavor such as a cherry flavor, a vanilla flavor, or a fruit flavor; a powder fragrance such as an apple micron, a banana micron, a peach micron, a strawberry micron, or an orange micron; vanillin; and ethyl vanillin.

Examples of the surfactant include sodium lauryl sulfate, dioctyl sodium sulfosuccinate, polysorbate, polyethylene glycol monostearate, polyoxyethylene castor oil, and polyoxyethylene hydrogenated castor oil.

Examples of the coating agent include hydroxypropyl methyl cellulose, an aminoalkyl methacrylate copolymer E, an aminoalkyl methacrylate copolymer RS, ethyl cellulose, cellulose acetate phthalate, hydroxypropyl methyl cellulose phthalate, a methacrylic acid copolymer L, a methacrylic acid copolymer LD, and a methacrylic acid copolymer S.

Examples of the plasticizer include triethyl citrate, macrogol, triacetin, and propylene glycol.

These additives may be used alone or in combination of two or more thereof.

Although the formulation amount of the additives is not particularly limited, the additives may be suitably formulated such that the effects thereof are sufficiently exhibited depending on the respective purposes.

The pharmaceutical composition to which an appropriate mixture has been added can be orally or parenterally administered according to a conventional method in the form of a tablet, a capsule, a powder, a syrup, a granule, a pill, a suspension, an emulsion, a solution, a powdered preparation, a suppository, an eye drop, a nasal drop, an ear drop, a patch, an ointment, an injection, or the like.

The administration method, dosage, and administration frequency of the compound represented by General Formula [1] or the salt thereof according to the embodiment of the present invention can be appropriately selected depending on the age, body weight, and symptoms of the patient. Usually, for an adult, 0.0001 to 1,000 mg/kg/day may be orally or parenterally administered in one to several divided doses.

EXAMPLES

Hereinafter, the present invention will be described with reference to Reference Examples and Examples, but the present invention is not limited thereto.

Unless otherwise specified, purification by column chromatography was carried out using an automated purification apparatus ISOLERA (manufactured by Biotage AB) or a medium-pressure liquid chromatograph YFLC-Wprep2XY.N (manufactured by Yamazen Corporation).

Unless otherwise specified, SNAPKP-Sil Cartridge (manufactured by Biotage AB), or HI-FLASH COLUMN W001, W002, W003, W004, or W005 (manufactured by Yamazen Corporation) was used as a carrier in silica gel column chromatography; SNAP KP-NH Cartridge (manufactured by Biotage AB) was used as a carrier in basic silica gel column chromatography; and CHROMATOREX Q-PACK Cartridge (manufactured by Fuji Silysia Chemical Ltd.) was used as a carrier in diol silica gel column chromatography.

In preparative thin layer chromatography, PLC glass plate silica gel $F_{60}$ (manufactured by Merck & Co., Inc.) was used.

The mixing ratio in the eluent was a volume ratio. For example, "hexane:ethyl acetate gradient elution=50:50 to 0:100" means that an eluent of 50% hexane/50% ethyl acetate was finally changed to an eluent of 0% hexane/100% ethyl acetate.

In addition, for example, "hexane:ethyl acetate gradient elution=50:50 to 0:100, methanol:ethyl acetate gradient elution=0:100 to 20:80" means that an eluent of 50% hexane/50% ethyl acetate was changed to an eluent of 0% hexane/100% ethyl acetate, and then the eluent was switched to an eluent of 0% methanol/100% ethyl acetate and finally changed to an eluent of 20% methanol/80% ethyl acetate.

SFC 30 (manufactured by Waters Corporation) was used for supercritical fluid chromatography.

Column: CHIRALPAK IA (5 μm, 10×250 mm), CHIRALPAK IC (5 μm, 10×250 mm), or CHIRALPAK AS-H (5 μm, 10×250 mm) (all manufactured by Daicel Chemical Industries, Ltd.)

Flow rate: 30 mL/min

Detection wavelength: 280 nm

Temperature: 40° C.

MS spectra were measured using an ACQUITY SQD LC/MS System (manufactured by Waters Corporation, ionization method: Electro Spray Ionization (ESI) method), a Model M-8000 (manufactured by Hitachi, Ltd., ionization method: ESI method), or an LCMS-2010EV (manufactured by Shimadzu Corporation, ionization method: method of carrying out ESI and Atmospheric Pressure Chemical Ionization (APCI) at the same time).

As a microwave reactor, Initiator Sixty (manufactured by Biotage AB) was used.

NMR spectra were measured using BrukerAV300 (manufactured by Bruker Corporation, 300 MHz) and using tetramethylsilane as an internal standard, and all b values were shown in ppm.

The retention time (RT) was measured using SQD (manufactured by Waters Corporation), and was shown in minutes (min).

Column: BEHC 18 1.7 μm, 2.1×30 mm (manufactured by Waters Corporation)

Solvent: liquid A: 0.1% formic acid-water liquid B: 0.10% formic acid-acetonitrile Gradient cycle: 0.00 min (liquidA/liquid B=95/5), 2.00 min (liquidA/liquid B=5/95), 3.00 min (liquid A/liquid B=5/95), 3.01 min (liquid A/liquid B=100/0), 3.80 min (liquid A/liquid B=100/0)

Flow rate: 0.5 mL/min

Column temperature: room temperature

Detection wavelength: 254 nm

Abbreviations in Examples have the following meanings.

Boc: tert-butoxycarbonyl

Bu: butyl

Et: ethyl

HATU: 1-(bis(dimethylamino)methylene)-1H-1,2,3-triazolo[4,5,b]pyridinium 3-oxide hexafluorophosphate M: mol/L Me: methyl MMTr: (4-methoxyphenyl)diphenylmethyl Pent: pentyl Ph: phenyl Pr: propyl RT (min): retention time (min)

*: bonding position

Reference Example 1

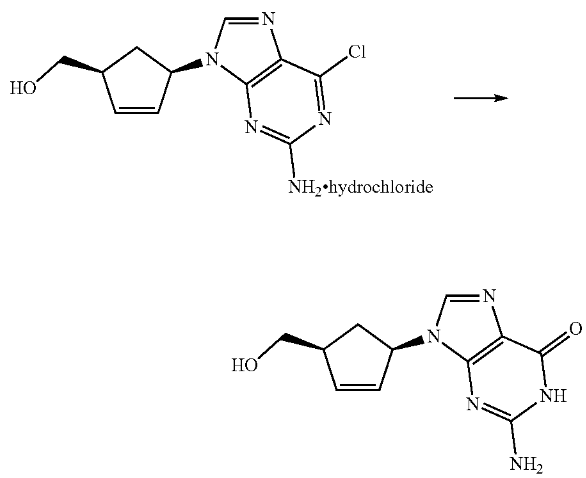

A mixture of (((1S,4R)-4-(2-amino-6-chloro-9H-purin-9-yl)cyclopent-2-en-1-yl)methanol hydrochloride (50 mg), sodium hydroxide (66 mg), and water (0.75 mL) was irradiated with microwave (microwave reactor, 130° C., 1 hour, 2.45 GHz, 0 to 240 W). The reaction solution was purified by diol silica gel column chromatography (methanol:ethyl acetate=0:100 to 30:70) to give 2-amino-9-((1R,4S)-4-(hydroxymethyl)cyclopent-2-en-1-yl)-1,9 -dihydro-6H-purin-6-one (55 mg) as a white solid.

MS (ESI m/z): 248 (M+H)

RT (min): 0.47

Reference Example 2-1

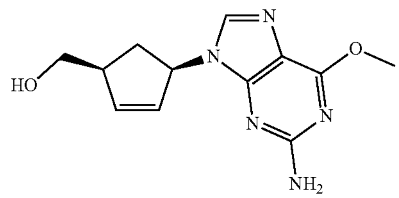 [SMILES: COc1nc(N)nc2c1ncn2[C@H]1C=C[C@@H](CO)C1]

A 5 M sodium methoxide/methanol solution (1.0 mL) was added to a mixture of (((1S,4R)-4-(2-amino-6-chloro-9H-purin-9-yl)cyclopent-2-en-1-yl)methanol hydrochloride (0.50 g) and methanol (5.0 mL) which was then stirred at room temperature for 6 hours. The solvent was distilled off under reduced pressure, and the obtained residue was purified by silica gel column chromatography (hexane:ethyl acetate=50:50 to 0:100, methanol:ethyl acetate=0:100 to 20:80) to give ((1S,4R)-4-(2-amino-6-methoxy-9H-purin-9-yl)cyclopent-2-en-1-yl)methanol (0.47 g) as a white solid.

MS (ESI m/z): 262 (M+H)

RT (min): 0.57

Reference Example 2-2

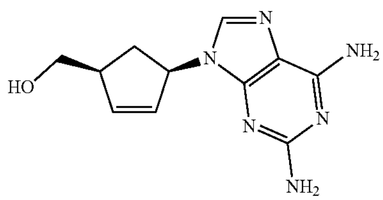 [SMILES: Nc1nc(N)c2ncn([C@H]3C=C[C@@H](CO)C3)c2n1]

A mixture of (((1S,4R)-4-(2-amino-6-chloro-9H-purin-9-yl)cyclopent-2-en-1-yl)methanol hydrochloride (0.10 g) and 7 M ammonia/methanol solution (1.4 mL) was irradiated with microwave (microwave reactor, 100° C., 1 hour, 120° C., 1 hour, 130° C., 30 minutes, 2.45 GHz, 0 to 240 W). The reaction solution was purified by basic silica gel column chromatography (methanol:ethyl acetate=0:100 to 12:88) to give ((1S,4R)-4-(2,6-diamino-9H-purin-9-yl))cyclopent-2-en-1-yl)methanol (60 mg) as a white solid.

MS (ESI m/z): 247 (M+H)

RT (min): 0.49

Reference Example 2-3

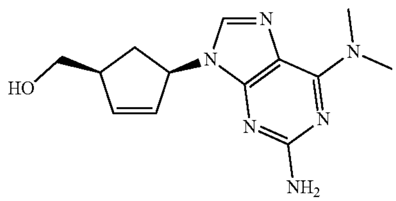 [SMILES: CN(C)c1nc(N)nc2c1ncn2[C@H]1C=C[C@@H](CO)C1]

A 50% aqueous dimethylamine solution (0.1 mL) was added to a mixture of (((1 S,4R)-4-(2-amino-6-chloro-9H-purin-9-yl)cyclopent-2-en-1-yl)methanol hydrochloride (20 mg) and ethanol (0.5 mL) which was then stirred at room temperature for 1 hour. The reaction solution was purified by silica gel column chromatography (hexane:ethyl acetate=50:50 to 0:100, methanol:ethyl acetate=0:100 to 20:80) to give ((1S,4R)-4-(2-amino-6-(dimethylamino)-9H-purin-9-yl)cyclopent-2-en-1-yl)methanol (20 mg) as a white solid.

MS (ESI m/z): 275 (M+H)

RT (min): 0.58

Reference Example 2-4

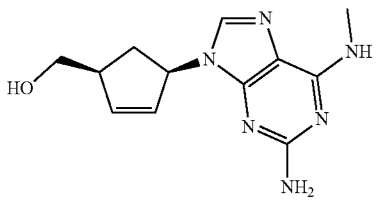 [SMILES: CNc1nc(N)nc2c1ncn2[C@H]1C=C[C@@H](CO)C1]

A 2 M methylamine/tetrahydrofuran solution (0.2 mL) was added to a mixture of (((1S,4R)-4-(2-amino-6-chloro-9H-purin-9-yl)cyclopent-2-en-1-yl)methanol hydrochloride (20 mg) and ethanol (0.5 mL) which was then irradiated with microwave (microwave reactor, 120° C., 1 hour, 2.45 GHz, 0 to 240 W). The reaction solution was purified by silica gel column chromatography (hexane:ethyl acetate=50:50 to 0:100, methanol:ethyl acetate=0:100 to 20:80) to give ((1S,4R)-4-(2-amino-6-(dimethylamino)-9H-purin-9-yl)cyclopent-2-en-1-yl)methanol (13 mg) as a white solid.

MS (ESI m/z): 261 (M+H)

RT (min): 0.51

Reference Example 2-5

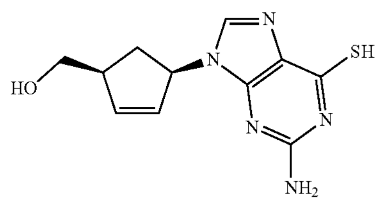 [SMILES: Nc1nc(S)c2ncn([C@H]3C=C[C@@H](CO)C3)c2n1]

A 15% aqueous sodium hydrosulfide solution (0.1 mL) was added to a mixture of (((1S,4R)-4-(2-amino-6-chloro-9H-purin-9-yl)cyclopent-2-en-1-yl)methanol hydrochloride (20 mg) and ethanol (0.5 mL) which was then stirred at room temperature for 18 hours. The reaction solution was purified by silica gel column chromatography (hexane:ethyl acetate=50:50 to 0:100, methanol:ethyl acetate=0:100 to 20:80) to give ((1S,4R)-4-(2-amino-6-mercapto-9H-purin-9-yl)cyclopent-2-en-1-yl)methanol (11 mg) as a white solid.

MS (ESI m/z): 264 (M+H)

RT (min): 0.52

Reference Example 2-6

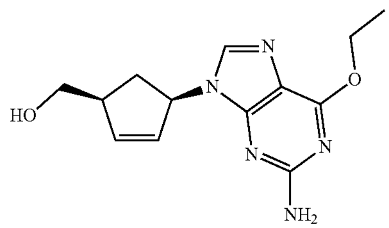 [SMILES: CCOc1nc(N)nc2c1ncn2[C@H]1C=C[C@@H](CO)C1]

A 20% sodium ethoxide/ethanol solution (0.1 mL) was added to a mixture of (((1 S,4R)-4-(2-amino-6-chloro-9H-purin-9-yl)cyclopent-2-en-1-yl)methanol hydrochloride (20 mg) and ethanol (0.5 mL) which was then stirred at room temperature for 18 hours. The reaction solution was purified by silica gel column chromatography (hexane:ethyl acetate=50:50 to 0:100, methanol:ethyl acetate=0:100 to 20:80) to give ((1S,4R)-4-(2-amino-6-ethoxy-9H-purin-9-yl)cyclopent-2-en-1-yl)methanol (16 mg) as a white solid.

MS (ESI m/z): 276 (M+H)

RT (min): 0.68

Reference Example 2-7

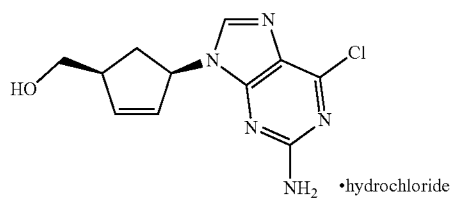

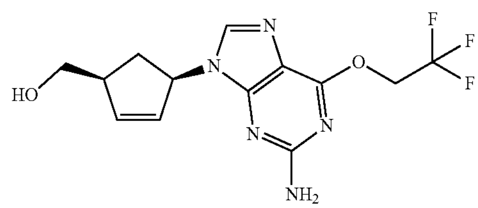

Under a nitrogen atmosphere, 2,2,2-trifluoroethanol (142 L) was added dropwise to a mixture of 60% sodium hydride (66 mg) and tetrahydrofuran which was then stirred at room temperature until the foaming subsided. (((1S,4R)-4-(2-amino-6-chloro-9H-purin-9-yl)cyclopent-2-en-1-yl)methanol hydrochloride (100 mg) was added to the reaction solution which was then stirred at 50° C. for 4 hours. The reaction solution was allowed to cool to room temperature, neutralized by adding 2 M hydrochloric acid, and concentrated under reduced pressure. The obtained residue was purified by silica gel column chromatography (ethyl acetate:hexane=30:70 to 100:0, methanol:ethyl acetate=0:100 to 18:82) to give ((1S,4R)-4-(2-amino-6-(2,2,2-trifluoroethyl)-9H-purin-9-yl)cyclopent-2-en-1-yl)methanol (32 mg) as a pale brown solid.

MS (ESI m/z): 330 (M+H)

RT (min): 0.85

Reference Example 2-8

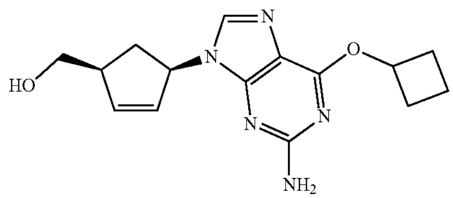 [SMILES: Nc1nc(OC2CCC2)c2ncn([C@H]3C=C[C@@H](CO)C3)c2n1]

The following compound was obtained in the same manner as in Reference Example 2-7.

((1S,4R)-4-(2-amino-6-cyclobutoxy-9H-purin-9-yl)cyclopent-2-en-1-yl)methanol

MS (ESI m/z): 302 (M+H)

RT (min): 0.81

Reference Example 2-9

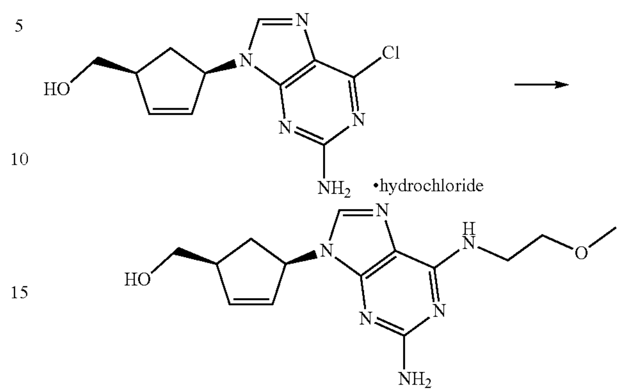

2-methoxyethylamine (141 L) was added to a mixture of ((1S,4R)-4-(2-amino-6-chloro-9H-purin-9-yl)cyclopent-2-en-1-yl)methanol hydrochloride (100 mg), ethanol (1 mL), and tetrahydrofuran (1 mL) which was then irradiated with microwave (microwave reactor, 120° C., 45 minutes, 2.45 GHz, 0 to 240 W). The reaction solution was purified by silica gel column chromatography (ethyl acetate:hexane=30:70 to 100:0, methanol:ethyl acetate=0:100 to 10:90) to give ((1S,4R)-4-(2-amino-6-((2-methoxyethyl)amino)-9H-purin-9-yl)cyclopent-2-en-1-yl)methanol (81 mg) as a pale brown solid.

MS (ESI m/z): 305 (M+H)

RT (min): 0.57

Reference Example 2-10

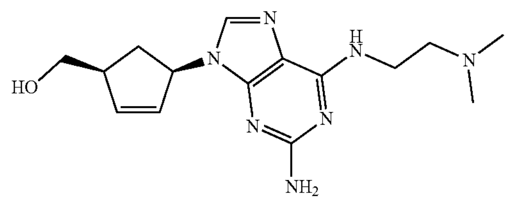

The following compound was obtained in the same manner as in Reference Example 2-9.

((1S,4R)-4-(2-amino-6-((2-(dimethylamino)ethyl)amino)-9H-purin-9-yl)cyclopent-2-en-1-yl)methanol MS (ESI m/z): 318 (M+H)

RT (min): 0.41

Reference Example 2-11

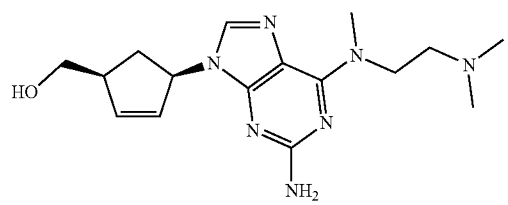 [SMILES: CN(C)CCN(C)c1nc(N)nc2c1ncn2[C@H]1C=C[C@@H](CO)C1]

The following compound was obtained in the same manner as in Reference Example 2-9.

((1S,4R)-4-(2-amino-6-((2-(dimethylamino)ethyl)(methyl)amino)-9H-purin-9-yl)cyclopent-2-en-1-yl)methanol MS (ESI m/z): 332 (M+H)
RT (min): 0.48

Reference Example 2-12

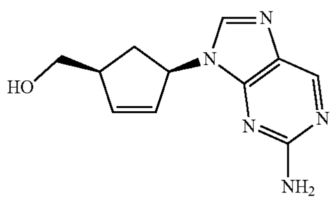 [SMILES: Nc1ncc2ncn([C@H]3C=C[C@@H](CO)C3)c2n1]

The following compound was obtained according to the method described in Nucleosides and Nucleotides, 14, (1995), 39.

((1S,4R)-4-(2-amino-9H-purin-9-yl)cyclopent-2-en-1-yl)methanol

MS (ESI m/z): 232 (M+H)
RT (min): 0.43

Reference Example 2-13

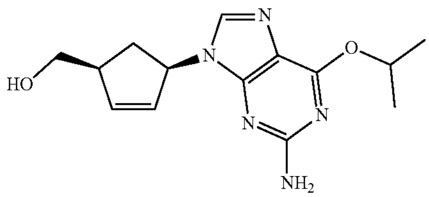 [SMILES: CC(C)Oc1nc(N)nc2c1ncn2[C@H]1C=C[C@@H](CO)C1]

The following compound was obtained according to the method described in U.S. Pat. No. 5,049,671A, 1991.

((1S,4R)-4-(2-amino-6-isopropoxy-9H-purin-9-yl)cyclopent-2-en-1-yl)methanol

MS (ESI m/z): 290 (M+H)
RT (min): 0.71

Reference Example 2-14

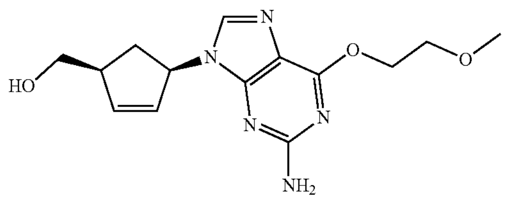 [SMILES: COCCOc1nc(N)nc2c1ncn2[C@H]1C=C[C@@H](CO)C1]

The following compound was obtained according to the method described in U.S. Pat. No. 5,049,671A, 1991.

((1S,4R)-4-(2-amino-6-(2-methoxyethoxy)-9H-purin-9-yl)cyclopent-2-en-1-yl)methanol MS (ESI m/z): 306 (M+H)
RT (min): 0.63

Reference Example 2-15

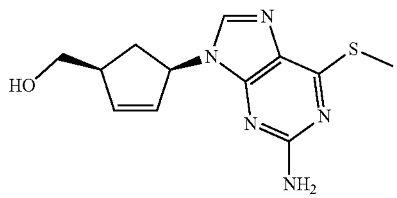 [SMILES: CSc1nc(N)nc2c1ncn2[C@H]1C=C[C@@H](CO)C1]

The following compound was obtained according to the method described in U.S. Pat. No. 5,049,671A, 1991.

((1S,4R)-4-(2-amino-6-(methylthio)-9H-purin-9-yl)cyclopent-2-en-1-yl)methanol

MS (ESI m/z): 278 (M+H)
RT (min): 0.70

Reference Example 2-16

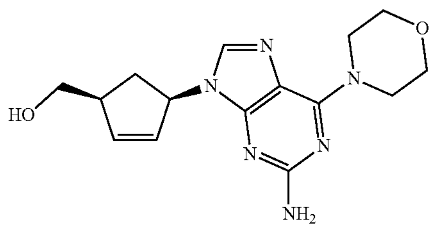 [SMILES: Nc1nc(N2CCOCC2)c2ncn([C@H]3C=C[C@@H](CO)C3)c2n1]

The following compound was obtained according to the method described in U.S. Pat. No. 5,049,671A, 1991.

((1S,4R)-4-(2-amino-6-morpholino-9H-purin-9-yl)cyclopent-2-en-1-yl)methanol

MS (ESI m/z): 317 (M+H)
RT (min): 0.61

Reference Example 2-17

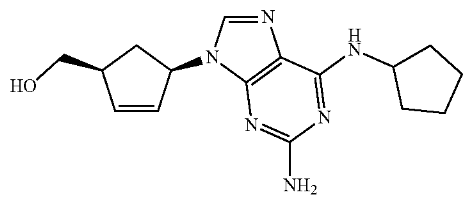 [SMILES: Nc1nc(NC2CCCC2)c2ncn([C@H]3C=C[C@@H](CO)C3)c2n1]

The following compound was obtained according to the method described in U.S. Pat. No. 5,034,394A, 1991.

((1S,4R)-4-(2-amino-6-(cyclopentylamino)-9H-purin-9-yl)cyclopent-2-en-1-yl)methanol MS (ESI m/z): 315 (M+H)

RT (min): 0.75

Reference Example 2-18

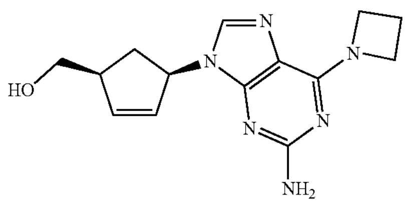 [SMILES: Nc1nc(N2CCC2)c2ncn([C@H]3C=C[C@@H](CO)C3)c2n1]

The following compound was obtained according to the method described in US2003/0040506A1.

((1S,4R)-4-(2-amino-6-(azetidin-1-yl)-9H-purin-9-yl)cyclopent-2-en-1-yl)methanol MS (ESI m/z): 287 (M+H)

RT (min): 0.55

Reference Example 3-1

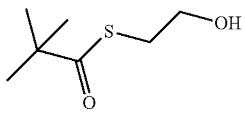

A mixture of pivaloyl chloride (1.3 mL) and methylene chloride (5 mL) was added dropwise to a mixture of 2-mercaptoethanol (0.75 mL), triethylamine (2.0 mL), and methylene chloride (25 mL) in an ice bath, which was followed by stirring at room temperature for 2 hours. Water (20 mL) was added to the reaction solution, and the organic layer was dried over anhydrous sodium sulfate. The solvent was distilled off under reduced pressure to give S-(2-hydroxyethyl) 2,2-dimethylpropanethioate (1.8 g) as a colorless oil.

$^{1}$H-NMR ($CDCl_3$) δ: 3.76 (t, 2H, J=6.1 Hz), 3.06 (t, 2H, J=6.1 Hz), 1.93 (br s, 1H), 1.25 (s, 9H).

Reference Example 3-2

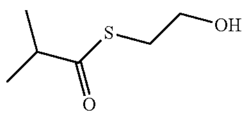

The following compound was obtained in the same manner as in Reference Example 3-1.

S-(2-hydroxyethyl) 2-methylpropanethioate $^{1}$H-NMR ($CDCl_3$) δ: 3.77 (t, 2H, J=6.3 Hz), 3.08 (t, 2H, J=6.3 Hz), 2.85-2.70 (m, 1H), 1.89 (br s, 1H), 1.21 (d, 6H, J=6.6 Hz).

Reference Example 3-3

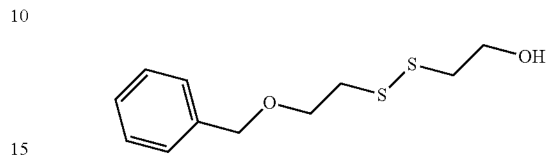

Under a nitrogen atmosphere, 60% sodium hydride (0.13 g) was added to a mixture of bis(2-hydroxyethyl)disulfide (0.50 g) and tetrahydrofuran (5.0 mL) which was then stirred at room temperature for 10 minutes. Benzyl bromide (0.38 mL) was added to the reaction solution which was then stirred for 3 hours, and water was added thereto, followed by extraction with ethyl acetate. The organic layer was washed with an aqueous saturated sodium chloride solution, the solvent was distilled off under reduced pressure, and then the obtained residue was purified by silica gel column chromatography (hexane:ethyl acetate=80:20 to 50:50) to give 2-((2-(benzyloxy)ethyl)disulfanyl)ethanol (0.39 g) as a colorless oil.

$^{1}$H-NMR ($CDCl_3$) δ: 7.39-7.27 (m, 5H), 4.56 (s, 2H), 3.92-3.81 (m, 2H), 3.75 (t, 2H, J=6.3 Hz), 2.94 (t, 2H, J=6.3 Hz), 2.83 (t, 2H, J=5.9 Hz), 2.12-1.95 (m, 1H).

MS (ESI m/z): 245 (M+H)

RT (min): 1.30

Reference Example 3-4

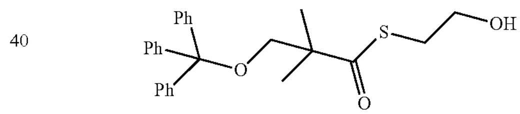

The following compound was obtained according to the method described in Bioorganic & Medicinal Chemistry 16 (2008) 7321-7329.

S-(2-hydroxyethyl) 2,2-dimethyl-3-(trityloxy)propanethioate

Reference Example 3-5

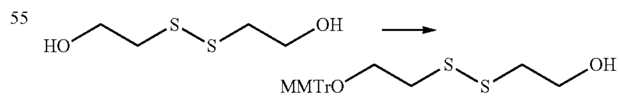

Under a nitrogen atmosphere, a mixture of bis(2-hydroxyethyl)disulfide (5.0 g), pyridine (30 mL), and 4-methoxytrityl chloride (6.6 g) was stirred under ice cooling for 100 minutes. Ethyl acetate was added to the reaction solution, the organic layer was washed with water, and then the solvent was distilled off under reduced pressure. The obtained residue was purified by silica gel column chromatography (hexane:ethyl acetate=100:0 to 40:60) to give 2-((2-((4-methoxyphenyl)diphenylmethoxy)ethyl)disulfanylethan-1-ol (6.3 g) as a yellow oil.

MS (ESI m/z): 449 (M+Na).

RT (min): 1.87

Reference Example 3-6

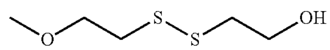

The following compound was obtained according to the method described in US2017/0233429A1.

2-((2-methoxyethyl)disulfanyl)ethan-1-ol

Reference Example 4-1

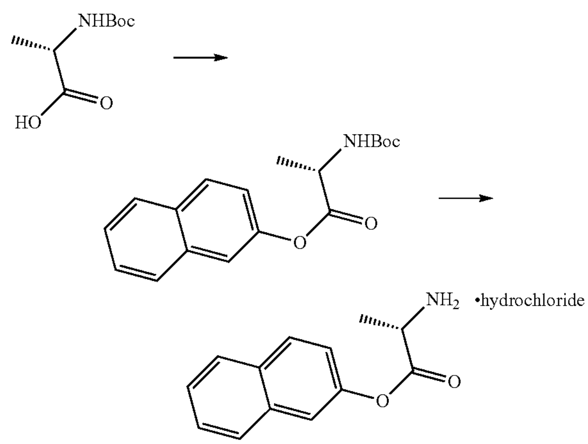

First Step

Triethylamine (2 mL) and HATU (4.8 g) were added to a mixture of N-(tert-butoxycarbonyl)-L-alanine (2.5 g), 2-naphthol (1.7 g), and methylene chloride (12 mL) which was then stirred overnight. Water was added to the reaction solution, extraction was carried out with ethyl acetate, the solvent was distilled off under reduced pressure, and then the obtained residue was purified by silica gel column chromatography (hexane:ethyl acetate=100:0 to 60:40) to give naphthalen-2-yl (tert-butoxycarbonyl)-L-alaninate (0.70 g).

MS (ESI m/z): 316 (M+H)

RT (min): 1.68

Second Step

A mixture of naphthalen-2-yl (tert-butoxycarbonyl)-L-alaninate (0.70 g) and 4 M hydrochloric acid/cyclopentyl methyl ether solution (5 mL) was stirred overnight at room temperature. After distilling off the solvent under reduced pressure, ethyl acetate was added to the obtained residue and the resulting solid was collected by filtration to give naphthalen-2-yl L-alaninate hydrochloride (0.26 g) as a white solid.

MS (ESI m/z): 216 (M+H)

RT (min): 0.81

Reference Example 4-2

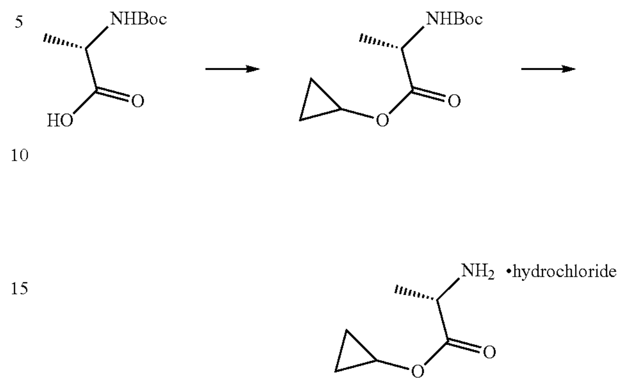

First Step

Triethylamine (2.0 mL) and HATU (5.5 g) were added to a mixture of N-(tert-butoxycarbonyl)-L-alanine (2.48 g), cyclopentanol (0.91 mL), and methylene chloride (25 mL) which was then stirred overnight. An aqueous saturated sodium hydrogencarbonate solution was added to the reaction solution, extraction was carried out with ethyl acetate, the solvent was distilled off under reduced pressure, and then the obtained residue was purified by silica gel column chromatography (hexane:ethyl acetate=100:0 to 70:30) to give cyclopropyl (tert-butoxycarbonyl)-L-alaninate (400 mg).

Second Step

A mixture of cyclopropyl (tert-butoxycarbonyl)-L-alaninate (400 mg) and 4 M hydrochloric acid/cyclopentyl methyl ether solution (3 mL) was stirred at room temperature for 30 minutes. 30% hydrochloric acid (1.5 mL) was added to the reaction solution which was then stirred at 50° C. for 1 hour. After distilling off the solvent under reduced pressure, toluene was added to the obtained residue and the solvent was distilled off under reduced pressure to give cyclopropyl L-alaninate hydrochloride (214 mg) as a white solid.

$^1$H-NMR ($CD_3OD$) δ: 4.32-4.25 (m, 1H), 4.11-3.97 (m, 1H), 1.57-1.47 (m, 3H), 0.82-0.73 (m, 4H).

Reference Example 4-3

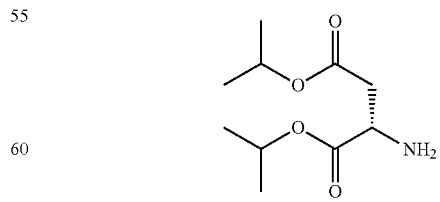

The following compound was obtained according to the method described in WO2018134399A1.

Diisopropyl L-aspartate

MS (ESI m/z): 218 (M+H)

Reference Example 5-1

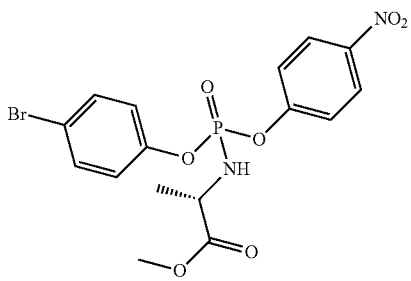 [SMILES: COC(=O)[C@H](C)NP(=O)(Oc1ccc(Br)cc1)Oc1ccc([N+](=O)[O-])cc1]

Under a nitrogen atmosphere, a mixture of 4-bromophenol (1.2 g), triethylamine (0.94 mL), and methylene chloride (15 mL) was added dropwise to a mixture of 4-nitrophenyl phosphorodichloridate (1.7 g) and methylene chloride (15 mL) at −78° C., which was followed by stirring at −78° C. for 30 minutes. A mixture of L-alanine methyl ester hydrochloride (0.94 g), triethylamine (1.9 mL), and methylene chloride (30 mL) was added dropwise to the reaction solution at −78° C., which was followed by stirring at −78° C. for 30 minutes and then at room temperature for 1 hour. After distilling off the solvent under reduced pressure, methylene chloride (10 mL) was added to the obtained residue, and the resulting solid was filtered off. After distilling off the solvent under reduced pressure, the obtained residue was purified by silica gel column chromatography (hexane:ethyl acetate=90:10 to 0:100) to give methyl ((4-bromophenoxy)(4-nitrophenoxy)phosphoryl)-L-alaninate (1.7 g) as a white solid.

MS (ESI m/z): 459, 461 (M+H)

RT (min): 1.56

Reference Example 5-2

The compounds in Tables 1-1 and 1-2 were obtained in the same manner as in Reference Example 5-1.

TABLE 1-1

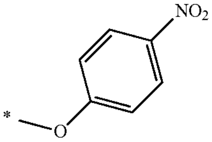

| Reference Example No. | R | Compound name | MS (ESI m/z) (M + H) | RT (min) |
|---|---|---|---|---|
| 5-2-1 | 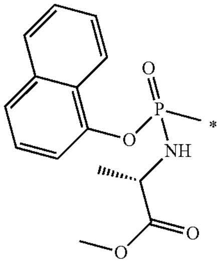 | Methyl ((naphthalen-1-yloxy)(4-nitrophenoxy) phosphoryl)-L-alaninate | 431 | 1.56 |
| 5-2-2 | 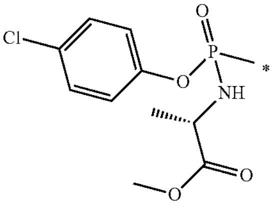 | Methyl ((4-chlorophenoxy)(4-nitrophenoxy) phosphoryl)-L-alaninate | 415<br>417 | 1.52 |
| 5-2-3 | 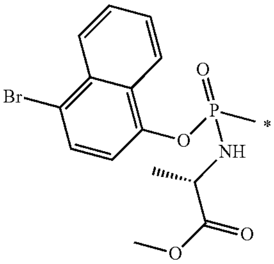 | Methyl (((4-bromonaphthalen-1-yl)oxy) (4-nitrophenoxy)phosphoryl)-L-alaninate | 509<br>511 | 1.75 |

TABLE 1-1-continued

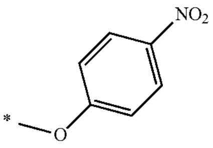

| Reference Example No. | R | Compound name | MS (ESI m/z) (M + H) | RT (min) |
|---|---|---|---|---|
| 5-2-4 | 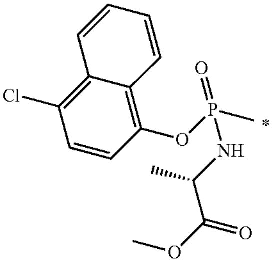 | Methyl (((4-chloronaphthalen-1-yl)oxy)(4-nitrophenoxy)phosphoryl)-L-alaninate | 465<br>467 | 1.72 |
| 5-2-5 | 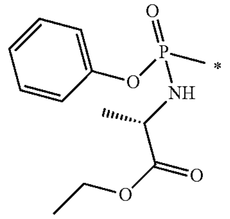 | Ethyl ((4-nitrophenoxy)(phenoxy)phosphoryl)-L-alaninate | 395 | 1.49 |
| 5-2-6 | 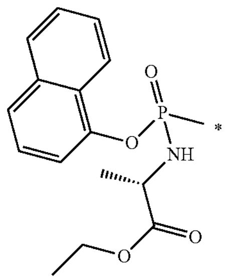 | Ethyl ((naphthalen-1-yloxy)(4-nitrophenoxy)phosphoryl)-L-alaninate | 445 | 1.65 |
| 5-2-7 | 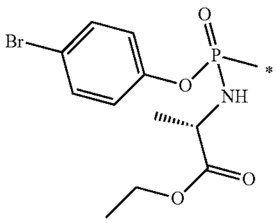 | Ethyl ((4-bromophenoxy)(4-nitrophenoxy)phosphoryl)-L-alaninate | 474<br>476 | 1.63 |
| 5-2-8 | 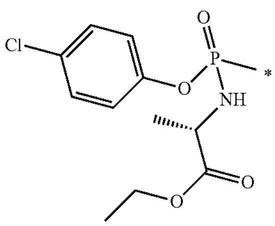 | Ethyl ((4-chlorophenoxy)(4-nitrophenoxy)phosphoryl)-L-alaninate | 429<br>431 | 1.61 |

TABLE 1-1-continued

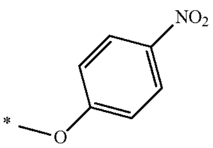

| Reference Example No. | R | Compound name | MS (ESI m/z) (M + H) | RT (min) |
|---|---|---|---|---|
| 5-2-9 | 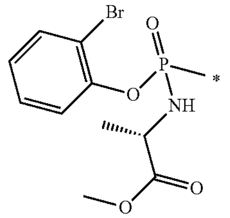 | Methyl ((2-bromophenoxy)(4-nitrophenoxy) phosphoryl)-L-alaninate | 459<br>461 | 1.52 |
| 5-2-10 | 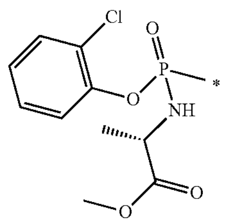 | Methyl ((2-chlorophenoxy)(4-nitrophenoxy) phosphoryl)-L-alaninate | 415<br>417 | 1.49 |
| 5-2-11 | 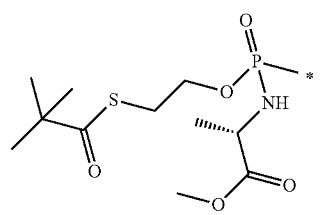 | Methyl ((4-nitrophenoxy)(2-(pivaloylthio) ethoxy)phosphoryl)-L-alaninate | 447<br>(M − H) | 1.56 |
| 5-2-12 | 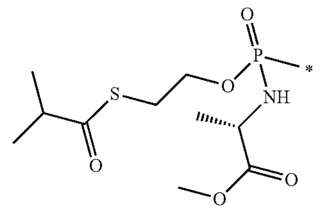 | Methyl ((2-isobutyrylthio)ethoxy))(4-nitrophenoxy)phosphoryl)-L-alaninate | 435 | 1.49 |
| 5-2-13 | 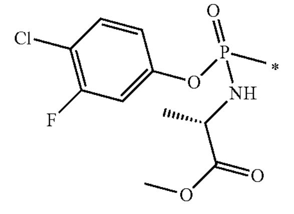 | Methyl ((4-chloro-3-fluorophenoxy) (4-nitrophenoxy)phosphoryl)-L-alaninate | 433<br>435 | 1.56 |
| 5-2-14 | 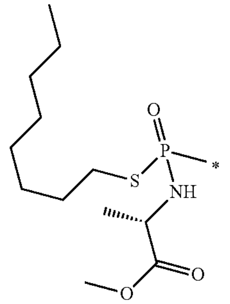 | Methyl ((4-nitrophenoxy)(octylthio) phosphoryl)-L-alaninate | 433 | 1.92 |

TABLE 1-1-continued

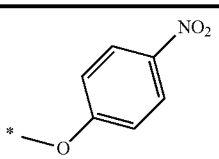

| Reference Example No. | R | Compound name | MS (ESI m/z) (M + H) | RT (min) |
|---|---|---|---|---|
| 5-2-15 | 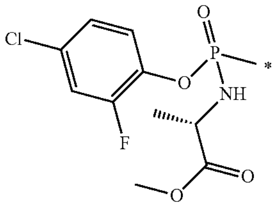 | Methyl ((4-chloro-2-fluorophenoxy) (4-nitrophenoxy)phosphoryl)-L-alaninate | 433 435 | 1.56 |
| 5-2-16 | 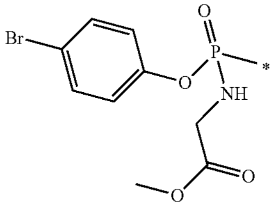 | Methyl ((4-bromophenoxy)(4-nitrophenoxy)phosphoryl) glycinate | 445 447 | 1.48 |
| 5-2-17 | 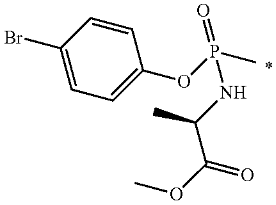 | Methyl ((4-bromophenoxy)(4-nitrophenoxy) phosphoryl)-D-alaninate | 459 461 | 1.55 |
| 5-2-18 | 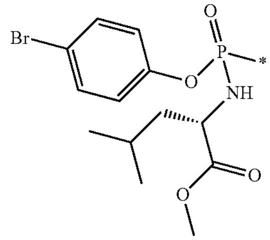 [SMILES: *P(=O)(N[C@@H](CC(C)C)C(=O)OC)Oc1ccc(Br)cc1] | Methyl ((4-bromophenoxy)(4-nitrophenoxy) phosphoryl)-L-leucinate | 501 503 | 1.77 |
| 5-2-19 | 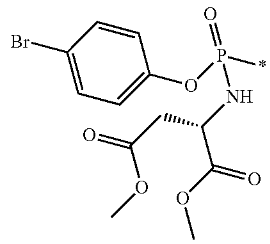 [SMILES: *P(=O)(N[C@@H](CC(=O)OC)C(=O)OC)Oc1ccc(Br)cc1] | Dimethyl ((4-bromophenoxy)(4-nitrophenoxy) phosphoryl)-L-aspartate | 517 519 | 1.53 |
| 5-2-20 | 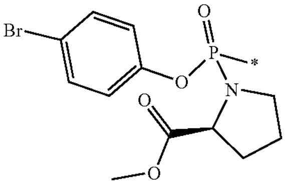 [SMILES: *P(=O)(Oc1ccc(Br)cc1)N1CCC[C@H]1C(=O)OC] | Methyl (4-bromophenoxy)(4-nitrophenoxy) phosphoryl)-L-prolinate | 485 487 | 1.68 |

TABLE 1-1-continued

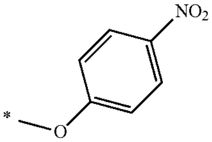

| Reference Example No. | R | Compound name | MS (ESI m/z) (M + H) | RT (min) |
|---|---|---|---|---|
| 5-2-21 | 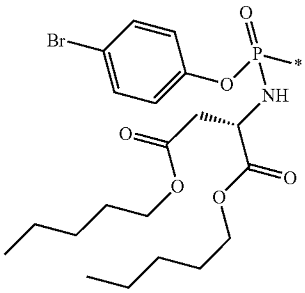 [SMILES: *P(=O)(N[C@@H](CC(=O)OCCCCC)C(=O)OCCCCC)Oc1ccc(Br)cc1] | Dipentyl ((4-bromophenoxy)(4-nitrophenoxy) phosphoryl)-L-aspartate | 629<br>631 | 2.14 |
| 5-2-22 | 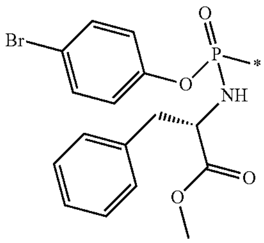 [SMILES: *P(=O)(N[C@@H](Cc1ccccc1)C(=O)OC)Oc1ccc(Br)cc1] | Methyl ((4-bromophenoxy)(4-nitrophenoxy) phosphoryl)-L-phenylalaninate | 535<br>537 | 1.75 |
| 5-2-23 | 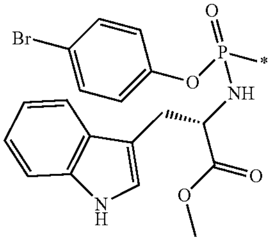 [SMILES: *P(=O)(N[C@@H](Cc1c[nH]c2ccccc12)C(=O)OC)Oc1ccc(Br)cc1] | Methyl ((4-bromophenoxy)(4-nitrophenoxy) phosphoryl)-L-tryptophanate | 574<br>576 | 1.71<br>1.73 |
| 5-2-24 | 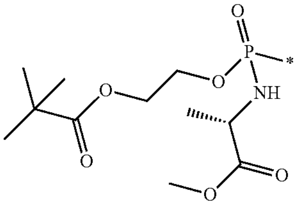 [SMILES: *P(=O)(N[C@@H](C)C(=O)OC)OCCOC(=O)C(C)(C)C] | 2-(((((S)-1-methoxy-1-oxo propan-2-yl)amino)(4-nitrophenoxy) phosphoryl)oxy)ethylpivalate | 433 | 1.44 |
| 5-2-25 | 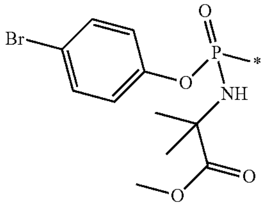 [SMILES: *P(=O)(NC(C)(C)C(=O)OC)Oc1ccc(Br)cc1] | Methyl 2-(((4-bromophenoxy)(4-nitrophenoxy) phosphoryl)amino)-2-methylpropanoate | 473<br>475 | 1.61 |

TABLE 1-1-continued

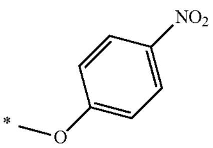

| Reference Example No. | R | Compound name | MS (ESI m/z) (M + H) | RT (min) |
|---|---|---|---|---|
| 5-2-26 | 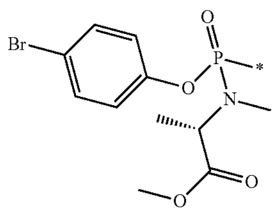 [SMILES: *P(=O)(Oc1ccc(Br)cc1)N(C)[C@@H](C)C(=O)OC] | Methyl N-((4-bromophenoxy)(4-nitrophenoxy) phosphoryl)-N-methyl-L-alaninate | 473<br>475 | 1.70 |
| 5-2-27 | 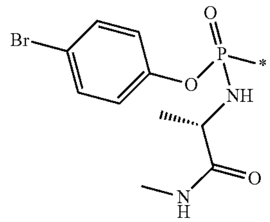 [SMILES: *P(=O)(N[C@@H](C)C(=O)NC)Oc1ccc(Br)cc1] | 4-bromophenyl (4-nitrophenyl)((S)-1-(methylamino)-1-oxopropan-2-yl)phosphoramidate | 458<br>460 | 1.31 |
| 5-2-28 | 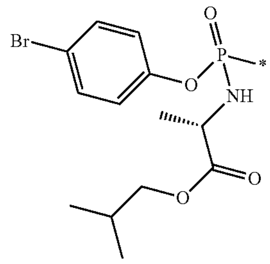 [SMILES: *P(=O)(N[C@@H](C)C(=O)OCC(C)C)Oc1ccc(Br)cc1] | Isobutyl ((4-bromophenoxy)(4-nitrophenoxy) phosphoryl)-L-alaninate | 501<br>503 | 1.80 |
| 5-2-29 | 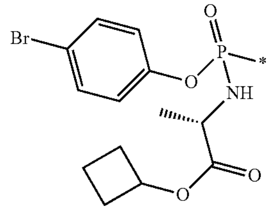 [SMILES: *P(=O)(N[C@@H](C)C(=O)OC1CCC1)Oc1ccc(Br)cc1] | Cyclobutyl ((4-bromophenoxy)(4-nitrophenoxy) phosphoryl)-L-alaninate | 500<br>502 | 1.75 |
| 5-2-30 | 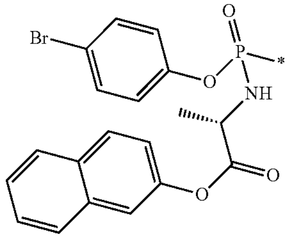 [SMILES: *P(=O)(N[C@@H](C)C(=O)Oc1ccc2ccccc2c1)Oc1ccc(Br)cc1] | Naphthalen-2-yl ((4-bromophenoxy))(4-nitrophenoxy) phosphoryl)-L-alaninate | 571<br>573 | 1.86 |
| 5-2-31 | 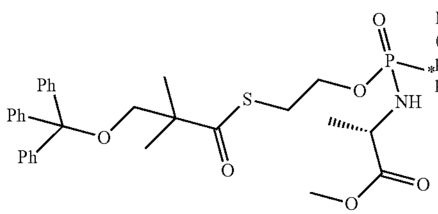 | Methyl ((2-((2,2-dimethyl-3-(trityloxy) propanoyl)thio)ethoxy)(4-nitrophenoxy) phosphoryl)-L-alaninate | 705<br>(M − H) | 2.11 |

TABLE 1-1-continued

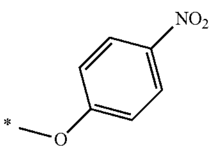

| Reference Example No. | R | Compound name | MS (ESI m/z) (M + H) | RT (min) |
|---|---|---|---|---|
| 5-2-32 | 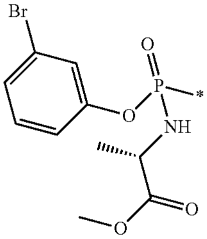 [SMILES: *P(=O)(N[C@@H](C)C(=O)OC)Oc1cccc(Br)c1] | Methyl ((3-bromophenoxy)(4-nitrophenoxy) phosphoryl)-L-alaninate | 459<br>461 | 1.55 |

TABLE 1-2

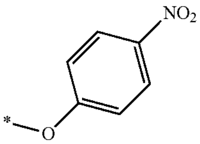 [SMILES: *Oc1ccc([N+](=O)[O-])cc1]

| Reference Example No. | R | Compound name | MS ESI (m/z) (M + H) | RT (min) |
|---|---|---|---|---|
| 5-2-33 | 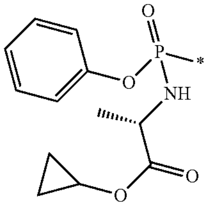 [SMILES: *P(=O)(N[C@@H](C)C(=O)OC1CC1)Oc1ccccc1] | Cyclopropyl ((4-nitrophenoxy)(phenoxy) phosphoryl)-L-alaninate | 407 | 1.5 |
| 5-2-34 | 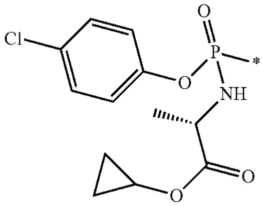 [SMILES: *P(=O)(N[C@@H](C)C(=O)OC1CC1)Oc1ccc(Cl)cc1] | Cyclopropyl ((4-chlorophenoxy)(4-nitrophenoxy)phosphoryl)-L-alaninate | 441<br>443 | 1.62 |
| 5-2-35 | 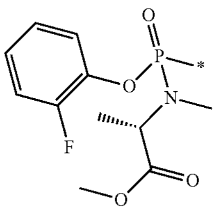 [SMILES: *P(=O)(Oc1ccccc1F)N(C)[C@@H](C)C(=O)OC] | Methyl ((2-fluorophenoxy)(4-nitrophenoxy)phosphoryl)-L-alaninate | 399 | 1.41 |

TABLE 1-2-continued

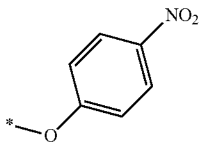

| Reference Example No. | R | Compound name | MS ESI (m/z) (M + H) | RT (min) |
|---|---|---|---|---|
| 5-2-36 | 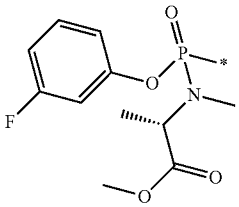 [SMILES: *P(=O)(Oc1cccc(F)c1)N(C)[C@@H](C)C(=O)OC] | Methyl ((3-fluorophenoxy)(4-nitrophenoxy)phosphoryl)-L-alaninate | 399 | 1.43 |
| 5-2-37 | 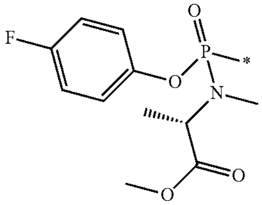 [SMILES: *P(=O)(Oc1ccc(F)cc1)N(C)[C@@H](C)C(=O)OC] | Methyl ((4-fluorophenoxy)(4-nitrophenoxy)phosphoryl)-L-alaninate | 399 | 1.41 |
| 5-2-38 | 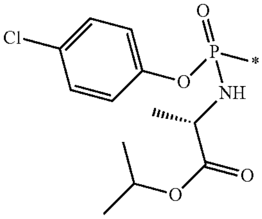 [SMILES: *P(=O)(N[C@@H](C)C(=O)OC(C)C)Oc1ccc(Cl)cc1] | Isopropyl ((4-chlorophenoxy)(4-nitrophenoxy)phosphoryl)-L-alaninate | 443<br>445 | 1.68 |
| 5-2-39 | 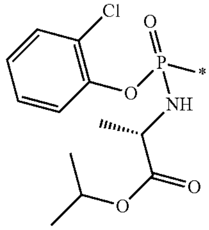 [SMILES: *P(=O)(N[C@@H](C)C(=O)OC(C)C)Oc1ccccc1Cl] | Isopropyl ((2-chlorophenoxy)(4-nitrophenoxy)phosphoryl)-L-alaninate | 443<br>445 | 1.66<br>1.67 |
| 5-2-40 | 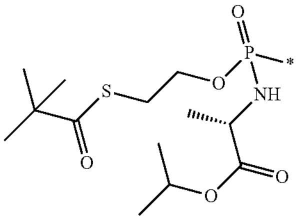 [SMILES: *P(=O)(N[C@@H](C)C(=O)OC(C)C)OCCSC(=O)C(C)(C)C] | Isopropyl ((4-nitrophenoxy)(2-(pivaloylthio)ethoxy) phosphoryl)-L-alaninate | 475<br>(M − H) | 1.73 |
| 5-2-41 | 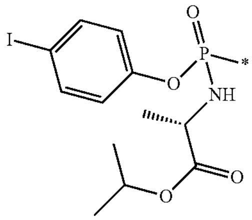 [SMILES: *P(=O)(N[C@@H](C)C(=O)OC(C)C)Oc1ccc(I)cc1] | Isopropyl ((4-iodophenoxy)(4-nitrophenoxy)phosphoryl)-L-alaninate | 535 | 1.74<br>1.75 |

TABLE 1-2-continued

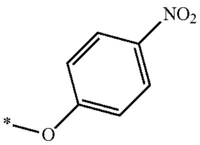

| Reference Example No. | R | Compound name | MS ESI (m/z) (M + H) | RT (min) |
|---|---|---|---|---|
| 5-2-42 | 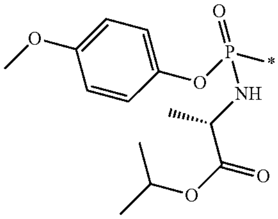 [SMILES: *P(=O)(N[C@@H](C)C(=O)OC(C)C)Oc1ccc(OC)cc1] | Isopropyl ((4-methoxyphenoxy)(4-nitrophenoxy)phosphoryl)-L-alaninate | 439 | 1.57 |
| 5-2-43 | 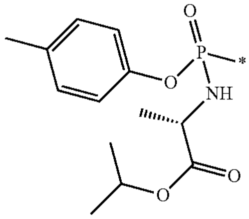 [SMILES: *P(=O)(N[C@@H](C)C(=O)OC(C)C)Oc1ccc(C)cc1] | Isopropyl ((4-nitrophenoxy)(p-toluyloxy) phosphoryl)-L-alaninate | 423 | 1.67 |
| 5-2-44 | 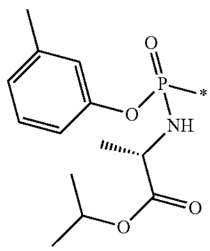 [SMILES: *P(=O)(N[C@@H](C)C(=O)OC(C)C)Oc1cccc(C)c1] | Isopropyl ((4-nitrophenoxy)(m-toluyloxy) phosphoryl)-L-alaninate | 423 | 1.67 |
| 5-2-45 | 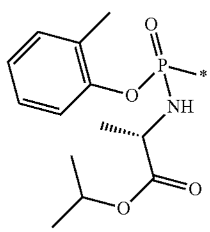 [SMILES: *P(=O)(N[C@@H](C)C(=O)OC(C)C)Oc1ccccc1C] | Isopropyl ((4-nitrophenoxy)(o-toluyloxy) phosphoryl)-L-alaninate | 423 | 1.66 |
| 5-2-46 | 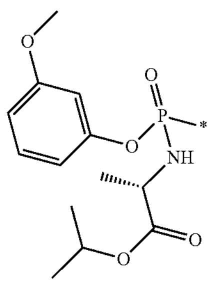 [SMILES: *P(=O)(N[C@@H](C)C(=O)OC(C)C)Oc1cccc(OC)c1] | Isopropyl ((3-methoxyphenoxy) (4-nitrophenoxy)phosphoryl)-L-alaninate | 439 | 1.59 |

TABLE 1-2-continued

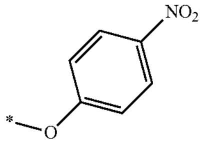

| Reference Example No. | R | Compound name | MS ESI (m/z) (M + H) | RT (min) |
|---|---|---|---|---|
| 5-2-47 | 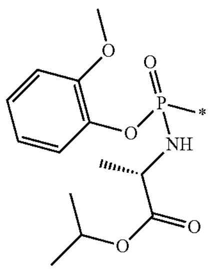 [SMILES: *P(=O)(N[C@@H](C)C(=O)OC(C)C)Oc1ccccc1OC] | Isopropyl ((3-(dimethylamino)phenoxy) (4-nitrophenoxy)phosphoryl)-L-alaninate | 452 | 1.64 |
| 5-2-48 | 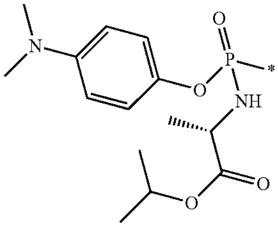 [SMILES: *P(=O)(N[C@@H](C)C(=O)OC(C)C)Oc1ccc(N(C)C)cc1] | Isopropyl ((2-methoxyphenoxy)(4-nitrophenoxy)phosphoryl)-L-alaninate | 439 | 1.57 |
| 5-2-49 | 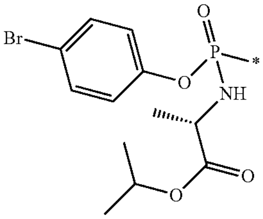 | Isopropyl ((4-(dimethylamino)phenoxy) (4-nitrophenoxy)phosphoryl)-L-alaninate | 452 | 1.43 |
| 5-2-50 | 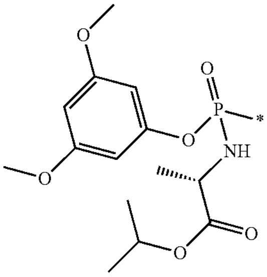 [SMILES: *P(=O)(N[C@@H](C)C(=O)OC(C)C)Oc1cc(OC)cc(OC)c1] | Isopropyl ((4-bromophenoxy)(4-nitrophenoxy)phosphoryl)-L-alaninate | 487 489 | 1.72 |
| 5-2-51 | | Isopropyl ((3,5-dimethoxyphenoxy)(4-nitrophenoxy)phosphoryl)-L-alaninate | 469 | 1.61 |

TABLE 1-2-continued

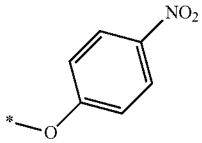

| Reference Example No. | R | Compound name | MS ESI (m/z) (M + H) | RT (min) |
|---|---|---|---|---|
| 5-2-52 | 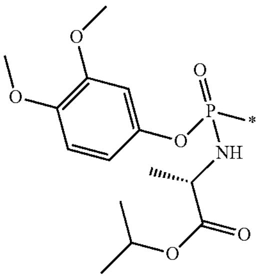 [SMILES: *P(=O)(N[C@@H](C)C(=O)OC(C)C)Oc1ccc(OC)c(OC)c1] | Isopropyl ((3,4-dimethoxyphenoxy)(4-nitrophenoxy)phosphoryl)-L-alaninate | 469 | 1.49 |
| 5-2-53 | 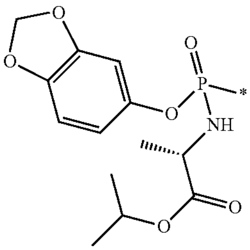 [SMILES: *P(=O)(N[C@@H](C)C(=O)OC(C)C)Oc1ccc2c(c1)OCO2] | Isopropyl ((benzo[d][1,3]dioxolo-5-yl oxy)(4-nitrophenoxy) phosphoryl)-L-alaninate | 453 | 1.55 |
| 5-2-54 | 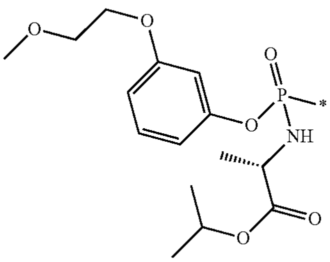 [SMILES: *P(=O)(N[C@@H](C)C(=O)OC(C)C)Oc1cccc(OCCOC)c1] | Isopropyl ((3-(2-methoxyethoxy) phenoxy(4-nitrophenoxy) phosphoryl)-L-alaninate | 483 | 1.56 |
| 5-2-55 | 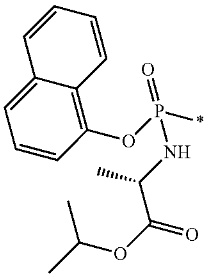 [SMILES: *P(=O)(N[C@@H](C)C(=O)OC(C)C)Oc1cccc2ccccc12] | Isopropyl ((naphthalen-1-yloxy)(4-nitrophenoxy)phosphoryl)-L-alaninate | 459 | 1.74 |
| 5-2-56 | 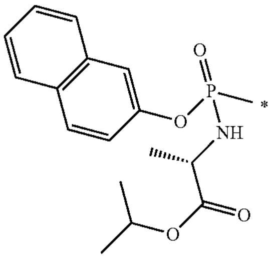 | Isopropyl ((naphthalen-2-yloxy)(4-nitrophenoxy)phosphoryl)-L-alaninate | 459 | 1.74 |

Reference Example 5-3

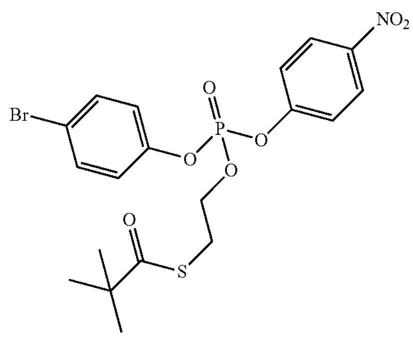 [SMILES: CC(C)(C)C(=O)SCCOP(=O)(Oc1ccc(Br)cc1)Oc1ccc([N+](=O)[O-])cc1]

The following compound was obtained in the same manner as in Reference Example 5-1.

S-(2-(((4-bromophenoxy)(4-nitrophenoxy)phosphoryl)oxy)ethyl) 2,2-dimethylpropanethioate $^1$H-NMR ($CDCl_3$) δ: 8.30-8.23 (m, 2H), 7.51-7.46 (m, 2H), 7.43-7.37 (m, 2H), 7.15-7.11 (m, 2H), 4.32 (dt, 2H, J=8.3, 6.6 Hz), 3.16 (td, 2H, J=6.6, 0.7 Hz), 1.22 (s, 9H).

Reference Example 6-1

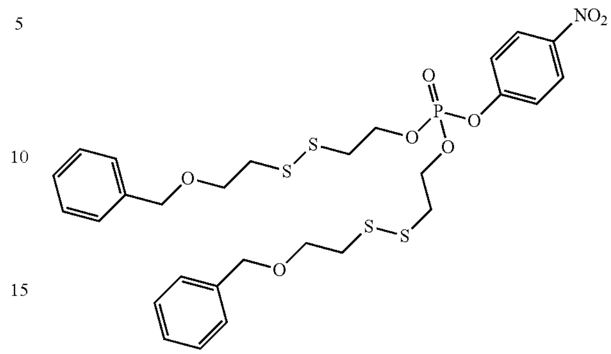

Under a nitrogen atmosphere, triethylamine (0.45 mL) was added to a mixture of 4-nitrophenyl phosphorodichloridate (0.16 g) and methylene chloride (2 mL) under ice cooling, and then 2-((2-(benzyloxy)ethyl)disulfanyl)ethanol (0.39 g) and methylene chloride (2 mL) were added thereto, which was followed by stirring at room temperature for 1.5 hours. The reaction solution was purified by silica gel column chromatography (hexane:ethyl acetate=80:20 to 25:75) to give bis(2-((2-(benzyloxy)ethyl)disulfanyl)ethyl) (4-nitrophenyl)phosphate (0.33 g) as a colorless oil.

$^1$H-NMR ($CDCl_3$) δ: 8.27-8.17 (m, 2H), 7.43-7.24 (m, 10H), 4.54 (s, 4H), 4.46-4.34 (m, 4H), 3.79-3.66 (m, 4H), 2.99-2.87 (m, 8H).

Reference Example 6-2

The compounds in Table 2 were obtained in the same manner as in Reference Example 6-1.

TABLE 2

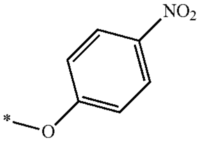 [SMILES: *Oc1ccc([N+](=O)[O-])cc1]

| Reference Example No. | R | Compound name | MS (ESI m/z) (M + H) | RT (min) |
|---|---|---|---|---|
| 6-2-1 | 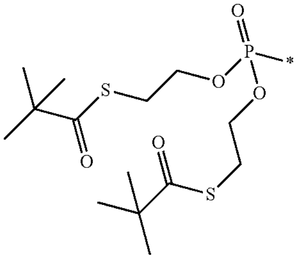 [SMILES: *P(=O)(OCCSC(=O)C(C)(C)C)OCCSC(=O)C(C)(C)C] | Bis(S-pivaloyl-2-mercaptoethan-1-yl) (4-nitrophenyl)phosphate | 508 | 1.96 |

TABLE 2-continued

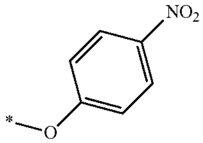

| Reference Example No. | R | Compound name | MS (ESI m/z) (M + H) | RT (min) |
|---|---|---|---|---|
| 6-2-2 | 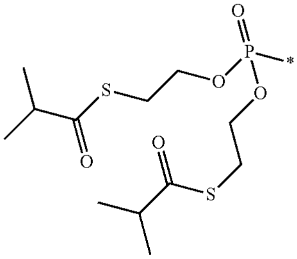 [SMILES: *P(=O)(OCCSC(=O)C(C)C)OCCSC(=O)C(C)C] | Bis(S-isobutyroyl-2-mercaptoethan-1-yl) (4-nitrophenyl)phosphate | 480 | 1.82 |
| 6-2-3 | 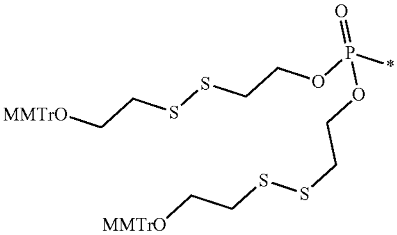 | Bis(2-((2-((4-methoxyphenyl) diphenylmethoxy)ethyl)disulfanyl)ethyl) (4-nitrophenyl)phosphate | 1058 (M + Na) | 2.49 |
| 6-2-4 | 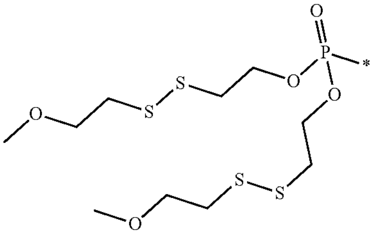 [SMILES: *P(=O)(OCCSSCCOC)OCCSSCCOC] | Bis(2-((2-methoxyethyl) disulfanyl)ethyl)(4-nitrophenyl) phosphate | 542 (M + N) | 1.63 |

Reference Example 7-1

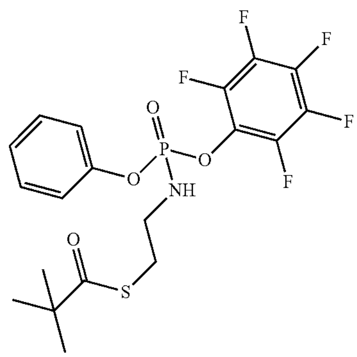 [SMILES: CC(C)(C)C(=O)SCCNP(=O)(Oc1ccccc1)Oc1c(F)c(F)c(F)c(F)c1F]

Under a nitrogen atmosphere, a mixture of perfluorophenol (0.62 g), triethylamine (0.47 mL), and methylene chloride (5 mL) was added dropwise to a mixture of phenyl phosphorodichloridate (0.5 mL) and methylene chloride (5 mL) at −78° C., which was followed by stirring at −78° C. for 1 hour. A mixture of S-(2-hydroxyethyl) 2,2-dimethylpropanethioate (0.54 g), triethylamine (0.94 mL), and methylene chloride (5 ml) was added dropwise to the reaction solution at −78° C., which was followed by stirring at −78° C. for 1.5 hours and then at room temperature for 40 minutes. After distilling off the solvent under reduced pressure, the obtained residue was purified by silica gel column chromatography (hexane:ethyl acetate=90:10 to 70:30) to give S-(2-(((perfluorophenoxy)(phenoxy)phosphoryl)oxy) ethyl) 2,2-dimethylpropanethioate (0.86 g) as a colorless oil.

MS (ESI m/z): 483 (M−H)

RT (min): 2.01

Reference Example 7-2

The compounds in Table 3 were obtained in the same manner as in Reference Example 7-1.

TABLE 3

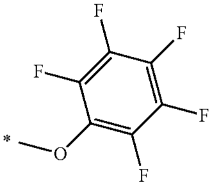

| Reference Example No. | R | Compound name | MS (ESI m/z) (M + H) | RT (min) |
|---|---|---|---|---|
| 7-2-1 | 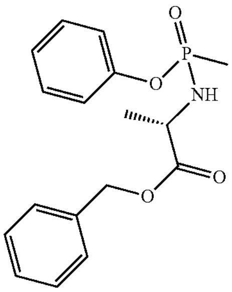 | Benzyl ((perfluorophenoxy)(phenoxy) phosphoryl)-L-alaninate | 502 | 1.84 |
| 7-2-2 | 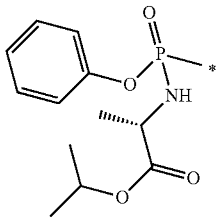 | Isopropyl ((perfluorophenoxy)(phenoxy) phosphoryl)-L-alaninate | 454 | 1.79 |
| 7-2-3 | 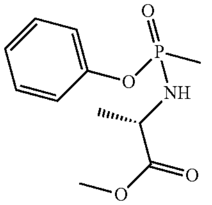 | Methyl ((perfluorophenoxy)(phenoxy) phosphoryl)-L-alaninate | 426 | 1.59 |
| 7-2-4 | 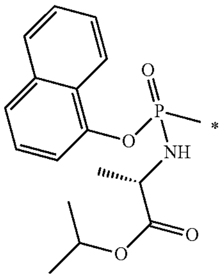 | Isopropyl ((naphthalen-1-yloxy) (perfluorophenoxy)phosphoryl)-L-alaninate | 504 | 1.92 |
| 7-2-5 | 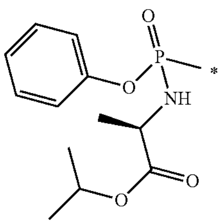 | Isopropyl ((perfluorophenoxy)(phenoxy) phosphoryl)-D-alaninate | 454 | 1.76 |

TABLE 3-continued

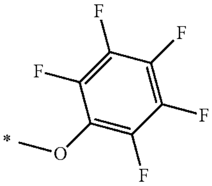

| Reference Example No. | R | Compound name | MS (ESI m/z) (M + H) | RT (min) |
|---|---|---|---|---|
| 7-2-6 | 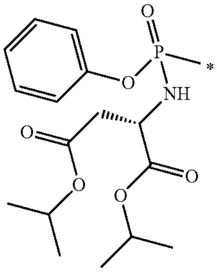 | Diisopropyl ((perfluorophenoxy)(phenoxy) phosphoryl)-L-aspartate | 540 | 1.86 |
| 7-2-7 | 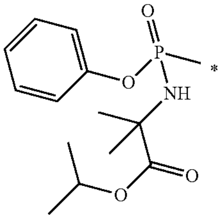 | Isopropyl 2-methyl-2-((perfluorophenoxy) (phenoxy)phosphoryl)amino) propanoate | 468 | 1.83 |
| 7-2-8 | 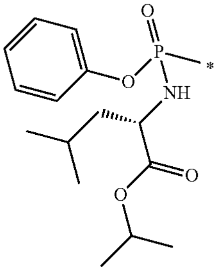 | Isopropyl ((perfluorophenoxy)(phenoxy) phosphoryl)-L-leucinate | 496 | 1.97 |

Reference Example 7-3

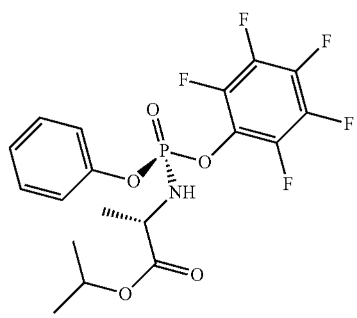

-continued

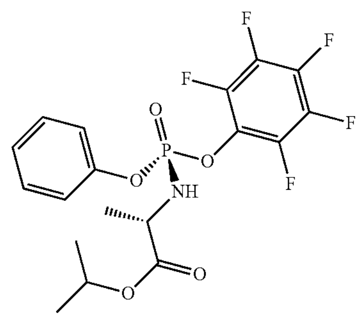

The following compounds were obtained according to the method described in WO2014197578A.

Reference Example 7-3-1

Isopropyl ((R)-(perfluorophenoxy)(phenoxy)phosphoryl)-L-alaninate $^1$H-NMR ($CDCl_3$) δ: 7.42-7.31 (m, 2H), 7.31-7.17 (m, 3H), 5.13-4.98 (m, 1H), 4.24- 4.08 (m, 1H), 4.08-3.91 (m, 1H), 1.44 (d, 3H, J=6.6 Hz), 1.30-1.23 (m, 6H).

MS (ESI m/z): 454 (M+H)

RT (min): 1.75

Reference Example 7-3-2

Isopropyl ((S)-(perfluorophenoxy)(phenoxy)phosphoryl)-L-alaninate $^1$H-NMR ($CDCl_3$) δ: 7.42-7.30 (m, 2H), 7.30-7.17 (m, 3H), 5.12-4.97 (m, 1H), 4.22-4.06 (m, 1H), 4.00-3.87 (m, 1H), 1.46 (d, 3H, J=7.3 Hz), 1.31-1.20 (m, 6H).

MS (ESI m/z): 454 (M+H)

RT (min): 1.75

Reference Example 8-1

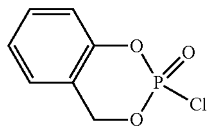 [SMILES: O=P1(Cl)OCc2ccccc2O1]

The following compound was obtained according to the method described in Chem. Eur. J. 2011, 17, 1649-1659.

2-chloro-4H-benzo[d][1,3,2]dioxaphosphinine 2-oxide

MS (ESI m/z): 205, 207 (M+H)

RT (min): 1.11

Reference Example 8-2

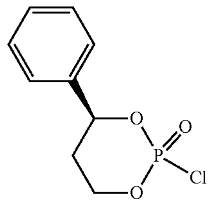 [SMILES: O=P1(Cl)OCC[C@@H](c2ccccc2)O1]

The following compound was obtained in the same manner as in Reference Example 8-1.

(4S)-2-chloro-4-phenyl-1,3,2-dioxaphosphinane 2-oxide

MS (ESI m/z): 233 (M+H)

RT (min): 1.16

Reference Example 9

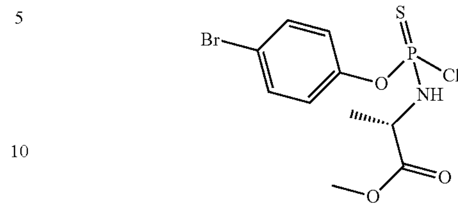

Under a nitrogen atmosphere, thiophosphoryl chloride (298 μL) and triethylamine (403 μL) were added to a mixture of 4-bromophenol (500 mg), methylene chloride (10 mL), and tetrahydrofuran (5.0 mL) at −40° C., and the temperature was raised to −5° C. over 1 hour. L-alanine methyl ester hydrochloride (403 mg) and triethylamine (806 μL) were added to the reaction solution which was then stirred at room temperature overnight. Tert-butyl methyl ether was added to the reaction solution, the resulting solid was filtered off, the solvent was distilled off under reduced pressure, and the obtained residue was purified by silica gel column chromatography (hexane:ethyl acetate=99:1 to 70:30) to give methyl ((4-bromophenoxy)chlorophosphorothioyl)-L-alaninate (161 mg) as a colorless oil.

MS (ESI m/z): 372, 374 (M+H)

RT (min): 1.75

Reference Example 10

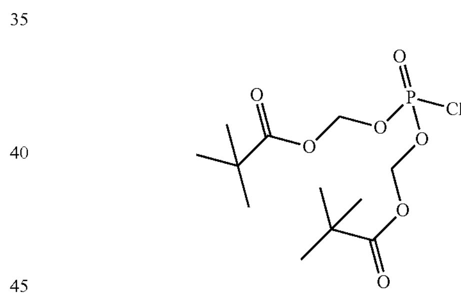

The following compound was obtained according to the method described in Org. Lett., Vol. 6, No. 10, 2004, 1555-1556.

((Chlorophosphoryl)bis(oxy))bis(methylene)bis(2,2-dimethylpropanoate)

Reference Example 11

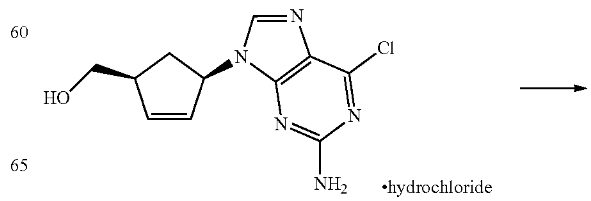

-continued

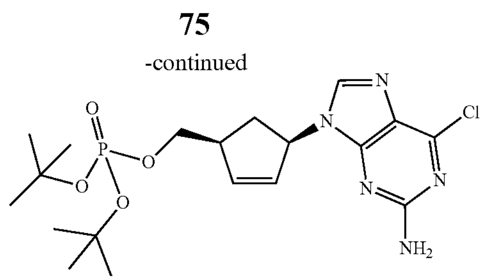

1H-tetrazole (3.5 g) and di-tert-butyl N,N-diisopropyl phosphoramidite (10.3 mL) were added to a mixture of ((1S,4R)-4-(2-amino-6-chloro-9H-purin-9-yl)cyclopent-2-en-1-yl)methanol hydrochloride (5 g) and dichloromethane (100 mL) which was then stirred at room temperature for 1 hour. Metachloroperbenzoic acid (4.1 g) was added thereto at −40° C., and the temperature was raised to −10° C. over 140 minutes. An aqueous sodium thiosulfate solution was added to the reaction solution, the aqueous layer was removed, and then the solvent was distilled off from the organic layer under reduced pressure. The obtained residue was purified by silica gel column chromatography (ethyl acetate:hexane=50:50 to 100:0, methanol:ethyl acetate=0:100 to 10:90) to give (((1S,4R)-4-(2-amino-6-chloro-9H-purin-9-yl)cyclopent-2-en-1-yl)methyl di-tert-butyl phosphate (5.4 g) as a colorless oil.

MS (ESI m/z): 458, 460 (M+H)

RT (min): 1.24

Example 1-1

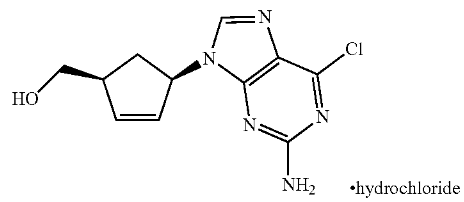

•hydrochloride

-continued

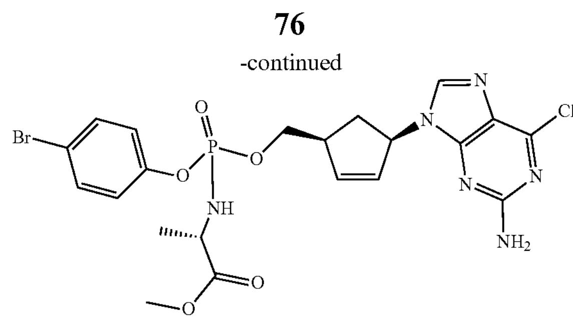

Under a nitrogen atmosphere, a 1.0 M tert-butyl magnesium chloride/tetrahydrofuran solution (330 μL) was added dropwise to a mixture of (((1S,4R)-4-(2-amino-6-chloro-9H-purin-9-yl)cyclopent-2-en-1-yl)methanol hydrochloride (20 mg) and tetrahydrofuran (0.8 mL), and then a mixture of (methyl ((4-bromophenoxy)(4-nitrophenoxy)phosphoryl)-L-alaninate (46 mg) and tetrahydrofuran (0.2 mL) was added thereto, which was followed by stirring at room temperature overnight. The reaction solution was purified by silica gel column chromatography (hexane:ethyl acetate=70:30 to 0:100, methanol:ethyl acetate=0:100 to 14:86) to give methyl ((((1S,4R)-4-(2-amino-6-chloro-9H-purin-9-yl)cyclopent-2-en-1-yl)methoxy)(4-bromophenoxy)phosphoryl)-L-alaninate (7.16 mg) as a pale yellow solid.

$^1$H-NMR ($CD_3OD$) δ: 8.02-7.99 (m, 1H), 7.49-7.41 (m, 2H), 7.16-7.03 (m, 2H), 6.22-6.11 (m, 1H), 6.02-5.94 (m, 1H), 5.66-5.53 (m, 1H), 4.30-4.14 (m, 2H), 3.99-3.77 (m, 1H), 3.68-3.61 (m, 3H), 3.29-3.10 (m, 1H), 2.87-2.72 (m, 1H), 1.90-1.67 (m, 1H), 1.39-1.22 (m, 3H).

MS (ESI m/z): 585, 587 (M+H)

RT (min): 1.25

Example 1-2

The compounds in Tables 4-1 to 4-9 were obtained in the same manner as in Example 1-1.

TABLE 4-1

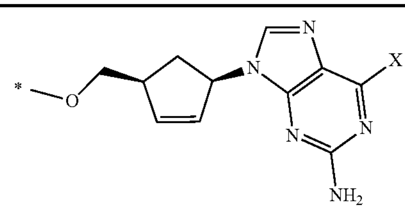

| Example No. | R | X | Compound name |
| --- | --- | --- | --- |
| 1-2-1 | 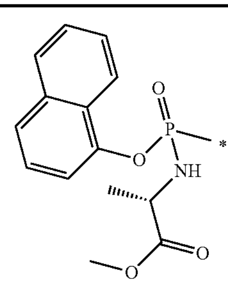 | OMe | Methyl ((((1S,4R)-4-(2-amino-6-methoxy-9H-purin-9-yl)cyclopent-2-en-1-yl)methoxy)(naphthalen-1-yloxy)phosphoryl)-L-alaninate |

TABLE 4-1-continued

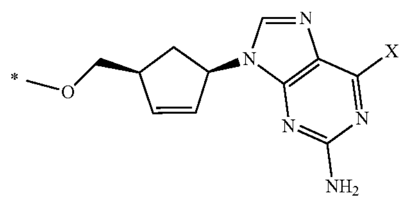

| | | | |
|---|---|---|---|
| 1-2-2 | 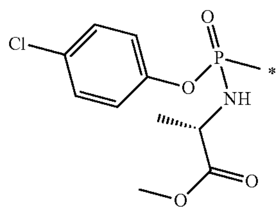 | OMe | Methyl ((((1S,4R)-4-(2-amino-6-methoxy-9H-purin-9-yl)cyclopent-2-en-1-yl)methoxy)(4-chlorophenoxy) phosphoryl)-L-alaninate |
| 1-2-3 | 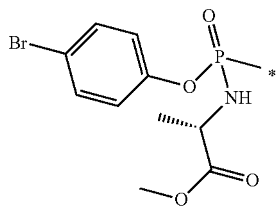 | OMe | Methyl ((((1S,4R)-4-(2-amino-6-methoxy-9H-purin-9-yl)cyclopent-2-en-1-yl)methoxy)(4-bromophenoxy)phosphoryl)-L-alaninate |
| 1-2-4 | 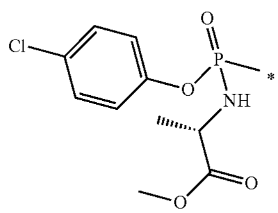 | Cl | Methyl ((((1S,4R)-4-(2-amino-6-chloro-9H-purin-9-yl)cyclopent-2-en-1-yl)methoxy)(4-chlorophenoxy) phosphoryl)-L-alaninate |
| 1-2-5 | 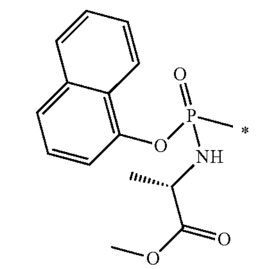 | Cl | Methyl ((((1S,4R)-4-(2-amino-6-chloro-9H-purin-9-yl)cyclopent-2-en-1-yl)methoxy)(naphthalen-1-yloxy) phosphoryl)-L-alaninate |
| 1-2-6 | 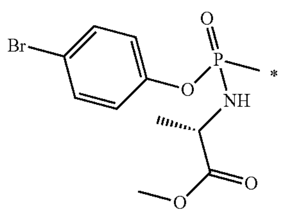 | NH2 | Methyl ((4-bromophenoxy)(((1S,4R)-4-(2,6-diamino-9H-purin-9-yl) cyclopent-2-en-1-yl)methoxy) phosphoryl)-L-alaninate |

TABLE 4-1-continued

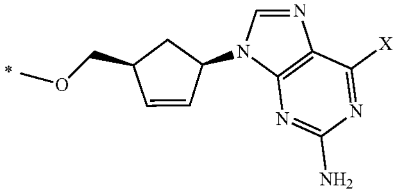

| | | | |
|---|---|---|---|
| 1-2-7 | 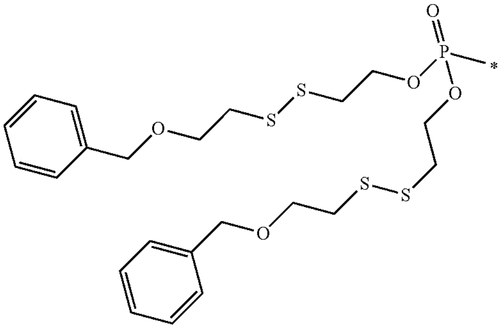 | Cl | ((1S,4R)-4-(2-amino-6-chloro-9H-purin-9-yl)cyclopent-2-en-1-yl)methylbis(2-((2-(benzyloxy)ethyl)disulfanyl)ethyl)phosphate |
| 1-2-8 | 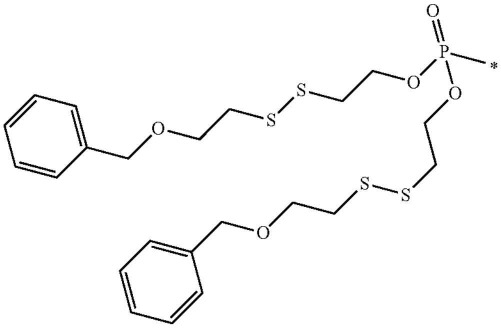 | OMe | ((1S,4R)-4-(2-amino-6-methoxy-9H-purin-9-yl)cyclopent-2-en-1-yl)methylbis(2-((2-(benzyloxy)ethyl)disulfanyl)ethyl)phosphate |
| 1-2-9 | 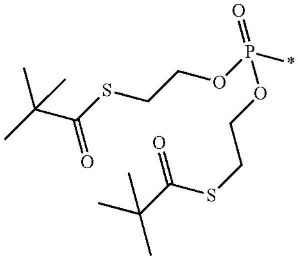 [SMILES: *P(=O)(OCCSC(=O)C(C)(C)C)OCCSC(=O)C(C)(C)C] | Cl | ((1S,4R)-4-(2-amino-6-chloro-9H-purin-9-yl)cyclopent-2-en-1-yl)methylbis(S-pivaloyl-2-mercaptoethan-1-yl)phosphate |
| 1-2-10 | 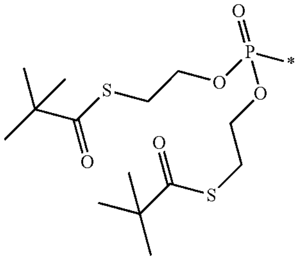 [SMILES: *P(=O)(OCCSC(=O)C(C)(C)C)OCCSC(=O)C(C)(C)C] | OMe | ((1S,4R)-4-(2-amino-6-methoxy-9H-purin-9-yl)cyclopent-2-en-1-yl)methylbis(S-pivaloyl-2-mercaptoethan-1-yl)phosphate |

TABLE 4-1-continued

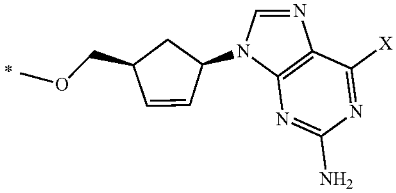

| Example No. | 1H-NMR | MS (ESI m/z) (M + H) | RT (min) |
|---|---|---|---|
| 1-2-1 | $^1$H-NMR ($CD_3OD$) δ: 8.14-8.03 (m, 1H), 7.88-7.79 (m, 1H), 7.75-7.59 (m, 2H), 7.55-7.30 (m, 4H), 6.11-6.02 (m, 1H), 5.96-5.85 (m, 1H), 5.58-5.45 (m, 1H), 4.26-4.14 (m, 2H), 4.07-3.92 (m, 4H), 3.59 (s, 3H), 3.22-3.09 (m, 1H), 2.79-2.62 (m, 1H), 1.73-1.58 (m, 1H), 1.36-1.23 (m, 3H). | 553 | 1.18 1.19 |
| 1-2-2 | $^1$H-NMR ($CD_3OD$) δ: 7.79-7.73 (m, 1H), 7.34-7.23 (m, 2H), 7.20-7.08 (m, 2H). 6.19-6.08 (m, 1H), 6.01-5.93 (m, 1H), 5.62-5.49 (m, 1H), 4.25-4.10 (m, 2H), 4.04 (s, 3H), 3.98-3.77 (m, 1H), 3.67-3.60 (m, 3H), 3.27-3.11 (m, 1H), 2.86-2.71 (m, 1H), 1.84-1.67 (m, 1H), 1.37-1.22 (m, 3H). | 537 539 | 1.15 |
| 1-2-3 | $^1$H-NMR ($CD_3OD$) δ: 7.80-7.76 (m, 1H), 7.49-7.40 (m, 2H), 7.15-7.04 (m, 2H), 6.20-6.11 (m, 1H), 6.02-5.91 (m, 1H), 5.62-5.50 (m, 1H), 4.29-4.13 (m, 2H), 4.05 (s, 3H), 3.98-3.80 (m, 1H), 3.69-3.62 (m, 3H), 3.29-3.10 (m, 1H), 2.87-2.72 (m, 1H), 1.84-1.66 (m, 1H), 1.38-1.25 (m, 3H). | 581 583 | 1.17 |
| 1-2-4 | $^1$H-NMR ($CDCl_3$) δ: 7.79 (s, 1H), 7.31-7.24 (m, 2H), 7.20-7.12 (m, 2H), 6.16-6.07 (m, 1H), 5.92-5.85 (m, 1H), 5.58-5.49 (m, 1H), 5.40-5.27 (m, 2H), 4.38-4.15 (m, 2H), 4.07-3.93 (m, 1H), 3.75-3.51 (m, 4H), 3.26-3.15 (m, 1H), 2.85-2.72 (m, 1H), 1.89-1.77 (m, 1H), 1.42-1.31 (m, 3H). | 541 543 | 1.23 |
| 1-2-5 | $^1$H-NMR ($CDCl_3$) δ: 8.14-8.04 (m, 1H), 7.88-7.72 (m, 2H), 7.69-7.46 (m, 4H), 7.42-7.31 (m, 1H), 6.09-6.03 (m, 1H), 5.88-5.79 (m, 1H), 5.56-5.31 (m, 3H), 4.42-4.03 (m, 3H), 3.84-3.59 (m, 4H), 3.25-3.11 (m, 1H), 2.79-2.62 (m, 1H), 1.82-1.71 (m, 1H), 1.41-1.30 (m, 3H). | 557 559 | 1.26 1.27 |
| 1-2-6 | $^1$H-NMR ($CD_3OD$) δ: 7.73-7.69 (m, 1H), 7.50-7.41 (m, 2H), 7.15-7.05 (m, 2H), 6.19-6.11 (m, 1H), 6.01-5.93 (m, 1H), 5.56-5.46 (m, 1H), 4.27-4.12 (m, 2H), 3.99-3.83 (m, 1H), 3.65 (s, 3H), 3.27-3.11 (m, 1H), 2.87-2.73 (m, 1H), 1.79-1.63 (m, 1H), 1.36-1.26 (m, 3H). | 566 568 | 1.01 |
| 1-2-7 | $^1$H-NMR ($CD_3OD$) δ: 7.98 (s, 1H), 7.36-7.14 (m, 10H), 6.20-6.08 (m, 1H), 6.02-5.89 (m, 1H), 5.62-5.50 (m, 1H), 4.54-4.42 (m, 4H), 4.31-4.10 (m, 6H), 3.77-3.60 (m, 4H), 3.23-3.10 (m, 1H), 2.99-2.70 (m, 9H), 1.90-1.71 (m, 1H). | 798 800 | 1.83 |
| 1-2-8 | $^1$H-NMR ($CD_3OD$) δ: 7.76 (s, 1H), 7.35-7.15 (m, 10H), 6.18-6.05 (m, 1H), 5.99-5.88 (m, 1H), 5.59-5.44 (m, 1H), 4.55-4.40 (m, 4H), 4.31-4.07 (m, 6H), 4.02 (s, 3H), 3.74-3.57 (m, 4H), 3.22-3.06 (m, 1H), 2.98-2.70 (m, 9H), 1.83-1.66 (m, 1H). | 794 | 1.77 |
| 1-2-9 | $^1$H-NMR ($CD_3OD$) δ: 8.04 (s, 1H), 6.23-6.11 (m, 1H), 6.05-5.94 (m, 1H), 5.68-5.55 (m, 1H), 4.27-4.14 (m, 2H), 4.14-3.98 (m, 7H), 3.27-3.17 (m, 1H), 3.17-3.03 (m, 4H), 2.93-2.75 (m, 1H), 1.97-1.80 (m, 1H), 1.20 (s, 18H). | 634 636 | 1.67 |
| 1-2-10 | $^1$H-NMR ($CD_3OD$) δ: 7.80 (s, 1H), 6.21-6.12 (m, 1H), 6.03-5.95 (m, 1H), 5.64-5.52 (m, 1H), 4.23-4.13 (m, 2H), 4.13-3.97 (m, 7H), 3.26-3.17 (m, 1H), 3.17-3.05 (m, 4H), 2.92-2.77 (m, 1H), 1.88-1.75 (m, 1H), 1.20 (s, 18H). | 630 | 1.60 |

TABLE 4-2

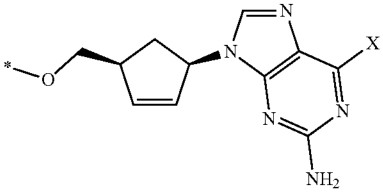

| Example No. | R | X | Compound name |
|---|---|---|---|
| 1-2-11 | 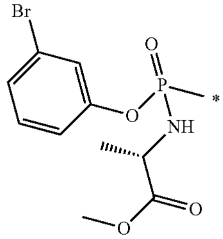 | OMe | Methyl ((((1S,4R)-4-(2-amino-6-methoxy-9H-purin-9-yl)cyclopent-2-en-1-yl) methoxy)(3-bromophenoxy) phosphoryl)-L-alaninate |
| 1-2-12 | 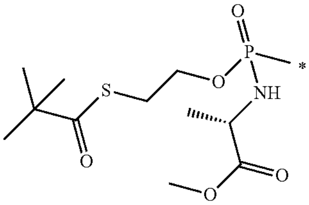 | OMe | Methyl ((((1S,4R)-4-(2-amino-6-methoxy-9H-purin-9-yl)cyclopent-2-en-1-yl) methoxy)(2-(pivaloylthio)ethoxy) phosphoryl)-L-alaninate |
| 1-2-13 | 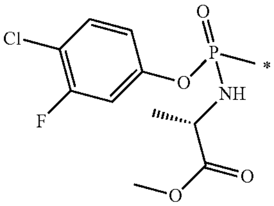 | OMe | Methyl ((((1S,4R)-4-(2-amino-6-methoxy-9H-purin-9-yl)cyclopent-2-en-1-yl) methoxy)(4-chloro-3-fluorophenoxy) phosphoryl)-L-alaninate |
| 1-2-14 | 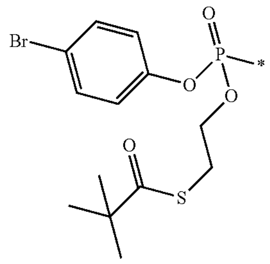 [SMILES: *P(=O)(OCCSC(=O)C(C)(C)C)Oc1ccc(Br)cc1] | OMe | S-(2-(((((1S,4R)-4-(2-amino-6-methoxy-9H-purin-9-yl)cyclopent-2-en-1-yl) methoxy)(4-bromophenoxy) phosphoryl)oxy)ethyl) 2,2-dimethylpropanethioate |
| 1-2-15 | 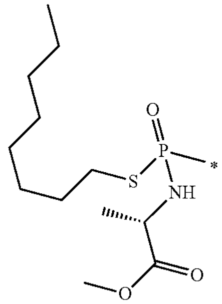 | OMe | Methyl ((((1S,4R)-4-(2-amino-6-methoxy-9H-purin-9-yl)cyclopent-2-en-1-yl) methoxy)(octylthio)phosphoryl)-L-alaninate |

TABLE 4-2-continued

| 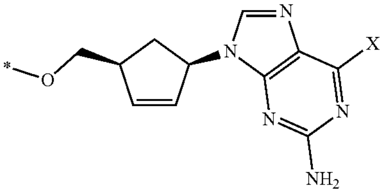 | | | |
|---|---|---|---|
| 1-2-16 | 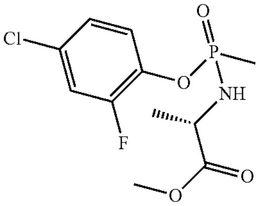 | OMe | Methyl ((((1S,4R)-4-(2-amino-6-methoxy-9H-purin-9-yl)cyclopent-2-en-1-yl) methoxy)(4-chloro-2-fluorophenoxy) phosphoryl)-L-alaninate |
| 1-2-17 | 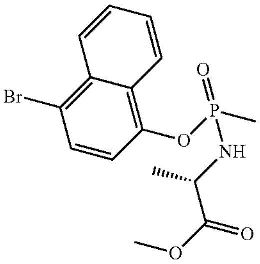 | OMe | Methyl ((((1S,4R)-4-(2-amino-6-methoxy-9H-purin-9-yl)cyclopent-2-en-1-yl) methoxy)((4-bromonaphthalen-1-yl)oxy)phosphoryl)-L-alaninate |
| 1-2-18 | 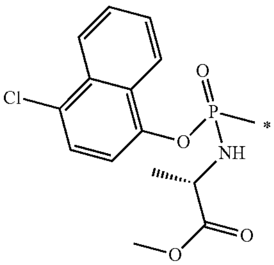 | OMe | Methyl ((((1S,4R)-4-(2-amino-6-methoxy-9H-purin-9-yl)cyclopent-2-en-1-yl) methoxy)((4-chloronaphthalen-1-yl)oxy)phosphoryl)-L-alaninate |
| 1-2-19 | 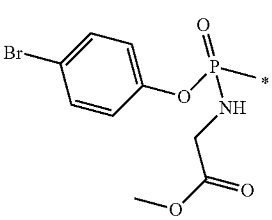 | OMe | Methyl ((((1S,4R)-4-(2-amino-6-methoxy-9 H-purin-9-yl)cyclopent-2-en-1-yl) methoxy)(4-bromophenoxy) phosphoryl)glycinate |

| Example No. | 1H-NMR | MS (ESI m/z) (M + H) | RT (min) |
|---|---|---|---|
| 1-2-11 | $^1$H-NMR ($CDCl_3$) δ: 7.62-7.57 (m, 1H), 7.42-7.36 (m, 1H), 7.31-7.26 (m, 1H), 7.20-7.14 (m, 2H), 6.11-6.05 (m, 1H), 5.93-5.88 (m, 1H), 5.58-5.50 (m, 1H), 5.01-4.92 (m, 2H), 4.31-4.16 (m, 2H), 4.09-3.96 (m, 4H), 3.74-3.52 (m, 4H), 3.23-3.13 (m, 1H), 2.83-2.73 (m, 1H), 1.82-1.74 (m, 1H), 1.42-1.34 (m, 3H). | 581<br>583 | 1.17 |

TABLE 4-2-continued

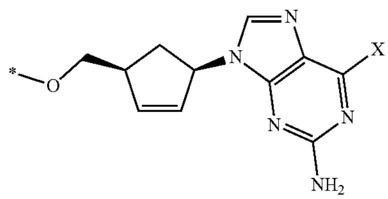

| | | | |
|---|---|---|---|
| 1-2-12 | $^{1}$H-NMR ($CDCl_3$) δ: 7.66-7.63 (m, 1H), 6.16-6.10 (m, 1H), 5.92-5.87 (m, 1H), 5.58-5.51 (m, 1H), 4.99-4.94 (m, 2H), 4.17-3.91 (m, 8H), 3.76-3.72 (m, 3H), 3.44-3.33 (m, 1H), 3.21-3.09 (m, 3H), 2.85-2.76 (m, 1H), 1.83-1.74 (m, 1H), 1.43-1.38 (m, 3H), 1.22 (s, 9H). | 571 | 1.22 |
| 1-2-13 | $^{1}$H-NMR ($CDCl_3$) δ: 7.66-7.58 (m, 1H), 7.36-7.27 (m, 1H), 7.14-7.04 (m, 1H), 7.03-6.93 (m, 1H), 6.14-6.06 (m, 1H), 5.97-5.88 (m, 1H), 5.61-5.48 (m, 1H), 5.05-4.92 (m, 2H), 4.33-3.92 (m, 6H), 3.78-3.54 (m, 4H), 3.26-3.11 (m, 1H), 2.87-2.72 (m, 1H), 1.84-1.73 (m, 1H), 1.45-1.33 (m, 3H). | 555<br>557 | 1.19 |
| 1-2-14 | $^{1}$H-NMR ($CDCl_3$) δ: 7.62-7.58 (m, 1H), 7.46-7.40 (m, 2H), 7.14-7.07 (m, 2H), 6.12-6.07 (m, 1H), 5.94-5.88 (m, 1H), 5.57-5.50 (m, 1H), 4.97 (s, 2H), 4.34-4.11 (m, 4H), 4.07 (s, 3H), 3.25-3.09 (m, 3H), 2.85-2.73 (m, 1H), 1.82-1.72 (m, 1H), 1.21 (s, 9H). | 640<br>642 | 1.58 |
| 1-2-15 | $^{1}$H-NMR ($CDCl_3$) δ: 7.65 (s, 1H), 6.16-6.10 (m, 1H), 5.94-5.87 (m, 1H), 5.61-5.51 (m, 1H), 4.96 (s, 2H), 4.26-3.94 (m, 6H), 3.79-3.62 (m, 4H), 3.24-3.12 (m, 1H), 2.88-2.70 (m, 3H), 1.83-1.73 (m, 1H), 1.70-1.58 (m, 2H), 1.47-1.17 (m, 13H), 0.87 (t, 3H, J = 6.6 Hz). | 555 | 1.55 |
| 1-2-16 | $^{1}$H-NMR ($CDCl_3$) δ: 7.63 (s, 1H), 7.38-7.31 (m, 1H), 7.18-7.12 (m, 1H), 7.08-7.03 (m, 1H), 6.13-6.06 (m, 1H), 5.94-5.88 (m, 1H), 5.59-5.49 (m, 1H), 5.01-4.91 (m, 2H), 4.31-4.18 (m, 2H), 4.14-3.98 (m, 4H), 3.75-3.59 (m, 4H), 3.26-3.11 (m, 1H), 2.85-2.73 (m, 1H), 1.84-1.70 (m, 1H), 1.44-1.34 (m, 3H). | 555<br>557 | 1.19 |
| 1-2-17 | $^{1}$H-NMR ($CDCl_3$) δ: 8.24-8.18 (m, 1H), 8.13-8.05 (m, 1H), 7.72-7.52 (m, 4H), 7.45-7.37 (m, 1H), 6.09-6.01 (m, 1H), 5.94-5.84 (m, 1H), 5.57-5.47 (m, 1H), 5.04-4.89 (m, 2H), 4.35-4.22 (m, 2H), 4.16-4.01 (m, 4H), 3.82-3.59 (m, 4H), 3.24-3.11 (m, 1H), 2.82-2.69 (m, 1H), 1.82-1.71 (m, 1H), 1.40-1.31 (m, 3H). | 631<br>633 | 1.35 |
| 1-2-18 | $^{1}$H-NMR ($CDCl_3$) δ: 8.28-8.20 (m, 1H), 8.15-8.06 (m, 1H), 7.68-7.54 (m, 3H), 7.50-7.42 (m, 2H), 6.09-6.01 (m, 1H), 5.93-5.84 (m, 1H), 5.56-5.47 (m, 1H), 5.02-4.89 (m, 2H), 4.36-4.19 (m, 2H), 4.16-4.00 (m, 4H), 3.79-3.57 (m, 4H), 3.24-3.10 (m, 1H), 2.81-2.68 (m, 1H), 1.81-1.71 (m, 1H), 1.40-1.31 (m, 3H). | 587<br>589 | 1.32<br>1.33 |
| 1-2-19 | $^{1}$H-NMR ($CDCl_3$) δ: 7.68-7.62 (m, 1H), 7.45-7.38 (m, 2H), 7.16-7.04 (m, 2H), 6.12-6.07 (m, 1H), 5.94-5.87 (m, 1H), 5.58-5.49 (m, 1H), 5.04-4.91 (m, 2H), 4.31-4.18 (m, 2H), 4.09-4.04 (m, 3H), 3.82-3.46 (m, 6H), 3.24-3.11 (m, 1H), 2.85-2.72 (m, 1H), 1.84-1.69 (m, 1H). | 567<br>569 | 1.11 |

TABLE 4-3

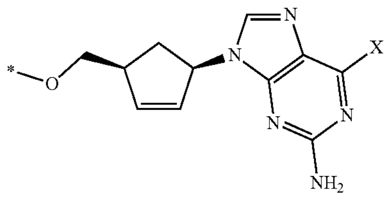

| Example No. | R | X | Compound name | $^1$H-NMR | MS (ESI m/z) (M + H) | RT (min) |
|---|---|---|---|---|---|---|
| 1-2-20 | 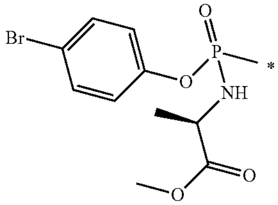 | OMe | Methyl ((((1S,4R)-4-(2-amino-6-methoxy-9H-purin-9-yl) cyclopent-2-en-1-yl)methoxy) (4-bromophenoxy) phosphoryl)-D-alaninate | $^1$H-NMR ($CDCl_3$) δ: 7.58-7.60 (m, 1H), 7.45-7.38 (m, 2H), 7.17-7.03 (m, 2H), 6.12-6.05 (m, 1H), 5.94-5.86 (m, 1H), 5.58-5.49 (m, 1H), 5.03-4.92 (m, 2H), 4.31-3.82 (m, 6H), 3.72-3.53 (m, 4H), 3.24-3.10 (m, 1H), 2.85-2.71 (m, 1H), 1.82-1.67 (m, 1H), 1.38-1.32 (m, 3H). | 581 583 | 1.18 |
| 1-2-21 | 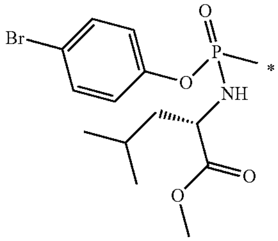 | OMe | Methyl ((((1S,4R)-4-(2-amino-6-methoxy-9H-purin-9-yl) cyclopent-2-en-1-yl) methoxy)(4-bromophenoxy) phosphoryl)-L-leucinate | $^1$H-NMR ($CDCl_3$) δ: 7.62 (s, 1H), 7.44-7.37 (m, 2H), 7.14-7.06 (m, 2H), 6.12-6.03 (m, 1H), 5.93-5.86 (m, 1H), 5.59-5.49 (m, 1H), 5.03-4.92 (m, 2H), 4.32-4.11 (m, 2H), 4.07 (s, 3H), 3.99-3.86 (m, 1H), 3.69-3.63 (m, 3H), 3.50-3.24 (m, 1H), 3.23-3.09 (m, 1H), 2.85-2.70 (m, 1H), 1.84-1.38 (m, 4H), 0.93-0.81 (m, 6H). | 623 625 | 1.41 |
| 1-2-22 | 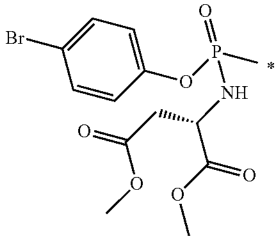 | OMe | Dimethyl ((((1S,4R)-4-(2-amino-6-methoxy-9H-purin-9-yl) cyclopent-2-en-1-yl) methoxy)(4-bromophenoxy) phosphoryl)-L-aspartate | $^1$H-NMR ($CDCl_3$) δ: 7.64-7.61 (m, 1H), 7.45-7.38 (m, 2H), 7.13-7.07 (m, 2H), 6.13-6.03 (m, 1H), 5.92-5.87 (m, 1H), 5.59-5.48 (m, 1H), 5.05-4.93 (m, 2H), 4.32-3.92 (m, 7H), 3.74-3.69 (m, 3H), 3.67-3.62 (m, 3H), 3.26-3.10 (m, 1H), 2.99-2.60 (m, 3H), 1.84-1.68 (m, 1H). | 639 641 | 1.17 |
| 1-2-23 | 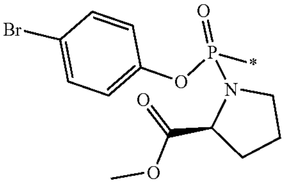 [SMILES: *P(=O)(Oc1ccc(Br)cc1)N1CCC[C@H]1C(=O)OC] | OMe | Methyl ((((1S,4R)-4-(2-amino-6-methoxy-9H-purin-9-yl) cyclopent-2-en-1-yl) methoxy)(4-bromophenoxy) phosphoryl)-L-prolinate | $^1$H-NMR ($CDCl_3$) δ: 7.70-7.60 (m, 1H), 7.45-7.38 (m, 2H), 7.19-7.10 (m, 2H), 6.13-6.04 (m, 1H), 5.93-5.84 (m, 1H), 5.61-5.49 (m, 1H), 5.04-4.89 (m, 2H), 4.39-4.23 (m, 2H), 4.17-4.04 (m, 4H), 3.70-3.62 (m, 3H), 3.46-3.09 (m, 3H), 2.88-2.71 (m, 1H), 2.23-1.67 (m, 5H). | 607 609 | 1.27 1.29 |

TABLE 4-3-continued

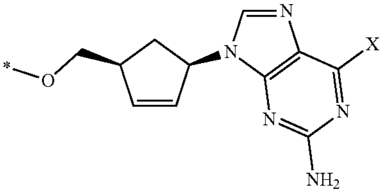

| Example No. | R | X | Compound name | $^1$H-NMR | MS (ESI m/z) (M + H) | RT (min) |
|---|---|---|---|---|---|---|
| 1-2-24 | 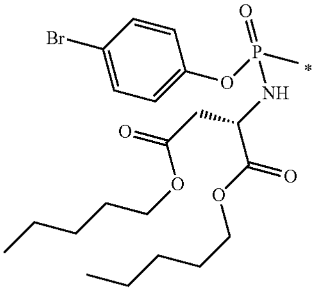 | OMe | Dipentyl ((((1S,4R)-4-(2-amino-6-methoxy-9H-purin-9-yl) -2-en-1-yl) methoxy)(4-bromophenoxy) phosphoryl)-L-aspartate | $^1$H-NMR ($CDCl_3$) δ: 7.63-7.60 (m, 1H), 7.44-7.38 (m, 2H), 7.13-7.07 (m, 2H), 6.12-6.02 (m, 1H), 5.91-5.86 (m, 1H), 5.58-5.48 (m, 1H), 5.00-4.91 (m, 2H), 4.32-3.90 (m, 11H), 3.25-3.11 (m, 1H), 2.99-2.88 (m, 1H), 2.86-2.58 (m, 2H), 1.84-1.51 (m, 5H), 1.37-1.21 (m, 8H), 0.93-0.84 (m, 6H). | 751 753 | 1.84 |
| 1-2-25 | 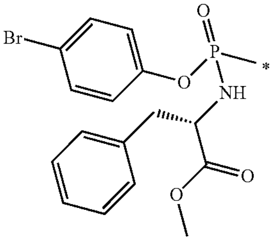 | OMe | Methyl ((((1S,4R)-4-(2-amino-6-methoxy-9H-purin-9-yl) cyclopent-2-en-1-yl) methoxy)(4-bromophenoxy) phosphoryl)-L-phenylalaninate | $^1$H-NMR ($CDCl_3$) δ: 7.62-7.56 (m, 1H), 7.42-6.95 (m, 9H), 6.03-5.96 (m, 1H), 5.91-5.82 (m, 1H), 5.57-5.46 (m, 1H), 5.04-4.92 (m, 2H), 4.37-3.64 (m, 9H), 3.51-3.35 (m, 1H), 3.15-2.64 (m, 4H), 1.72-1.60 (m, 1H). | 657 659 | 1.40 |
| 1-2-26 | 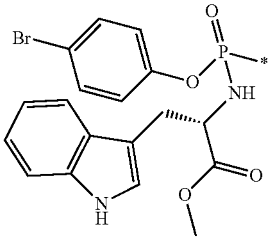 [SMILES: *P(=O)(N[C@@H](Cc1c[nH]c2ccccc12)C(=O)OC)Oc1ccc(Br)cc1] | OMe | Methyl ((((1S,4R)-4-(2-amino-6-methoxy-9H-purin-9-yl) cyclopent-2-en-1-yl) methoxy)(4-bromophenoxy) phosphoryl)-L-tryptophanate | $^1$H-NMR ($CDCl_3$) δ: 8.52 (s, 1H), 7.57-7.52 (m, 1H), 7.51-7.45 (m, 1H), 7.37-7.25 (m, 3H), 7.19-6.91 (m, 5H), 5.97-5.74 (m, 2H), 5.51-5.41 (m, 1H), 5.03-4.93 (m, 2H), 4.35-4.16 (m, 1H), 4.10-3.51 (m, 9H), 3.25-2.85 (m, 3H), 2.73-2.53 (m, 1H), 1.64-1.47 (m, 1H). | 696 698 | 1.37 |
| 1-2-27 | 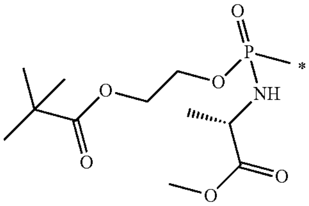 | OMe | 2-(((((1S,4R)-4-(2-amino-6-methoxy-9H-purin-9-yl) cyclopent-2-en-1-yl) methoxy)(((S)-1-methoxy-1-oxopropan-2-yl)amino) phosphoryl)oxy)ethyl) ethylpivalate | $^1$H-NMR ($CDCl_3$) δ: 7.63 (s, 1H), 6.15-6.09 (m, 1H), 5.93-5.87 (m, 1H), 5.60-5.51 (m, 1H), 4.99 (s, 2H), 4.30-4.05 (m, 9H), 3.98-3.89 (m, 1H), 3.75-3.72 (m, 3H), 3.49-3.35 (m, 1H), 3.23-3.11 (m, 1H), 2.87-2.74 (m, 1H), 1.83-1.70 (m, 1H), 1.43-1.38 (m, 3H), 1.21-1.19 (m, 9H). | 555 | 1.11 |
| 1-2-28 | 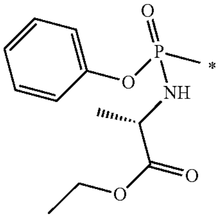 | Cl | Ethyl ((((1S,4R)-4-(2-amino-6-chloro-9-H-purin-9-yl) cyclopent-2-en-1-yl) methoxy)(phenoxy) phosphoryl)-L-alaninate | $^1$H-NMR ($CDCl_3$) δ: 7.79-7.75 (m, 1H), 7.35-7.10 (m, 5H), 6.15-6.07 (m, 1H), 5.89-5.83 (m, 1H), 5.58-5.48 (m, 1H), 5.34-5.25 (m, 2H), 4.37-4.09 (m, 4H), 4.08-3.92 (m, 1H), 3.56-3.48 (m, 1H), 3.27-3.14 (m, 1H), 2.84-2.70 (m, 1H), 1.89-1.75 (m, 1H), 1.42-1.31 (m, 3H), 1.29-1.20 (m, 3H). | 521 523 | 1.19 |

TABLE 4-4

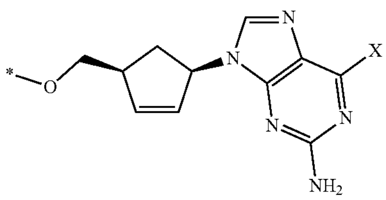

| Example No. | R | X | Compound name | $^1$H-NMR | MS (ESI m/z) (M + H) | RT (min) |
|---|---|---|---|---|---|---|
| 1-2-29 | 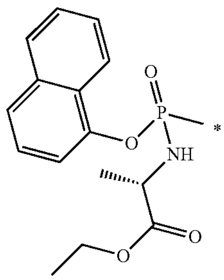 | Cl | Ethyl ((((1S,4R)-4-(2-amino-6-chloro-9 H-purin-9-yl) cyclopent-2-en-1-yl) methoxy) (naphthalen-1-yloxy) phosphoryl)-L-alaninate | $^1$H-NMR ($CDCl_3$) δ: 8.13-8.05 (m, 1H), 7.88-7.77 (m, 1H), 7.77-7.71 (m, 1H), 7.69-7.59 (m, 1H), 7.56-7.46 (m, 3H), 7.42-7.31 (m, 1H), 6.09-6.03 (m, 1H), 5.86-5.78 (m, 1H), 5.54-5.43 (m, 1H), 5.37-5.25 (m, 2H), 4.44-4.21 (m, 2H), 4.17-4.01 (m, 3H), 3.79-3.58 (m, 1H), 3.25-3.11 (m, 1H), 2.81-2.61 (m, 1H), 1.86-1.71 (m, 1H), 1.43-1.30 (m, 3H), 1.30-1.14 (m, 3H). | 571<br>573 | 1.35<br>1.36 |
| 1-2-30 | 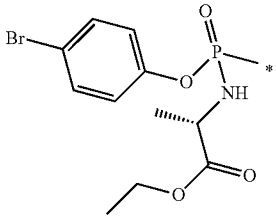 | Cl | Ethyl ((((1S,4R)-4-(2-amino-6-chloro-9 H-purin-9-yl) cyclopent-2-en-1-yl) methoxy)(4-bromophenoxy) phosphoryl)-L-alaninate | $^1$H-NMR ($CDCl_3$) δ: 7.78 (s, 1H), 7.45-7.37 (m, 2H), 7.14-7.06 (m, 2H), 6.15-6.07 (m, 1H), 5.90-5.85 (m, 1H), 5.58-5.49 (m, 1H), 5.34-5.25 (m, 2H), 4.38-4.10 (m, 4H), 4.05-3.89 (m, 1H), 3.68-3.47 (m, 1H), 3.26-3.14 (m, 1H), 2.85-2.71 (m, 1H), 1.90-1.76 (m, 1H), 1.42-1.32 (m, 3H), 1.29-1.21 (m, 3H). | 599<br>601 | 1.34 |
| 1-2-31 | 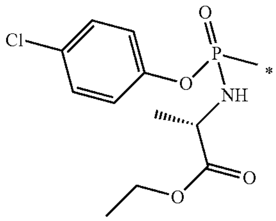 | Cl | Ethyl ((((1S,4R)-4-(2-amino-6-chloro-9 H-purin-9-yl) cyclopent-2-en-1-yl) methoxy)(4-chlorophenoxy) phosphoryl)-L-alaninate | $^1$H-NMR ($CDCl_3$) δ: 7.80 (s, 1H), 7.31-7.24 (m, 2H), 7.21-7.13 (m, 2H), 6.17-6.09 (m, 1H), 5.92-5.86 (m, 1H), 5.60-5.50 (m, 1H), 5.37-5.27 (m, 2H), 4.40-4.12 (m, 4H), 4.07-3.92 (m, 1H), 3.71-3.50 (m, 1H), 3.28-3.16 (m, 1H), 2.87-2.73 (m, 1H), 1.92-1.78 (m, 1H), 1.44-1.33 (m, 3H), 1.31-1.22 (m, 3H). | 555<br>557 | 1.31 |
| 1-2-32 | 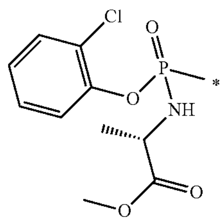 | Cl | Methyl ((((1S,4R)-4-(2-amino-6-chloro-9 H-purin-9-yl) cyclopent-2-en-1-yl)methoxy)(2-chlorophenoxy) phosphoryl)-L-alaninate | $^1$H-NMR ($CDCl_3$) δ: 7.78 (s, 1H), 7.50-7.44 (m, 1H), 7.43-7.36 (m, 1H), 7.26-7.16 (m, 1H), 7.14-7.04 (m, 1H), 6.15-6.06 (m, 1H), 5.89-5.84 (m, 1H), 5.58-5.49 (m, 1H), 5.32-5.24 (m, 2H), 4.40-4.19 (m, 2H), 4.17-4.03 (m, 1H), 3.74-3.60 (m, 4H), 3.27-3.14 (m, 1H), 2.84-2.70 (m, 1H), 1.89-1.77 (m, 1H), 1.45-1.32 (m, 3H). | 541<br>543 | 1.19<br>1.20 |
| 1-2-33 | 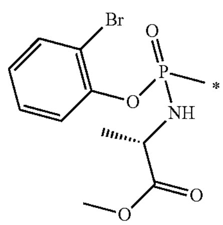 | Cl | Methyl ((((1S,4R)-4-(2-amino-6-chloro-9 H-purin-9-yl) cyclopent-2-en-1-yl) methoxy)(2-bromophenoxy) phosphoryl)-L-alaninate | $^1$H-NMR ($CDCl_3$) δ: 7.80 (s, 1H), 7.61-7.46 (m, 2H), 7.31-7.21 (m, 1H), 7.09-6.99 (m, 1H), 6.18-6.08 (m, 1H), 5.91-5.85 (m, 1H), 5.59-5.50 (m, 1H), 5.35-5.26 (m, 2H), 4.42-4.24 (m, 2H), 4.19-4.08 (m, 1H), 3.78-3.65 (m, 4H), 3.30-3.16 (m, 1H), 2.85-2.72 (m, 1H), 1.91-1.76 (m, 1H), 1.46-1.34 (m, 3H). | 585<br>587 | 1.20<br>1.21 |

TABLE 4-4-continued

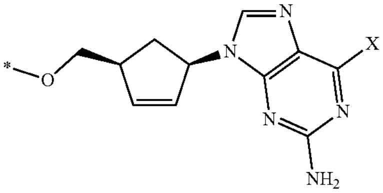

| Example No. | R | X | Compound name | $^1$H-NMR | MS (ESI m/z) (M + H) | RT (min) |
|---|---|---|---|---|---|---|
| 1-2-34 | 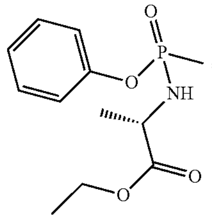 | OMe | Ethyl ((((1S,4R)-4-(2-amino-6-methoxy-9H-purin-9-yl) cyclopent-2-en-1-yl) methoxy)(phenoxy) phosphoryl)-L-alaninate | $^1$H-NMR ($CDCl_3$) δ: 7.62-7.57 (m, 1H), 7.36-7.09 (m, 5H), 6.13-6.05 (m, 1H), 5.91-5.84 (m, 1H), 5.59-5.49 (m, 1H), 5.00-4.91 (m, 2H), 4.32-3.94 (m, 8H), 3.65-3.44 (m, 1H), 3.23-3.10 (m, 1H), 2.86-2.70 (m, 1H), 1.82-1.68 (m, 1H), 1.44-1.33 (m, 3H), 1.31-1.19 (m, 3H). | 517 | 1.11 |
| 1-2-35 | 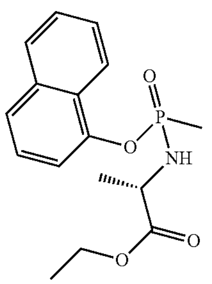 | OMe | Ethyl ((((1S,4R)-4-(2-amino-6-methoxy-9H-purin-9-yl) cyclopent-2-en-1-yl) methoxy) (naphthalen-1-yloxy) phosphoryl)-L-alaninate | $^1$H-NMR ($CDCl_3$) δ: 8.14-8.06 (m, 1H), 7.88-7.79 (m, 1H), 7.68-7.60 (m, 1H), 7.59-7.46 (m, 4H), 7.42-7.32 (m, 1H), 6.08-5.99 (m, 1H), 5.89-5.80 (m, 1H), 5.56-5.46 (m, 1H), 5.01-4.89 (m, 2H), 4.35-4.20 (m, 2H), 4.16-4.00 (m, 6H), 3.77-3.56 (m, 1H), 3.22-3.10 (m, 1H), 2.80-2.64 (m, 1H), 1.78-1.66 (m, 1H), 1.43-1.32 (m, 3H), 1.30-1.14 (m, 3H). | 567 | 1.27<br>1.28 |
| 1-2-36 | 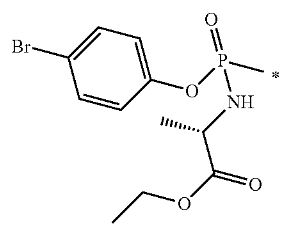 | OMe | Ethyl ((((1S,4R)-4-(2-amino-6-methoxy-9H-purin-9-yl) cyclopent-2-en-1-yl) methoxy)(4-bromophenoxy) phosphoryl)-L-alaninate | $^1$H-NMR ($CDCl_3$) δ: 7.66-7.59 (m, 1H), 7.46-7.37 (m, 2H), 7.17-7.05 (m, 2H), 6.14-6.04 (m, 1H), 5.94-5.86 (m, 1H), 5.59-5.49 (m, 1H), 5.04-4.91 (m, 2H), 4.33-3.90 (m, 8H), 3.72-3.47 (m, 1H), 3.26-3.12 (m, 1H), 2.87-2.69 (m, 1H), 1.85-1.72 (m, 1H), 1.45-1.32 (m, 3H), 1.32-1.20 (m, 3H). | 595<br>597 | 1.26 |
| 1-2-37 | 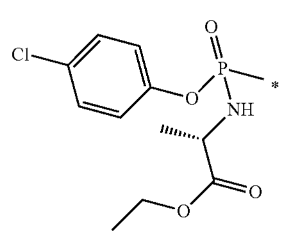 | OMe | Ethyl ((((1S,4R)-4-(2-amino-6-methoxy-9H-purin-9-yl) cyclopent-2-en-1-yl) methoxy)(4-chlorophenoxy) phosphoryl)-L-alaninate | $^1$H-NMR ($CDCl_3$) δ: 7.64-7.59 (m, 1H), 7.31-7.22 (m, 2H), 7.20-7.11 (m, 2H), 6.12-6.04 (m, 1H), 5.93-5.87 (m, 1H), 5.59-5.49 (m, 1H), 5.01-4.91 (m, 2H), 4.31-3.92 (m, 8H), 3.68-3.45 (m, 1H), 3.25-3.11 (m, 1H), 2.87-2.71 (m, 1H), 1.83-1.70 (m, 1H), 1.43-1.32 (m, 3H), 1.30-1.19 (m, 3H). | 551<br>553 | 1.24 |

TABLE 4-5

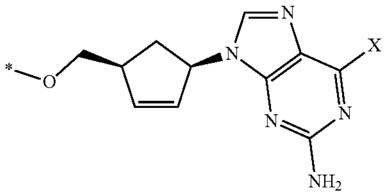

| Example No. | R | X | Compound name | $^1$H-NMR | MS (ESI m/z) (M + H) | RT (min) |
|---|---|---|---|---|---|---|
| 1-2-38 | 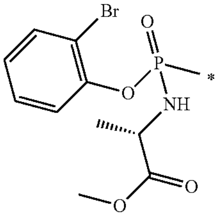 | OMe | Methyl ((((1S,4R)-4-(2-amino-6-methoxy-9H-purin-9-yl) cyclopent-2-en-1-yl) methoxy)(2-bromophenoxy) phosphoryl)-L-alaninate | $^1$H-NMR ($CDCl_3$) δ: 7.60 (s, 1H), 7.59-7.47 (m, 2H), 7.31-7.21 (m, 1H), 7.07-6.98 (m, 1H), 6.13-6.04 (m, 1H), 5.91-5.84 (m, 1H), 5.59-5.49 (m, 1H), 5.00-4.90 (m, 2H), 4.34-4.20 (m, 2H), 4.18-4.04 (m, 4H), 3.77-3.59 (m, 4H), 3.25-3.12 (m, 1H), 2.84-2.71 (m, 1H), 1.81-1.68 (m, 1H), 1.46-1.33 (m, 3H). | 581<br>583 | 1.13<br>1.14 |
| 1-2-39 | 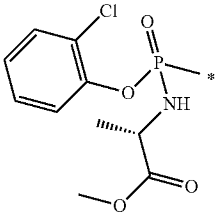 | OMe | Methyl ((((1S,4R)-4-(2-amino-6-methoxy-9H-purin-9-yl) cyclopent-2-en-1-yl) methoxy)(2-chlorophenoxy) phosphoryl)-L-alaninate | $^1$H-NMR ($CDCl_3$) δ: 7.60 (s, 1H), 7.52-7.45 (m, 1H), 7.43-7.36 (m, 1H), 7.25-7.16 (m, 1H), 7.14-7.04 (m, 1H), 6.12-6.04 (m, 1H), 5.91-5.85 (m, 1H), 5.58-5.48 (m, 1H), 5.01-4.91 (m, 2H), 4.34-4.19 (m, 2H), 4.18-4.05 (m, 4H), 3.79-3.58 (m, 4H), 3.25-3.12 (m, 1H), 2.84-2.70 (m, 1H), 1.82-1.68 (m, 1H), 1.47-1.32 (m, 3H). | 537<br>539 | 1.11<br>1.12 |
| 1-2-40 | 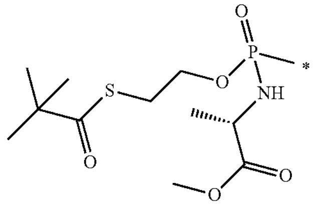 | Cl | Methyl ((((1S,4R)-4-(2-amino-6-chloro-9 H-purin-9-yl) cyclopent-2-en-1-yl) methoxy)(2-(pivaloylthio)ethoxy) phosphoryl)-L-alaninate | $^1$H-NMR ($CDCl_3$) δ: 7.84-7.80 (m, 1H), 6.20-6.13 (m, 1H), 5.91-5.85 (m, 1H), 5.60-5.50 (m, 1H), 5.38-5.30 (m, 2H), 4.28-3.88 (m, 5H), 3.79-3.71 (m, 3H), 3.51-3.33 (m, 1H), 3.26-3.09 (m, 3H), 2.89-2.72 (m, 1H), 1.95-1.79 (m, 1H), 1.47-1.37 (m, 3H), 1.32-1.20 (m, 9H). | 575<br>577 | 1.30 |
| 1-2-41 | 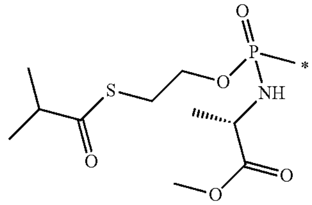 | Cl | Methyl ((((1S,4R)-4-(2-amino-6-chloro-9 H-purin-9-yl) cyclopent-2-en-1-yl) methoxy)(2-(isobutyrylthio) ethoxy) phosphoryl)-L-alaninate | $^1$H-NMR ($CDCl_3$) δ: 7.84-7.80 (m, 1H), 6.20-6.13 (m, 1H), 5.92-5.84 (m, 1H), 5.60-5.51 (m, 1H), 5.37-5.27 (m, 2H), 4.30-3.88 (m, 5H), 3.81-3.72 (m, 3H), 3.48-3.32 (m, 1H), 3.26-3.07 (m, 3H), 2.89-2.67 (m, 2H), 1.95-1.78 (m, 1H), 1.49-1.36 (m, 3H), 1.32-1.14 (m, 6H). | 561<br>563 | 1.22 |

TABLE 4-5-continued

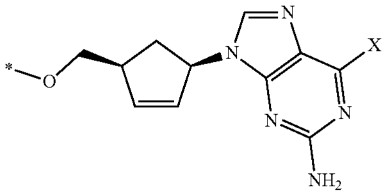

| Example No. | R | X | Compound name | $^1$H-NMR | MS (ESI m/z) (M + H) | RT (min) |
|---|---|---|---|---|---|---|
| 1-2-42 | 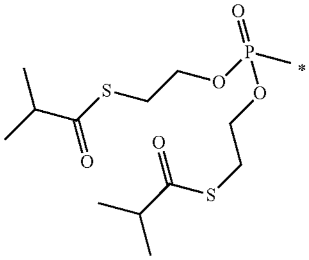 | Cl | ((1S,4R)-4-(2-amino-6-chloro-9H-purin-9-yl) cyclopent-2-en-1-yl) methylbis(S-isobutyroyl-2-mercaptoethan-1-yl)phosphate | $^1$H-NMR ($CDCl_3$) δ: 7.80 (s, 1H), 6.20-6.14 (m, 1H), 5.93-5.87 (m, 1H), 5.60-5.51 (m, 1H), 5.32 (br s, 2H), 4.34-4.18 (m, 2H), 4.16-4.08 (m, 4H), 3.28-3.19 (m, 1H), 3.16 (t, 4H, J = 6.6 Hz), 2.90-2.67 (m, 3H), 1.90 (ddd, 1H, J = 13.9, 5.9, 5.9 Hz), 1.18 (d, 12H, J = 6.6 Hz). | 606 608 | 1.53 |
| 1-2-43 | 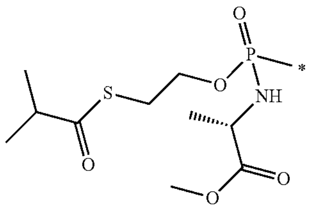 | OMe | Methyl ((((1S,4R)-4-(2-amino-6-methoxy-9H-purin-9-yl) cyclopent-2-en-1-yl) methoxy)(2-(isobutyrylthio) ethoxy) phosphoryl)-L-alaninate | $^1$H-NMR ($CDCl_3$) δ: 7.66-7.63 (m, 1H), 6.16-6.09 (m, 1H), 5.93-5.87 (m, 1H), 5.60-5.51 (m, 1H), 4.97 (br s, 2H), 4.22-3.88 (m, 8H), 3.82-3.70 (m, 3H), 3.47-3.30 (m, 1H), 3.24-3.08 (m, 3H), 2.89-2.68 (m, 2H), 1.88-1.73 (m, 1H), 1.50-1.35 (m, 3H), 1.35-1.15 (m, 6H). | 557 | 1.15 |
| 1-2-44 | 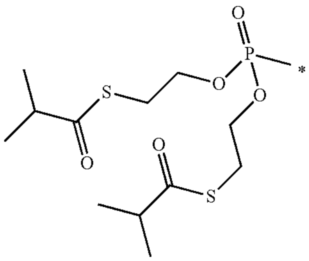 | OMe | ((1S,4R)-4-(2-amino-6-methoxy-9 H-purin-9-yl) cyclopent-2-en-1-yl) methylbis(S-isobutyroyl-2-mercaptoethan-1-yl)phosphate | $^1$H-NMR ($CDCl_3$) δ: 7.63 (s, 1H), 6.17-6.11 (m, 1H), 5.94-5.90 (m, 1H), 5.60-5.50 (m, 1H), 4.99 (br s, 2H), 4.26-4.04 (m, 9H), 3.25-3.11 (m, 5H), 2.89-2.68 (m, 3H), 1.85-1.74 (m, 1H), 1.19 (d, 12H, J = 7.3 Hz). | 602 | 1.46 |
| 1-2-45 | 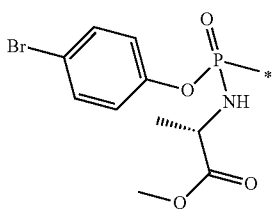 | $NMe_2$ | Methyl ((((1S,4R)-4-(2-amino-6-(dimethyl amino)-9H-purin-9-yl)cyclopent-2-en-1-yl)methoxy) (4-bromophenoxy) phosphoryl)-L-alaninate | $^1$H-NMR ($CD_3OD$) δ: 7.62-7.60 (m, 1H), 7.47-7.40 (m, 2H), 7.12-7.04 (m, 2H), 6.20-6.11 (m, 1H), 6.01-5.96 (m, 1H), 5.55-5.45 (m, 1H), 4.21-4.10 (m, 2H), 3.99-3.81 (m, 1H), 3.67-3.62 (m, 3H), 3.40 (s, 6H), 3.27-3.09 (m, 1H), 2.87-2.72 (m, 1H), 1.80-1.60 (m, 1H), 1.36-1.25 (m, 3H). | 594 596 | 1.08 |
| 1-2-46 | 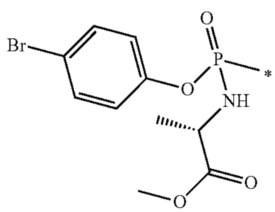 | NHMe | Methyl ((((1S,4R)-4-(2-amino-6-(methylamino)-9H-purin-9-yl) cyclopent-2-en-1-yl)methoxy)(4-bromophenoxy) phosphoryl)-L-alaninate | $^1$H-NMR ($CD_3OD$) δ: 7.66-7.63 (m, 1H), 7.49-7.40 (m, 2H), 7.12-7.06 (m, 2H), 6.19-6.11 (m, 1H), 6.01-5.95 (m, 1H), 5.55-5.45 (m, 1H), 4.24-4.10 (m, 2H), 3.99-3.82 (m, 1H), 3.65 (s, 3H), 3.27-3.11 (m, 1H), 3.04 (s, 3H), 2.87-2.72 (m, 1H), 1.81-1.61 (m, 1H), 1.37-1.25 (m, 3H). | 580 582 | 1.03 |

TABLE 4-6

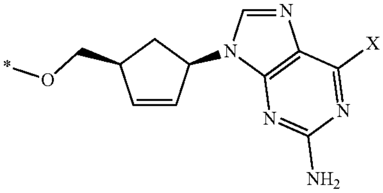

| Example No. | R | X | Compound name | 1H-NMR | MS (ESI m/z) (M + H) | RT (min) |
|---|---|---|---|---|---|---|
| 1-2-47 | 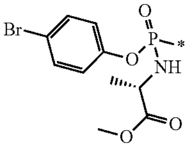 [SMILES: *P(=O)(N[C@@H](C)C(=O)OC)Oc1ccc(Br)cc1] | SH | Methyl ((((1S,4R)-4-(2-amino-6-mercapto-9H-purin-9-yl)cyclopent-2-en-1-yl) methoxy)(4-bromophenoxy) phosphoryl)-L-alaninate | $^1$H-NMR ($CD_3OD$) δ: 7.82-7.75 (m, 1H), 7.50-7.42 (m, 2H), 7.15-7.06 (m, 2H), 6.18-6.10 (m, 1H), 5.98-5.92 (m, 1H), 5.57-5.43 (m, 1H), 4.26-4.12 (m, 2H), 3.97-3.85 (m, 1H), 3.67-3.64 (m, 3H), 3.27-3.10 (m, 1H), 2.83-2.68 (m, 1H), 1.84-1.63 (m, 1H), 1.38-1.27 (m, 3H). | 583 585 | 1.11 |
| 1-2-48 | 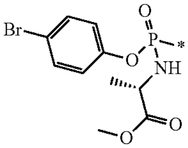 [SMILES: *P(=O)(N[C@@H](C)C(=O)OC)Oc1ccc(Br)cc1] | OEt | Methyl ((((1S,4R)-4-(2-amino-6-ethoxy-9H-purin-9-yl)cyclopent-2-en-1-yl) methoxy)(4-bromophenoxy) phosphoryl)-L-alaninate | $^1$H-NMR ($CD_3OD$) δ: 7.79-7.74 (m, 1H), 7.49-7.39 (m, 2H), 7.14-7.04 (m, 2H), 6.19-6.11 (m, 1H), 6.01-5.95 (m, 1H), 5.61-5.50 (m, 1H), 4.53 (q, 2H, J = 7.0 Hz), 4.24-4.12 (m, 2H), 3.96-3.85 (m, 1H), 3.66-3.53 (m, 3H), 3.27-3.11 (m, 1H), 2.87-2.72 (m, 1H), 1.84-1.65 (m, 1H), 1.43 (t, 3H, J = 7.0 Hz), 1.37-1.27 (m, 3H). | 595 597 | 1.24 |
| 1-2-49 | 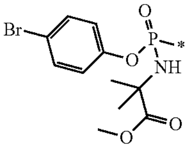 [SMILES: *P(=O)(NC(C)(C)C(=O)OC)Oc1ccc(Br)cc1] | OMe | Methyl 2-(((((1S,4R)-4-(2-amino-6-methoxy-9H-purin-9-yl)cyclopent-2-en-1-yl) methoxy)(4-bromophenoxy) phosphoryl)amino)-2-methylpropanoate | $^1$H-NMR ($CDCl_3$) δ: 7.64-7.58 (m, 1H), 7.44-7.37 (m, 2H), 7.16-7.05 (m, 2H), 6.10-6.05 (m, 1H), 5.92-5.85 (m, 1H), 5.57-5.48 (m, 1H), 5.02-4.91 (m, 2H), 4.31-4.15 (m, 2H), 4.07 (s, 3H), 3.93-3.86 (m, 1H), 3.73-3.70 (m, 3H), 3.24-3.08 (m, 1H), 2.84-2.70 (m, 1H), 1.80-1.74 (m, 1H), 1.56-1.46 (m, 6H). | 595 597 | 1.23 |
| 1-2-50 | 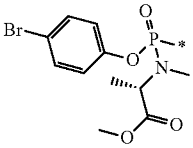 [SMILES: *P(=O)(Oc1ccc(Br)cc1)N(C)[C@@H](C)C(=O)OC] | OMe | Methyl N-((((1S,4R)-4-(2-amino-6-methoxy-9 H-purin-9-yl)cyclopent-2-en-1-yl) methoxy)(4-bromophenoxy) phosphoryl)- N-methyl-L-alaninate | $^1$H-NMR ($CDCl_3$) δ: 7.69-7.62 (m, 1H), 7.48-7.39 (m, 2H), 7.19-7.09 (m, 2H), 6.16-6.06 (m, 1H), 5.95-5.86 (m, 1H), 5.63-5.51 (m, 1H), 5.04-4.86 (m, 2H), 4.58-4.36 (m, 1H), 4.33-4.04 (m, 5H), 3.70-3.60 (m, 3H), 3.27-3.11 (m, 1H), 2.90-2.75 (m, 1H), 2.71-2.54 (m, 3H), 1.84-1.70 (m, 1H), 1.42-1.22 (m, 3H). | 595 597 | 1.29 1.31 |
| 1-2-51 | 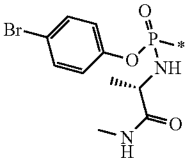 [SMILES: *P(=O)(N[C@@H](C)C(=O)NC)Oc1ccc(Br)cc1] | OMe | ((1S,4R)-4-(2-amino-6-methoxy-9H-purin-9-yl)cyclopent-2-en-1-yl)methyl) 4-bromophenyl)((S)-1-(methylamino)-1-oxopropan-2-yl)phosphoramidate | $^1$H-NMR ($CDCl_3$) δ: 7.67-7.64 (m, 1H), 7.46-7.37 (m, 2H), 7.15-7.00 (m, 2H), 6.61-6.40 (m, 1H), 6.14-6.05 (m, 1H), 5.97-5.88 (m, 1H), 5.59-5.49 (m, 1H), 5.05-4.93 (m, 2H), 4.32-4.12 (m, 2H), 4.09-4.04 (m, 3H), 3.89-3.45 (m, 2H), 3.23-3.10 (m, 1H), 2.89-2.69 (m, 4H), 1.82-1.68 (m, 1H), 1.36-1.16 (m, 3H). | 580 582 | 0.98 1.00 |
| 1-2-52 | 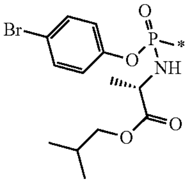 [SMILES: *P(=O)(N[C@@H](C)C(=O)OCC(C)C)Oc1ccc(Br)cc1] | Cl | Isobutyl ((((1S,4R)-4-(2-amino-6-chloro-9H-purin-9-yl)cyclopent-2-en-1-yl) methoxy)(4-(bromophenoxy) phosphoryl)-L-alaninate | $^1$H-NMR ($CDCl_3$) δ: 7.79 (s, 1H), 7.44-7.38 (m, 2H), 7.14-7.07 (m, 2H), 6.16-6.07 (m, 1H), 5.90-5.85 (m, 1H), 5.58-5.49 (m, 1H), 5.32-5.23 (m, 2H), 4.37-4.16 (m, 2H), 4.07-3.94 (m, 1H), 3.94-3.81 (m, 2H), 3.66-3.48 (m, 1H), 3.26-3.15 (m, 1H), 2.86-2.70 (m, 1H), 1.97-1.74 (m, 2H), 1.44-1.32 (m, 3H), 0.95-0.87 (m, 6H). | 627 629 | 1.52 |
| 1-2-53 | 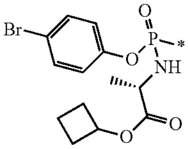 [SMILES: *P(=O)(N[C@@H](C)C(=O)OC1CCC1)Oc1ccc(Br)cc1] | Cl | Cyclobutyl ((((1S,4R)-4-(2-amino-6-chloro-9H-purin-9-yl)cyclopent-2-en-1-yl) methoxy)(4-bromophenoxy) phosphoryl)-L-alaninate | $^1$H-NMR ($CDCl_3$) δ: 7.79 (s, 1H), 7.44-7.39 (m, 2H), 7.14-7.06 (m, 2H), 6.16-6.06 (m, 1H), 5.91-5.85 (m, 1H), 5.59-5.49 (m, 1H), 5.33-5.23 (m, 2H), 5.02-4.90 (m, 1H), 4.30-4.24 (m, 2H), 4.00-3.89 (m, 1H), 3.59-3.46 (m, 1H), 3.27-3.15 (m, 1H), 2.85-2.72 (m, 1H), 2.40-2.25 (m, 2H), 2.09-1.95 (m, 2H), 1.91-1.74 (m, 3H), 1.40-1.32 (m, 3H). | 625 627 | 1.46 |

TABLE 4-6-continued

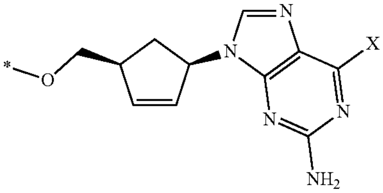

| Example No. | R | X | Compound name | 1H-NMR | MS (ESI m/z) (M + H) | RT (min) |
|---|---|---|---|---|---|---|
| 1-2-54 | 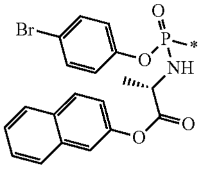 [SMILES: *P(=O)(N[C@@H](C)C(=O)Oc1ccc2ccccc2c1)Oc1ccc(Br)cc1] | Cl | Naphthalen-2-yl ((((1S,4R)-4-(2-amino-6-chloro-9H-purin-9-yl)cyclopent-2-en-1-yl)methoxy)(4-bromophenoxy) phosphoryl)-L-alaninate | $^1$H-NMR ($CDCl_3$) δ: 7.88-7.76 (m, 4H), 7.52-7.41 (m, 5H), 7.20-7.09 (m, 3H), 6.16-6.07 (m, 1H), 5.90-5.83 (m, 1H), 5.57-5.45 (m, 1H), 5.32-5.22 (m, 2H), 4.43-4.23 (m, 3H), 3.81-3.57 (m, 1H), 3.28-3.16 (m, 1H), 2.84-2.71 (m, 1H), 1.92-1.78 (m, 1H), 1.64-1.53 (m, 3H). | 697 699 | 1.61 |

TABLE 4-7

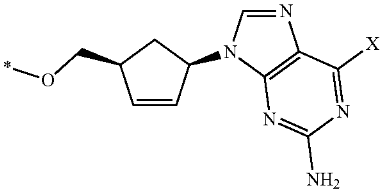

| Example No. | R | X | Compound name | 1H—NMR | MS (ESI m/z) (M + H) | RT (min) |
|---|---|---|---|---|---|---|
| 1-2-55 | 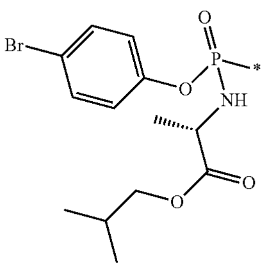 [SMILES: *P(=O)(N[C@@H](C)C(=O)OCC(C)C)Oc1ccc(Br)cc1] | OMe | Isobutyl ((((1S,4R)-4-(2-amino-6-methoxy-9H-purin-9-yl)cyclopent-2-en-1-yl) methoxy)(4-bromophenoxy) phosphoryl)-L-alaninate | $^1$H—NMR ($CDCl_3$) δ: 7.63-7.60 (m, 1 H), 7.44-7.37 (m, 2H), 7.15-7.06 (m, 2H), 6.12-6.05 (m, 1H), 5.92-5.85 (m, 1H), 5.59-5.49 (m, 1H), 5.01-4.93 (m, 2H), 4.28-4.15 (m, 2H), 4.07 (s, 3H), 4.06-3.94 (m, 1H), 393-3.80 (m, 2H), 3.71-3.51 (m, 1H), 3.25-371 (m, 1H), 2.86-2.71 (m, 1H), 1.97-1.84 (m, 1H), 1.82-1.72 (m, 1H), 1.43-1.32 (m, 3H), 0.93-0.88 (6H, m). | 623 625 | 1.44 |
| 1-2-56 | 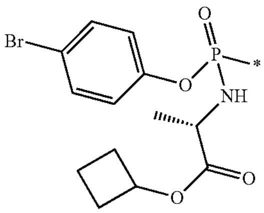 [SMILES: *P(=O)(N[C@@H](C)C(=O)OC1CCC1)Oc1ccc(Br)cc1] | OMe | Cyclobutyl ((((1S,4R)-4-(2-amino-6-methoxy-9H-purin-9-yl) cyclopent-2-en-1-yl) methoxy)(4-bromophenoxy) phosphoryl)-L-alaninate | $^1$H—NMR ($CDCl_3$) δ: 7.64-7.60 (m, 1H), 7.45-7.37 (m, 2H), 7.14-7.06 (m. 2H), 6.12-6.04 (m, 1H), 5.93-5.87 (m, 1H), 5.59-5.48 (m, 1H), 5.02-491 (m, 3H), 4.30-4.15 (m, 2H), 4.07 (s, 3H), 4.00-3.89 (m, 1H), 3.66-3.46 (m, 1H) 3.25-3.10 (m, 1H). 2.86-2.70 (m, 1H), 2.39-2.26 (m, 2H), 2.10-1.94 (m, 2H), 1.86-1.54 (m, 3H), 1.41-1.32 (m, 3H). | 621 623 | 1.38 |
| 1-2-57 | 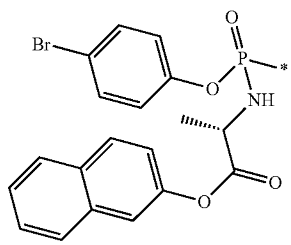 [SMILES: *P(=O)(N[C@@H](C)C(=O)Oc1ccc2ccccc2c1)Oc1ccc(Br)cc1] | OMe | Naphthalen-2-yl((((1S,4R)-4-(2-amino-6-methoxy-9H-purin-9-yl) cyclopent-2-en-1-yl) methoxy(4-bromophenoxy) phosphoryl)-L-alaninate | $^1$H—NMR ($CDCl_3$) δ: 7.88-7.76 (m, 3H), 7.65-7.62 (m, 1H), 7.54-7.37 (m, 5H), 7 21-7.08 (m, 3H), 6.13-6.07 (m, 1H), 5.93-5.87 (m, 1H), 5.57-5.48 (m, 1H), 5.00-4.92 (m, 2H), 4.35-4.24 (m, 3H), 4.05 (s, 3H), 3.82-3.56 (m, 1H), 3.26-3.13 (m, 1H), 2.86-2.71 (m, 1H), 1.86-1.75 (m, 1H), 1.29-1.22 (m, 3H). | 693 695 | 1.54 |

TABLE 4-7-continued

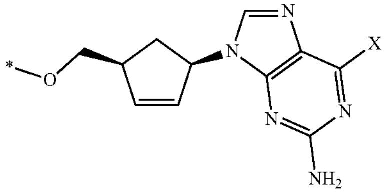

| Example No. | R | X | Compound name | 1H—NMR | MS (ESI m/z) (M + H) | RT (min) |
|---|---|---|---|---|---|---|
| 1-2-58 | 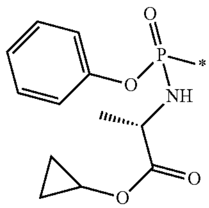 [SMILES: *P(=O)(N[C@@H](C)C(=O)OC1CC1)Oc1ccccc1] | OMe | Cyclopropyl ((((1S,4R)-4-(2-amino-6-methoxy-9H-purin-9-yl) cyclopent-2-en-1-yl) methoxy) (phenoxy) phosphoryl)-L-alaninate | $^1$H—NMR ($CD_3OD$) δ: 7.78-7.75 (m, 1H), 7.37-7.10 (m, 5H), 6.20-6.10 (m, 1H), 6.02-5.92 (m, 1H), 5.63-5.51 (m, 1H), 4.25-4.01 (m, 6H), 3.91-3.80 (m, 1H), 3.27-3.11 (m, 1H), 2.87-2.71 (m, 1H), 1.84-1.64 (m, 1H), 1 33-1.22 (m, 3H), 0.72-0.56 (m, 4H). | 529 | 1.13 1.14 |
| 1-2-59 | 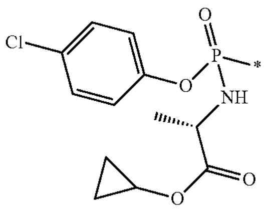 [SMILES: *P(=O)(N[C@@H](C)C(=O)OC1CC1)Oc1ccc(Cl)cc1] | OMe | Cyclopropyl ((((1S,4R)-4-(2-amino-6-methoxy-9H-purin-9-yl) cyclopent-2-en-1-yl) methoxy)(4-chlorophenoxy) phosphoryl)-L-alaninate | $^1$H—NMR ($CD_3OD$) δ: 7.79-7.77 (m, 1H), 7.34-7 26 (m, 2H), 7.19-7.11 (m. 2H), 6.19-6.12 (m, 1H), 6.02-5.94 (m, 1H), 5.63-5.51 (m, 1 H), 4.24-4.13 (m, 2H), 4.12-4.01 (m, 4H), 3.92-3 77 (m, 1 H), 328-3 12 (m, 1H), 2 86-2.73 (m, 1H), 1.84-1.67 (m, 1H), 1.34-1.22 (m, 3H), 0.73-0.56 (m, 4H). | 563 535 | 1.26 |
| 1-2-60 | 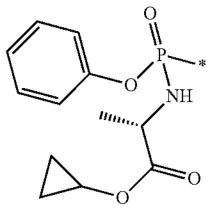 | Cl | Cyclopropyl ((((1S,4R)4-(2-amino-6-chloro-9H-purin-9-yl) cyclopent-2-en-1-yl)methoxy) (phenoxy) phosphoryl)-L-alaninate | $^1$H—NMR ($CD_3OD$) δ: 8 02-7.98 (m, 1H), 7.36-7.10 (m, 5H), 6.22-6.12 (m, 1H), 6.03-5.92 (m, 1H), 5.66-5.55 (m, 1H), 4.31-4.02 (m, 3H), 3.93-3.79 (m, 1H), 3.28-3.15 (m, 1H), 2.88-2.72 (m, 1H), 1.92-1.72 (m, 1H), 1 32-1.23 (m, 3H), 0.72-0.56 (m, 4H). | 533 535 | 1.21 |
| 1-2-61 | 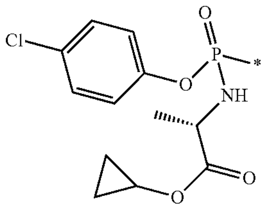 [SMILES: *P(=O)(N[C@@H](C)C(=O)OC1CC1)Oc1ccc(Cl)cc1] | Cl | Cyclopropyl ((((1S,4R)-4-(2-amino-6-chloro-9H-purin-9-yl)cyclopent-2-en-1-yl) methoxy)(4-chlorophenoxy) phosphoryl)-L-alaninate | $^1$H—NMR ($CD_3OD$) δ: 8.03-8.00 (m, 1H), 7.35-7.27 (m, 2H), 7.20-7.12 (m, 2H), 6 22-6.12 (m, 1H), 6.02-5.96 (m, 1H), 5 67-5.55 (m, 1H), 4.28-4.02 (m, 3H), 3.93-3.78 (m, 1H), 3.28-3 14 (m, 1H) 2.89-2.72 (m, 1H), 1.94-1.72 (m, 1H), 1.34-1.20 (m, 3H), 0.74-0.55 (m, 4H). | 567 569 | 1.33 |
| 1-2-62 | 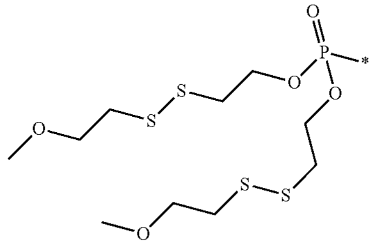 [SMILES: *P(=O)(OCCSSCCOC)OCCSSCCOC] | Cl | ((1S,4R)-4-(2-amino-6-chloro-9H-purin-9-yl) cyclopent-2-en-1-yl) methylbis (2-((2-methoxyethyl) disulfanyl)ethyl) phosphate | $^1$H—NMR ($CDCl_3$) δ: 7.80 (s, 1 H), 6.22-6.14 (m, 1H), 5.95-5.87 (m, 1H), 5.61-5.50 (m, 1H), 5.34 (br s, 2H), 4.47-4.19 (m, 6H), 3.63 (t, 4H, J = 6.3 Hz), 3.37 (s, 6H), 3.32-3.15 (m, 1H), 3.10-2.76 (m, 9H), 1.97-1.85 (m, 1H). | 646 635 | 1.33 |

TABLE 4-8

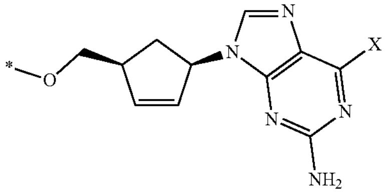

| Example No. | R | X | Compound name | 1H—NMR | MS (ESI m/z) (M + H) | RT (min) |
|---|---|---|---|---|---|---|
| 1-2-63 | 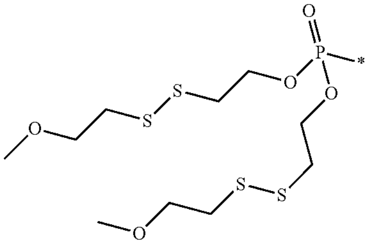 [SMILES: *P(=O)(OCCSSCCOC)OCCSSCCOC] | OMe | ((1S,4R)-4-(2-amino-6-methoxy-9H-purin-9-yl) cyclopent-2-en-1-yl) methylbis(2-((2-methoxyethyl) disulfanyl) ethyl) phosphate | $^1$H—NMR ($CDCl_3$) δ: 7.63 (s, 1H), 6.18-6.12 (m, 1H), 5.96-5.89 (m, 1H), 5.62-5.51 (m, 1H), 497 (br s, 2H), 4.40-4.14 (m, 6H), 4.07 (s, 3h), 3.63 (t, 4H, J = 6.3 Hz), 3.37 (s, 6H), 3.28-3.14 (m, 1H), 3.04-2.76 (m, 9H), 1.88-1.76 (m, 1H). | 642 | 1.26 |
| 1-2-64 | 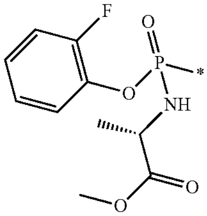 [SMILES: *P(=O)(N[C@@H](C)C(=O)OC)Oc1ccccc1F] | Cl | Methyl ((((1S,4R)-4-(2-amino-6-chloro-9H-purin-9-yl) cyclopent-2-en-1-yl) methoxy)(2-fluorophenoxy) phosphoryl)-L-alaninate | $^1$H—NMR ($CDCl_3$) δ: 7.81-7.76 (m, 1H), 7.45-7.33 (m, 1H), 7 16-7.01 (m, 3H), 6.17-6.07 (m. 1H), 5.96-5.84 (m, 1H), 5.61-5.49 (m, 1H), 5.36-5.08 (m, 2H), 4.40-4.18 (m. 2H). 4.15-3 97 (m, 1H), 389-353 (m. 4H). 328-313 (m, 1H), 2.91-2.72 (m, 1H), 1.91-1.59 (m, 1H), 1.45-1 33 (m. 3H). | 525<br>527 | 1.12 |
| 1-2-65 | 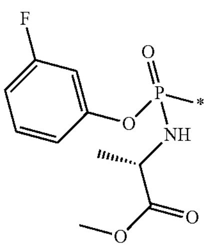 | Cl | Methyl ((((1S,4R)-4-(2-amino-6-chloro-9H-purin-9-yl) cyclopent-2-en-l-yl) methoxy)(3-fluorophenoxy) phosphoryl)-L-alaninate | $^1$H—NMR ($CDCl_3$) δ: 7.79-7 76 (m, 1 H), 7.33-7.20 (m, 1H), 7.06-6.81 (m, 3H), 6.17-6.08 (m, 1H), 5.96-5.86 (m, 1H), 5.60-5.49 (m, 1H), 5.37-5.11 (m, 2H), 4.39-4.17 (m, 2H), 4.10-3.94 (m, 1H), 3.87-3.52 (m, 4H), 3.30-3.11 (m, 1H), 2.92-2.72 (m, 1H), 1.91-1.61 (m, 1 H), 1.45-1.33 (m, 3H). | 525<br>527 | 1.14 |
| 1-2-66 | 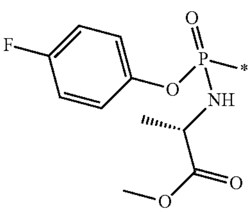 [SMILES: *P(=O)(N[C@@H](C)C(=O)OC)Oc1ccc(F)cc1] | Cl | Methyl ((((1S,4R)-4-(2-amino-6-chloro-9H-purin-9-yl) cyclopent-2-en-1-yl) methoxy)(4-fluorophenoxy) phosphoryl)-L-alaninate | $^1$H—NMR ($CDCl_3$) δ: 7.81-7.76 (m, 1H), 7.22-7.10 (m, 2H), 7.05-6.94 (m, 2H), 6.16-6.07 (m, 1H) 5.97-5.85 (m, 1H), 5.59-5.49 (m, 1H), 5.35-5.09 (m, 2H), 4.38-4.14 (m, 2H). 4.03-3.94 (m, 1H), 3.85-3.68 (m, 3H), 3.64-3.44 (m, 1H), 3.27-3.13 (m, 1H), 2.89-2 68 (m, 1H), 1.90-1.57 (m, 1H), 1.44-1.31 (m, 3H) | 525<br>527 | 1.13 |
| 1-2-67 | 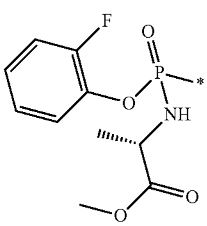 [SMILES: *P(=O)(N[C@@H](C)C(=O)OC)Oc1ccccc1F] | OMe | Methyl((((1S, 4RM-(2-amino-6-methoxy-9H-purin-9-yl) cyclopent-2-en-1-yl) methoxy)(2-fluorophenoxy) phosphoryl)-L-alaninate | $^1$H—NMR ($CDCl_3$) δ: 7.64-7.58 (m, 1H), 7.44-7.32 (m, 1H), 7.17-7.02 (m, 3H), 6.13-6.05 (m, 1H), 5.97-5.85 (m, 1H), 5.60-5.49 (m, 1H), 5.05-4.82 (m, 2H), 4.32-417 (m, 2H), 4.10-4.00 (m, 4H), 3.88-3.46 (m, 4H), 3.26-3.10 (m, 1H), 2.89-2.71 (m, 1H), 1.82-1.66 (m, 1H), 1.49-1.33 (m, 3H) | 521 | 1.04 |

TABLE 4-8-continued

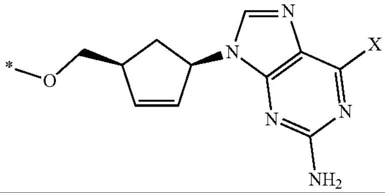

| Example No. | R | X | Compound name | 1H—NMR | MS (ESI m/z) (M + H) | RT (min) |
|---|---|---|---|---|---|---|
| 1-2-68 | 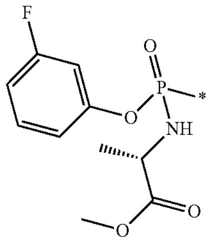 [SMILES: *P(=O)(N[C@@H](C)C(=O)OC)Oc1cccc(F)c1] | OMe | Methyl ((((1S,4R)-4-(2-amino-6-methoxy-9H-purin-9-yl) cyclopent-2-en-1-yl) methoxy)(3-fluorophenoxy) phosphoryl)-L-alaninate | [1]H—NMR ($CDCl_3$) δ: 7.64-7.57 (m, 1H), 7.31-7.21 (m, 1H), 7 06-6.82 (m, 3H), 6.14-6.04 (m, 1H). 5.97-5.87 (m, 1H), 5.60-5.50 (m, 1H), 5.01-484 (m, 2H), 4.36-3.94 (m, 6H), 3.36-3.51 (m, 4H), 3.28-3.09 (m, 1H), 2 89-2.72 (m, 1H), 1.83-1.70 (m, 1H), 1.43-1.32 (m, 3H) | 521 | 1.07 |
| 1-2-69 | 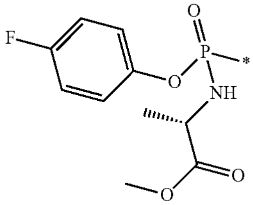 [SMILES: *P(=O)(N[C@@H](C)C(=O)OC)Oc1ccc(F)cc1] | OMe | Methyl ((((1S,4R)-4-(2-amino-6-methoxy-9H-purin-9-yl) cyclopent-2-en-1-yl) methoxy)(4-fluorophenoxy) phosphoryl)-L-alaninate | [1]H—NMR ($CDCl_3$) δ: 7.65-7.59 (m, 1H), 7.22-7.10 (m, 2H), 7.04-6.93 (m, 2H), 6.12-6.04 (m, 1H), 5 98-5.86 (m, 1H), 5.60-5.49 (m, 1H), 5.04-4.85 (m, 2H), 4.33-3.93 (m, 6H), 3.85-3.45 (m, 4H), 3.24-3.09 (m, 1H), 2 90-2 71 (m, 1H), 1.82-1.58 (m, 1H), 1.44-1.30 (m, 3H). | 521 | 1.06 |
| 1-2-70 | 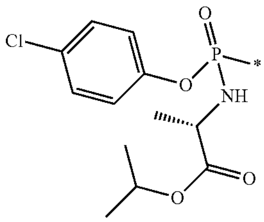 [SMILES: *P(=O)(N[C@@H](C)C(=O)OC(C)C)Oc1ccc(Cl)cc1] | Cl | Isopropyl ((((1S,4R)-4-(2-amino-6-chloro-9H-purin-9-yl)cyclopent-2-en-1-yl) methoxy)(4-chlorophenoxy) phosphoryl)-L-alaninate | [1]H—NMR ($CDCl_3$) δ: 7.80-7.75 (m, 1H), 7.30-7.23 (m, 2H), 7.20-7.11 (m, 2H), 6.18-6.07 (m, 1H), 5.93-5.83 (m, 1H), 5.63-5.47 (m, 1H), 5.37-5.21 (m, 2H), 5.05-492 (m, 1H), 4.40-4 15 (m, 2H), 4.03-3.87 (m, 1H), 3.68-3.48 (m, 1H), 3.28-3.13 (m, 1H), 2.92-2.71 (m, 1H), 1.90-1.77 (m, 1H), 1.40-1.30 (m, 3H), 1.25-1.18 (m, 6H). | 569<br>571 | 1.40 |

TABLE 4-9

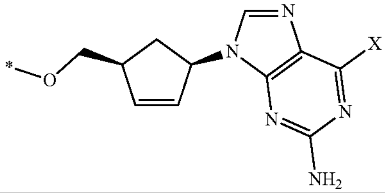

| Example No. | R | X | Compound name | 1H—NMR | MS (ESI m/z) (M + H) | RT (min) |
|---|---|---|---|---|---|---|
| 1-2-71 | 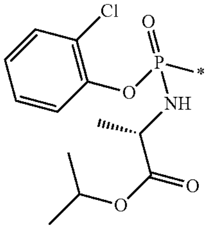 [SMILES: *P(=O)(N[C@@H](C)C(=O)OC(C)C)Oc1ccccc1Cl] | OMe | Isopropyl ((((1S,4R)-4-(2-amino-6-methoxy-9H-purin-9-yl) cyclopent-2-en-1-yl) methoxy)(2-chlorophenoxy) phosphoryl)-L-alaninate | [1]H—NMR ($CDCl_3$) δ: 7.63-7.55 (m, 1H), 7.52-7.46 (m, 1H) 7.42-7.35 (m, 1H), 7.25-7.15 (m, 1H) 7.13-7.03 (m, 1H), 6.12-6.04 (m, 1H), 5.90-5 84 (m, 1H), 5.58-5.49 (m, 1H), 5.07-4.89 (m, 3H), 4.34-4.17 (m, 2H), 4.10-3.97 (m, 4H), 3.77-3.65 (m, 1H), 3.25-3.11 (m, 1H), 2.83-2.70 (m, 1H), 1.80-1.67 (m, 1H), 1.43-1.32 (m, 3H), 1.27-1.18 (m, 6H). | 565<br>567 | 1.28<br>1.29 |

TABLE 4-9-continued

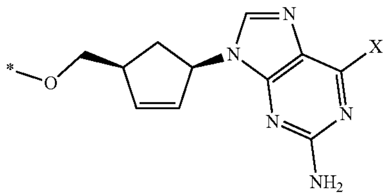

| Example No. | R | X | Compound name | 1H—NMR | MS (ESI m/z) (M + H) | RT (min) |
|---|---|---|---|---|---|---|
| 1-2-72 | 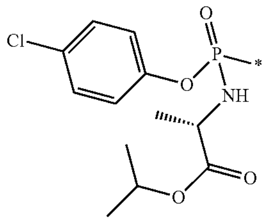 [SMILES: *P(=O)(N[C@@H](C)C(=O)OC(C)C)Oc1ccc(Cl)cc1] | OMe | Isopropyl ((((1S,4R)-4-(2-amino-6-methoxy-9H-purin-9-yl) cyclopent-2-en-1-yl) methoxy)(4-chlorophenoxy) phosphoryl)- L-alaninate | $^1$H—NMR ($CDCl_3$) δ: 7.64-7.58 (m, 1H), 7.30-7.08 (m, 4H), 6.12-6.04 (m, 1H), 5.93-5.85 (m, 1H), 5.59-5.49 (m, 1H), 5.06-4.87 (m, 3H), 4.32-4.12 (m, 2H), 4.07 (s, 3H), 4.01-3.87 (m, 1H), 3.72-3.52 (m, 1H), 3.25-3.10 (m, 1H), 2.86-2.71 (m, 1H), 1.82-1.69 (m, 1H), 1.40-1.31 (m, 3H), 1 25-1.18 (m, 6H). | 565 567 | 1.32 |
| 1-2-73 | 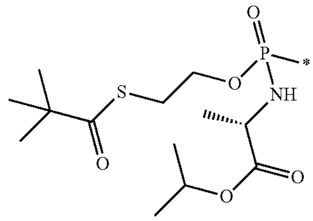 [SMILES: *P(=O)(N[C@@H](C)C(=O)OC(C)C)OCCSC(=O)C(C)(C)C] | Cl | Isopropyl ((((1S,4R)-4-(2-amino-6-chloro-9H-purin-9-yl) cyclopent-2-en-1-yl)methoxy) (2-(pivaloylthio) ethoxy) phosphoryl)- L-alaninate | $^1$H—NMR ($CDCl_3$) δ: 7.83-7.79 (m, 1H), 6.20-6.14 (m, 1H), 5.90-5.85 (m, 1H), 5.60-5.50 (m, 1H), 5.36 (br s, 2H), 5.09-4.94 (m, 1H), 4.29-3.82 (m, 5H), 3.51-3.35 (m, 1 H), 3.25-3.07 (m, 3H), 2.87-2.73 (m, 1H), 1.94-1.77 (m, 1 H), 1.42-1.36 (m, 3H), 1.28-1.19 (m, 15H). | 603 605 | 1.44 |
| 1-2-74 | 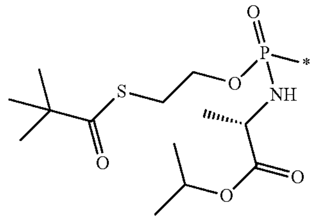 [SMILES: *P(=O)(N[C@@H](C)C(=O)OC(C)C)OCCSC(=O)C(C)(C)C] | OMe | Isopropyl ((((1S,4R)-4-(2-amino-6-methoxy-9H-purin-9-yl) cyclopent-2-en-1-yl)methoxy)(2-(pivaloylthio) ethoxy) phosphoryl)- L-alaninate | $^1$H—NMR ($CDCl_3$) δ: 7.68-7.63 (m, 1H), 6.17-6.08 (m, 1 H), 5.93-5.86 (m, 1 H), 5.61-5.50 (m, 1H), 5.09-4.93 (m, 3H), 4.21-3.81 (m, 8H), 3.50-3.35 (m, 1H), 3.26-3.08 (m, 3H), 2.88-2.73 (m, 1 H), 1.84-1.69 (m, 1H), 1.42-1.35 (m, 3H), 1.27-1.21 (m, 15H). | 599 | 1.37 |
| 1-2-75 | 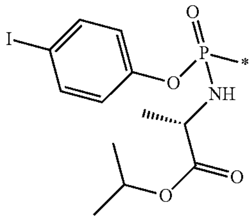 [SMILES: *P(=O)(N[C@@H](C)C(=O)OC(C)C)Oc1ccc(I)cc1] | Cl | Isopropyl ((((1S,4R)-4-(2-amino-6-chloro-9H-purin-9-yl) cyclopent-2-en-1-yl)methoxy)(4-iodophenoxy) phosphoryl)- L-alaninate | $^1$H—NMR ($CDCl_3$) δ: 7.80-7.76 (m, 1H), 7.66-7.54 (m, 2H), 7.03-6.94 (m, 2H), 6.16-6.07 (m, 1H). 5.90-5.85 (m, 1H), 5.59-5.48 (m, 1H), 5.39-5.28 (m, 2H), 5.09-4.90 (m, 1H) 4.39-4.13 (m, 2H), 4.02-3.85 (m, 1H), 3.71-3.53 (m, 1H), 3.28-3.13 (m, 1H) 2.85-2.71 (m, 1H) 1.89-1.75 (m, 1H), 1.40-1.31 (m, 3H), 1.28-1.18 (m, 6H). | 661 663 | 1.45 |

TABLE 4-9-continued

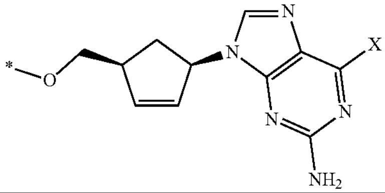

| Example No. | R | X | Compound name | 1H—NMR | MS (ESI m/z) (M + H) | RT (min) |
|---|---|---|---|---|---|---|
| 1-2-76 | 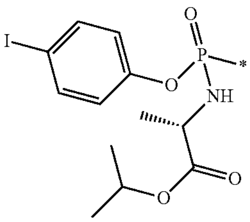 [SMILES: *P(=O)(N[C@@H](C)C(=O)OC(C)C)Oc1ccc(I)cc1] | OMe | Isopropyl ((((1S,4R)-4-(2-amino-6-methoxy-9H-purin-9-yl) cyclopent-2-en-1-yl)methoxy) (4-iodophenoxy) phosphoryl)-L-alaninate | $^{1}$H—NMR ($CDCl_3$) δ: 7.06-7.54 (m, 3H), 7.03-6.93 (m, 2H), 6.12-6.05 (m, 1H), 5.93-5.86 (m, 1H), 5.59-5.49 (m, 1H), 5.07-4.87 (m, 3H), 4.36-3.86 (m, 6H), 3.71-3.52 (m, 1H), 3.26-3.09 (m, 1H), 2 85-2.70 (m, 1H), 1.82-1.68 (m, 1H), 1.39-1.31 (m, 3H), 1.27-1.17 (m, 6H). | 657 | 1.37 |
| 1-2-77 | 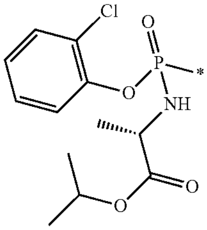 [SMILES: *P(=O)(N[C@@H](C)C(=O)OC(C)C)Oc1ccccc1Cl] | Cl | Isopropyl ((((1S,4R)-4-(2-amino-6-chloro-9H-purin-9-yl) cyclopent-2-en-1-yl) methoxy)(2-chlorophenoxy) phosphoryl)-L-alaninate | $^{1}$H—NMR ($CDCl_3$) δ: 7.80-7.75 (m, 1H), 7.51-7.34 (m, 2H), 7.25-7.04 (m, 2H), 6.15-6.05 (m, 1H), 5.89-5.83 (m, 1H), 5.58-5.47 (m, 1H), 5.42-5.23 (m, 2H), 5.07-4.93 (m, 1H), 4.42-3.97 (m, 3H), 3.79-3.65 (m, 1H), 3.29-3.10 (m, 1H), 2.84-2.69 (m, 1H), 1.89-1.75 (m, 1H), 1.43-1.31 (m, 3H), 1.25-1.19 (m, 6H). | 569<br>571 | 1.36<br>1.37 |

Example 2-1

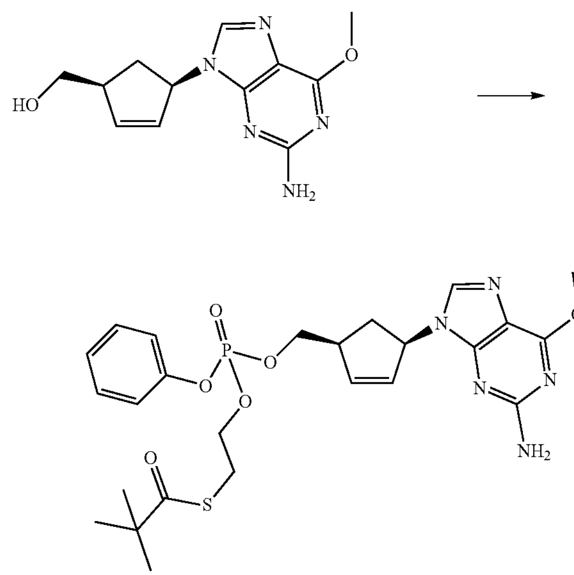

Under a nitrogen atmosphere, a 1.0 M tert-butyl magnesium chloride/tetrahydrofuran solution (0.25 mL) was added dropwise to a mixture of ((1S,4R)-4-(2-amino-6-methoxy-9H-purin-9-yl)cyclopent-2-en-1-yl)methanol (20 mg) and tetrahydrofuran (0.2 mL) which was then stirred at room temperature for 20 minutes. A mixture of S-(2-(((perfluorophenoxy)(phenoxy)phosphoryl)oxy)ethyl) 2,2-dimethylpropanethioate (30 mg) and tetrahydrofuran (0.15 mL) was added to the reaction solution which was then stirred at room temperature for 11 hours. An aqueous saturated ammonium chloride solution was added to the reaction solution, which was followed by extraction with ethyl acetate and washing with an aqueous saturated sodium chloride solution. The solvent was distilled off under reduced pressure, and the obtained residue was purified by silica gel column chromatography (hexane:ethyl acetate=50:50 to 0:100, methanol:ethyl acetate=0:100 to 5:95) to give S-(2-(((((1S,4R)-4-(2-amino-6-methoxy-9H-purin-9-yl)cyclopent-2-en-1-yl) methoxy)(phenoxy)phosphoryl)oxy)ethyl) 2,2-dimethylpropanethioate (3.9 mg) as a pale yellow solid.

$^{1}$H-NMR (MeOD) δ: 7.77-7.67 (m, 1H), 7.38-7.26 (m, 2H), 7.23-7.09 (m, 3H), 6.17-6.08 (m, 1H), 6.02-5.92 (m, 1H), 5.60-5.49 (m, 1H), 4.33-4.22 (m, 2H), 4.22-4.08 (m, 2H), 4.04 (s, 3H), 3.26-3.04 (m, 3H), 2.86-2.72 (m, 1H), 1.80-1.66 (m, 1H), 1.18 (s, 9H).

MS (ESI m/z): 562 (M+H)

RT (min): 1.44

Example 2-2

The compounds in Tables 5-1 to 5-6 were obtained in the same manner as in Example 2-1.

TABLE 5-11

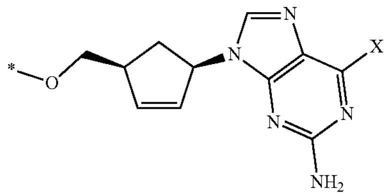

| Example No. | R | X | Compound name | $^1H$—NMR | MS (ESI m/z) (M + H) | RT (min) |
|---|---|---|---|---|---|---|
| 2-2-1 | 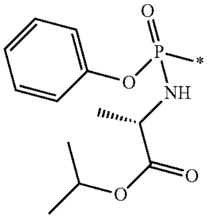 | Cl | Isopropyl ((((1S,4R)-4-(2-amino-6-chloro-9H-purin-9-yl) cyclopent-2-en-1-yl) methoxy) (phenoxy) phosphoryl)-L-alaninate | $^1H$—NMR ($CD_3OD$) δ: 8.01-7.98 (m, 1H), 7.35-7.27 (m, 2H), 7.20-7.11 (m, 3H), 6.20-6.12 (m, 1H), 6.00-5.96 (m, 1H), 5.65-5.55 (m, 1H), 4.95-4.85 (m, 1H), 4.25-4.14 (m, 2H), 3.92-3.79 (m, 1H), 3.26-3.12 (m, 1H), 2.85-2.73 (m, 1H), 1.87-1.72 (m, 1H), 1.33-1.26 (m, 3H), 1.21-1.17 (m, 6H). | 535<br>537 | 1.39<br>1.40 |
| 2-2-2 | 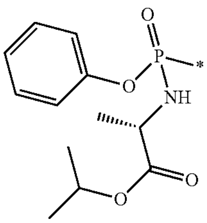 [SMILES: *P(=O)(N[C@@H](C)C(=O)OC(C)C)Oc1ccccc1] | NHcycloPr | Isopropyl ((((1S,4R)-4-(2-amino-6-(cyclopropyl-amino)-9H-purin-9-yl) cyclopent-2-en-1-yl)methoxy) (phenoxy) phosphoryl)-L-alaninate | $^1H$—NMR ($CD_3OD$) δ: 7.66-7.63 (m, 1H), 7.35-7.27 (m, 2H), 7.20-7.11 (m, 3H), 6.18-6.10 (m, 1H), 5.99-5.93 (m, 1H), 5.55-5.46 (m, 1H), 4.96-485 (m, 1H), 4.25-4.06 (m, 2H), 3.91-3.78 (m, 1H), 3.24-3.10 (m, 1H), 2.95-2.72 (m, 2H), 1.77-1.62 (m, 1H), 1.33-1.15 (m, 9H), 0.88-0.80 (m, 2H), 0.63-0.56 (m, 2H). | 556 | 1.22<br>1.23 |
| 2-2-3 | 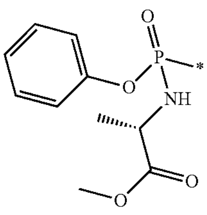 [SMILES: *P(=O)(N[C@@H](C)C(=O)OC)Oc1ccccc1] | NHcycloPr | Methyl ((((1S,4R)-4-(2-amino-6-(cyclopropyl-amino)-9H-purin-9-yl) cyclopent-2-en-1-yl)methoxy) (phenoxy) phosphoryl)-L-alaninate | $^1H$—NMR ($CD_3OD$) δ: 7.68-7.63 (m, 1H), 7.37-7.26 (m, 2H), 7.21-7.11 (m, 3H), 6.20-6.09 (m, 1H), 6.00-5.92 (m, 1H), 5.56-5.45 (m, 1H), 4.26-4.03 (m, 2H), 3.98-3.83 (m, 1H), 3.68-3.62 (m, 3H), 3.26-3.11 (m, 1H), 2.96-2.70 (m, 2H), 1.78-1.61 (m, 1 H), 1.37-1.19 (m, 3H), 0.90-0.79 (m, 2H), 0.65-0 55 (m. 2H). | 528 | 1.08 |
| 2-2-4 | 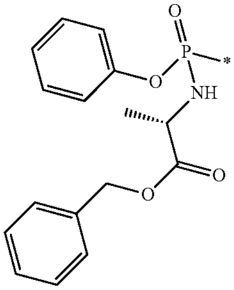 [SMILES: *P(=O)(N[C@@H](C)C(=O)OCc1ccccc1)Oc1ccccc1] | NHcycloPr | Benzyl ((((1S,4R)-4-(2-amino-6-(cyclopropyl-amino)-9H-purin-9-yl) cyclopent-2-en-1-yl)methoxy) (phenoxy) phosphoryl)-L-alaninate | $^1H$—NMR ($CD_3OD$) δ: 7.63-7.60 (m, 1H), 7.34-7.24 (m, 7H), 7.18-7.10 (m, 3H), 6.12-6.01 (m, 1H), 5.94-5.88 (m, 1H), 5.53-5.42 (m, 1H), 5.13-5.03 (m, 2H), 4.18-3.88 (m, 3H), 3.16-3.00 (m, 1H), 2.93-2.83 (m, 1H), 2.79-2.65 (m, 1H), 1.69-1.55 (m, 1H), 1.35-1.26 (m, 3H), 0.87-0.79 (m, 2H), 0.61-0.54 (m, 2H). | 604 | 1.33 |
| 2-2-5 | 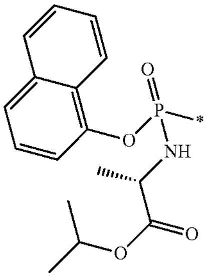 [SMILES: *P(=O)(N[C@@H](C)C(=O)OC(C)C)Oc1cccc2ccccc12] | NHcycloPr | Isopropyl ((((1S,4R)-4-(2-amino-6-(cyclopropyl-amino)-9H-purin-9-yl) cyclopent-2-en-1-yl)methoxy) (naphthalen-1-yloxy) phosphoryl)-L-alaninate | $^1H$—NMR ($CD_3OD$) δ: 8.14-8.06 (m, 1H), 7.89-7.82 (m, 1H), 7.71-7.62 (m, 1H), 7.61-7.57 (m, 1H), 7.55-7.45 (m, 2H), 7.44-7.32 (m, 2H), 6.11-6.06 (m, 1H), 5.96-5.88 (m, 1H), 5.52-5.42 (m, 1H), 4.94-4.83 (m, 1H), 4.25-4.14 (m, 2H), 3.99-3.87 (m, 1H), 3.20-3.09 (m, 1H), 2.95-2.84 (m, 1H), 2.79-2.63 (m, 1H), 1.70-1.54 (m, 1H), 1.32-1.25 (m, 3H), 1.19-1.12 (m, 6H), 0 88-0.79 (m. 2H), 0.62-0.54 (m. 2H). | 606 | 1.35<br>1.37 |

TABLE 5-11-continued

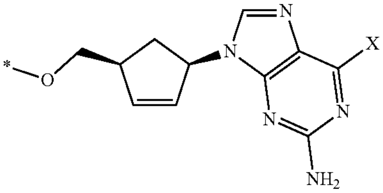

| Example No. | R | X | Compound name | $^1$H—NMR | MS (ESI m/z) (M + H) | RT (min) |
|---|---|---|---|---|---|---|
| 2-2-6 | 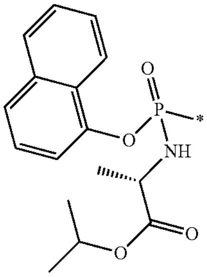 [SMILES: *P(=O)(N[C@@H](C)C(=O)OC(C)C)Oc1cccc2ccccc12] | Cl | Isopropyl ((((1S,4R)-4-amino-6-chloro-9H-purin-9-yl) cyclopent-2-en-1-yl)methoxy) (naphthalen-1-yloxy) phosphoryl)-L-alaninate | $^1$H—NMR ($CD_3OD$) δ: 8.15-8.07 (m, 1H), 7 97-7.93 (m, 1H), 7.90-7.80 (m, 1H), 7.70-7.62 (m, 1H), 7.55-7.32 (m, 4H), 6.12-6.06 (m, 1H), 5 97-5 89 (m, 1H), 5.61-5.50 (m, 1H). 4.94-4.83 (m, 1H), 4.29-4.16 (m, 2H), 4.01-3.88 (m, 1H) 3.22-3.09 (m, 1H), 2.77-2.61 (m, 1H), 1.76-1.62 (m, 1H), 1.35-1.26 (m, 3H), 1.20-1.11 (m, 6H). | 585<br>587 | 1.54<br>1.56 |
| 2-2-7 | 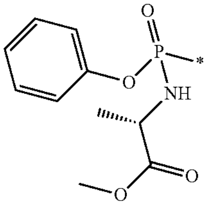 [SMILES: *P(=O)(N[C@@H](C)C(=O)OC)Oc1ccccc1] | Cl | Methyl ((((1S,4R)-4-(2-amino-6-chloro-9H-purin-9-yl) cyclopent-2-en-1-yl)methoxy) (phenoxy) phosphoryl)-<br><br>L-alaninate | $^1$H—NMR ($CD_3OD$) δ: 8.01-7 99 (m, 1H), 7.36-7.26 (m, 2H), 7.21-7.11 (m, 3H), 6.21-6.12 (m, 1H), 6.00-5.94 (m, 1H), 5.65-5.54 (m, 1H), 4.29-4.14 (m, 2H), 3.99-3.84 (m, 1H), 3.66-3.63 (m, 3H), 3.25-3.12 (m, 1H), 2.87-2,72 (m, 1H), 1.88-1.71 (m, 1H) 1.36-1.25 (m, 3H). | 507<br>509 | 1.24 |
| 2-2-8 | 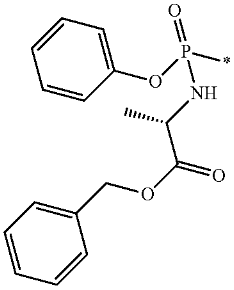 [SMILES: *P(=O)(N[C@@H](C)C(=O)OCc1ccccc1)Oc1ccccc1] | Cl | Benzyl ((((1S,4R)-4-(2-amino-6-chloro-9H-purin-9-yl) cyclopent-2-en-1-yl)methoxy) (phenoxy) phosphoryl)-L-alaninate | $^1$H—NMR ($CD_3OD$) δ: 7.97 (s, 1H), 7.37-7.23 (m, 7H), 7.21-7.09 (m, 3H), 6.14-6.03 (m, 1H), 5.97-5.88 (m, 1H), 5.62-5.51 (m, 1H), 5.14-5.07 (m, 2H), 4.22-3.90 (m, 3H), 3.19-3.02 (m, 1H), 2.79-2.64 (m, 1H), 1.78-1.63 (m, 1H), 1.38-1.25 (m, 3H). | 583<br>585 | 1.50 |
| 2-2-9 | 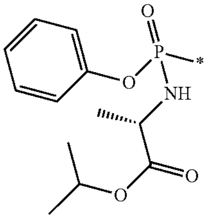 | OH | Isopropyl ((((1S,4R)-4-(2-amino-6-hydroxy-9H-purin-9-yl) cyclopent-2-en-1-yl)methoxy) (phenoxy) phosphoryl)-L-alaninate | $^1$H—NMR ($CD_3OD$) δ: 10.59 (s, 1 H), 7.56 (s, 1H), 7.39-7.30 (m, 2H), 7.21-7.08 (m, 3H), 6.45 (s, 2H), 6.11-5.88 (m, 3H), 5.42-5.32 (m, 1H), 4.90-475 (m, 1H), 4.13-4.04 (m, 2H), 3.82-3.66 (m, 1H), 3.17-3.03 (m, 1H), 2.74-2.57 (m, 1H), 1.69-1.53 (m, 1H), 1.23-1.08 (m, 9H). | 517 | 1.06<br>1.07 |

TABLE 5-2

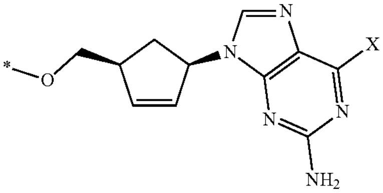

| Example No. | R | X | Compound name | $^1$H—NMR | MS (ESI m/z) (M +H) | RT (min) |
|---|---|---|---|---|---|---|
| 2-2-10 | 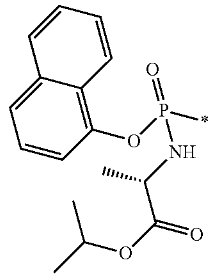 [SMILES: *P(=O)(N[C@@H](C)C(=O)OC(C)C)Oc1cccc2ccccc12] | OH | Isopropyl ((((1S,4R)-4-(2-amino-6-hydroxy-9H-purin-9-yl) cyclopent-2-en-1-yl)methoxy) (naphthalen-1-yloxy) phosphoryl)-L-alaninate | $^1$H—NMR (DWSO-$D_6$) δ: 10.62 (s, 1H), 8.15-8.07 (m, 1H), 8.00-7.90 (m, 1H), 7.78-7.68 (m, 1H), 7.62-7.52 (m, 3H), 7.50-7.39 (m, 2H), 6.46 (s, 2H), 6.21-6.09 (m, 1H), 6.06-6.01 (m, 1H), 5.95-5.89 (m, 1H), 5.41-5.31 (m, 1H), 4.89-4.76 (m, 1H), 4.20-4.00 (m, 2H), 3.94-3.78 (m, 1H), 3.17-2.99 (m, 1H). 2.68-2.53 (m, 1H), 1.66-1.53 (m, 1H), 1.29-1.05 (m, 9H). | 567 | 1.20 1.23 |
| 2-2-11 | 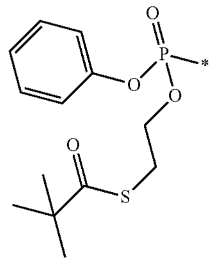 [SMILES: *P(=O)(OCCSC(=O)C(C)(C)C)Oc1ccccc1] | Cl | S-(2-(((((1S,4R)-4-(2-amino-6-chloro-9H-purin-9-yl) cyclopent-2-en-1-yl)methoxy) (phenoxy) phosphoryl) oxy)ethyl) 2,2-dimethyl-propanethioate | $^1$H—NMR ($CD_3OD$) δ: 8.00-7.90 (m, 1 H), 7.38-7.23 (m, 2H), 7.23-7.10 (m, 3H), 6.19-6.10 (m, 1H), 6.03-5.94 (m, 1H), 5.64-5.53 (m, 1H), 4.37-4.23 (m, 2H), 4.23-4.07 (m, 2H), 3.26-3.04 (m, 3H), 2.86-2.72 (m, 1H), 1.87-1.73 (m 1H), 1.17 (s, 9H). | 566 568 | 1.52 |
| 2-2-12 | 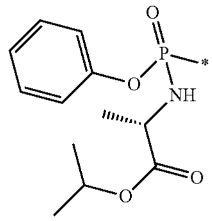 [SMILES: *P(=O)(N[C@@H](C)C(=O)OC(C)C)Oc1ccccc1] | OMe | Isopropyl ((((1S,4R)-4-(2-amino-6-methoxy-9H-purin-9-yl) cyclopent-2-en-1-yl)methoxy) (phenoxy) phosphoryl)-L-alaninate | $^1$H—NMR ($CD_3OD$) δ: 7.78-7.72 (m, 1H). 7.35-7.22 (m, 2H), 7.20-7.07 (m. 3H). 6.16-0.07 (m, 1H), 6.00-5.90 (m, 1H), 5.60-5.48 (m, 1H), 4.98-4.81 (m, 1H), 4.21-3.97 (m, 5H), 3.93-3.77 (m, 1H), 3.23-3.09 (m, 1H). 2.84-2.69 (m, 1H), 1.76-1.63 (m. 1H). 1.35-1.11 (m, 9H). | 531 | 1.21 |
| 2-2-13 | 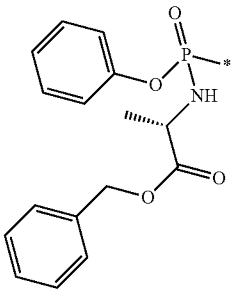 [SMILES: *P(=O)(N[C@@H](C)C(=O)OCc1ccccc1)Oc1ccccc1] | OMe | Benzyl ((((1S,4R)-4-(2-amino-6-methoxy-9H-purin-9-yl) cyclopent-2-en-1-yl)methoxy) (phenoxy) phosphoryl)-L-alaninate | $^1$H NMR ($CD_3OD$) δ: 7.75-7 69 (m, 1H), 7 34-7.22 (m, 7H), 7.19-7.08 (m, 3H), 6.12-5.99 (m, 1H), 5.94-5.86 (m, 1H), 5.57-5.46 (m, 1H), 5.08 (s, 2H), 4.19-3.88 (m, 6H), 3.17-2.99 (m, 1H), 2.79-2.62 (m, 1H), 1.73-1.55 (m, 1H), 1.37-1.24 (m, 3H). | 579 | 1.31 1.32 |
| 2-2-14 | 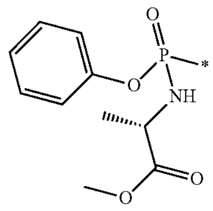 [SMILES: *P(=O)(N[C@@H](C)C(=O)OC)Oc1ccccc1] | OH | Methyl ((((1S,4R)-4-(2-amino-6-hydroxy-9H-purin-9-yl) cyclopent-2-en-1-yl)methoxy) (phenoxy) phosphoryl)-L-alaninate | $^1$H—NMR ($CD_3OD$) δ: 7 67-7 62 (m, 1H), 7.37-7.26 (m, 2H), 7.23-7.11 (m, 3H), 6.16-6.07 (m, 1H), 5.96-5.90 (m, 1H), 5.57-5.45 (m, 1H), 4.25-4.07 (m, 2H), 3.99-3.85 (m, 1H), 3.67-3.59 (m, 3H), 3.25-3.08 (m, 1H), 2.85-2.67 (m, 1H), 1.82-1.63 (m, 1H), 1.36-1.24 (m, 3H). | 489 | 0.89 0.91 |

TABLE 5-2-continued

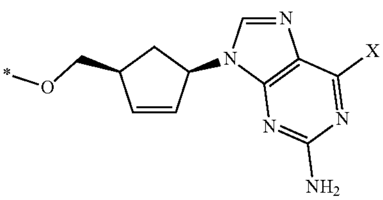

| Example No. | R | X | Compound name | $^1$H—NMR | MS (ESI m/z) (M +H) | RT (min) |
|---|---|---|---|---|---|---|
| 2-2-15 | 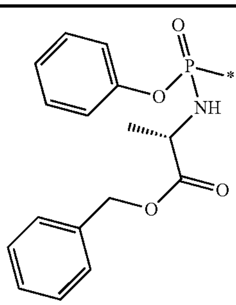 | $NH_2$ | Benzyl ((((1S,4R)-4-(2,6-diamino-9H-purin-9-yl) cyclopent-2-en-1-yl)methoxy) (phenoxy) phosphoryl)-L-alaninate | $^1$H—NMR ($CDCl_3$) δ: 7.53-7.49 (m, 1H), 7.39-7.24 (m, 7H), 7.21-7.09 (m, 3H), 6.08-5.98 (m, 1H), 5.88-5.81 (m, 1H), 5.59 (s, 2H), 5.53-5.43 (m, 1H), 5.16-5.07 (m, 2H), 4.90 (s, 2H), 4.26-3.96 (m, 4H), 3.18-3.02 (m, 1H), 2.81-2.65 (m, 1H), 1.74-1.60 (m, 1H), 1.41-1.32 (m, 3H). | 564 | 1.15 |
| 2-2-16 | 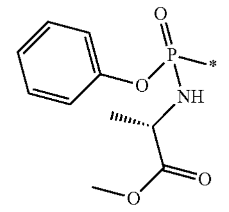 [SMILES: *P(=O)(N[C@@H](C)C(=O)OC)Oc1ccccc1] | OMe | Methyl ((((1S,4R)-4-(2-amino-6-methoxy-9H-purin-9-yl)cyclopent-2-en-1-yl) methoxy) (phenoxy) phosphoryl)-L-alaninate | $^1$H—NMR ($CDCl_3$) δ: 7 63-7.58 (m, 1H), 7.34-7.27 (m, 2H), 7.24-7.11 (m, 3H), 6.10-6.04 (m, 1H), 5.91-5.84 (m, 1H), 5.57-5.49 (m, 1H), 5.08-4.98 (m, 2H), 4.29-4.14 (m, 2H), 4.09-3.97 (m, 4H), 3.78-3.59 (m, 4H), 3.20-3.10 (m, 1H), 2.82-2.70 (m, 1H), 1.79-1.69 (m, 1H), 1.42-1.32 (m, 3H). | 503 | 1.03 |

TABLE 5-3

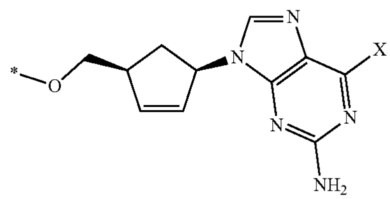

| Example No. | R | X | Compound name | $^1$H—NMR | MS (ESI m/z) (M + H) | RT (min) |
|---|---|---|---|---|---|---|
| 2-2-17 | 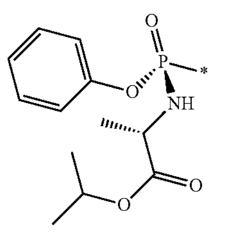 [SMILES: *[P@](=O)(N[C@@H](C)C(=O)OC(C)C)Oc1ccccc1] | OEt | Isopropyl ((R)-(((1S,4R)-4-(2-amino-6-ethoxy-9H-purin-9-yl) cyclopent-2-en-1-yl)methoxy) (phenoxy) phosphoryl)-L-alaninate | $^1$H—NMR ($CDCl_3$) δ: 7.57 (s, 1H), 7.34-7.10 (m, 5H), 6.11-6.06 (m, 1H), 5 89-5.83 (m, 1H), 5.58-5.50 (m, 1H), 5.05-4.88 (m, 3H), 4.55 (q, 2H, J = 7.0 Hz), 4.32-4.13 (m, 2H), 4.04-3.90 (m, 1H), 3 61-3.50 (m, 1H), 3.25-3.12 (m, 1H), 2 84-2.71 (m, 1H), 1.79-1 68 (m, 1H), 1.46 (t, 3H, J = 6.9 Hz), 1.34 (d, 3H, J = 7.3 Hz), 1.24-1.17 (m, 6H). | 545 | 1.19 |

TABLE 5-3-continued

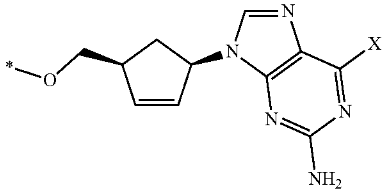

| Example No. | R | X | Compound name | $^1H$—NMR | MS (ESI m/z) (M + H) | RT (min) |
|---|---|---|---|---|---|---|
| 2-2-18 | 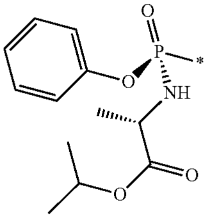 [SMILES: *[P@@](=O)(N[C@@H](C)C(=O)OC(C)C)Oc1ccccc1] | OEt | Isopropyl ((S)-(((1S,4R)-4-(2-amino-6-ethoxy-9H-purin-9-yl) cyclopent-2-en-1-yl)methoxy) (phenoxy) phosphoryl)-L-alaninate | $^1H$—NMR ($CDCl_3$) δ: 7.60 (s, 1H), 7.34-7.11 (m, 5H), 6.10-6.04 (m, 1H), 5.91-5.85 (m, 1H), 5.57-5.49 (m, 1H), 5.07-4.88 (m, 3H), 4.55 (q, 2H, J = 7.0 Hz), 4.30-4.13 (m, 2H), 4.03-3.90 (m, 1H), 3.66-3.55 (m, 1H), 3.22-3.10 (m, 1H), 2.83-2.70 (m, 1H), 1.80-1.68 (m, 1 H), 1.46 (t, 3H, J = 7.1 Hz), 1.37 (d, 3H, J = 6.9 Hz). 1.22 (d, 6H, J = 6.3 Hz). | 545 | 1.20 |
| 2-2-19 | 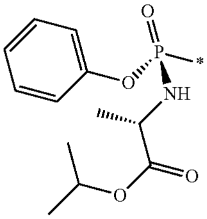 [SMILES: *[P@](=O)(N[C@@H](C)C(=O)OC(C)C)Oc1ccccc1] | OiPr | Isopropyl ((R)-(((1S,4R)-4-(2-amino-6-isopropoxy-9H-purin-9-yl) cyclopent-2-en-1-yl)methoxy) (phenoxy) phosphoryl)-L-alaninate | $^1H$—NMR ($CDCl_3$) δ: 7.57 (s, 1H), 7.35-7.10 (m, 5H), 6.12-6.05 (m, 1 H), 5.90-5.83 (m, 1H), 5.64-5.49 (m, 2H). 5.05-4.86 (m, 3H), 4.30-4.14 (m, 2H), 4.04-3.90 (m, 1H), 3.64-3.53 (m, 1H), 3.23-3.12 (m, 1H), 2.84-2.71 (m. 1H). 1.79-1.67 (m, 1H), 1 42 (d, 6H, J = 5.9 Hz), 1.34 (d, 3H, J = 6.9 Hz). 1.24-1.17 (m, 6H). | 559 | 1.26 |
| 2-2-20 | 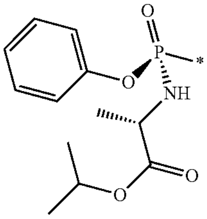 [SMILES: *[P@@](=O)(N[C@@H](C)C(=O)OC(C)C)Oc1ccccc1] | OiPr | Isopropyl ((S)-(((1S,4R)-4-(2-amino-6-isopropoxy-9H-purin-9-yl)cyclopent-2-en-1-yl) methoxy) (phenoxy) phosphoryl)- L-alaninate | $^1H$—NMR ($CDCl_3$) δ: 7.59 (s, 1H), 7.35-7.10 (m, 5H), 6.10-6.04 (m, 1H), 5 90-5.85 (m, 1H), 5.64-5.49 (m, 2H), 5.06-488 (m, 3H), 4.29-408 (m, 2H), 4.03-3.89 (m, 1H), 3.69-3.59 (m, 1H), 3.23-3.07 (m, 1H), 2.82-2.70 (m, 1H), 1.77-1.66 (m, 1 H), 1.42 (d, 6H, J = 6.3 Hz). 1.37 (d, 3H, J = 6.9 Hz), 1.22 (d, 6H, J = 6.3 Hz). | 559 | 1.27 |
| 2-2-21 | 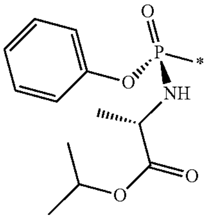 [SMILES: *[P@](=O)(N[C@@H](C)C(=O)OC(C)C)Oc1ccccc1] | $OCH_2CH_2OMe$ | Isopropyl ((R)-(((1S,4R)-4-(2-amino-6-(2-methoxyethoxy)-9H-purin-9-yl) cyclopent-2-en-1-yl)methoxy) (phenoxy) phosphoryl)-L-alaninate | $^1H$—NMR ($CDCl_3$) δ: 7.58 (s, 1H), 7.34-7 10 (m, 5H), 6.11-6 .06 (m, 1H), 5 89-5.83 (m, 1H), 5.58-5.49 (m, 1H), 5.05-4.92 (m, 3H), 4.68-4.62 (m, 2H), 4.30-4.15 (m, 2H), 4.05-3.91 (m, 1H), 3.83-3.78 (m, 2H), 3.62-3.52 (m, 1H), 3.43 (s, 3H), 3.24-3.12 (m, 1H), 2.86-2.70 (m, 1H), 1.80-1.67 (m, 1H), 1.34 (d, 3H, J = 6.9 Hz). 1 24-1.18 (m, 6H). | 575 | 1.21 |
| 2-2-22 | 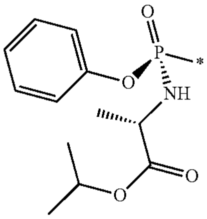 [SMILES: *[P@@](=O)(N[C@@H](C)C(=O)OC(C)C)Oc1ccccc1] | $OCH_2CH_2OMe$ | Isopropyl ((S)-(((1S,4R)-4-(2-amino-6-(2-methoxyethoxy)-9H-purin-9-yl) cyclopent-2-en-1-yl)methoxy) (phenoxy) phosphoryl)-L-alaninate | $^1H$—NMR ($CDCl_3$) δ: 7.60 (s, 1H), 7.35-7.11 (m, 5H), 6.10-6.04 (m, 1H), 5.90-5.85 (m, 1H), 5.57-5.48 (m, 1H), 5.07-4.93 (m, 3H), 4.68-4.61 (m, 2H), 4.30-4.12 (m, 2H), 4.03-3.89 (m, 1H), 3 84-3.77 (m, 2H), 3.69-3.58 (m, 1H), 3.43 (s, 3H), 3.21-3.09 (m, 1H), 2.82-2.69 (m, 1H), 1.78-1.67 (m, 1H), 1.37 (d, 3H, J = 6.9 Hz), 1.22 (d, 6H, J = 6.3 Hz). | 575 | 1.22 |

TABLE 5-3-continued

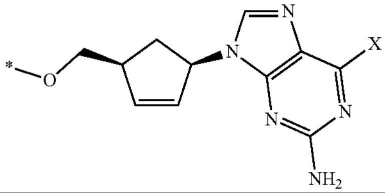

| Example No. | R | X | Compound name | $^1$H—NMR | MS (ESI m/z) (M + H) | RT (min) |
|---|---|---|---|---|---|---|
| 2-2-23 | 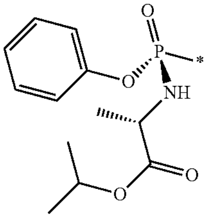 [SMILES: *[P@](=O)(N[C@@H](C)C(=O)OC(C)C)Oc1ccccc1] | $OCH_2CF_3$ | Isopropyl ((R)-(((1S,4R)-4-(2-amino-6-(2,2,2-trifluoroethoxy)-9H-purin-9-yl)cyclopent-2-en-1-yl)methoxy)(phenoxy)phosphoryl)-L-alaninate | $^1$H—NMR ($CDCl_3$) δ: 7.64 (s, 1H), 7.34-7.10 (m, 5H), 6.14-6.07 (m, 1H), 5.90-5.82 (m, 1H), 5.58-5.48 (m, 1H), 5.17-4.83 (m, 5H), 4.33-418 (m, 2H), 4.05-3.90 (m, 1H), 3 65-3.55 (m, 1H), 3 25-3.12 (m, 1H), 2.84-2.70 (m, 1H), 1.84-1.72 (m, 1H), 1.34 (d, 3H, J = 6.9 Hz), 1.24-1.17 (m, 6H). | 599 | 1.42 |
| 2-2-24 | 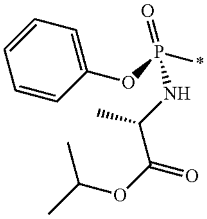 [SMILES: *[P@@](=O)(N[C@@H](C)C(=O)OC(C)C)Oc1ccccc1] | $OCH_2CF_3$ | Isopropyl ((S)-(((1S,4R)-4-(2-amino-6-(2,2,2-trifluoroethoxy)-9H-purin-9-yl)cyclopent-2-en-1-yl)methoxy)(phenoxy)phosphoryl)-L-alaninate | $^1$H—NMR ($CDCl_3$) δ: 7.66 (s, 1H), 7.35-7.11 (m, 5H), 6.11-6.05 (m, 1H), 5 90-5.84 (m, 1H), 5.57-5.49 (m, 1H), 5.14-4.86 (m, 5H), 4.35-4.14 (m, 2H), 4.03-3.89 (m, 1H), 3.70-3.58 (m, 1H), 3 24-3.09 (m, 1H), 2.82-2.70 (m, 1H), 1.82-1.72 (m, 1H), 1.37 (d, 3H, J = 6.9 Hz), 1.22 (d, 6H, J = 6.3 Hz) | 599 | 1.43 |

TABLE 5-4

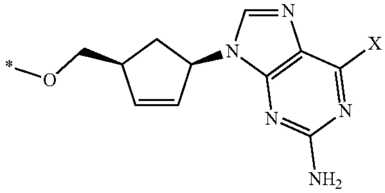

| Example No. | R | X | Compound name | $^1$H—NMR | MS (ESI m/z) (M + H) | RT (min) |
|---|---|---|---|---|---|---|
| 2-2-25 | 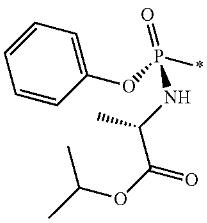 | $NMe_2$ | Isopropyl ((R)-(((1S,4R)-4-(2-amino-6-(dimethylamino)-9H-purin-9-yl)cyclopent-2-en-1-yl)methoxy)(phenoxy)phosphoryl)-L-alaninate | $^1$HNMR ($CDCl_3$) δ: 7.47 (s, 1H), 7.35-7.09 (m, 5H), 6.10-6.04 (m, 1H), 5.92-5.85 (m, 1H), 5.59-5.50 (m, 1H), 5.05-4 92 (m, 1H), 4.68 (br s, 2H), 4.23-4 08 (m, 2H), 4.04-389 (m, 1H), 3 63-3.32 (m, 7H), 3.22-3.10 (m, 1H), 2.86-2.72 (m, 1H), 1.70-1.58 (m, 1H), 1.33 (d, 3H, J = 7.3 Hz), 1.24-1.17 (m, 6H). | 544 | 1.12 |
| 2-2-26 | 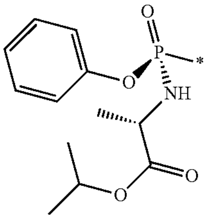 [SMILES: *[P@@](=O)(N[C@@H](C)C(=O)OC(C)C)Oc1ccccc1] | $NMe_2$ | Isopropyl ((S)-(((1S,4R)-4-(2-amino-6-(dimethylamino)-9H-purin-9-yl)cyclopent-2-en-1-yl)methoxy)(phenoxy)phosphoryl)-L-alaninate | $^1$HNMR ($CDCl_3$) δ: 7.48 (s, 1H), 7.35-7.10 (m, 5H), 6.10-6.04 (m, 1H), 5.93-5.86 (m, 1H), 5.58-5.49 (m, 1H), 5.05-4.93 (m, 1H), 4.70 (br s, 2H), 4.21-4.07 (m, 2H), 4.03-3.89 (m, 1H), 3.71-3.61 (m, 1H), 3.45 (br s, 6H), 3.19-3.07 (m, 1H), 2.83-2.70 (m, 1H), 1 69-1.57 (m, 1H), 1.37 (d, 3H, J = 6.9 Hz), 1.25-1.18 (m, 6H). | 544 | 1.13 |

TABLE 5-4-continued

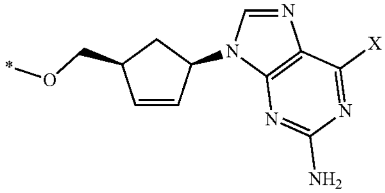

| Example No. | R | X | Compound name | $^1$H—NMR | MS (ESI m/z) (M + H) | RT (min) |
|---|---|---|---|---|---|---|
| 2-2-27 | 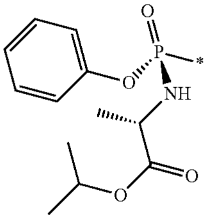 | $NHCH_2CH_2OMe$ | Isopropyl ((R)-(((1S,4R)-4-(2-amino-6-((2-methoxyethyl) amino)-9H-purin-9-yl) cyclopent-2-en-1-yl)methoxy) (phenoxy) phosphoryl)-L-alaninate | $^1$HNMR ($CDCl_3$) δ: 7.46 (s, 1H). 7.34-7.10 (m, 5H), 6.11-5.97 (m, 2H), 5.90-5.84 (m, 1H), 5.56-5.48 (m, 1H), 5.05-4.92 (m, 1H), 4.83 (br s, 2H), 4.25-4.11 (m, 2H), 4.04-3.90 (m, 1H), 3.86-3.54 (m, 5H), 3.38 (s, 3H), 3.22-3.10 (m, 1H), 2.84-2.71 (m, 1H), 1.73-1.62 (m, 1H), 1.34 (d, 3H, J = 6.9 Hz), 1 24-1.18 (m, 6H). | 574 | 1.12 |
| 2-2-28 | 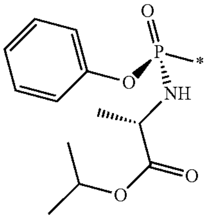 [SMILES: *[P@@](=O)(N[C@@H](C)C(=O)OC(C)C)Oc1ccccc1] | $NHCH_2CH_2OMe$ | Isopropyl ((S)-(((1S,4R)-4-(2-amino-6-((2-methoxyethyl) amino)-9H-purin-9-yl) cyclopent-2-en-1-yl)methoxy) (phenoxy) phosphoryl)-L-alaninate | $^1$HNMR ($CDCl_3$) δ: 7.49 (s, 1H), 7.35-7.10 (m, 5H), 6.10-5.96 (m, 2H), 5 92-5.86 (m, 1H), 5.56-5.47 (m, 1H), 5.05-4.93 (m, 1H), 4.83 (br s, 2H), 4.23-4.10 (m, 2H), 4.03-3.89 (m, 1H), 3.87-3.68 (m, 3H), 3.61-3.55 (m, 2H), 3.38 (s, 3H), 3.19-3.07 (m, 1H), 2.83-2.69 (m, 1H), 1 72-1.61 (m, 1H), 1.36 (d, 3H, J = 6.9 Hz), 1.25-1.18 (m, 6H). | 574 | 1.13 |
| 2-2-29 | 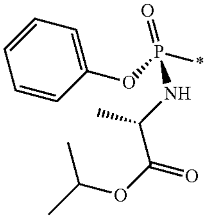 | NHMe | Isopropyl ((R)-(((1S,4R)-4-(2-amino-6-(methylamino)-9H-purin-9-yl)cyclopent-2-en-1-yl) methoxy(phenoxy) phosphoryl)-L-alaninate | $^1$HNMR ($CDCl_3$) δ: 7.45 (s, 1H), 7.34-7.09 (m, 5H), 6.10-6.04 (m, 1H), 5.90-5.79 (m, 2H), 5.56-5.47 (m, 1H), 5.05-4.84 (m, 3H), 4.26-4.10 (m, 2H), 4.04-3.79 (m, 2H), 3.22-3.01 (m, 4H), 2.84-2.71 (m, 1H), 1.73-1.61 (m, 1H), 1.34 (d, 3H, J = 6 9 Hz), 1.24-1.17 (m, 6H). | 530 | 1.07 |
| 2-2-30 | 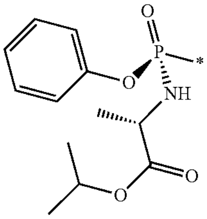 | NHMe | Isopropyl ((S)-(((1S,4R)-4-(2-amino-6-(methylamino)-9H-purin-9-yl) cyclopent-2-en-1-yl) methoxy(phenoxy) phosphoryl)-L-alaninate | $^1$HNMR ($CDCl_3$) δ: 7.48 (s, 1H), 7.34-7.10 (m, 5H), 6.09-6.03 (m, 1 H), 5 92-5.83 (m, 2H), 5.56-5.47 (m, 1H), 5.05-4.85 (m, 3H), 4.23-4.08 (m, 2H), 4.03-3.90 (m, 2H), 3.1 9-3.03 (m, 4H), 2 83-2.70 (m, 1H). 1 72-1 60 (m, 1H), 1.36 (d, 3H, J = 6.3 Hz), 1.25-1.17 (m, 6H). | 530 | 1.08 |
| 2-2-31 | 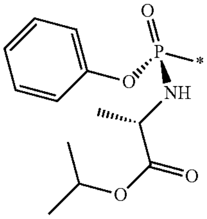 | $NMeCH_2CH_2NMe_2$ | Isopropyl ((R)-(((1S,4R)-4-(2-amino-6-((2-(dimethylamino) ethyl)(methyl) amino)-9H-purin-9-yl)cyclopent-2-en-l-yl) methoxy)(phenoxy) phosphoryl)-L-alaninate | $^1$HNMR ($CDCl_3$) δ: 7.45 (s, 1H), 7.33-7.11 (m, 5H), 6.10-6.05 (m, 1H), 5.91-5.86 (m, 1H), 5.58-5.50 (m, 1H), 5.05-4.92 (m, 1H), 4.64 (br s, 2H), 4.24-3.88 (m, 5H), 3.67-3.30 (m, 4H), 3.22-3.10 (m, 1H), 2.85-2.72 (m, 1H), 2.63-2.55 (m, 2H), 2.32 (s, 6H), 1.70-1.59 (m, 1H), 1.34 (d, 3H, J = 6.9 Hz), 1.24-1.18 (m, 6H). | 601 | 1.03 |

TABLE 5-4-continued

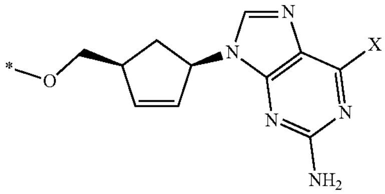

| Example No. | R | X | Compound name | $^1H$—NMR | MS (ESI m/z) (M + H) | RT (min) |
|---|---|---|---|---|---|---|
| 2-2-32 | 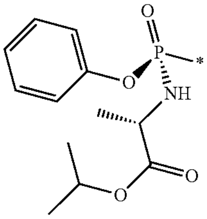 [SMILES: *[P@@](=O)(N[C@@H](C)C(=O)OC(C)C)Oc1ccccc1] | $NMeCH_2CH_2NMe_2$ | Isopropyl ((S)-(((1S,4R)-4-(2-amino-6-((2-(dimethylammo) ethyl)(methyl) amino)-9H-purin-9-yl) cyclopent-2-en-1-yl)methoxy) (phenoxy) phosphoryl)-L-alaninate | $^1HNMR$ ($CDCl_3$) δ: 7.47 (s, 1H), 7.34-7.11 (m, 5H), 6.08-6.03 (m, 1H), 5.91-5.86 (m, 1H), 5.58-5.50 (m, 1H), 5.06-4.93 (m, 1H), 4.64 (br s, 2H), 4.23-3.88 (m, 5H), 3.69-3.26 (m, 4H), 3.20-3.07 (m, 1H), 2.83-2.71 (m, 1 H), 2.62-2.54 (m, 2H), 2.32 (s, 6H), 1.68-1.58 (m, 1H), 1.37 (d, 3H, J = 7.3 Hz), 1.24-1.19 (m, 6H). | 601 | 1.04 |

TABLE 5-5

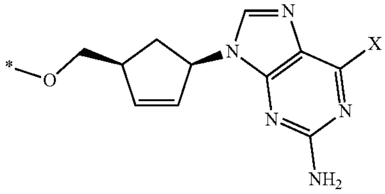

| Example No. | R | X | Compound name | $^1H$—NMR | MS (ESI m/z) (M + H) | RT (min) |
|---|---|---|---|---|---|---|
| 2-2-33 | 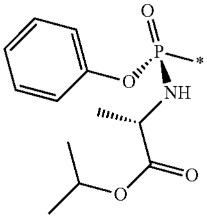 | $NMeCH_2CH_2NMe_2$ | Isopropyl ((R)-(((1S,4R)-4-(2-amino-6-((2-(dimethylamino)ethyl) amino)-9H-purin-9-yl)cyclopent-2-en-1-yl) methoxy)(phenoxy) phosphoryl)-L-alaninate | $^1H$—NMR ($CDCl_3$) δ: 7.45 (s, 1H), 7.33-7.10, (m, 9H), 6.17-6.05 (m, 1H), 5.90-5.89 (m, 1H), 5.56-5.48 (m, 1H), 5.05-4.82 (m, 1H), 4.77 (br s, 2H), 4.25-4.12 (m, 2H), 4.04-3.90 (m, 1H), 3.75-3.52 (m, 1H), 3.22-3.10 (m, 1H), 2.85-2.73 (m, 1H), 2.58-2.51 (m, 2H), 2.27 (s, 6H), 1.73-1.52 (m, 1H), 1.34 (d, 3H, J = 6.9 Hz), 1.24-1.15 (m, 6H). | 557 | 1.02 |
| 2-2-34 | 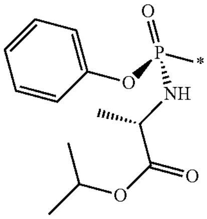 [SMILES: *[P@@](=O)(N[C@@H](C)C(=O)OC(C)C)Oc1ccccc1] | $NMeCH_2CH_2NMe_2$ | Isopropyl ((S)-(((1S,4R)-4-(2-amino-6-((2-(dimethylamino) ethyl)amino)-9H-purin-9-yl) cyclopent-2-en-1-yl)methoxy) (phenoxy)phosphoryl)-L-alaninate | $^1H$—NMR ($CDCl_3$) δ: 7.48 (s, 1H), 7.34-7.10, (m, 9H), 6.12-6.01 (m, 2H), 5.91-5.88 (m, 1H), 5.56-5.47 (m, 1H), 5.05-4.63 (m, 1H), 4.77 (br s, 2H), 4.23-4.09 (m, 2H), 4.03-3.89 (m, 1H), 3.78-3.52 (m, 1H), 3.20-3.07 (m, 1H), 2.82-2.70 (m, 1H), 2.56-2.50 (m, 2H), 2.26 (s, 6H), 1.72-1.61 (m, 1H), 1.37 (d, 3H, J = 6.9 Hz), 1.24-1.19 (m, 6H). | 557 | 1.01 |

TABLE 5-5-continued

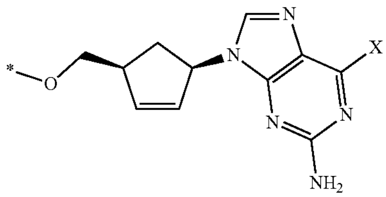

| Example No. | R | X | Compound name | $^1H$—NMR | MS (ESI m/z) (M + H) | RT (min) |
|---|---|---|---|---|---|---|
| 2-2-35 | 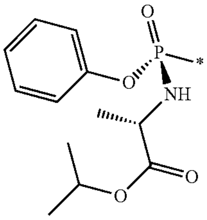 | OcycloBu | Isopropyl ((R)-(((1S,4R)-4-(2-amino-6-cyclo butoxy-9H-purin-9-yl)cyclopent-2-en-1-yl) methoxy)(phenoxy) phosphoryl)-L-alaninate | $^1H$—NMR ($CDCl_3$) δ: 7.59 (s, 1H), 7.34-7.09, (m, 5H), 6.12-6.05 (m, 1H), 5.89-5.84 (m, 1H), 5.58-5.48 (m, 1H), 5.46-4.35 (m, 1H), 5.05-4.85 (m, 3H), 4.33-4.09 (m, 2H), 4.04-3.90 (m, 1H), 3.63-3.53(m, 1H), 3.23-3.11 (m, 1H), 2.83-2.70 (m, 1H), 2.53-2.39 (m, 2H), 2.37-2.20 (m, 2H), 1.92-1.57 (m, 3H), 1.34 (d, 3H, J = 6.9 Hz), 1.24-1.17 (m, 6H). | 571 | 1.38 |
| 2-2-36 | 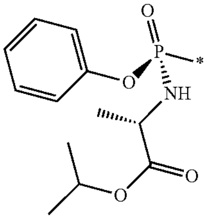 [SMILES: *[P@@](=O)(N[C@@H](C)C(=O)OC(C)C)Oc1ccccc1] | OcycloBu | Isopropyl ((S)-(((1S,4R)-4-(2-amino-6-cyclobutoxy-9H-purin-9-yl)cyclopent-2-en-1-yl) methoxy)(phenoxy) phosphoryl)-L-alaninate | $^1H$—NMR ($CDCl_3$) δ: 7.80 (s, 1H), 7.35-7.10, (m, 5H), 6.10-6.03 (m, 1H), 5.90-5.84 (m, 1H), 5.57-5.48 (m, 1H), 5.47-4.35 (m, 1H), 5.06-4.89 (m, 3H), 4.33-4.09 (m, 2H), 4.03-3.89 (m, 1H), 3.70-3.60 (m, 1H), 3.21-3.08 (m, 1H), 2.82-2.69 (m, 1H), 2.53-2.40 (m, 2H), 2.37-2.21 (m, 2H), 1.92-1.58 (m, 3H), 1.37 (d, 3H, J = 6.9 Hz), 1.22 (d, 6H, J = 6.3 Hz). | 571 | 1.39 |
| 2-2-37 | 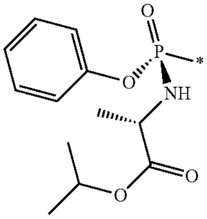 | 1-azetidinyl | Isopropyl ((R)-(((1S,4R)-4-(2-amino-6-(azetidin-1-yl)-9H-purin-9-yl)cyclopent-2-en-1-yl) methoxy)(phenoxy) phosphoryl)-L-alaninate | $^1H$—NMR ($CDCl_3$) δ: 7.46 (s, 1H), 7.34-7.10 (m, 5H), 6.10-6.04 (m, 1H), 5.90-5.84 (m, 1H), 5.96-5.46 (m, 1H), 5.06-4.91 (m, 1H), 4.83 (br s, 2H), 4.43 (br s, 4H), 4.04-4.09 (m, 2H), 4.04-3.90 (m, 1H), 3.68-3.85 (m, 1H), 3.21-3.09 (m, 1H), 2.84-2.70 (m, 1H), 2.52-2.40 (m, 2H), 1.71-1.59 (m, 1H), 1.33 (d, 3H, J = 7.3 Hz), 1.24-1.18 (m, 6H). | 556 | 1.09 |
| 2-2-38 | 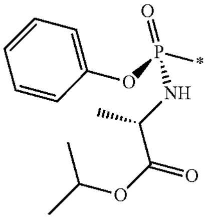 [SMILES: *[P@@](=O)(N[C@@H](C)C(=O)OC(C)C)Oc1ccccc1] | 1-azetidinyl | Isopropyl ((S)-(((1S,4R)-4-(2-amino-6-(azetidin-1-yl)-9H-purin-9-yl) cyclopent-2-en-1-yl) methoxy)(phenoxy) phosphoryl)-L-alaninate | $^1H$—NMR ($CDCl_3$) δ: 7.47 (s, 1H), 7.34-7.10 (m, 5H), 6.10-6.03 (m, 1H), 5.92-5.85 (m, 1H), 5.55-5.46 (m, 1H), 5.06-4.92 (m, 1H), 4.82 (br s, 2H), 4.42 (br s, 4H), 4.21-4.08 (m, 2H), 4.04-3.89 (m, 1H), 3.76-3.84 (m, 1H), 3.19-3.07 (m, 1H), 2.82-2.09 (m, 1H), 2.52-2.39 (m, 2H), 1.69-1.58 (m, 1H), 1.37 (d, 3H, J = 6.9 Hz), 1.22 (d, 6H, J = 6.3 Hz). | 556 | 1.10 |
| 2-2-39 | 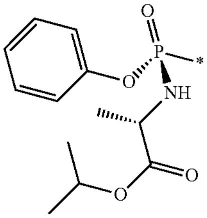 | 4-morpholinyl | Isopropyl ((R)-(((1S,4R)-4-(2-amino-6-morpholino-9H-purin-9-yl) cyclopent-2-en-1-yl) methoxy)(phenoxy) phosphoryl)-L-alaninate | $^1H$—NMR ($CDCl_3$) δ: 7.48 (s, 1H), 7.35-7.10 (m, 5H), 6.12-6.05 (m, 1H), 5.91-5.84 (m, 1H), 5.59-5.51 (m, 1H), 5.05-4.92 (m, 1H), 4.72 (br s, 2H), 4.34-4.07 (m, 6H), 4.04-4.89 (m, 1H), 3.84-3.74 (m, 4H), 3.63-3.51 (m, 1H), 3.23-3.09 (m, 1H), 2.85-2.71 (m, 1H), 1.72-1.60 (m, 1H), 1.33 (d, 3H, J = 7.3 Hz), 1.25-1.16 (m, 6H). | 586 | 1.17 |

TABLE 5-5-continued

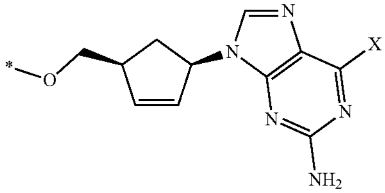

| Example No. | R | X | Compound name | $^1$H—NMR | MS (ESI m/z) (M + H) | RT (min) |
|---|---|---|---|---|---|---|
| 2-2-40 | 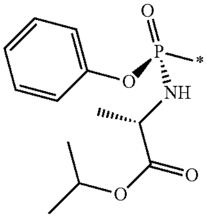 [SMILES: *[P@@](=O)(N[C@@H](C)C(=O)OC(C)C)Oc1ccccc1] | 4-morpholinyl | Lsopropyl ((S)-(((1S,4R)-4-(2-amino-6-morpholino-9H-purin-9-yl)cyclopent-2-en-1-yl) methoxy)(phenoxy) phosphoryl)-L-alaninate | $^1$H—NMR ($CDCl_3$) δ: 7.48 (s, 1H), 7.34-7.09 (m, 5H), 6.10-6.05 (m, 1H), 5.93-5.86 (m, 1H), 9.58-5.50 (m, 1H), 9.05-4.92 (m, 1H), 4.72 (br s, 2H), 4.32-4.08 (m, 6H), 4.03-4.89 (m, 1H), 3.85-3.74 (m, 4H), 3.72-3.61 (m, 1H), 3.20-3.07 (m, 1H), 2.84-2.70 (m, 1H), 1.71-1.59 (m, 1H), 1.37 (d, 3H, J = 8.9 Hz), 1.25-1.18 (m, 6H). | 586 | 1.18 |

TABLE 5-6

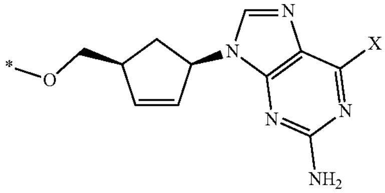

| Example No. | R | X | Compound name | $^1$H—NMR | MS (ESI m/z) (M + H) | RT (min) |
|---|---|---|---|---|---|---|
| 2-2-41 | 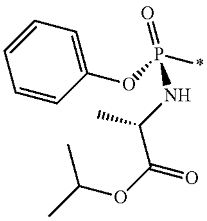 | SMe | Isopropyl ((R)-(((1S,4R)-4-(2-amino-6-(methylthio)-9H-purin-9-yl) cyclopent-2-en-1-yl)methoxy) (phenoxy) phosphoryl)-L-alaninate | $^1$H—NMR ($CDCl_3$) δ: 7.63 (s, 1 H), 7.34-7.09 (m, 5H), 6.12-6.07 (m, 1H), 5 89-5.83 (m, 1H), 5.58-5.49 (m, 1H), 5.10-4.92 (m, 3H), 4.33-4.13 (m, 2H), 4.07-3.88 (m, 1H), 3 62-3.52 (m, 1H), 3 24-3.11 (m, 1H), 2.83-2.70 (m, 1H), 2.63 (s, 3H), 1.80-1.69 (m, 1H), 1 34 (d, 3H, J = 6.9 Hz), 1 24-1.17 (m, 6H). | 547 | 1.31 |
| 2-2-42 | 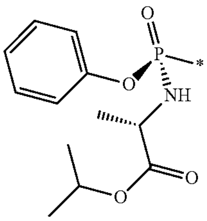 [SMILES: *[P@@](=O)(N[C@@H](C)C(=O)OC(C)C)Oc1ccccc1] | SMe | Isopropyl ((S)-(((1S ,4R)-4-(2-amino-6-(methylthio)-9H-purin-9-yl) cyclopent-2-en-1-yl)methoxy) (phenoxy) phosphoryl)-L-alaninate | $^1$H—NMR ($CDCl_3$) δ: 7.65 (s, 1H), 7.35-7.10 (m, 5H), 6.11-6.05 (m, 1H), 5.90-5.84 (m, 1H), 5.57-5.48 (m, 1H), 5.13-4.91 (m, 3H), 4.31-4.10 (m, 2H), 4.03-3.89 (m, 1H), 3.69-3.58 (m, 1H), 3.22-3.10 (m, 1H), 2.82-2 69 (m, 1H), 2.63 (s, 3H), 1.78-1.67 (m, 1H), 1 37 (d, 3H, J = 6.9 Hz), 1 24-1.19 (m, 6H). | 547 | 1.32 |
| 2-2-43 | 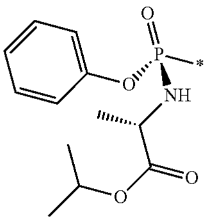 | NHcycloPen | Isopropyl ((R)-(((1S,4R)-4-(2-amino-6-(cyclopentylamino)-9H-purin-9-yl) cyclopent-2-en-1-yl)methoxy) (phenoxy) phosphoryl)-L-alaninate | $^1$H—NMR ($CDCl_3$) δ: 7.45 (s, 1H), 7.35-7.08 (m, 5H), 6.10-6.04 (m, 1H), 5.90-5.83 (m, 1H), 5.70-5.47 (m, 2H), 5.06-4.92 (m, 1H), 4.79 (br s, 2H), 4.56 (br s, 1H), 4.26-4.10 (m, 2H), 4.04-3.89 (m, 1H), 3.71-3.60 (m, 1H), 3.23-3.09 (m, 1H), 2.85-2.70 (m, 1 H), 2.15-2.01 (m, 2H), 1.82-1.45 (m, 7H), 1.34 (d, 3H, J = 7.3 Hz), 1.24-1.16 (m, 6H). | 584 | 1.30 |

TABLE 5-6-continued

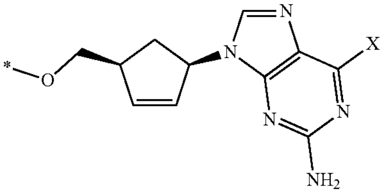

| Example No. | R | X | Compound name | $^1H$—NMR | MS (ESI m/z) (M + H) | RT (min) |
|---|---|---|---|---|---|---|
| 2-2-44 | 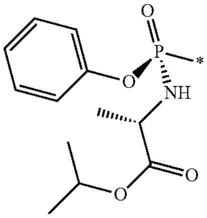 [SMILES: *[P@@](=O)(N[C@@H](C)C(=O)OC(C)C)Oc1ccccc1] | NHcycloPent | Isopropyl ((S)-(((1S,4R)-4-(2-amino-6-(cyclopentylamino)-9H-purin-9-yl) cyclopent-2-en-1-yl) methoxy)(phenoxy) phosphoryl)-L-alaninate | $^1H$—NMR ($CDCl_3$) δ: 7.47 (s, 1H), 7.35-7.10 (m, 5H), 6.10-6.02 (m, 1H), 5.93-5.85 (m, 1H), 5.69-5.45 (m, 2H), 5.06-4.91 (m, 1H), 4.79 (br s, 2H), 4.56 (br s, 1H). 4.23-4.09 (m, 2H), 4.03-3.88 (m, 1 H), 3.82-3.69 (m, 1 H), 3.20-3.06 (m, 1H). 2.83-2.68 (m, 1H), 2.14-2.01 (m, 2H), 1.81-1.44 (m, 7H), 1.37 (d, 3H. J = 6 9 Hz), 1.25-1.18 (m, 6H). | 584 | 1.31 |
| 2-2-45 | 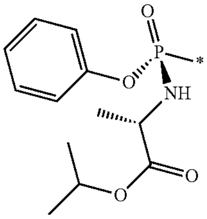 | $NH_2$ | Isopropyl ((R)-(((1S,4R)-4-(2,6-diamino-9H-purin-9-yl)cyclopent-2-en-1-yl) methoxy)(phenoxy) phosphoryl)-L-alaninate | $^1H$—NMR ($CDCl_3$) δ: 750 (s, 1 H), 7.34-7.09 (m, 5H), 6.10-6.03 (m, 1H), 5.91 (br s, 2H), 5.86-5.80 (m, 1 H), 5.55-5.45 (m, 1H), 5.14 (br s, 2H), 5.05-4.91 (m, 1H), 4.62-4.50 (m, 1H), 4.30-4.13 (m, 2H), 4.08-3.93 (m, 1H), 3.22-3.09 (m, 1H), 2 85-2.70 (m, 1H), 1.76-1.62 (m, 1H), 1.34 (d, 3H, J = 7.3 Hz), 1.24-1.17 (m, 6H). | 516 | 1.03 |
| 2-2-46 | 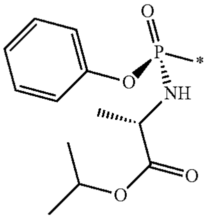 | $NH_2$ | Isopropyl ((S)-(((1S,4R)-4-(2,6-diamino-9H-purin-9-yl)cyclopent-2-en-1-yl) methoxy) (phenoxy)phosphoryl)-L-alaninate | $^1H$—NMR ($CDCl_3$) δ: 7.53 (s, 1H), 7.35-7.09 (m, 5H), 6.09-6.02 (m, 1H), 5.98-5.84 (m, 3H), 5.55-5.46 (m, 1H), 5.14-4.90 (m, 3H), 4.43-429 (m, 1H), 4.25-4.07 (m. 2H), 4 03-3.87 (m, 1H), 3.20-3.07 (m, 1H), 2.83-2.70 (m, 1H), 1.74-1.62 (m, 1H), 1.35 (d, 3H, J = 6.9 Hz). 1.23-1 17 (m, 6H). | 516 | 1.04 |
| 2-2-47 | 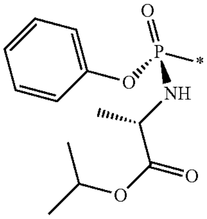 | H | Isopropyl ((R)-(((1S,4R)-4-(2-amino-9H-purin-9-yl)cyclopent-2-en-1-yl) methoxy)(phenoxy) phosphoryl)-L-alaninate | $^1H$—NMR ($CDCl_3$) δ: 8 67 (s, 1H), 7.74 (s, 1H), 7.34-7.10 (m, 5H), 6.16-6.09 (m. 1 H), 5.89-5.83 (m, 1H), 5.63-5.53 (m, 1H), 5.24 (br s, 2H), 5.05-4.92 (m, 1H), 4.33-4.17 (m, 2H), 4.05-390 (m, 1H). 3 87-3.77 (m, 1H), 3 26-3.14 (m, 1H), 2.86-2.72 (m, 1H), 1.85-1.71 (m, 1H), 1.33 (d, 3H, J = 6.9 Hz), 1.25-1.17(m, 6H). | 501 | 1.06 |
| 2-2-48 | 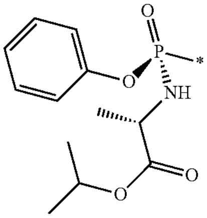 [SMILES: *[P@@](=O)(N[C@@H](C)C(=O)OC(C)C)Oc1ccccc1] | H | Isopropyl ((S)-(((1S,4R)-4-(2-amino-9H-purin-9-yl)cyclopent-2-en-1-yl)methoxy) (phenoxy)phosphoryl)-L-alaninate | $^1H$—NMR ($CDCl_3$) δ: 8.68 (s, 1H), 7.77 (s, 1H), 7.35-7.10 (m, 5H), 6.12-6.06 (m, 1H), 5.91-5.85 (m, 1H), 5.62-5.53 (m, 1H), 5.28 (br s, 2H), 5.07-4.92 (m, 1H), 4.34-4.14 (m, 2H), 4.03-3.82 (m, 2H), 3.24-3.11 (m, 1H), 2.85-2.70 (m, 1H), 1.83-1.71 (m, 1H), 1.37 (d, 3H, J = 6.6 Hz), 1.25-1.18 (m, 6H). | 501 | 1.08 |

Example 3-1

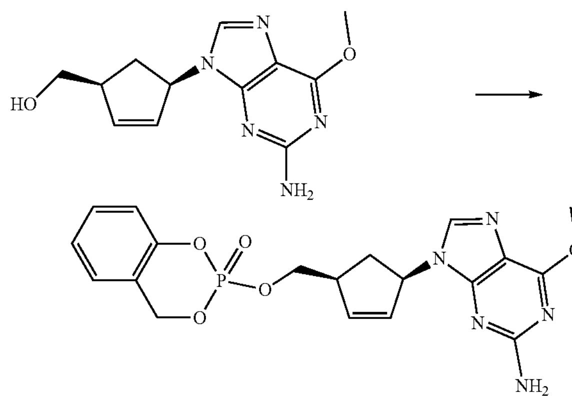

Under a nitrogen atmosphere, ((1S,4R)-4-(2-amino-6-methoxy-9H-purin-9-yl)cyclopent-2-en-1-yl)methanol (20 mg) and N-methylimidazole (36 μL) were added to a mixture of 2-chloro-4H-benzo[d][1,3,2]dioxaphosphinine 2-oxide (47 mg) and acetonitrile (1.0 mL) which was then stirred at room temperature for 30 minutes. The reaction solution was purified by silica gel column chromatography (hexane: ethyl acetate=70:30 to 0:100, methanol:ethyl acetate=0:100 to 16:84) to give 2-(((1S,4R)-4-(2-amino-6-methoxy-9H-purin-9-yl)cyclopent-2-en-1-yl)methoxy)-4H-benzo[d][1,3,2]dioxaphosphinine 2-oxide (14 mg) as a pale yellow solid.

$^1$H-NMR ($CDCl_3$) δ: 7.57-7.46 (m, 1H), 7.34-7.26 (m, 1H), 7.17-7.01 (m, 3H), 6.13-6.06 (m, 1H), 5.92-5.84 (m, 1H), 5.56-5.48 (m, 1H), 5.44-5.28 (m, 2H), 4.96 (s, 2H), 4.42-4.26 (m, 2H), 4.08-4.06 (m, 3H), 3.27-3.14 (m, 1H), 2.85-2.72 (m, 1H), 1.77-1.63 (m, 1H).

MS (ESI m/z): 430 (M+H)

RT (min): 0.94, 0.96

Example 3-2

The compounds in Table 6 were obtained in the same manner as in Example 3-1.

TABLE 6

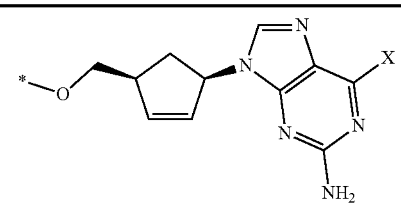

| Example No. | R | X | Compound name | 1H-NMR | MS (ESI m/z) (M +H) | RT (min) |
|---|---|---|---|---|---|---|
| 3-2-1 | 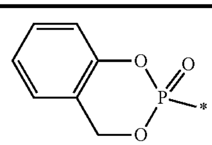 | Cl | 2-(((1S,4R)-4-(2-amino-6-chloro-9H-purin-9-yl)cyclopent-2-en-1-yl)methoxy)-4H-benzo[d][1,3,2] dioxaphosphinine 2-oxide | $^1$HNMR ($CDCl_3$) δ: 7.75-7.66 (m, 1H), 7.36-7.25 (m, 1H), 7.19-7.00 (m, 3H), 6.20-6.11 (m, 1H), 5.93-5.85 (m, 1H), 5.58-5.48 (m, 1H), 5.45-4.17 (m, 4H), 4.51-4.29 (m, 2H), 3.31-3.16 (m, 1H), 2.67-2.72 (m, 1H), 1.86-1.71 (m, 1H). | 434<br>438 | 1.01<br>1.03 |
| 3-2-2 | 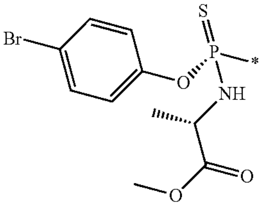 [SMILES: *[P@](=S)(N[C@@H](C)C(=O)OC)Oc1ccc(Br)cc1] | OMe | Methyl ((((1S,4R)-4-(2-amino-6-methoxy-9H-purin-9-yl)cyclopent-2-en-1-yl) methoxy)(4-bromophenoxy) phosphorothioyl)-L-alaninate | $^1$HNMR ($CDCl_3$) δ: 7.85 (s, 1H), 7.45-7.39 (m, 2H), 7.11-7.04 (m, 2H), 6.15-6.06 (m, 1H), 5.95-5.89 (m, 1H), 5.61-5.51 (m, 1H), 4.93-4.83 (m, 2H), 4.25-3.85 (m, 7H), 3.74-3.69 (m, 3H), 3.25-3.09 (m, 1H), 2.88-2.74 (m, 1H), 1.86-1.70 (m, 1H), 1.44-1.35 (m, 3H). | 597<br>599 | 1.47<br>1.49 |
| 3-2-3 | 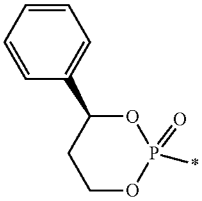 [SMILES: *P1(=O)OCC[C@@H](c2ccccc2)O1] | OMe | (4S)-2-(((1S,4R)-4-(2-amino-6-methoxy-9H-purin-9-yl)cyclopent-2-en-1-yl)methoxy)-4-phenyl-1,3,2-dioxaphosphinane 2-oxide | $^1$HNMR ($CDCl_3$) δ: 7.63 (s, 1H), 7.44-7.32 (m, 5H), 6.19-6.14 (m, 1H), 5.96-5.92 (m, 1H), 5.61-5.53 (m, 1H), 5.42-5.36 (m, 1H), 4.93 (s, 2H), 4.52-4.20 (m, 4H), 4.07 (s, 3H), 3.33-3.21 (m, 1H), 2.93-2.81 (m, 1H), 2.40-2.22 (m, 1H), 2.01-1.92 (m, 1H), 1.86-1.76 (m, 3H). | 458 | 1.01 |
| 3-2-4 | 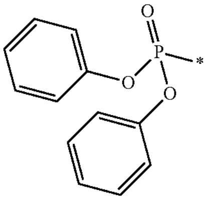 [SMILES: *P(=O)(Oc1ccccc1)Oc1ccccc1] | OMe | ((1S,4R)-4-(2-amino-6-methoxy-9H-purin-9-yl)cyclopent-2-en-1-yl) methyldiphenylphosphate | $^1$HNMR ($CDCl_3$) δ: 7.54 (s, 1H), 7.37-7.13 (m, 10H), 6.08-6.03 (m, 1H), 5.90-5.84 (m, 1H), 5.58-5.47 (m, 1H), 4.97 (s, 2H), 4.44-4.31 (m, 2H), 4.07 (s, 3H), 3.25-3.14 (m, 1H), 2.81-2.69 (m, 1H), 1.76-1.67 (m, 1H). | 494 | 1.28 |

TABLE 6-continued

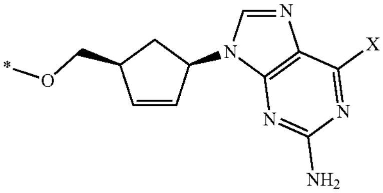

| Example No. | R | X | Compound name | 1H-NMR | MS (ESI m/z) (M +H) | RT (min) |
|---|---|---|---|---|---|---|
| 3-2-5 | 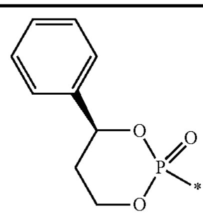 | Cl | (4S)-2-(((1S,4R)-4-(2-amino-6-chloro-9H-purin-9-yl)cyclopent-2-en-1-yl)methoxy)-4-phenyl-1,3,2-dioxaphosphinane 2-oxide | $^1$HNMR ($CDCl_3$) δ: 7.85-7.78 (m, 1H), 7.44-7.28 (m, 5H), 6.25-6.17 (m, 1H), 5.96-5.87 (m, 1H), 5.67-5.51 (m, 1H), 5.45-5.25 (m, 3H), 4.73-4.21 (m, 4H), 3.36-3.23 (m, 1H), 2.93-2.75 (m, 1H), 2.41-2.21 (m, 1H), 2.12-1.82 (m, 2H). | 462 464 | 1.05 1.09 |
| 3-2-6 | 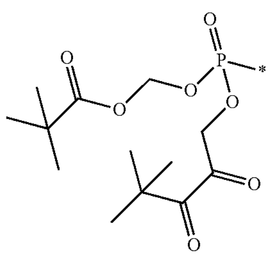 [SMILES: *P(=O)(OCOC(=O)C(C)(C)C)OCC(=O)C(=O)C(C)(C)C] | Cl | ((1R,4S)-4-(2-amino-6-methoxy-9H-purin-9-yl)cydopent-2-en-1-yl)methylbis(pivaloyl-oxymethyl) phosphate | $^1$HNMR ($CDCl_3$) δ: 7.61 (s, 1H), 6.15-6.11 (m, 1H), 5.93-5.89 (m, 1H), 5.70-5.61 (m, 4H), 5.59-5.51 (m, 1H), 4.96 (s, 2H), 4.27-4.18 (m, 2H), 4.07 (s, 3H), 3.25-3.13 (m, 1H), 2.86-2.75 (m, 1H), 1.82-1.72 (m, 1H), 1.23 (s, 9H), 1.82-1.72 (m, 1H), 1.23 (s, 9H), 1.22 (s, 9H). | 570 572 | 1.42 |

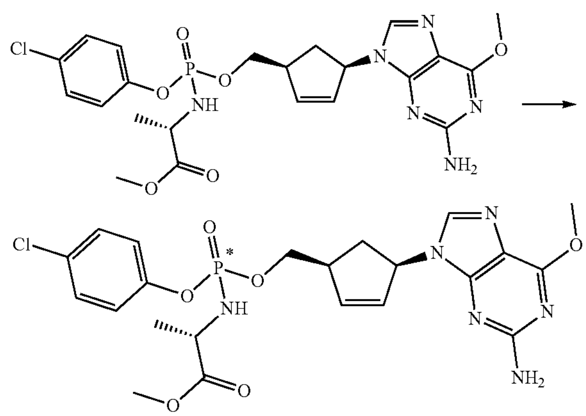

Example 4-1

Methyl ((((1S,4R)-4-(2-amino-6-methoxy-9H-purin-9-yl) cyclopent-2-en-1-yl)methoxy)(4-chlorophenoxy)phosphoryl)-L-alaninate obtained in Example 1-2-2 was subjected to chiral resolution by supercritical fluid chromatography to give optically active substance A and optically active substance B.

Example 4-1-1 (Optically Active Substance A)

$^1$H-NMR ($CDCl_3$) δ: 7.63 (s, 1H), 7.30-7.24 (m, 2H), 7.19-7.13 (m, 2H), 6.11-6.07 (m, 1H), 5.91-5.87 (m, 1H), 5.58-5.52 (m, 1H), 4.96 (s, 2H), 4.29-4.18 (m, 2H), 4.06 (s, 3H), 4.05-3.94 (m, 1H), 3.69 (s, 3H), 3.58-3.46 (m, 1H), 3.23-3.14 (m, 1H), 2.84-2.75 (m, 1H), 1.83-1.73 (m, 1H), 1.34 (d, 3H, J=7.1 Hz).

MS (ESI m/z): 537, 539 (M+H)

RT (min): 1.15

Example 4-1-2 (Optically Active Substance B)

$^1$H-NMR ($CDCl_3$) δ: 7.64 (s, 1H), 7.32-7.24 (m, 2H), 7.17-7.11 (m, 2H), 6.10-6.05 (m, 1H), 5.93-5.88 (m, 1H), 5.58-5.50 (m, 1H), 4.98 (s, 2H), 4.29-3.95 (m, 6H), 3.71 (s, 3H), 3.69-3.58 (m, 1H), 3.22-3.12 (m, 1H), 2.82-2.72 (m, 1H), 1.80-1.72 (m, 1H), 1.39 (d, 3H, J=7.1 Hz).

MS (ESI m/z): 537, 539 (M+H)

RT (min): 1.15

(Conditions for Supercritical Fluid Chromatography)

Column: CHIRALPAK IA (manufactured by Daicel Chemical Industries, Ltd.)

Mobile phase: carbon dioxide/methanol (volume ratio: 87/13)

Retention time: 15.65 min (optically active substance A), 18.77 min (optically active substance B)

Example 4-2

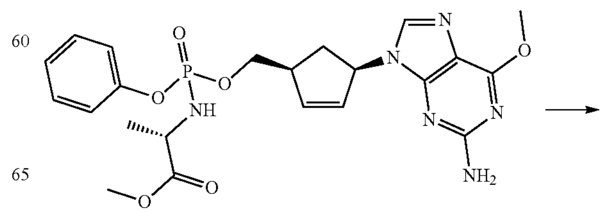

-continued

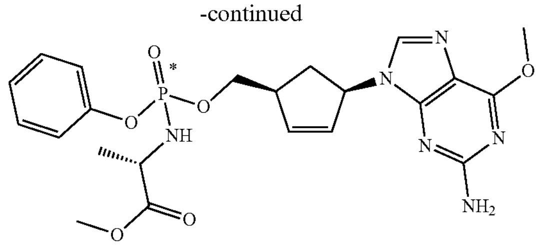

Methyl ((((1S,4R)-4-(2-amino-6-methoxy-9H-purin-9-yl)cyclopent-2-en-1-yl)methoxy)(phenoxy)phosphoryl)-L-alaninate obtained in Example 2-2-16 was subjected to chiral resolution by supercritical fluid chromatography to give optically active substance A and optically active substance B.

Example 4-2-1 (Optically Active Substance A)

$^{1}$H-NMR ($CDCl_3$) δ: 7.59 (s, 1H), 7.35-7.27 (m, 2H), 7.24-7.10 (m, 3H), 6.11-6.07 (m, 1H), 5.89-5.84 (m, 1H), 5.58-5.50 (m, 1H), 4.95 (s, 2H), 4.30-4.15 (M, 2H), 4.10-3.98 (m, 4H), 3.69 (s, 3H), 3.55-3.45 (m, 1H), 3.24-3.11 (m, 1H), 2.84-2.72 (m, 1H), 1.81-1.70 (m, 1H), 1.35 (d, 3H, J=6.9 Hz).

MS (ESI m/z): 503 (M+H)

RT (min): 1.02

Example 4-2-2 (Optically Active Substance B)

$^{1}$H-NMR ($CDCl_3$) δ: 7.61 (s, 1H), 7.35-7.26 (m, 2H), 7.23-7.11 (m, 3H), 6.09-6.04 (m, 1H), 5.90-5.86 (m, 1H), 5.57-5.49 (m, 1H), 4.99 (s, 2H), 4.29-4.13 (m, 2H), 4.09-3.94 (m, 4H), 3.72-3.61 (m, 4H), 3.21-3.10 (m, 1H), 2.82-2.70 (m, 1H), 1.80-1.68 (m, 1H), 1.39 (d, 3H, J=7.3 Hz).

MS (ESI m/z): 503 (M+H)

RT (min): 1.03

(Conditions for Supercritical Fluid Chromatography)

Column: CHIRALPAK IC (manufactured by Daicel Chemical Industries, Ltd.)

Mobile phase: carbon dioxide/methanol (volume ratio: 75/25)

Retention time: 12.31 min (optically active substance A), 13.85 min (optically active substance B)

Example 4-3

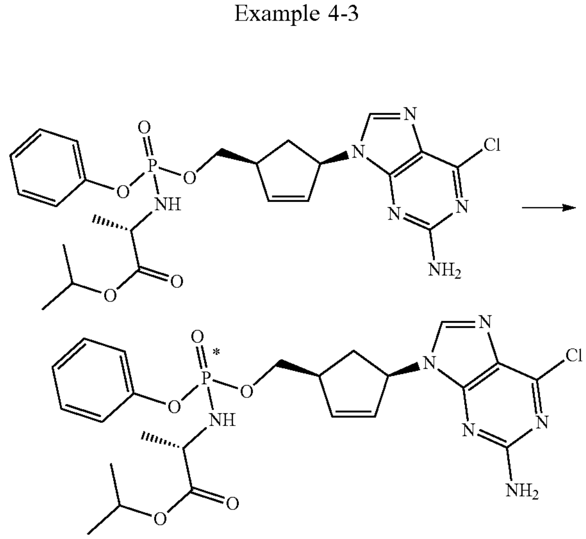

Isopropyl ((((1S,4R)-4-(2-amino-6-chloro-9H-purin-9-yl)cyclopent-2-en-1-yl)methoxy)(phenoxy)phosphoryl)-L-alaninate obtained in Example 2-2-1 was subjected to chiral resolution by supercritical fluid chromatography to give optically active substance A and optically active substance B.

Example 4-3-1 (Optically Active Substance A)

$^{1}$H-NMR ($CDCl_3$) δ: 7.76 (s, 1H), 7.34-7.09 (m, 5H), 6.16-6.10 (m, 1H), 5.88-5.82 (m, 1H), 5.58-5.49 (m, 1H), 5.29 (br s, 2H), 5.04-4.93 (m, 1H), 4.33-4.24 (m, 2H), 4.03-3.92 (m, 1H), 3.59-3.47 (m, 1H), 3.27-3.15 (m, 1H), 2.83-2.70 (m, 1H), 1.89-1.78 (m, 1H), 1.34 (d, 3H, J=7.3 Hz), 1.25-1.18 (m, 6H).

MS (ESI m/z): 535, 537 (M+H)

RT (min): 1.27

Example 4-3-2 (Optically Active Substance B)

$^{1}$H-NMR ($CDCl_3$) δ: 7.77 (s, 1H), 7.35-7.11 (m, 5H), 6.13-6.07 (m, 1H), 5.88-5.83 (m, 1H), 5.56-5.47 (m, 1H), 5.31 (br s, 2H), 5.05-4.95 (m, 1H), 4.41-4.30 (m, 1H), 4.25-4.15 (m, 1H), 4.01-3.90 (m, 1H), 3.64-3.52 (m, 1H), 3.26-3.12 (m, 1H), 2.84-2.70 (m, 1H), 1.87-1.76 (m, 1H), 1.37 (d, 3H, J=6.6 Hz), 1.23 (d, 6H, J=5.9 Hz).

MS (ESI m/z): 535, 537 (M+H)

RT (min): 1.28

(Conditions for Supercritical Fluid Chromatography)

Column: CHIRALPAK IA (manufactured by Daicel Chemical Industries, Ltd.)

Mobile phase: carbon dioxide/methanol (volume ratio: 78/22)

Retention time: 2.92 min (optically active substance A), 5.61 min (optically active substance B)

Example 4-4

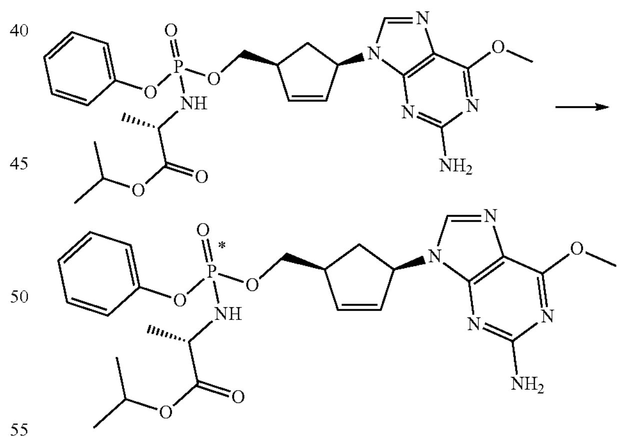

Isopropyl ((((1S,4R)-4-(2-amino-6-methoxy-9H-purin-9-yl)cyclopent-2-en-1-yl)methoxy)(phenoxy)phosphoryl)-L-alaninate obtained in Example 2-2-12 was subjected to chiral resolution by supercritical fluid chromatography to give optically active substance A and optically active substance B.

Example 4-4-1 (Optically Active Substance A)

$^{1}$H-NMR ($CDCl_3$) δ: 7.57 (s, 1H), 7.35-7.10 (m, 5H), 6.13-6.06 (m, 1H), 5.90-5.83 (m, 1H), 5.59-5.49 (m, 1H), 5.04-4.89 (m, 3H), 4.32-4.14 (m, 2H), 4.07 (s, 3H), 4.03-3.92 (m, 1H), 3.58-3.46 (m, 1H), 3.24-3.12 (m, 1H), 2.85-2.71 (m, 1H), 1.81-1.69 (m, 1H), 1.34 (d, 3H, J=7.3 Hz), 1.25-1.18 (m, 6H).

MS (ESI m/z): 531 (M+H)

RT (min): 1.19

Example 4-4-2 (Optically Active Substance B)

$^1$H-NMR ($CDCl_3$) δ: 7.60 (s, 1H), 7.35-7.10 (m, 5H), 6.10-6.05 (m, 1H), 5.90-5.85 (m, 1H), 5.57-5.49 (m, 1H), 5.05-4.91 (m, 3H), 4.30-4.13 (m, 2H), 4.07 (s, 3H), 4.02-3.91 (m, 1H), 3.63-3.53 (m, 1H), 3.23-3.10 (m, 1H), 2.83-2.70 (m, 1H), 1.80-1.68 (m, 1H), 1.37 (d, 3H, J=7.3 Hz), 1.22 (d, 6H, J=6.6 Hz).

MS (ESI m/z): 531 (M+H)

RT (min): 1.21

(Conditions for Supercritical Fluid Chromatography)

Column: CHIRALPAK IA (manufactured by Daicel Chemical Industries, Ltd.)

Mobile phase: carbon dioxide/methanol (volume ratio: 83/17)

Retention time: 3.69 min (optically active substance A), 5.88 min (optically active substance B)

Example 4-5

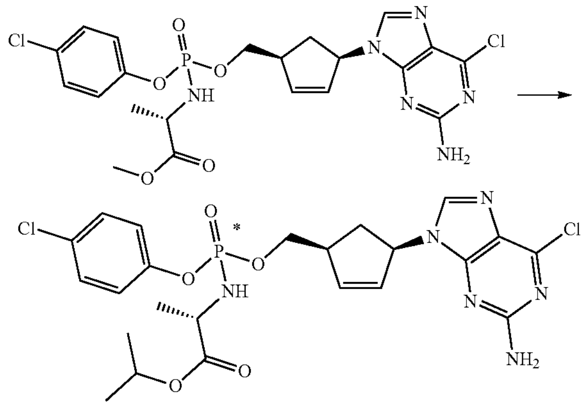

Methyl ((((1S,4R)-4-(2-amino-6-chloro-9H-purin-9-yl) cyclopent-2-en-1 -yl)methoxy)(4-chlorophenoxy)phosphoryl)-L-alaninate obtained in Example 1-2-4 was subjected to chiral resolution by supercritical fluid chromatography to give optically active substance A and optically active substance B.

Example 4-5-1 (Optically Active Substance A)

$^1$H-NMR ($CDCl_3$) δ: 7.78 (s, 1H), 7.30-7.23 (m, 2H), 7.19-7.12 (m, 2H), 6.16-6.11 (m, 1H), 5.90-5.85 (m, 1H), 5.58-5.50 (m, 1H), 5.27 (br s, 2H), 4.32-4.23 (m, 2H), 4.07-3.94 (m, 1H), 3.71 (s, 3H), 3.54-3.43 (m, 1H), 3.28-3.15 (m, 1H), 2.86-2.72 (m, 1H), 1.90-1.79 (m, 1H), 1.34 (d, 3H, J=6.6 Hz)

MS (ESI m/z): 541 (M+H)

RT (min): 1.22

Example 4-5-2 (Optically Active Substance B)

$^1$H-NMR ($CDCl_3$) δ: 7.78 (s, 1H), 7.30-7.23 (m, 2H), 7.19-7.11 (m, 2H), 6.13-6.06 (m, 1H), 5.91-5.84 (m, 1H), 5.57-5.48 (m, 1H), 5.30 (br s, 2H), 4.40-4.29 (m, 1H), 4.25-4.16 (m, 1H), 4.06-3.94 (m, 1H), 3.72 (s, 3H), 3.65-3.53 (m, 1H), 3.26-3.12 (m, 1H), 2.85-2.71 (m, 1H), 1.88-1.77 (m, 1H), 1.39 (d, 3H, J=7.3 Hz).

MS (ESI m/z): 541 (M+H)

RT (min): 1.22

(Conditions for Supercritical Fluid Chromatography)

Column: CHIRALPAK IA (manufactured by Daicel Chemical Industries, Ltd.)

Mobile phase: carbon dioxide/methanol (volume ratio: 78/22)

Retention time: 5.12 min (optically active substance A), 7.83 min (optically active substance B)

Example 4-6

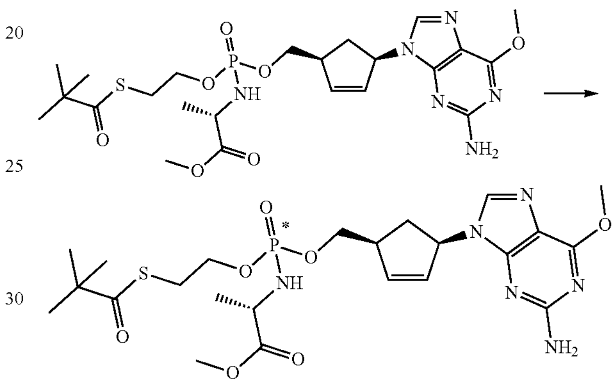

Methyl ((((1S,4R)-4-(2-amino-6-methoxy-9H-purin-9-yl) cyclopent-2-en-1-yl)methoxy)(2-(pivaloylthio)ethoxy) phosphoryl)-L-alaninate obtained in Example 1-2-12 was subjected to chiral resolution by supercritical fluid chromatography to give optically active substance A and optically active substance B.

Example 4-6-1 (Optically Active Substance A)

$^1$H-NMR ($CDCl_3$) δ: 7.64 (s, 1H), 6.17-6.11 (m, 1H), 5.92-5.87 (m, 1H), 5.60-5.51 (m, 1H), 4.95 (br s, 2H), 4.19-3.87 (m, 8H), 3.74 (s, 3H), 3.38-3.27 (m, 1H), 3.24-3.08 (m, 3H), 2.87-2.75 (m, 1H), 1.85-1.73 (m, 1H), 1.40 (d, 3H, J=6.6 Hz), 1.22 (s, 9H).

MS (ESI m/z): 571 (M+H)

RT (min): 1.21

Example 4-6-2 (Optically Active Substance B)

$^1$H-NMR ($CDCl_3$) δ: 7.64 (s, 1H), 6.15-6.09 (m, 1H), 5.93-5.86 (m, 1H), 5.61-5.50 (m, 1H), 4.97 (br s, 2H), 4.24-3.90 (m, 8H), 3.73 (s, 3H), 3.44-3.33 (m, 1H), 3.24-3.08 (m, 3H), 2.89-2.72 (m, 1H), 1.83-1.70 (m, 1H), 1.41 (d, 3H, J=7.3 Hz), 1.22 (s, 9H).

MS (ESI m/z): 571 (M+H)

RT (min): 1.22

(Conditions for Supercritical Fluid Chromatography)

Column: CHIRALPAK IC (manufactured by Daicel Chemical Industries, Ltd.)

Mobile phase: carbon dioxide/ethanol (volume ratio: 78/22)

Retention time: 15.08 min (optically active substance A), 19.18 min (optically active substance B)

Example 4-7

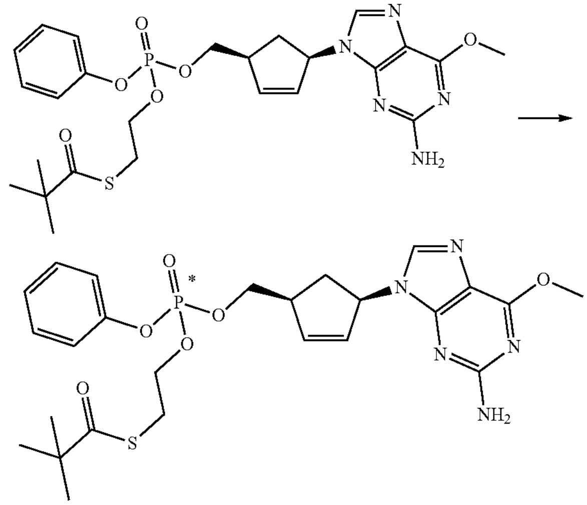

S-(2-(((((1S,4R)-4-(2-amino-6-methoxy-9H-purin-9-yl) cyclopent-2-en-1-yl)methoxy)(phenoxy)phosphoryl)oxy) ethyl) 2,2-dimethylpropanethioate obtained in Example 2-1 was subjected to chiral resolution by supercritical fluid chromatography to give optically active substance A and optically active substance B.

Example 4-7-1 (Optically Active Substance A)

$^1$H-NMR ($CDCl_3$) δ: 7.59 (s, 1H), 7.36-7.13 (m, 5H), 6.12-6.06 (m, 1H), 5.93-5.86 (m, 1H), 5.58-5.48 (m, 1H), 4.96 (br s, 2H), 4.34-4.25 (m, 2H), 4.25-4.13 (m, 2H), 4.07 (s, 3H), 3.26-3.08 (m, 3H), 2.85-2.71 (m, 1H), 1.83-1.69 (m, 1H), 1.21 (s, 9H).

MS (ESI m/z): 562 (M+H)

RT (min): 1.44

Example 4-7-2 (Optically Active Substance B)

$^1$H-NMR ($CDCl_3$) δ: 7.57 (s, 1H), 7.36-7.12 (m, 5H), 6.12-6.06 (m, 1H), 5.91-5.85 (m, 1H), 5.58-5.48 (m, 1H), 4.95 (br s, 2H), 4.37-4.24 (m, 2H), 4.24-4.13 (m, 2H), 4.07 (s, 3H), 3.26-3.09 (m, 3H), 2.85-2.71 (m, 1H), 1.81-1.69 (m, 1H), 1.21 (s, 9H).

MS (ESI m/z): 562 (M+H)

RT (min): 1.44

(Conditions for Supercritical Fluid Chromatography)

Column: CHIRALPAK IA (manufactured by Daicel Chemical Industries, Ltd.)

Mobile phase: carbon dioxide/(ethanol/isopropyl alcohol/isopropylamine=650/350/1) (volume ratio: 88/12)

Retention time: 18.18 min (optically active substance A), 23.30 min (optically active substance B)

Example 4-8

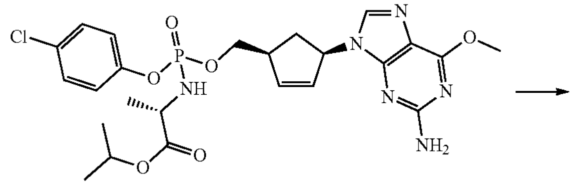

-continued

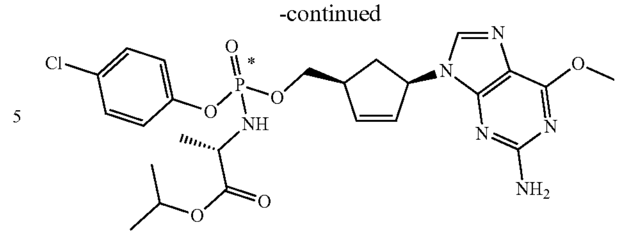

Isopropyl ((((1S,4R)-4-(2-amino-6-methoxy-9H-purin-9-yl)cyclopent-2-en-1-yl)methoxy)(4-chlorophenoxy)phosphoryl)-L-alaninate obtained in Example 1-2-72 was subjected to chiral resolution by supercritical fluid chromatography to give optically active substance A and optically active substance B.

Example 4-8-1 (Optically Active Substance A)

$^1$H-NMR ($CDCl_3$) δ: 7.60 (s, 1H), 7.30-7.23 (m, 2H), 7.20-7.13 (m, 2H), 6.12-6.06 (m, 1H), 5.92-5.86 (m, 1H), 5.60-5.49 (m, 1H), 5.05-4.87 (m, 3H), 4.34-4.14 (m, 2H), 4.07 (s, 3H), 4.01-3.85 (m, 1H), 3.57-3.47 (m, 1H), 3.26-3.11 (m, 1H), 2.86-2.73 (m, 1H), 1.83-1.72 (m, 1H), 1.34 (d, 3H, J=7.3 Hz), 1.25-1.18 (m, 6H).

MS (ESI m/z): 565 (M+H)

RT (min): 1.31

Example 4-8-2 (Optically Active Substance B)

$^1$H-NMR ($CDCl_3$) δ: 7.62 (s, 1H), 7.29-7.22 (m, 2H), 7.18-7.11 (m, 2H), 6.10-6.05 (m, 1H), 5.92-5.87 (m, 1H), 5.58-5.49 (m, 1H), 5.07-4.91 (m, 3H), 4.32-4.13 (m, 2H), 4.07 (s, 3H), 4.03-3.88 (m, 1H), 3.65-3.55 (m, 1H), 3.22-3.09 (m, 1H), 2.84-2.71 (m, 1H), 1.81-1.70 (m, 1H), 1.37 (d, 3H, J=7.3 Hz), 1.23 (d, 6H, J=5.9 Hz).

MS (ESI m/z): 565 (M+H)

RT (min): 1.32

(Conditions for Supercritical Fluid Chromatography)

Column: CHIRALPAK IA (manufactured by Daicel Chemical Industries, Ltd.)

Mobile phase: carbon dioxide/methanol (volume ratio: 83/17)

Retention time: 5.08 min (optically active substance A), 9.33 min (optically active substance B)

Example 4-9

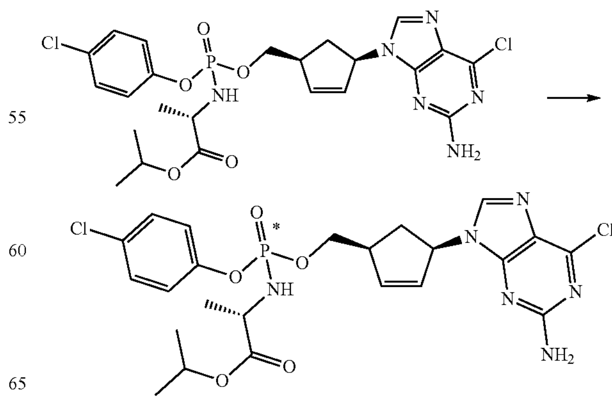

Isopropyl ((((1S,4R)-4-(2-amino-6-chloro-9H-purin-9-yl) cyclopent-2-en-1-yl)methoxy)(4-chlorophenoxy)phosphoryl)-L-alaninate obtained in Example 1-2-70 was subjected to chiral resolution by supercritical fluid chromatography to give optically active substance A and optically active substance B.

Example 4-9-1 (Optically Active Substance A)

$^{1}$H-NMR ($CDCl_3$) δ: 7.78 (s, 1H), 7.32-7.23 (m, 2H), 7.20-7.12 (m, 2H), 6.18-6.09 (m, 1H), 5.93-5.84 (m, 1H), 5.61-5.49 (m, 1H), 5.28 (br s, 2H), 5.06-4.91 (m, 1H), 4.40-4.22 (m, 2H), 4.05-3.87 (m, 1H), 3.61-3.46 (m, 1H), 3.30-3.14 (m, 1H), 2.86-2.71 (m, 1H), 1.91-1.79 (m, 1H), 1.34 (d, 3H, J=7.3 Hz), 1.27-1.18 (m, 6H).

MS (ESI m/z): 569, 571 (M+H)

RT (min): 1.39

Example 4-9-2 (Optically Active Substance B)

$^{1}$H-NMR ($CDCl_3$) δ: 7.78 (s, 1H), 7.32-7.23 (m, 2H), 7.19-7.11 (m, 2H), 6.14-6.06 (m, 1H), 5.92-5.84 (m, 1H), 5.57-5.48 (m, 1H), 5.31 (br s, 2H), 5.08-4.93 (m, 1H), 4.42-4.29 (m, 1H), 4.26-4.14 (m, 1H), 4.02-3.86 (m, 1H), 3.68-3.53 (m, 1H), 3.27-3.13 (m, 1H), 2.84-2.71 (m, 1H), 1.88-1.76 (m, 1H), 1.37 (d, 3H, J=7.3 Hz), 1.23 (d, 6H, J=5.9 Hz).

MS (ESI m/z): 569, 571 (M+H)

RT (min): 1.40

(Conditions for Supercritical Fluid Chromatography)

Column: CHIRALPAK IA (manufactured by Daicel Chemical Industries, Ltd.)

Mobile phase: carbon dioxide/methanol (volume ratio: 80/20)

Retention time: 4.44 min (optically active substance A), 9.99 min (optically active substance B)

Example 5-1

First Step

The following compound was obtained in the same manner as in Example 1-1.

Methyl ((((1S,4R)-4-(2-amino-6-chloro-9H-purin-9-yl)cyclopent-2-en-1-yl)methoxy)(2-((2,2-dimethyl-3-(trityloxy)propanoyl)thio)ethoxy)phosphoryl)-L-alaninate MS (ESI m/z): 833, 835 (M+H)

RT (min): 1.91

Second Step

A mixture of methyl ((((1S,4R)-4-(2-amino-6-chloro-9H-purin-9-yl)cyclopent-2-en-1-yl)methoxy)(2-((2,2-dimethyl-3-(trityloxy)propanoyl)thio)ethoxy)phosphoryl)-L-alaninate (16 mg), 4 M hydrochloric acid/cyclopentyl methyl ether (0.1 mL), and acetonitrile (0.5 mL) was stirred at room temperature for 3 hours. The solvent was distilled off under reduced pressure, and the obtained residue was purified by preparative thin layer chromatography (methanol:ethyl acetate=5:95) to give methyl ((((1S,4R)-4-(2-amino-6-chloro-9H-purin-9-yl)cyclopent-2-en-1-yl)methoxy)(2-((3-hydroxy-2,2-dimethylpropanoyl)thio)ethoxy)phosphoryl)-L-alaninate (9.7 mg) as a colorless oil.

$^{1}$H-NMR ($CDCl_3$) δ: 7.89-7.85 (m, 1H), 6.20-6.11 (m, 1H), 5.92-5.85 (m, 1H), 5.62-5.53 (m, 1H), 5.28-5.20 (m, 2H), 4.25-4.05 (m, 4H), 4.00-3.84 (m, 1H), 3.77-3.70 (m, 3H), 3.67-3.60 (m, 2H), 3.56-3.37 (m, 1H), 3.25-3.07 (m, 3H), 2.90-2.76 (m, 1H), 1.92-1.79 (m, 1H), 1.45-1.35 (m, 3H), 1.29-1.20 (m, 6H).

MS (ESI m/z): 591, 593 (M+H)

RT (min): 1.02

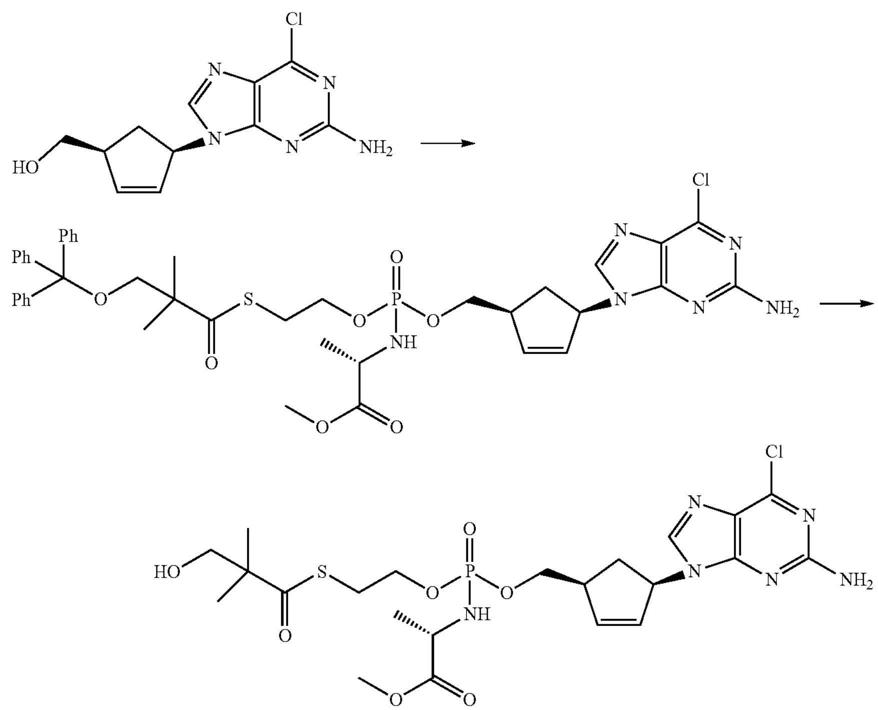

Example 5-2

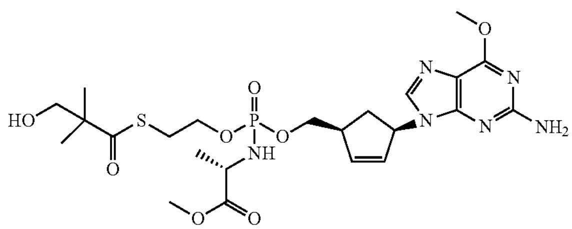 [SMILES: COC(=O)[C@H](C)NP(=O)(OCCSC(=O)C(C)(C)CO)OC[C@@H]1C=C[C@H](n2cnc3c(OC)nc(N)nc32)C1]

The following compound was obtained in the same manner as in Example 5-1.

Methyl ((((1S,4R)-4-(2-amino-6-methoxy-9H-purin-9-yl)cyclopent-2-en-1-yl)methoxy)(2-((3-hydroxy-2,2-dimethylpropanoyl)thio)ethoxy)phosphoryl)-L-alaninate $^1$H-NMR ($CDCl_3$) δ: 7.72-7.67 (m, 1H), 6.17-6.07 (m, 1H), 5.94-5.86 (m, 1H), 5.62-5.53 (m, 1H), 5.00-4.92 (m, 2H), 4.20-4.04 (m, 7H), 4.01-3.85 (m, 1H), 3.77-3.70 (m, 3H), 3.66-3.60 (m, 2H), 3.47-3.34 (m, 1H), 3.21-3.08 (m, 3H), 2.89-2.76 (m, 1H), 1.85-1.73 (m, 1H), 1.44- 1.34 (m, 3H), 1.29-1.19 (m, 6H).

MS (ESI m/z): 587 (M+H)

RT (min): 0.60

Example 5-3

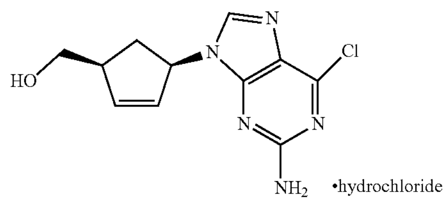

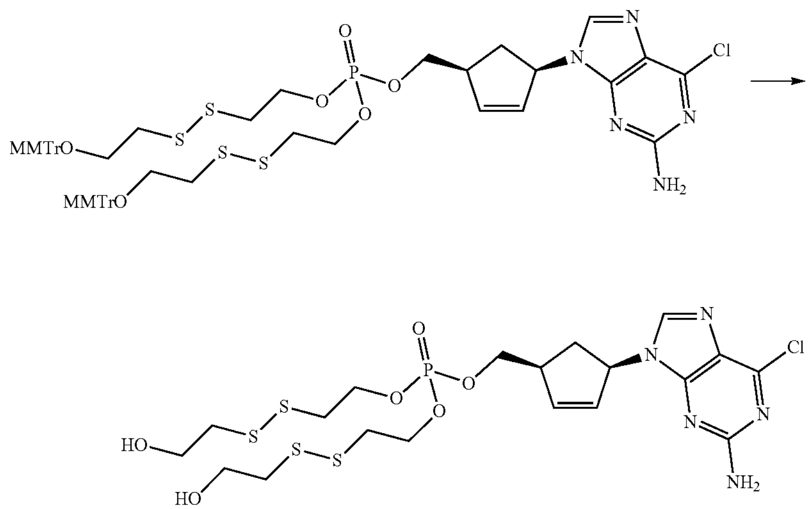

First Step

The following compound was obtained in the same manner as in Example 1-1.

(1S,4R)-4-(2-amino-6-chloro-9H-purin-9-yl)cyclopent-2-en-1-yl)methylbis(2-((2-((4-methoxyphenyl)diphenylmethoxy)ethyl)disulfanyl)ethyl)phosphate MS (ESI m/z): 1184 (M+Na)

RT (min): 2.37

Second Step

A mixture of (1S,4R)-4-(2-amino-6-chloro-9H-purin-9-yl)cyclopent-2-en-1-yl)methylbis(2-((2-((4-methoxyphenyl)diphenylmethoxy)ethyl)disulfanyl)ethyl)phosphate (47 mg), acetic acid (800 μL), and methanol (200 μL) was stirred at room temperature for 9 hours. Acetic acid (1 mL) was added to the reaction solution which was then stirred at room temperature for 4 hours. After distilling off the solvent under reduced pressure, the obtained residue was purified by silica gel column chromatography (hexane:ethyl acetate=80:20 to 0:100, methanol:ethyl acetate=0:100 to 20:80) to give (1S,4R)-4-(2-amino-6-chloro-9H-purin-9-yl)cyclopent-2-en-1-yl)methylbis(2-((2-hydroxyethyl)disulfanyl)ethyl)phosphate (10 mg).

$^1$H-NMR ($CDCl_3$) δ: 7.89 (s, 1H), 6.22-6.14 (m, 1H), 5.96-5.89 (m, 1H), 5.66-5.54 (m, 1H), 5.23 (br s, 2H), 4.47-4.16 (m, 6H), 4.01-3.80 (m, 4H), 3.52-3.30 (m, 2H), 3.28-3.16 (m, 1H), 3.12-2.79 (m, 9H), 1.93-1.83 (m, 1H).

MS (ESI m/z): 618, 620 (M+H)

RT (min): 0.99

Example 5-4

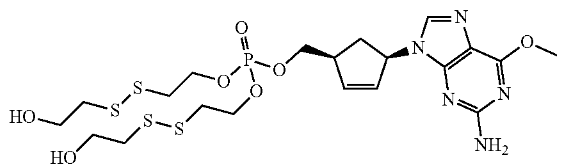 [SMILES: COc1nc(N)nc2c1ncn2[C@H]1C=C[C@@H](COP(=O)(OCCSSCCO)OCCSSCCO)C1]

The following compound was obtained in the same manner as in Example 5-3.

(1S,4R)-4-(2-amino-6-methoxy-9H-purin-9-yl)cyclopent-2-en-1-yl)methylbis(2-((2-hydroxyethyl) disulfanyl)ethyl)phosphate $^1$H-NMR ($CDCl_3$) δ: 7.71 (s, 1H), 6.21-6.10 (m, 1H), 6.00-5.89 (m, 1H), 5.66-5.54 (m, 1H), 4.95 (br s, 2H), 4.43-4.03 (m, 9H), 3.99-3.64 (m, 6H), 3.27-3.13 (m, 1H), 3.09-2.79 (m, 9H), 1.89-1.76 (m, 1H).

MS (ESI m/z): 614 (M+H)

RT (min): 0.94

Example 6-1

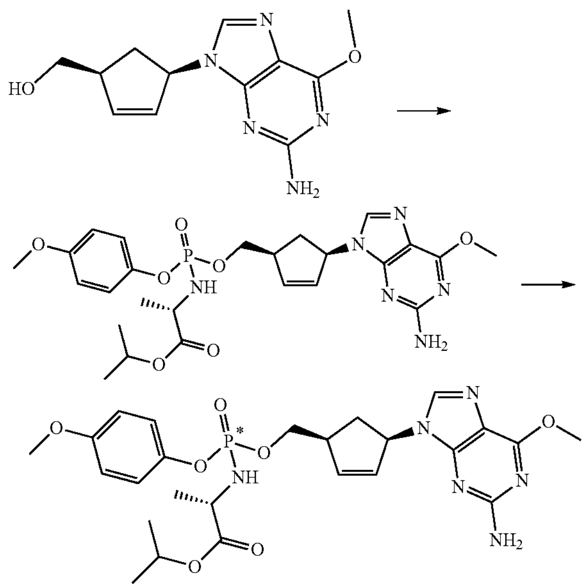

First Step

The following compound was obtained in the same manner as in Example 1-1.

Isopropyl ((((1S,4R)-4-(2-amino-6-methoxy-9H-purin-9-yl)cyclopent-2-en-1-yl)methoxy)(4-methoxyphenoxy)phosphoryl)-L-alaninate Second Step Isopropyl ((((1S,4R)-4-(2-amino-6-methoxy-9H-purin-9-yl)cyclopent-2-en-1-yl)methoxy)(4-methoxyphenoxy)phosphoryl)-L-alaninate obtained in the first step was subjected to chiral resolution by supercritical fluid chromatography to give optically active substance A and optically active substance B.

Example 6-1-1 (Optically Active Substance A)

$^1$H-NMR ($CDCl_3$) δ: 7.61 (s, 1H), 7.16-7.09 (m, 2H), 6.84-6.77 (m, 2H), 6.13-6.06 (m, 1H), 5.90-5.84 (m, 1H), 5.58-5.49 (m, 1H), 5.06-4.92 (m, 3H), 4.28-4.15 (m, 2H), 4.07 (s, 3H), 4.03-3.89 (m, 1H), 3.76 (s, 3H), 3.58-3.47 (m, 1H), 3.23-3.12 (m, 1H), 2.84-2.71 (m, 1H), 1.81-1.70 (m, 1H), 1.33 (d, 3H. J=7.3 Hz), 1.25-1.18 (m, 6H).

MS (ESI m/z): 561 (M+H)

RT (min): 1.19

Example 6-1-2 (Optically Active Substance B)

$^1$H-NMR ($CDCl_3$) δ: 7.62 (s, 1H), 7.15-7.08 (m, 2H), 6.84-6.77 (m, 2H), 6.10-6.05 (m, 1H), 5.91-5.85 (m, 1H), 5.57-5.49 (m, 1H), 5.07-4.94 (m, 3H), 4.29-4.11 (m, 2H), 4.07 (s, 3H), 4.02-3.88 (m, 1H), 3.77 (s, 3H), 3.62-3.51 (m, 1H), 3.21-3.10 (m, 1H), 2.82-2.70 (m, 1H), 1.79-1.68 (m, 1H), 1.37 (d, 3H, J=6.9 Hz), 1.22 (d, 6H, J=6.3 Hz).

MS (ESI m/z): 561 (M+H)

RT (min): 1.20

Conditions for Supercritical Fluid Chromatography

Column: CHIRALPAK IA (manufactured by Daicel Chemical Industries, Ltd.)

Mobile phase: carbon dioxide/methanol (volume ratio: 82/18)

Retention time: 3.97 min (optically active substance A), 6.44 min (optically active substance B)

Example 6-2

The compounds in Tables 7-1 to 7-4 were obtained in the same manner as in Example 6-1.

TABLE 7-1

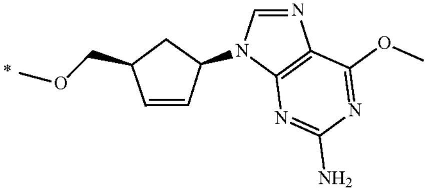

| Example No. | R | Compound name | $^1$H-NMR | MS (ESI m/z) (M + H) | Supercritical fluid chromatography RT (min) | Column Mobile phase | Retention time (min) |
|---|---|---|---|---|---|---|---|
| 6-2-1 (Optically active substance A) | 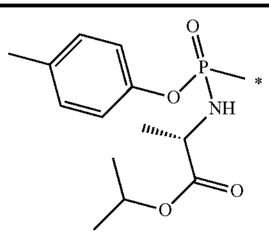 | Isopropyl ((((1S,4R)-4-(2-amino-6-methoxy-9H-purin-9-yl)cyclopent-2-en-1 -yl)methoxy)(p-toluyloxy)phosphoryl)-L-alaninate | $^1$H-NMR ($CDCl_3$) δ: 7.59 (s, 1H), 7.08 (s, 4H), 6.12-6.06 (m, 1H), 5.89-5.83 (m, 1H), 5.58-5.50 (m, 1H), 5.05-4.92 (m, 3H), 4.32-4.12 (m, 2H), 4.07 (s, 3H), 4.03-3.89 (m, 1H), 3.61-3.51 (m, 1H), 3.23-3.12 (m, 1H), 2.84-2.71 (m, 1H), 2.29 (s, 3H), 1.80-1.69 (m, 1H), 1.34 (d, 3H, J = 6.9 Hz), 1.24-1.17 (m, 6H). | 545 | 1.28 | CHIRALPAK IA carbon dioxide/methanol (volume ratio: 85/15) | 5.08 |
| 6-2-2 (Optically active substance B) | 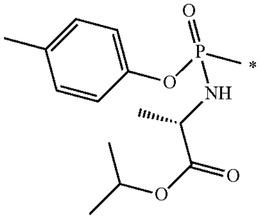 | Isopropyl ((((1S,4R)-4-(2-amino-6-methoxy-9H-purin-9-yl)cyclopent-2-en-1-yl)methoxy)(p-toluyloxy)phosphoryl)-L-alaninate | $^1$H-NMR ($CDCl_3$) δ: 7.61 (s, 1H), 7.08 (s, 4H), 6.11-6.05 (m, 1H), 5.90-5.85 (m, 1H), 5.57-5.49 (m, 1H), 5.07-4.93 (m, 3H), 4.31-4.10 (m, 2H), 4.07 (s, 3H), 4.03-3.89 (m, 1H), 3.68-3.57 (m, 1H), 3.22-3.08 (m, 1H), 2.82-2.70 (m, 1H), 2.29 (s, 3H), 1.78-1.67 (m, 1H), 1.37 (d, 3H, J = 6.9 Hz), 1.22 (d, 6H, J = 6.3 Hz) | 545 | 1.29 | | 8.03 |
| 6-2-3 (Optically active substance A) | 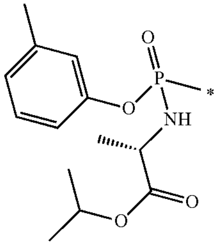 | Isopropyl ((((1S,4R)-4-(2-amino-6-methoxy-9H-purin-9-yl)cyclopent-2-en-1-yl)methoxy)(m-amino-6-methoxy-9H-purin-9-toluyloxy)phosphoryl)-L-alaninate | $^1$H-NMR ($CDCl_3$) δ: 7.58 (s, 1H), 7.21-7.13 (m, 1H), 7.06-6.91 (m, 3H), 6.12-6.06 (m, 1H), 5.89-5.83 (m, 1H), 5.58-5.49 (m, 1H), 5.05-4.92 (m, 3H), 4.32-4.13 (m, 2H), 4.07 (s, 3H), 4.05-3.90 (m, 1H), 3.64-3.53 (m, 1H), 3.24-3.12 (m, 1H), 2.83-2.71 (m, 1H), 2.30 (s, 3H), 1.81-1.70 (m, 1H), 1.35 (d, 3H, J = 6.9 Hz), 1.24-1.17 (m, 6H). | 545 | 1.27 | CHIRALPAK IA carbon dioxide/methanol (volume ratio: 88/12) | 5.32 |

TABLE 7-1-continued

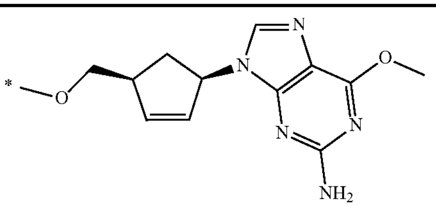

| Example No. | R | Compound name | $^1$H-NMR | MS (ESI m/z) (M + H) | Supercritical fluid chromatography RT (min) | Column Mobile phase | Retention time (min) |
|---|---|---|---|---|---|---|---|
| 6-2-4 (Optically active substance B) | 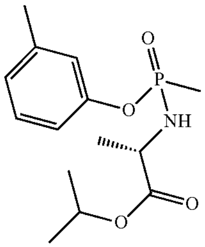 | Isopropyl ((((1S,4R)-4-(2-amino-6-methoxy-9H-purin-9-yl)cyclopent-2-en-1-yl)methoxy)(m-toluyloxy)phosphoryl)-L-alaninate | $^1$H-NMR ($CDCl_3$) δ: 7.61 (s, 1H), 7.21-7.13 (m, 1H), 7.04-6.92 (m, 3H), 6.11-6.05 (m, 1H), 5.90-5.85 (m, 1H), 5.58-5.49 (m, 1H), 5.07-4.93 (m, 3H), 4.31-4.11 (m, 2H), 4.07 (s, 3H), 4.04-3.89 (m, 1H), 3.72-3.59 (m, 1H), 3.23-3.10 (m, 1H), 2.83-2.70 (m, 1H), 2.31 (s, 3H), 1.80-1.68 (m, 1H), 1.37 (d, 3H, J = 6.9 Hz), 1.22 (d, 6H, J = 6.3 Hz). | 545 | 1.29 | | 9.55 |
| 6-2-5 (Optically active substance A) | 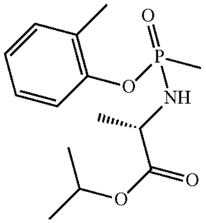 | Isopropyl ((((1S,4R)-4-(2-amino-6-methoxy-9H-purin-9-yl)cyclopent-2-en-1-yl)methoxy)(o-toluyloxy)phosphoryl)-L-alaninate | $^1$H-NMR ($CDCl_3$) δ: 7.55 (s, 1H), 7.34-7.29 (m, 1H), 7.20-6.99 (m, 3H), 6.09-6.04 (m, 1H), 5.88-5.83 (m, 1H), 5.57-5.48 (m, 1H), 5.07-4.93 (m, 3H), 4.31-4.11 (m, 2H), 4.09-3.93 (m, 4H), 3.66-3.56 (m, 1H), 3.22-3.10 (m, 1H), 2.81-2.69 (m, 1H), 2.28 (s, 3H), 1.76-1.65 (m, 1H), 1.37 (d, 3H, J = 6.9 Hz), 1.25-1.19 (m, 6H). | 545 | 1.27 | CHIRALPAK IA carbon dioxide/methanol (volume ratio: 85/15) | 3.68 |
| 6-2-6 (Optically active substance B) | 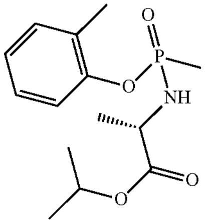 | Isopropyl ((((1S,4R)-4-(2-amino-6-methoxy-9H-purin-9-yl)cyclopent-2-en-1-yl)methoxy)(o-toluyloxy)phosphoryl)-L-alaninate | $^1$H-NMR ($CDCl_3$) δ: 7.57 (s, 1H), 7.33-7.28 (m, 1H), 7.20-7.01 (m, 3H), 6.06-6.01 (m, 1H), 5.89-5.84 (m, 1H), 5.56-5.48 (m, 1H), 5.07-4.93 (m, 3H), 4.29-4.11 (m, 2H), 4.09-3.91 (m, 4H), 3.71-3.61 (m, 1H), 3.20-3.08 (m, 1H), 2.80-2.68 (m, 1H), 2.28 (s, 3H), 1.77-1.66 (m, 1H), 1.40 (d, 3H, J = 7.3 Hz), 1.23 (d, 6H, J = 6.3 Hz). | 545 | 1.28 | | 5.98 |

TABLE 7-1-continued

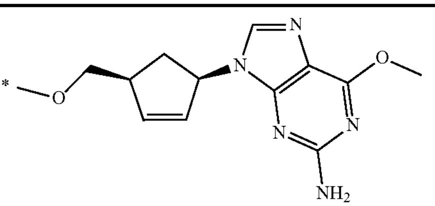

| Example No. | R | Compound name | $^1$H-NMR | MS (ESI m/z) (M + H) | Supercritical fluid chromatography RT (min) | Column Mobile phase | Retention time (min) |
|---|---|---|---|---|---|---|---|
| 6-2-7 (Optically active substance A) | 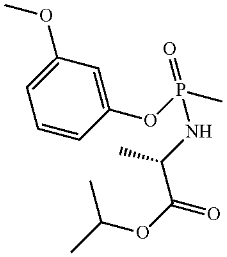 | Isopropyl ((((1S,4R)-4-(2-amino-6-methoxy-9H-purin-9-yl)cyclopent-2-en-1-yl)methoxy)(3-methoxyphenoxy)phosphoryl)-L-alaninate | $^1$H-NMR ($CDCl_3$) δ: 7.60 (s, 1H), 7.22-7.15 (m, 1H), 6.84-6.77 (m, 2H), 6.72-6.66 (m, 1H), 6.13-6.07 (m, 1H), 5.90-5.84 (m, 1H), 5.58-5.50 (m, 1H), 5.06-4.92 (m, 3H), 4.31-4.16 (m, 2H), 4.07 (s, 3H), 4.04-3.90 (m, 1H), 3.77 (s, 3H), 3.64-3.54 (m, 1H), 3.24-3.13 (m, 1H), 2.84-2.72 (m, 1H), 1.81-1.70 (m, 1H), 1.35 (d, 3H, J = 7.3 Hz), 1.24-1.18 (m, 6H). | 561 | 1.21 | CHIRALPAK IA carbon dioxide/methanol (volume ratio: 85/15) | 4.09 |
| 6-2-8 (Optically active substance B) | 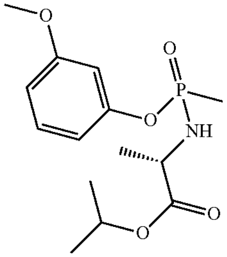 | Isopropyl ((((1S,4R)-4-(2-amino-6-methoxy-9H-purin-9-yl)cyclopent-2-en-1-yl)methoxy)(3-methoxyphenoxy)phosphoryl)-L-alaninate | $^1$H-NMR ($CDCl_3$) δ: 7.61 (s, 1H), 7.23-7.15 (m, 1H), 6.83-6.76 (m, 2H), 6.73-6.67 (m, 1H), 6.11-6.06 (m, 1H), 5.91-5.85 (m, 1H), 5.57-5.49 (m, 1H), 5.07-4.91 (m, 3H), 4.32-4.13 (m, 2H), 4.07 (s, 3H), 4.04-3.90 (m, 1H), 3.78 (s, 3H), 3.68-3.58 (m, 1H), 3.23-3.11 (m, 1H), 2.83-2.71 (m, 1H), 1.80-1.70 (m, 1H), 1.37 (d, 3H, J = 7.3 Hz), 1.22 (d, 6H, J = 6.3 Hz). | 561 | 1.22 | | 6.63 |

TABLE 7-2

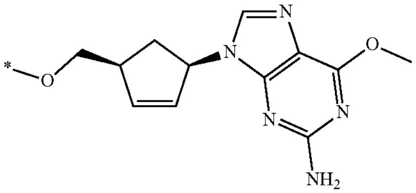

| Example No. | R | Compound name | $^1$H-NMR | MS (ESI m/z (M + H) | RT (min) | Supercritical fluid chromatography Column Mobile phase | Retention time (min) |
|---|---|---|---|---|---|---|---|
| 6-2-9 (Optically active substance A) | 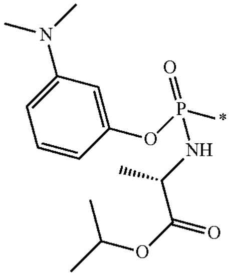 [SMILES: *P(=O)(N[C@@H](C)C(=O)OC(C)C)Oc1cccc(N(C)C)c1] | Isopropyl ((((1S,4R)-4-(2-amino-6-methoxy-9H-purin-9-yl)cyclopent-2-en-1 -yl)methoxy)(3-(dimethylamino)phenoxy)phosphoryl)-L-alaninate | $^1$H-NMR ($CDCl_3$) δ: 7.60 (s, 1H), 7.15-7.08 (m, 1H), 6.57-6.44 (m, 3H), 6.13-6.08 (m, 1H), 5.89-5.83 (m, 1H), 5.58-5.49 (m, 1H), 5.06-4.89 (m, 3H), 4.31-4.13 (m, 2H), 4.09-3.91 (m, 4H), 3.59-3.48 (m, 1H), 3.24-3.11 (m, 1H), 2.91 (s, 6H), 2.83-2.71 (m, 1H), 1.80-1.70 (m, 1H), 1.35 (d, 3H, J = 6.9 Hz), 1.24-1.18 (m, 6H). | 574 | 1.20 | CHIRALPAK IA carbon dioxide/methanol (volume ratio: 82/18) | 3.49 |
| 6-2-10 (Optically active substance B) | 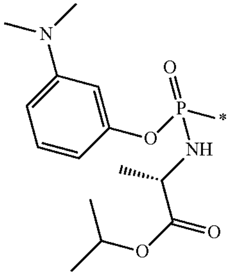 [SMILES: *P(=O)(N[C@@H](C)C(=O)OC(C)C)Oc1cccc(N(C)C)c1] | Isopropyl ((((1S,4R)-4-(2-amino-6-methoxy-9H-purin-9-yl)cyclopent-2-en-1-yl)methoxy)(3-(dimethylamino)phenoxy) phosphoryl)-L-alaninate | $^1$H-NMR ($CDCl_3$) δ: 7.62 (s, 1H), 7.17-7.08 (m, 1H), 6.57-6.45 (m, 3H), 6.11-6.06 (m, 1H), 5.89-5.84 (m, 1H), 5.57-5.49 (m, 1H), 5.06-4.94 (m, 3H), 4.30-4.12 (m, 2H), 4.10-3.90 (m, 4H), 3.66-3.56 (m, 1H), 3.22-3.10 (m, 1H), 2.92 (s, 6H), 2.82-2.70 (m, 1H), 1.79-1.69 (m, 1H), 1.37 (d, 3H, J = 6.9 Hz), 1.22 (d, 6H, J = 6.3 Hz). | 574 | 1.21 | | 5.94 |

TABLE 7-2-continued

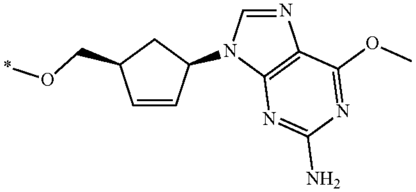

| Example No. | R | Compound name | $^1$H-NMR | MS (ESI m/z (M + H) | RT (min) | Supercritical fluid chromatography Column Mobile phase | Retention time (min) |
|---|---|---|---|---|---|---|---|
| 6-2-11 (Optically active substance A) | 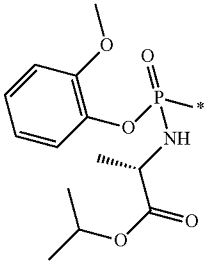 [SMILES: *P(=O)(N[C@@H](C)C(=O)OC(C)C)Oc1ccccc1OC] | Isopropyl ((((1S,4R)-4-(2-amino-6-methoxy-9H-purin-9-yl)cyclopent-2-en-1 -yl)methoxy)(2-methoxyphenoxy)phosphoryl)-L-alaninate | $^1$H-NMR ($CDCl_3$) δ: 7.61 (s, 1H), 7.33-7.28 (m, 1H), 7.14-7.07 (m, 1H), 6.95-6.84 (m, 2H), 6.13-6.08 (m, 1H), 5.88-5.83 (m, 1H), 5.59-5.50 (m, 1H), 5.07-4.92 (m, 3H), 4.30-4.21 (m, 2H), 4.14-3.95 (m, 4H), 3.85 (s, 3H), 3.75-3.66 (m, 1H), 3.25-3.12 (m, 1H), 2.84-2.72 (m, 1H), 1.81-1.70 (m, 1H), 1.29 (d, 3H, J = 6.9 Hz), 1.24-1.17 (m, 6H). | 561 | 1.19 | CHIRALPAK IA carbon dioxide/methanol (volume ratio: 85/15) | 4.47 |
| 6-2-12 (Optically active substance B) | 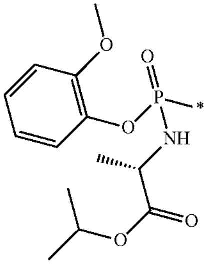 [SMILES: *P(=O)(N[C@@H](C)C(=O)OC(C)C)Oc1ccccc1OC] | Isopropyl ((((1S,4R)-4-(2-amino-6-methoxy-9H-purin-9-yl)cyclopent-2-en-1 -yl)methoxy)(2-methoxyphenoxy)phosphoryl)-L-alaninate | $^1$H-NMR ($CDCl_3$) δ: 7.62 (s, 1H), 7.33-7.26 (m, 1H), 7.14-7.07 (m, 1H), 6.95-6.85 (m, 2H), 6.14-6.08 (m, 1H), 5.90-5.84 (m, 1H), 5.59-5.50 (m, 1H), 5.06-4.91 (m, 3H), 4.32-4.18 (m, 2H), 4.12-3.96 (m, 4H), 3.91-3.81 (m, 4H), 3.25-3.11 (m, 1H), 2.83-2.70 (m, 1H), 1.82-1.71 (m, 1H), 1.37 (d, 3H, J = 6.9 Hz), 1.25-1.17 (m, 6H). | 561 | 1.20 | | 6.98 |
| 6-2-13 (Optically active substance A) | 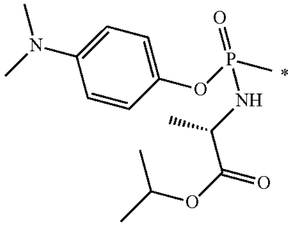 | Isopropyl ((((1S,4R)-4-(2-amino-6-methoxy-9H-purin-9-yl)cyclopent-2-en-1-yl)methoxy)(4-(dimethylamino)phenoxy) phosphoryl)-L-alaninate | $^1$H-NMR ($CDCl_3$) δ: 7.61 (s, 1H), 7.10-7.04 (m, 2H), 6.66-6.59 (m, 2H), 6.12-6.08 (m, 1H), 5.88-5.83 (m, 1H), 5.57-5.49 (m, 1H), 5.06-4.93 (m, 3H), 4.27-4.14 (m, 2H), 4.10-3.90 (m, 4H), 3.55-3.46 (m, 1H), 3.24-3.11 (m, 1H), 2.88 (s, 6H), 2.83-2.71 (m, 1H), 1.80-1.69 (m, 1H), 1.34 (d, 3H, J = 7.3 Hz), 1.25-1.17 (m, 6H). | 574 | 0.97 | CHIRALPAK IA carbon dioxide/methanol (volume ratio: 88/12) | 5.70 |

TABLE 7-2-continued

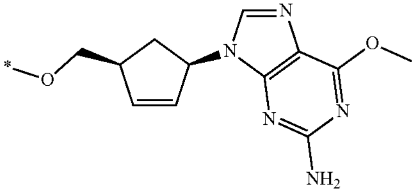

| Example No. | R | Compound name | $^1$H-NMR | MS (ESI m/z (M + H) | Supercritical fluid chromatography RT (min) | Column Mobile phase | Retention time (min) |
|---|---|---|---|---|---|---|---|
| 6-2-14 (Optically active substance B) | 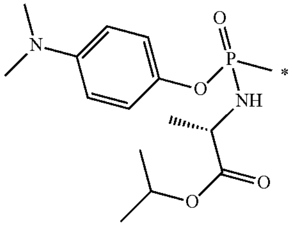 | Isopropyl ((((1S,4R)-4-(2-amino-6-methoxy-9H-purin-9-yl)cyclopent-2-en-1- yl)methoxy)(4-(dimethylamino)phenoxy) phosphoryl)-L-alaninate | $^1$H-NMR ($CDCl_3$) δ: 7.63 (s, 1H), 7.10-7.03 (m, 2H), 6.66-6.60 (m, 2H), 6.11-6.06 (m, 1H), 5.89-5.84 (m, 1H), 5.57-5.49 (m, 1H), 5.06-4.93 (m, 3H), 4.27-4.10 (m, 2H), 4.07 (s, 3H), 4.02-3.89 (m, 1H), 3.62-3.52 (m, 1H), 3.22-3.07 (m, 1H), 2.89 (s, 6H), 2.82-2.70 (m, 1H), 1.78-1.68 (m, 1H), 1.37 (d, 3H, J = 7.3 Hz), 1.22 (d, 6H, J = 6.3 Hz). | 574 | 0.98 | | 9.00 |
| 6-2-15 (Optically active substance A) | 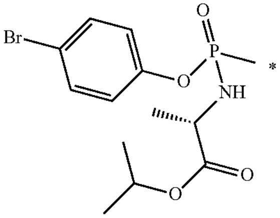 | Isopropyl ((((1S,4R)-4-(2-amino-6-methoxy-9H-purin-9-yl)cyclopent-2-en-1-yl)methoxy)(4-bromophenoxy)phosphoryl)-L-alaninate | $^1$H-NMR ($CDCl_3$) δ: 7.61 (s, 1H), 7.45-7.38 (m, 2H), 7.15-7.08 (m, 2H), 6.12-6.06 (m, 1H), 5.92-5.86 (m, 1H), 5.59-5.50 (m, 1H), 5.07-4.90 (m, 3H), 4.32-4.16 (m, 2H), 4.07 (s, 3H), 4.00-3.86 (m, 1H), 3.66-3.56 (m, 1H), 3.25-3.13 (m, 1H), 2.85-2.73 (m, 1H), 1.82-1.71 (m, 1H), 1.34 (d, 3H, J = 6.9 Hz), 1.24-1.17 (m, 6H). | 609<br>611 | 1.34 | CHIRALPAK AS-H carbon dioxide/methanol (volume ratio: 88/12) | 2.57 |
| 6-2-16 (Optically active substance B) | 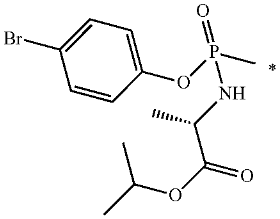 | Isopropyl ((((1S,4R)-4-(2-amino-6-methoxy-9H-purin-9-yl)cyclopent-2-en-1-yl)methoxy)(4-bromophenoxy)phosphoryl)-L-alaninate | $^1$H-NMR ($CDCl_3$) δ: 7.62 (s, 1H), 7.44-7.37 (m, 2H), 7.13-7.06 (m, 2H), 6.10-6.05 (m, 1H), 5.93-5.87 (m, 1H), 5.58-5.49 (m, 1H), 5.06-4.91 (m, 3H), 4.32-4.13 (m, 2H), 4.07 (s, 3H), 4.02-3.87 (m, 1H), 3.72-3.61 (m, 1H), 3.22-3.10 (m, 1H), 2.84-2.71 (m, 1H), 1.81-1.69 (m, 1H), 1.37 (d, 3H, J = 6.9 Hz), 1.22 (d, 6H, J = 6.3 Hz). | 609<br>611 | 1.35 | | 6.18 |

TABLE 7-3

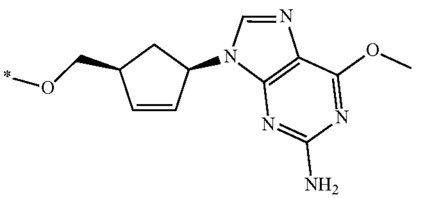

| Example No. | R | Compound name | $^{1}$H-NMR | MS (ESI m/z) (M + H) | Supercritical fluid chromatography RT (min) | Column Mobile phase | Retention time (min) |
|---|---|---|---|---|---|---|---|
| 6-2-17 (Optically active substance A) | 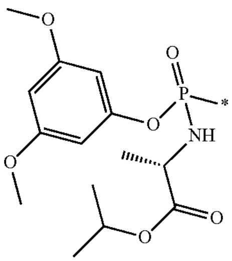 [SMILES: *P(=O)(N[C@@H](C)C(=O)OC(C)C)Oc1cc(OC)cc(OC)c1] | Isopropyl ((((1S,4R)-4-(2-amino-6-methoxy-9H-purin-9-yl)cyclopent-2-en-1-yl)methoxy)(3,5-dimethoxyphenoxy)phosphoryl)-L-alaninate | $^{1}$H-NMR ($CDCl_3$) δ: 7.62 (s, 1H), 6.43-6.38 (m, 2H), 6.27-6.23 (m, 1H), 6.13-6.07 (m, 1H), 5.91-5.86 (m, 1H), 5.58-5.50 (m, 1H), 5.06-4.92 (m, 3H), 4.31-4.15 (m, 2H), 4.07 (s, 3H), 4.03-3.90 (m, 1H), 3.74 (s, 6H), 3.64-3.55 (m, 1H), 3.25-3.14 (m, 1H), 2.85-2.71 (m, 1H), 1.83-1.72 (m, 1H), 1.35 (d, 3H, J = 6.9 Hz), 1.24-1.18 (m, 6H). | 591 | 1.24 | CHIRALPAK AS-H carbon dioxide/methanol (volume ratio: 88/12) | 2.34 |
| 6-2-18 (Optically active substance B) | 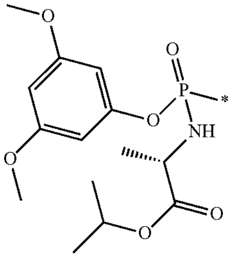 [SMILES: *P(=O)(N[C@@H](C)C(=O)OC(C)C)Oc1cc(OC)cc(OC)c1] | Isopropyl ((((1S,4R)-4-(2-amino-6-methoxy-9H-purin-9-yl)cyclopent-2-en-1-yl)methoxy)(3,5-dimethoxyphenoxy)phosphoryl)-L-alaninate | $^{1}$H-NMR ($CDCl_3$) δ: 7.63 (s, 1H), 6.42-6.38 (m, 2H), 6.27-6.24 (m, 1H), 6.12-6.07 (m, 1H), 5.91-5.86 (m, 1H), 5.57-5.49 (m, 1H), 5.06-4.93 (m, 3H), 4.32-4.12 (m, 2H), 4.06 (s, 3H), 4.03-3.90 (m, 1H), 3.75 (s, 6H), 3.70-3.60 (m, 1H), 3.23-3.11 (m, 1H), 2.84-2.72 (m, 1H), 1.81-1.71 (m, 1H), 1.38 (d, 3H, J = 6.9 Hz), 1.22 (d, 6H, J = 6.3 Hz). | 591 | 1.24 | | 5.88 |

TABLE 7-3-continued

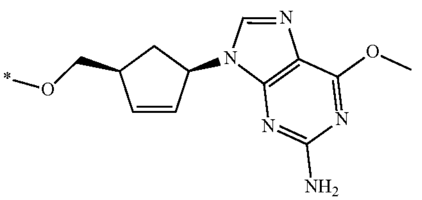

| Example No. | R | Compound name | $^1$H-NMR | MS (ESI m/z) (M + H) | Supercritical fluid chromatography RT (min) | Column Mobile phase | Retention time (min) |
|---|---|---|---|---|---|---|---|
| 6-2-19 (Optically active substance A) | 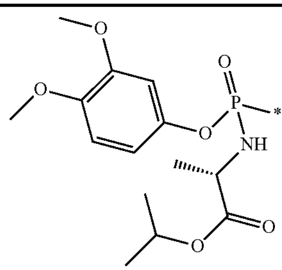 | Isopropyl ((((1S,4R)-4-(2-amino-6-methoxy-9H-purin-9-yl)cyclopent-2-en-1-yl)methoxy)(3,4-dimethoxyphenoxy)phosphoryl)-L-alaninate | $^1$H-NMR ($CDCl_3$) δ: 7.63 (s, 1H), 6.83-6.73 (m, 3H), 6.13-6.07 (m, 1H), 5.91-5.85 (m, 1H), 5.60-5.50 (m, 1H), 5.06-4.91 (m, 3H), 4.31-4.11 (m, 2H), 4.07 (s, 3H), 4.03-3.89 (m, 1H), 3.85 (s, 3H), 3.84 (s, 3H), 3.59-3.50 (m, 1H), 3.25-3.13 (m, 1H), 2.85-2.73 (m, 1H), 1.83-1.72 (m, 1H), 1.33 (d, 3H, J = 7.3 Hz), 1.24-1.17 (m, 6H). | 591 | 1.12 | CHIRALPAK IA carbon dioxide/methanol (volume ratio: 80/20) | 2.86 |
| 6-2-20 (Optically active substance B) | 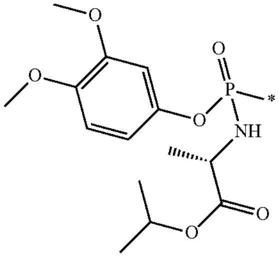 [SMILES: *P(=O)(N[C@@H](C)C(=O)OC(C)C)Oc1ccc(OC)c(OC)c1] | Isopropyl ((((1S,4R)-4-(2-amino-6-methoxy-9H-purin-9-yl)cyclopent-2-en-1-yl)methoxy)(3,4-dimethoxyphenoxy)phosphoryl)-L-alaninate | 1H-NMR ($CDCl_3$) δ: 7.64 (s, 1H), 6.83-6.72 (m, 3H), 6.11-6.06 (m, 1H), 5.92-5.86 (m, 1H), 5.58-5.49 (m, 1H), 5.07-4.93 (m, 3H), 4.32-4.12 (m, 2H), 4.06 (s, 3H), 4.04-3.89 (m, 1H), 3.85 (s, 3H), 3.84 (s, 3H), 3.66-3.57 (m, 1H), 3.23-3.10 (m, 1H), 2.84-2.71 (m, 1H), 1.81-1.69 (m, 1H), 1.38 (d, 3H, J = 6.9 Hz), 1.25-1.20 (m, 6H). | 591 | 1.13 | | 4.80 |
| 6-2-21 (Optically active substance A) | 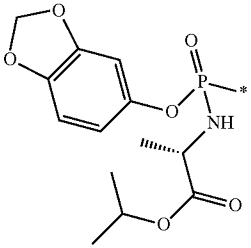 [SMILES: *P(=O)(N[C@@H](C)C(=O)OC(C)C)Oc1ccc2c(c1)OCO2] | Isopropyl ((((1S,4R)-4-(2-amino-6-methoxy-9H-purin-9-yl)cyclopent-2-en-1-yl)methoxy)(benzo[d][1,3]dioxolo-5-yloxy)phosphoryl)-L-alaninate | $^1$H-NMR ($CDCl_3$) δ: 7.61 (s, 1H), 6.78-6.62 (m, 3H), 6.14-6.07 (m, 1H), 5.98-5.85 (m, 3H), 5.58-5.49 (m, 3H), 4.03-3.88 (m, 1H), 3.62-3.50 (m, 1H), 3.25-3.12 1H), 5.07-4.94 (m, 3H), 4.32-4.12 (m, 2H), 4.07 (s, (m, 1H), 2.85-2.72 (m, 1H), 1.82-1.71 (m, 1H), 1.35 (d, 3H, J = 7.3 Hz), 1.27-1.18 (m, 6H). | 575 | 1.18 | CHIRALPAK AS-H carbon dioxide/methanol (volume ratio: 87/13) | 2.45 |

TABLE 7-3-continued

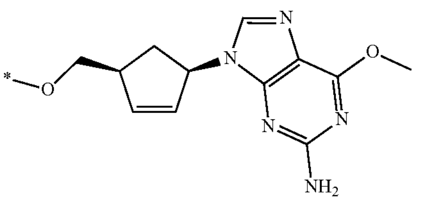

| Example No. | R | Compound name | $^1$H-NMR | MS (ESI m/z) (M + H) | Supercritical fluid chromatography RT (min) | Column Mobile phase | Retention time (min) |
|---|---|---|---|---|---|---|---|
| 6-2-22 (Optically active substance B) | 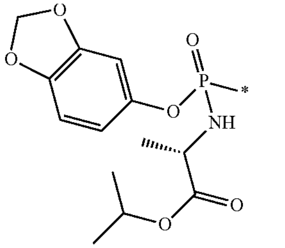 [SMILES: *P(=O)(N[C@@H](C)C(=O)OC(C)C)Oc1ccc2c(c1)OCO2] | Isopropyl ((((1S,4R)-4-(2-amino-6-methoxy-9H-purin-9-yl)cyclopent-2-en-1-yl)methoxy)(benzo[d][1,3]dioxolo-5-yloxy)phosphoryl)-L-alaninate | $^1$H-NMR ($CDCl_3$) δ: 7.61 (s, 1H), 6.77-6.61 (m, 3H), 6.13-6.06 (m, 1H), 5.99-5.86 (m, 3H), 5.58-5.49 (m, 3H), 4.02-3.88 (m, 1H), 3.68-3.56 (m, 1H), 3.23-3.10 1H), 5.09-4.90 (m, 3H), 4.32-4.12 (m, 2H), 4.07 (s, (m, 1H), 2.84-2.71 (m, 1H), 1.80-1.69 (m, 1H), 1.38 (d, 3H, J = 6.9 Hz), 1.23 (d, 6H, J = 6.3 Hz). | 575 | 1.18 | | 5.27 |
| 6-2-23 (Optically active substance A) | 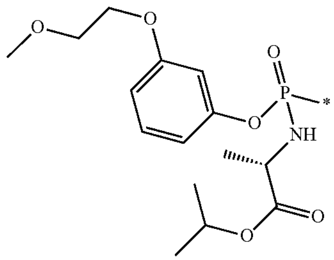 [SMILES: *P(=O)(N[C@@H](C)C(=O)OC(C)C)Oc1cccc(OCCOC)c1] | Isopropyl ((((1S,4R)-4-(2-amino-6-methoxy-9H-purin-9-yl)cyclopent-2-en-1-yl)methoxy)(3-(2-methoxyethoxy)phenoxy)phosphoryl)-L-alaninate | $^1$H-NMR ($CDCl_3$) δ: 7.60 (s, 1H), 7.21-7.14 (m, 1H), 6.86-6.69 (m, 3H), 6.14-6.06 (m, 1H), 5.91-5.84 (m, 1H), 5.59-5.48 (m, 1H), 5.06-4.92 (m, 3H), 4.32-3.89 (m, 8H), 3.75-3.69 (m, 2H), 3.63-3.52 (m, 1H), 3.43 (s, 3H), 3.24-3.11 (m, 1H), 2.84-2.71 (m, 1H), 1.82-1.70 (m, 1H), 1.34 (d, 3H, J = 7.3 Hz), 1.24-1.18 (m, 6H). | 605 | 1.20 | CHIRALPAK AS-H carbon dioxide/methanol (volume ratio: 87/13) | 1.94 |

TABLE 7-3-continued
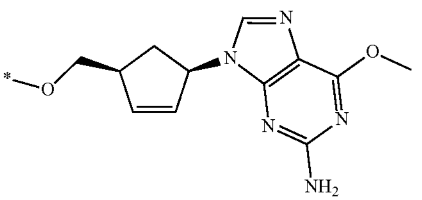
| Example No. | R | Compound name | $^1$H-NMR | MS (ESI m/z) (M + H) | RT (min) | Supercritical fluid chromatography Column Mobile phase | Retention time (min) |
|---|---|---|---|---|---|---|---|
| 6-2-24 (Optically active substance B) | 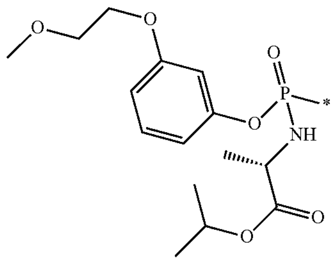 [SMILES: *P(=O)(N[C@@H](C)C(=O)OC(C)C)Oc1cccc(OCCOC)c1] | Isopropyl ((((1S,4R)-4-(2-amino-6-methoxy-9H-purin-9-yl)cyclopent-2-en-1-yl)methoxy)(3-(2-methoxyethoxy)phenoxy)phosphoryl)-L-alaninate | $^1$H-NMR ($CDCl_3$) δ: 7.62 (s, 1H), 7.22-7.14 (m, 1H), 6.84-6.69 (m, 3H), 6.10-6.04 (m, 1H), 5.90-5.85 (m, 1H), 5.57-5.48 (m, 1H), 5.09-4.91 (m, 3H), 4.32-3.88 (m, 8H), 3.76-3.58 (m, 3H), 3.43 (s, 3H), 3.23-3.10 (m, 1H), 2.83-2.70 (m, 1H), 1.81-1.69 (m, 1H), 1.37 (d, 3H, J = 6.9 Hz), 1.22 (d, 6H, J = 6.3 Hz). | 605 | 1.20 | | 4.93 |

TABLE 7-4

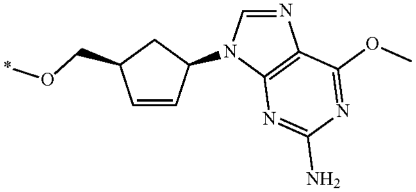

| Example No. | R | Compound name | $^1$H-NMR | MS (ESI m/z) (M+H) | Supercritical fluid chromatography RT (min) | Column Mobile phase | Retention time (min) |
|---|---|---|---|---|---|---|---|
| 6-2-25 (Optically active substance A) | 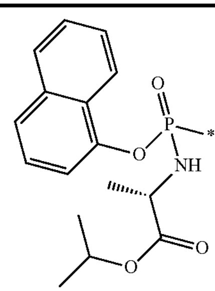 | Isopropyl ((((1S,4R)-4-(2-amino-6-methoxy-9H-purin-9-yl)cyclopent-2-en-1-yl)methoxy)(naphthalen-1-yloxy)phosphoryl)-L-alaninate | $^1$H-NMR ($CDCl_3$) δ: 8.15-8.05 (m, 1H), 7.85-7.77 (m, 1H), 7.66-7.58 (m, 1H), 7.56-7.46 (m, 4H), 7.39-7.32 (m, 1H), 6.04-5.98 (m, 1H), 5.85-5.79 (m, 1H), 5.53-5.44 (m, 1H), 5.01-4.87 (m, 3H), 4.32-4.19 (m, 2H), 4.12-3.98 (m, 4H), 3.73-3.62 (m, 1H), 3.21-3.08 (m, 1H), 2.76-2.63 (m, 1H), 1.74-1.63 (m, 1H), 1.34 (d, 3H, J = 6.9 Hz), 1.20-1.12 (m, 6H). | 581 | 1.35 | CHIRALPAK AS-H carbon dioxide/methanol (volume ratio: 83/17) | 1.92 |
| 6-2-26 (Optically active substance B) | 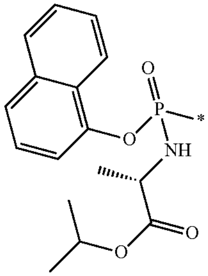 [SMILES: *P(=O)(N[C@@H](C)C(=O)OC(C)C)Oc1cccc2ccccc12] | Isopropyl ((((1S,4R)-4-(2-amino-6-methoxy-9H-purin-9-yl)cyclopent-2-en-1 -yl)methoxy)(naphthalen-1-yloxy)phosphoryl)-L-alaninate | $^1$H-NMR ($CDCl_3$) δ: 8.13-8.05 (m, 1H), 7.87-7.80 (m, 1H), 7.68-7.61 (m, 1H), 7.57 (s, 1H), 7.54-7.47 (m, 3H), 7.42-7.34 (m, 1H), 6.07-6.01 (m, 1H), 5.89-5.83 (m, 1H), 5.55-5.46 (m, 1H), 5.05-4.89 (m, 3H), 4.34-4.16 (m, 2H), 4.12-3.97 (m, 4H), 3.83-3.72 (m, 1H), 3.20-3.08 (m, 1H), 2.79-2.65 (m, 1H), 1.77-1.66 (m, 1H), 1.36 (d, 3H, J = 7.3 Hz), 1.19 (d, 6H, J = 6.3 Hz). | 581 | 1.36 | | 3.91 |

TABLE 7-4-continued

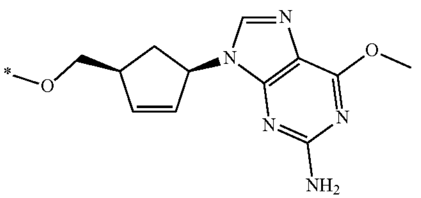

| Example No. | R | Compound name | $^1$H-NMR | MS (ESI m/z) (M+H) | RT (min) | Supercritical fluid chromatography Column Mobile phase | Retention time (min) |
|---|---|---|---|---|---|---|---|
| 6-2-27 (Optically active substance A) | 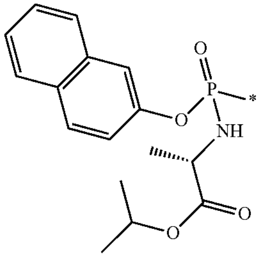 [SMILES: *P(=O)(N[C@@H](C)C(=O)OC(C)C)Oc1ccc2ccccc2c1] | Isopropyl ((((1S,4R)-4-(2-amino-6-methoxy-9H-purin-9-yl)cyclopent-2-en-1-yl)methoxy)(naphthalen-2-yloxy)phosphoryl)-L-alaninate | $^1$H-NMR ($CDCl_3$) δ: 7.83-7.65 (m, 4H), 7.59 (s, 1H), 7.49-7.32 (m, 3H), 6.11-6.05 (m, 1H), 5.86-5.80 (m, 1H), 5.55-5.47 (m, 1H), 5.08-4.88 (m, 3H), 4.35-4.19 (m, 2H), 4.08-3.94 (m, 4H), 3.73-3.63 (m, 1H), 3.24-3.13 (m, 1H), 2.82-2.69 (m, 1H), 1.82-1.71 (m, 1H), 1.35 (d, 3H, J = 6.9 Hz), 1.20-1.14 (m, 6H). | 581 | 1.35 | CHIRALPAK AS-H carbon dioxide/methanol (volume ratio: 83/17) | 1.91 |
| 6-2-28 6-2-28 (Optically active substance B) | 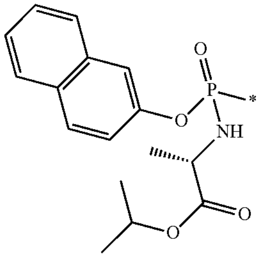 [SMILES: *P(=O)(N[C@@H](C)C(=O)OC(C)C)Oc1ccc2ccccc2c1] | Isopropyl ((((1S,4R)-4-(2-amino-6-methoxy-9H-purin-9-yl)cyclopent-2-en-1-yl)methoxy)(naphthalen-2-yloxy)phosphoryl)-L-alaninate | $^1$H-NMR ($CDCl_3$) δ: 7.83-7.66 (m, 4H), 7.63 (s, 1H), 7.50-7.30 (m, 3H), 6.12-6.05 (m, 1H), 5.90-5.83 (m, 1H), 5.57-5.47 (m, 1H), 5.06-4.90 (m, 3H), 4.35-4.16 (m, 2H), 4.09-3.93 (m, 4H), 3.78-3.66 (m, 1H), 3.23-3.11 (m, 1H), 2.83-2.69 (m, 1H), 1.81-1.70 (m, 1H), 1.38 (d, 3H, J = 7.3 Hz), 1.22-1.15 (m, 6H). | 581 | 1.36 | | 4.61 |

Example 7-1

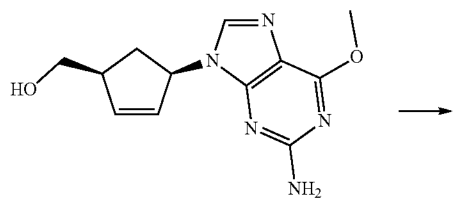

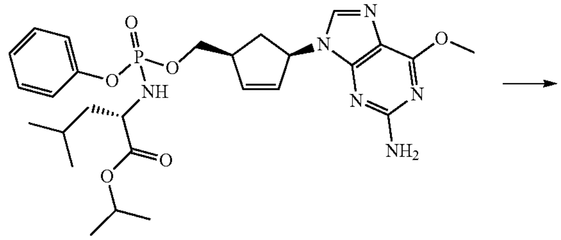

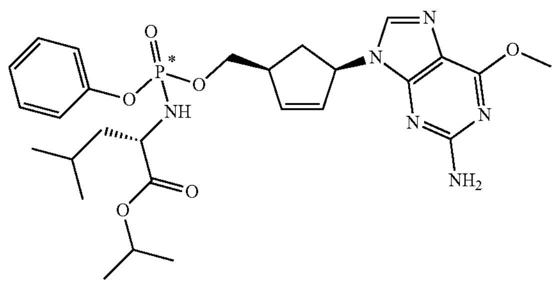

First Step

The following compound was obtained in the same manner as in Example 2-1.

Isopropyl ((((1S,4R)-4-(2-amino-6-methoxy-9H-purin-9-yl)cyclopent-2-en-1-yl)methoxy)(phenoxy)phosphoryl)-L-leucinate Second Step Isopropyl ((((1S,4R)-4-(2-amino-6-methoxy-9H-purin-9-yl)cyclopent-2-en-1-yl)methoxy)(phenoxy)phosphoryl)-L-leucinate obtained in the first step was subjected to chiral resolution by supercritical fluid chromatography to give optically active substance A and optically active substance B.

Example 7-1-1 (Optically Active Substance A)

$^{1}$H-NMR ($CDCl_3$) δ: 7.56 (s, 1H), 7.34-7.08 (m, 5H), 6.11-6.05 (m, 1H), 5.88-5.82 (m, 1H), 5.58-5.48 (m, 1H), 5.06-4.89 (m, 3H), 4.32-4.11 (m, 2H), 4.07 (s, 3H), 3.96-3.81 (m, 1H), 3.39-3.28 (m, 1H), 3.22-3.10 (m, 1H), 2.82-2.69 (m, 1H), 1.79-1.61 (m, 2H), 1.57-1.37 (m, 2H), 1.24-1.15 (m, 6H), 0.91-0.84 (m, 6H).

MS (ESI m/z): 573 (M+H)

RT (min): 1.43

Example 7-1-2 (Optically Active Substance B)

$^{1}$H-NMR ($CDCl_3$) δ: 7.59 (s, 1H), 7.34-7.09 (m, 5H), 6.08-6.02 (m, 1H), 5.89-5.83 (m, 1H), 5.57-5.47 (m, 1H), 5.07-4.90 (m, 3H), 4.31-4.01 (m, 5H), 3.96-3.81 (m, 1H), 3.52-3.41 (m, 1H), 3.20-3.08 (m, 1H), 2.80-2.68 (m, 1H), 1.80-1.63 (m, 2H), 1.59-1.37 (m, 2H), 1.24-1.17 (m, 6H), 0.94-0.84 (m, 6H).

MS (ESI m/z): 573 (M+H)

RT (min): 1.45

(Conditions for Supercritical Fluid Chromatography)

Column: CHIRALPAK IA (manufactured by Daicel Chemical Industries, Ltd.)

Mobile phase: carbon dioxide/methanol (volume ratio: 85/15)

Retention time: 3.43 min (optically active substance A), 5.68 min (optically active substance B)

Example 7-2

The compounds in Table 8 were obtained in the same manner as in Example 7-1.

TABLE 8

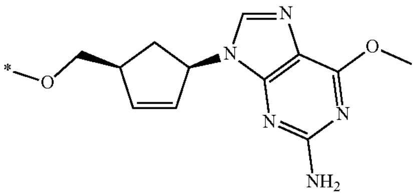

| Example No. | R | Compound name | $^1$H-NMR | MS (ESI m/z) (M + H) | Supercritical fluid chromatography RT (min) | Column Mobile phase | Retention time (min) |
|---|---|---|---|---|---|---|---|
| 7-2-1 (Optically active substance A) | 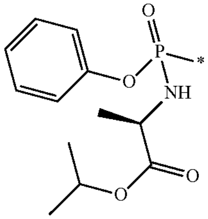 [SMILES: *P(=O)(N[C@H](C)C(=O)OC(C)C)Oc1ccccc1] | Isopropyl ((((1S,4R)-4-(2-amino-6-methoxy-9H-purin-9-yl)cyclopent-2-en-1-yl)methoxy)(phenoxy) phosphoryl)-D-alaninate | $^1$H-NMR ($CDCl_3$) δ: 7.63 (s, 1H), 7.35-7.11 (m, 5H), 6.13-6.06 (m, 1H), 5.93-5.86 (m, 1H), 5.58-5.49 (m, 1H), 5.05-4.93 (m, 3H), 4.32-4.16 (m, 2H), 4.12-3.92 (m, 4H), 3.64-3.52 (m, 1H), 3.24-3.11 (m, 1H), 2.85-2.71 (m, 1H), 1.81-1.71 (m, 1H), 1.34 (d, 3H, J = 6.9 Hz), 1.25-1.18 (m, 6H). | 531 | 1.19 | CHIRALPAK IA carbon dioxide/methanol (volume ratio: 88/12) | 7.15 |
| 7-2-2 (Optically active substance B) | 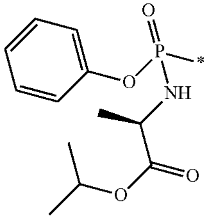 [SMILES: *P(=O)(N[C@H](C)C(=O)OC(C)C)Oc1ccccc1] | Isopropyl ((((1S,4R)-4-(2-amino-6-methoxy-9H-purin-9-yl)cyclopent-2-en-1-yl)methoxy)(phenoxy) phosphoryl)-D-alaninate | $^1$H-NMR ($CDCl_3$) δ: 7.58 (s, 1H), 7.36-7.11 (m, 5H), 6.11-6.05 (m, 1H), 5.88-5.82 (m, 1H), 5.57-5.49 (m, 1H), 5.06-4.91 (m, 3H), 4.32-4.11 3.51 (m, 1H), 3.23-3.10 (m, 1H), 2.83-2.70 (m, (m, 2H), 4.07 (s, 3H), 3.97-3.82 (m, 1H), 3.63-1H), 1.76-1.65 (m, 1H), 1.34 (d, 3H, J = 7.3 Hz), 1.24-1.17 (m, 6H). | 531 | 1.20 | | 8.54 |
| 7-2-3 (Optically active substance A) | 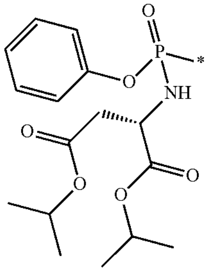 [SMILES: *P(=O)(N[C@@H](CC(=O)OC(C)C)C(=O)OC(C)C)Oc1ccccc1] | Diisopropyl ((((1S,4R)-4-(2-amino-6-methoxy-9H-purin-9-yl)cyclopent-2-en-1-yl)methoxy)(phenoxy) phosphoryl)-L-aspartate | $^1$H-NMR ($CDCl_3$) δ: 7.59 (s, 1H), 7.34-7.11 (m, 5H), 6.13-6.08 (m, 1H), 5.88-5.83 (m, 1H), 5.58-5.49 (m, 1H), 5.10-4.90 (m, 4H), 4.34-4.14 (m, 3H), 4.07 (s, 3H), 3.98-3.88 (m, 1H), 3.26-3.13 (m, 1H), 2.93-2.72 (m, 2H), 2.57 (dd, 1H, J = 16.8, 5.0 Hz), 1.81-1.70 (m, 1H), 1.25-1.16 (m, 12H). | 617 | 1.34 | CHIRALPAK AS-H carbon dioxide/methanol (volume ratio: 90/10) | 2.23 |

TABLE 8-continued

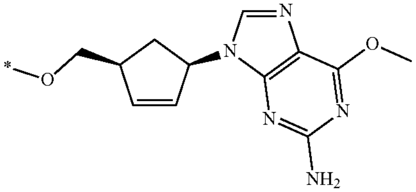

| Example No. | R | Compound name | $^1$H-NMR | MS (ESI m/z) (M + H) | Supercritical fluid chromatography RT (min) | Column Mobile phase | Retention time (min) |
|---|---|---|---|---|---|---|---|
| 7-2-4 (Optically active substance B) | 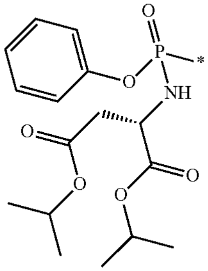 [SMILES: *P(=O)(N[C@@H](CC(=O)OC(C)C)C(=O)OC(C)C)Oc1ccccc1] | Diisopropyl ((((1S,4R)-4-(2-amino-6-methoxy-9H-purin-9-yl)cyclopent-2-en-1-yl)methoxy)(phenoxy) phosphoryl)-L-aspartate | $^1$H-NMR ($CDCl_3$) δ: 7.58 (s, 1H), 7.35-7.11 (m, 5H), 6.07-6.01 (m, 1H), 5.89-5.83 (m, 1H), 5.56-5.48 (m, 1H), 5.11-4.91 (m, 4H), 4.33-3.99 (m, 7H), 3.22-3.08 (m, 1H), 2.90 (dd, 1H, J = 16.7, 4.1 Hz), 2.81-2.67 (m, 2H), 1.76-1.66 (m, 1H), 1.25-1.16 (m, 12H). | 617 | 1.35 | | 4.25 |
| 7-2-5 (Optically active substance A) | 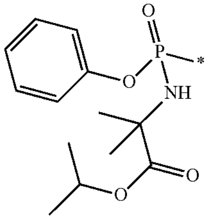 [SMILES: *P(=O)(NC(C)(C)C(=O)OC(C)C)Oc1ccccc1] | Isopropyl 2-(((((1S,4R)-4-(2-amino-6-methoxy-9H-purin-9-yl)methoxy)(phenoxy)phosph yl)cyclopent-2-en-1-oryl)amino)-2-methylpropanoate | $^1$H-NMR ($CDCl_3$) δ: 7.55 (s, 1H), 7.34-7.09 (m, 5H), 6.09-6.04 (m, 1H), 5.87-5.81 (m, 1H), 5.57-5.48 (m, 1H), 5.07-4.90 (m, 3H), 4.31-4.11 (m, 2H), 4.07 (s, 3H), 3.98 (d, 1H, J = 8.9 Hz), 3.22-3.09 (m, 1H), 2.81-2.69 (m, 1H), 1.76-1.65 (m, 1H), 1.53 (s, 3H), 1.50 (s, 3H), 1.27-1.19 (m, 6H). | 545 | 1.26 | CHIRALPAK AS-H carbon dioxide/ isopropanol (volume ratio: 88/12) | 6.07 |
| 7-2-6 (Optically active substance B) | 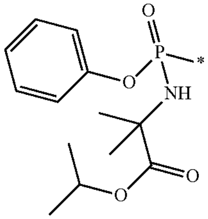 [SMILES: *P(=O)(NC(C)(C)C(=O)OC(C)C)Oc1ccccc1] | Isopropyl 2-(((((1S,4R)-4-(2-amino-6-methoxy-9H-purin-9-yl)cyclopent-2-en-1-yl)methoxy)(phenoxy) phosphoryl)amino)-2-methylpropanoate | $^1$H-NMR ($CDCl_3$) δ: 7.60 (s, 1H), 7.35-7.09 (m, 5H), 6.11-6.04 (m, 1H), 5.91-5.84 (m, 1H), 5.56-5.48 (m, 1H), 5.08-4.90 (m, 3H), 4.32-4.13 (m, 2H), 4.07 (s, 3H), 4.01 (d, 1H, J = 8.6 Hz), 3.21-3.09 (m, 1H), 2.82-2.68 (m, 1H), 1.79-1.68 (m, 1H), 1.53 (s, 3H), 1.52 (s, 3H), 1.28-1.20 (m, 6H). | 545 | 1.26 | | 8.50 |

Example 8

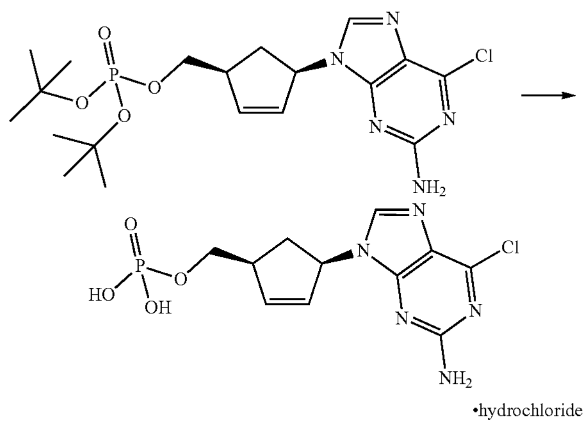

4 M hydrochloric acid/cyclopentyl methyl ether (20 mL) was added to a mixture of ((1S,4R)-4-(2-amino-6-chloro-9H-purin-9-yl)cyclopent-2-en-1-yl)methyl di-tert-butyl phosphate (4.8 g) and ethyl acetate (50 mL) which was then stirred at room temperature for 3 hours. The resulting solid was collected by filtration and washed with ethyl acetate to give ((1S,4R)-4-(2-amino-6-chloro-9H-purin-9-yl)cyclopent-2-en-1-yl)methyl dihydrogen phosphate hydrochloride (4.2 g) as a white solid.

$^1$H-NMR (DMSO-d$_6$) δ: 8.11 (s, 1H), 6.16-6.11 (m, 1H), 5.97-5.92 (m, 1H), 5.55-5.46 (m, 1H), 4.00-3.86 (m, 2H), 3.15-3.02 (m, 1H), 2.76-2.63 (m, 1H), 1.79-1.67 (m, 1H).

MS (ESI m/z): 346, 348 (M+H)

RT (min): 0.51

Example 9

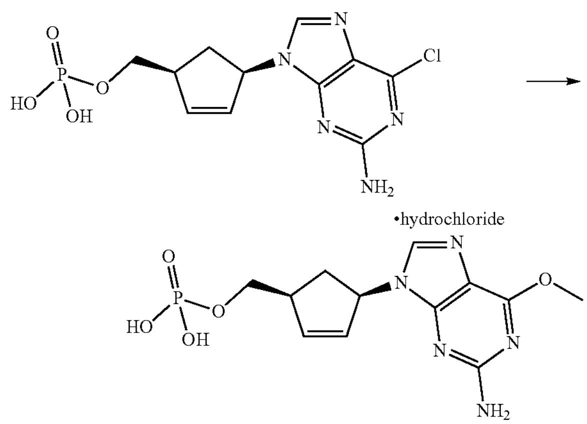

A 5 M sodium methoxide/methanol solution (44 μL) was added to a mixture of (1S,4R)-4-(2-amino-6-chloro-9H-purin-9-yl)cyclopent-2-en-1-yl)methyl dihydrogen phosphate hydrochloride (21 mg) and methanol (1 mL) which was then irradiated with microwave (microwave reactor, 50° C., 30 minutes, 60° C., 2 hours, 2.45 GHz, 0 to 240 W). Acetic acid (12 μL) was added to the reaction solution, the solvent was distilled off under reduced pressure, isopropanol was added thereto, and the resulting solid was collected by filtration to give ((1S,4R)-4-(2-amino-6-methoxy-9H-purin-9-yl)cyclopent-2-en-1-yl)methyl dihydrogen phosphate (4.3 mg) as a white solid.

$^1$H-NMR (DMSO-d$_6$) δ: 7.81 (s, 1H), 6.50-6.40 (m, 2H), 6.13-6.06 (m, 1H), 5.86-5.78 (m, 1H), 5.47-5.39 (m, 1H), 3.95 (s, 3H), 3.78-3.61 (m, 2H), 3.02-2.90 (m, 1H), 2.69-2.55 (m, 1H), 1.77-1.55 (m, 1H).

MS (ESI m/z): 342 (M+H)

RT (min): 0.45

Example 10-1

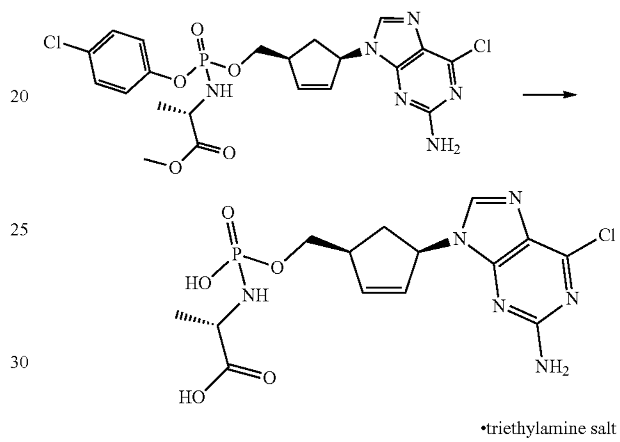

A mixture of methyl ((((1S,4R)-4-(2-amino-6-chloro-9H-purin-9-yl)cyclopent-2-en-1-yl)methoxy)(4-chlorophenoxy)phosphoryl)-L-alaninate (22 mg) obtained in Example 1-2-4, water (1 mL), and triethylamine (1 mL) was irradiated with microwave (microwave reactor, 50° C., 70 minutes, 2.45 GHz, 0 to 240 W). The solvent was distilled off from the aqueous layer under reduced pressure to give a triethylamine salt (20 mg) of ((((1S,4R)-4-(2-amino-6-chloro-9H-purin-9-yl)cyclopent-2-en-1-yl)methoxy)(hydroxy)phosphoryl)-L-alanine as a pale yellow solid.

$^1$H-NMR (DMSO-d$_6$) δ: 8.09 (s, 1H), 6.99-6.92 (m, 2H), 6.15-6.09 (m, 1H), 5.90-5.85 (m, 1H), 5.52-5.44 (m, 1H), 4.21-4.00 (m, 1H), 3.81-3.63 (m, 2H), 3.60-3.40 (m, 1H), 3.08-2.96 (m, 1H), 2.94-2.76 (m, 6H), 2.72-2.59 (m, 1H), 1.82-1.71 (m, 1H), 1.14-1.04 (m, 12H).

MS (ESI m/z): 417, 419 (M+H)

RT (min): 0.60

Example 10-2

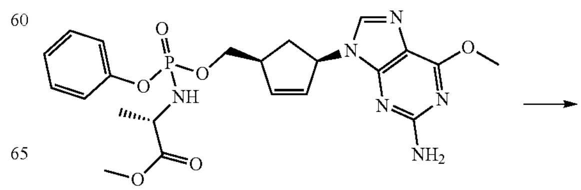

-continued

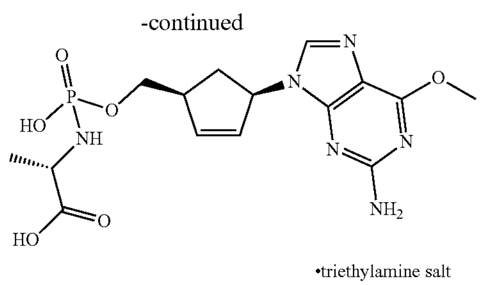

•triethylamine salt

A mixture of methyl ((((1S,4R)-4-(2-amino-6-methoxy-9H-purin-9-yl)cyclopent-2-en-1-yl)methoxy)(phenoxy)phosphoryl)-L-alaninate (13.5 mg) obtained in Example 2-2-16, water (0.5 mL), and triethylamine (0.5 mL) was irradiated with microwave (microwave reactor, 60° C., 1 hour, 2.45 GHz, 0 to 240 W). The solvent was distilled off from the aqueous layer under reduced pressure to give a triethylamine salt (3.8 mg) of ((((1S,4R)-4-(2-amino-6-methoxy-9H-purin-9-yl)cyclopent-2-en-1-yl)methoxy)(hydroxy)phosphoryl)-L-alanine as a pale yellow solid.

$^1$H-NMR (DMSO-$d_6$) δ: 7.80 (s, 1H), 6.47-6.41 (m, 2H), 6.13-6.08 (m, 1H), 5.90-5.84 (m, 1H), 5.49-5.42 (m, 1H), 3.95 (s, 3H), 3.76-3.62 (m, 2H), 3.60-3.40 (m, 1H), 3.05-2.95 (m, 1H), 2.85-2.70 (m, 6H), 2.70-2.58 (m, 1H), 1.72-1.63 (m, 1H), 1.11-1.00 (m, 12H).

MS (ESI m/z): 413 (M+H)

RT (min): 0.55

Example 10-3

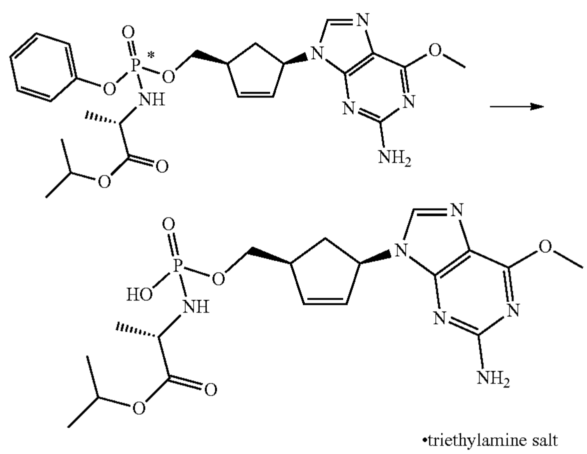

•triethylamine salt

A mixture of optically active substance A (50 mg) of isopropyl ((((1S,4R)-4-(2-amino-6-methoxy-9H-purin-9-yl)cyclopent-2-en-1-yl)methoxy)(phenoxy)phosphoryl)-L-alaninate obtained in Example 4-4-1, water (4.7 mL), and triethylamine (4.7 mL) was stirred at 35° C. for 5 hours. After allowing the reaction solution to cool to room temperature, the solvent was distilled off under reduced pressure and water was added to the obtained residue which was then washed with chloroform. The solvent was distilled off from the aqueous layer under reduced pressure, and the residue was purified by diol silica gel column chromatography (methanol:ethyl acetate=0:100 to 25:75) to give a triethylamine salt (3.7 mg) of isopropyl ((((1S,4R)-4-(2-amino-6-methoxy-9H-purin-9-yl)cyclopent-2-en-1-yl)methoxy)(hydroxy)phosphoryl)-L-alaninate as a pale brown solid.

$^1$H-NMR ($CDCl_3$) δ: 13.14 (1H, s), 7.76 (1H, s), 6.19-6.14 (1H, m), 5.81-5.76 (1H, m), 5.58-5.50 (1H, m), 5.02-4.89 (3H, m), 4.06 (3H, s), 3.92-3.82 (3H, m), 3.16-2.97 (7H, m), 2.76 (1H, dt, J=13.9, 8.8 Hz), 1.83-1.73 (1H, m), 1.35-1.23 (12H, m), 1.23-1.17 (6H, m).

MS (ESI m/z): 455 (M+H)

RT (min): 0.78

Comparative Example 1 (Reference Example 1)

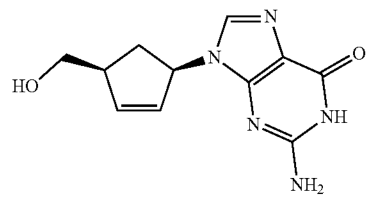 [SMILES: Nc1nc2c(ncn2[C@H]2C=C[C@@H](CO)C2)c(=O)[nH]1]

2-Amino-9-((1R,4S)-4-(hydroxymethyl)cyclopent-2-en-1-yl)-1,9-dihydro-6H-purin-6-one Test Example 1: Evaluation of Anti-Adenovirus Activity A system in which CRL-11516 cells (available from ATCC) were infected with adenovirus type 6 (hereinafter, referred to as ADV6) was constructed, and a test for evaluating the anti-adenovirus activity of the compound according to the embodiment of the present invention and the compound of Comparative Example was carried out using the system. The test for evaluating the anti-adenovirus activity was carried out according to the method described below.

CRL-11516 cells were added to a 96-well plate at a cell density of $1\times10^4$ cells/well and cultured at 37° C. for 24 hours. After the culture was completed, the cell culture liquid was removed, and a serial dilution (100 μL) of the compound according to the embodiment of the present invention or the compound of Comparative Example was added. ADV6 (corresponding to $50TCID_{50}$) was added thereto, followed by culturing at 37° C. for 48 hours.

After the culture was completed, the infected cells were stained using Adeno-X Rapid Titer Kit (manufactured by Takara Bio Inc.). 100% methanol was added thereto and the cells were fixed at −20° C. for 10 minutes. The plate was washed three times with phosphate buffered saline (hereinafter, referred to as PBS) and then Mouse Anti-Hexon Antibody was added thereto, followed by incubation at 37° C. for 1 hour. After the incubation was completed, the plate was washed three times with PBS, and Rat Anti-Mouse Antibody was added thereto, followed by incubation at 37° C. for 1 hour. After the incubation was completed, a mixed staining solution of Stable Peroxidase Buffer:DAB Substrate=10:1 was added thereto, followed by incubation at room temperature for 10 minutes for staining of the cells.

The number of dark brown-stained cells was counted under a microscope, and the concentration of the test drug that reduces the dark brown-stained cells by 50% was defined as $EC_{50}$. $EC_{50}$ values were calculated for the triplicate test results, and a mean value and a standard deviation thereof were determined. The results are shown in Table 9 below.

Evaluation Standards

TABLE 9

| Example No. | Anti-AdV activity $EC_{50}$ (μmol/L) | Example No. | Anti-AdV activity $EC_{50}$ (μmol/L) | Comparative Example No. | Anti-AdV activity $EC_{50}$ (μmol/L) |
|---|---|---|---|---|---|
| 1-2-2 | ++++ | 2-2-29 | +++ | 1 | + |
| 1-2-3 | ++++ | 2-2-35 | +++ | | |
| 1-2-4 | ++++ | 2-2-36 | ++ | | |
| 1-2-6 | ++ | 2-2-37 | +++ | | |
| 1-2-8 | +++ | 4-2-1 | +++ | | |
| 1-2-12 | ++++ | 4-2-2 | +++ | | |
| 1-2-34 | +++ | 4-3-1 | +++ | | |
| 1-2-45 | ++++ | 4-3-2 | ++ | | |
| 1-2-46 | ++++ | 4-4-1 | +++ | | |
| 1-2-49 | ++++ | 4-4-2 | ++ | | |
| 1-2-58 | +++ | 4-5-1 | ++++ | | |
| 1-2-70 | +++ | 4-5-2 | +++ | | |
| 1-2-72 | +++ | 4-6-1 | ++++ | | |
| 1-2-73 | ++++ | 4-6-2 | ++++ | | |
| 1-2-74 | +++ | 4-7-1 | +++ | | |
| 2-1 | ++++ | 4-7-2 | +++ | | |
| 2-2-1 | ++ | 4-8-1 | +++ | | |
| 2-2-2 | ++ | 4-8-2 | ++++ | | |
| 2-2-3 | +++ | 4-9-1 | +++ | | |
| 2-2-7 | +++ | 4-9-2 | ++++ | | |
| 2-2-12 | ++ | 5-1 | ++ | | |
| 2-2-16 | +++ | 6-2-7 | +++ | | |
| 2-2-17 | ++++ | 6-2-21 | +++ | | |
| 2-2-18 | ++ | 6-2-23 | ++++ | | |
| 2-2-19 | +++ | 6-2-25 | ++++ | | |
| 2-2-20 | ++ | 6-2-26 | +++ | | |
| 2-2-21 | +++ | 7-1-1 | +++ | | |
| 2-2-25 | +++ | 7-1-2 | ++ | | |
| 2-2-26 | ++ | | | | |

Evaluation standards
++++: 0.01 μM > $EC_{50}$
+++: 0.1 μM > $EC_{50}$ ≥ 0.01 μM
++: 1 μM > $EC_{50}$ ≥ 0.1 μM
+: 10 μM > $EC_{50}$ ≥ 1 μM
−: $EC_{50}$ ≥ 10 μM The compound according to the embodiment of the present invention had an excellent anti-adenovirus activity.

Test Example 2: Evaluation of ADV DNA Polymerase Inhibitory Activity

Recombinant ADV DNA polymerase was constructed, and a test for evaluating the DNA polymerase inhibitory activity of the triethylamine salt of (cis-4-(2-amino-6-oxo-1,6 -dihydro-9H-purin-9-yl)cyclopent-2-en-1-yl)methyl tetrahydrogen triphosphate (manufactured by Toronto Research Chemicals Inc.) was carried out. The test for evaluating the DNA polymerase inhibitory activity was carried out according to the method described below.

1) Purification of Recombinant ADV DNA Polymerase

Full-length human adenovirus 19 DNA polymerase (AFA46720.1) was totally synthesized as a cDNA optimized for insect cell expression, a His tag sequence was added to the C-terminus thereof, and then the resulting construct was inserted into pFastBac™ 1 (available from Invitrogen Corporation).

A bacmid was constructed by introducing the above vector into MAX Efficiency® DH10Bac™ competent cells (available from Invitrogen Corporation). It was confirmed by sequencing that the constructed bacmid contained the full-length human adenovirus 19 DNA polymerase.

Sf9 cells were transfected with the bacmid using Cellfectin II (available from Invitrogen Corporation). The culture supernatant containing recombinant baculoviruses was recovered after 7 days, and an operation of infecting Sf9 cells with baculoviruses was repeated twice to obtain a sufficient amount of baculoviruses for protein expression. The baculovirus titer was measured using BacPAK™ Baculovirus Rapid Titer Kit (manufactured by Takara Bio Inc.).

$0.8\times10^6$ cells/mL of Sf9 cells were infected with baculoviruses in Grace's Insect medium (manufactured by Gibco Corporation) supplemented with 10% fetal bovine serum (hereinafter, referred to as FBS, manufactured by Gibco Corporation) and 0.1% F-68 (manufactured by Gibco Corporation), such that the multiplicity of infection was about 0.3. After 3 days, Sf9 cells were recovered and the cell pellet was frozen at −80° C.

The frozen cell pellet was suspended in a cell lysis solution (50 mM sodium phosphate buffer (pH 7.0), 10% glycerol, 300 mM sodium chloride, 1% Triton® X-100, cOmplete™ EDTA-free Protease Inhibitor Cocktail (manufactured by F. Hoffmann-La Roche AG)) which was then allowed to stand on ice for 15 minutes. After vortexing for 30 seconds, centrifugation was carried out at 15,000 rpm to obtain a supernatant containing human adenovirus 19 DNA polymerase.

The supernatant containing human adenovirus 19 DNA polymerase was added to TALON® Superflow Metal Affinity Resin (manufactured by Takara Bio Inc.) which was then stirred at 4° C. for 2.5 hours with a rotator. The TALON (registered trademark) Superflow Metal Affinity Resin was washed five times with a wash solution 1 (10 mM imidazole, 50 mM sodium phosphate buffer (pH 7.0), 10% glycerol, 300 mM sodium chloride) and three times with a wash solution 2 (25 mM imidazole, 50 mM sodium phosphate buffer (pH 7.0), 10% glycerol, 300 mM sodium chloride). Then, an eluate (50 mM and 100 mM imidazole, 50 mM sodium phosphate buffer (pH 7.0), 10% glycerol, 300 mM sodium chloride) was added to the TALON® Superflow Metal Affinity Resin to elute the human adenovirus 19 DNA polymerase. The eluate was concentrated with Amicon Ultra-15 Centrifugal Filter Units, MWCO 50K (manufactured by MilliporeSigma Corporation), and then replaced with stock buffer (50 mM sodium phosphate buffer (pH 7.0), 10% glycerol, 300 mM sodium chloride) by a dialysis method using Slide-A-Lyzer MINI Dialysis Devices, 20K MWCO (manufactured by Thermo Fisher Scientific Inc.) prior to use for testing. The concentration of human adenovirus 19 DNA polymerase was measured using Pierce™ BCA Protein Assay Kit.

2) Test for Evaluating ADV DNA Polymerase Inhibitory Activity 1.5 μM primer oligo DNA (IRDye800-5'-GTAAAACGACGGCCAGT-3') (SEQ ID NO: 1) and 1 μM template oligo DNA (5'-CCGGG-GATCCTCTAGAGTCGACCTGCAGG-CATGCAAGCTTGGCACTGGCCGTCGTT TTA-CAACGTCGTGA-3') (SEQ ID NO: 2) were incubated in annealing buffer (10 mM Tris-HCl buffer (pH 8.0), 1 mM ethylenediaminetetraacetic acid (hereinafter, referred to as EDTA), 50 mM sodium chloride) at 95° C. for 5 minutes, and then the temperature was gradually returned to room temperature for annealing.

Human adenovirus 19 DNA polymerase, primer oligo DNA/template oligo DNA, dNTPs (manufactured by Nippon Gene Co., Ltd.), and a triethylamine salt of (cis-4-(2-amino-6-oxo-1,6-dihydro-9H-purin-9-yl)cyclopent-2-en-1-yl)methyl tetrahydrogen triphosphate were diluted in assay buffer (50 mM Tris-HCl buffer (pH 7.5), 1 mM dithiothreitol, 4% glycerol, 5 mM magnesium chloride, 0.1% bovine serum albumin).

40 nM human adenovirus 19 DNA polymerase (5 μL), the triethylamine salt (5 μL) of (cis-4-(2-amino-6-oxo-1,6-dihydro-9H-purin-9-yl)cyclopent-2-en-1-yl)methyl tetrahydrogen triphosphate at a concentration four times the final concentration, and 40 μM dNTPs (5 μL) were mixed and incubated at 37° C. for 5 minutes.

120 nM/80 nM primer oligo DNA/template oligo DNA (5 μL) was added to start an enzymatic reaction. After the enzymatic reaction at 37° C. for 10 minutes, 20 μL of 2× sample buffer (98% formamide, 10 mM EDTA, 0.2% bromophenol blue) was added to stop the reaction.

After incubating at 70° C. for 10 minutes, a part of the reaction solution was applied to Novex TBE-Urea gels, 15%, 15 well (manufactured by Thermo Fisher Scientific Inc.), and DNA was separated by electrophoresis. The extension of the primer oligo DNA by the DNA polymerase activity was evaluated by detecting IRDye800 with Odyssey (manufactured by LI-COR, Inc.). The results are shown in FIG. 1.

The compound according to the embodiment of the present invention had an excellent inhibitory activity on the DNA extension reaction by ADV DNA polymerase.

The compound represented by General Formula [1] or a salt thereof according to the embodiment of the present invention is useful as an anti-adenoviral agent. The compound represented by General Formula [1] or a salt thereof according to the embodiment of the present invention is useful as an agent for treating adenovirus.

SEQUENCE LISTING

International Application 18F01187W1JP19029447_93.app under the Patent Cooperation Treaty.

What is claimed is:

1. A method for suppressing adenovirus, comprising administering a compound represented by General Formula [1] or a salt thereof to a subject,

[1]

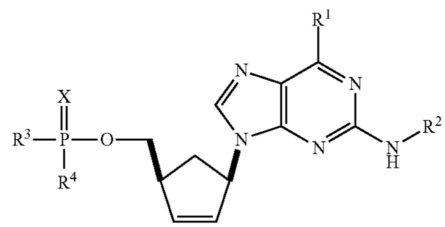

in the formula, $R^1$ represents a hydrogen atom, a halogen atom, an amino group which may be substituted, a monocyclic nitrogen-containing heterocyclic ring group which may be substituted (provided that a nitrogen atom forming the ring is bonded to a carbon atom to which $R^1$ is bonded), a monocyclic nitrogen- and oxygen-containing heterocyclic ring group which may be substituted (provided that a nitrogen atom forming the ring is bonded to a carbon atom to which $R^1$ is bonded), a $C_{1-6}$ alkoxy group which may be substituted, a $C_{3-8}$ cycloalkoxy group which may be substituted, a $C_{1-6}$ alkylthio group which may be substituted, a hydroxyl group which may be protected, or a thiol group which may be protected;

$R^2$ represents a hydrogen atom or an amino protecting group;

$R^3$ represents a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, a hydroxyl group which may be protected, or —O—P(O)(OH)—O—$PO_3H$;

$R^4$ represents a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, or a hydroxyl group which may be protected; or $R^3$ and $R^4$, together with a phosphorus atom to which $R^3$ and $R^4$ are bonded, may be combined to form a 5- to 10-membered nitrogen- and phosphorus-containing heterocyclic ring which may be substituted, a 5- to 10-membered oxygen- and phosphorus-containing heterocyclic ring which may be substituted, or a 5- to 10-membered nitrogen-, oxygen-, and phosphorus-containing heterocyclic ring which may be substituted; and X represents an oxygen atom or a sulfur atom; or a salt thereof.

2. The method for suppressing adenovirus according to claim 1, wherein $R^2$ is a hydrogen atom.

3. The method for suppressing adenovirus according to claim 1, wherein X is an oxygen atom.

4. The method for suppressing adenovirus according to claim 1, wherein $R^1$ is a halogen atom, an amino group which may be substituted, a monocyclic nitrogen-containing heterocyclic ring group which may be substituted (provided that a nitrogen atom forming the ring is bonded to a carbon atom to which $R^1$ is bonded), a monocyclic nitrogen- and oxygen-containing heterocyclic ring group which may be substituted (provided that a nitrogen atom forming the ring is bonded to a carbon atom to which $R^1$ is bonded), a $C_{1-6}$ alkoxy group which may be substituted, a $C_{3-8}$ cycloalkoxy group which may be substituted, a $C_{1-6}$ alkylthio group which may be substituted, a hydroxyl group which may be protected, or a thiol group which may be protected.

5. The method for suppressing adenovirus according to claim 4, wherein $R^1$ is a halogen atom, an amino group which may be substituted with one or more substituents selected from Substituent group A, a monocyclic nitrogen-containing heterocyclic ring group which may be substituted with one or more substituents selected from Substituent group A (provided that a nitrogen atom forming the ring is bonded to a carbon atom to which $R^1$ is bonded), a monocyclic nitrogen- and oxygen-containing heterocyclic ring group which may be substituted with one or more substituents selected from Substituent group A (provided that a nitrogen atom forming the ring is bonded to a carbon atom to which $R^1$ is bonded), a $C_{1-6}$ alkoxy group which may be substituted with one or more substituents selected from Substituent group A, a $C_{3-8}$ cycloalkoxy group which may be substituted with one or more substituents selected from Substituent group A, a $C_{1-6}$ alkylthio group which may be substituted with one or more substituents selected from Substituent group A, a hydroxyl group which may be protected, or a thiol group which may be protected, Substituent group A:

a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; an amino group which may be substituted with one or more substituents selected from Substituent group B; a $C_{1-6}$ alkoxycarbonyl group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B, Substituent group B:

a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an aryloxycarbonyl group; an aryl $C_{1-6}$ alkoxycarbonyl group; an aryl group; an aryloxy group; a heterocyclic oxy group which may be substituted with one or more substituents selected from a hydroxyl group and a hydroxymethyl group; an aryl $C_{1-6}$ alkoxy group; and an acyloxy group.

6. The method for suppressing adenovirus according to claim 4, wherein $R^1$ is a halogen atom, an amino group which may be substituted with one or more substituents selected from Substituent group A, a monocyclic nitrogen-containing heterocyclic ring group which may be substituted with one or more substituents selected from Substituent group A (provided that a nitrogen atom forming the ring is bonded to a carbon atom to which $R^1$ is bonded), a monocyclic nitrogen- and oxygen-containing heterocyclic ring group which may be substituted with one or more substituents selected from Substituent group A (provided that a nitrogen atom forming the ring is bonded to a carbon atom to which $R^1$ is bonded), a $C_{1-6}$ alkoxy group which may be substituted with one or more substituents selected from Substituent group A, a hydroxyl group which may be protected, or a thiol group which may be protected.

7. The method for suppressing adenovirus according to claim 4, wherein $R^1$ is a halogen atom, an amino group which may be substituted with one or more substituents selected from Substituent group A, a monocyclic nitrogen-containing heterocyclic ring group which may be substituted with one or more substituents selected from Substituent group A (provided that a nitrogen atom forming the ring is bonded to a carbon atom to which $R^1$ is bonded), a monocyclic nitrogen- and oxygen-containing heterocyclic ring group which may be substituted with one or more substituents selected from Substituent group A (provided that a nitrogen atom forming the ring is bonded to a carbon atom to which $R^1$ is bonded), a $C_{1-6}$ alkoxy group which may be substituted with one or more substituents selected from Substituent group A, or a hydroxyl group.

8. The method for suppressing adenovirus according to claim 1, wherein $R^3$ is a $C_{1-20}$ alkoxy group which may be substituted, a $C_{3-8}$ cycloalkoxy group which may be substituted, a $C_{1-20}$ alkylthio group which may be substituted, an aryloxy group which may be substituted, a heterocyclic ring group which may be substituted, a heterocyclic oxy group which may be substituted, an amino group which may be substituted, or —O—P(O)(OH)—O—$PO_3$H.

9. The method for suppressing adenovirus according to claim 8, wherein $R^3$ is a $C_{1-20}$ alkoxy group which may be substituted with one or more substituents selected from Substituent group A, a $C_{3-8}$ cycloalkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, an amino group which may be substituted with one or more substituents selected from Substituent group A, or —O—P(O)(OH)—O—$PO_3$H, Substituent group A:

a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; an amino group which may be substituted with one or more substituents selected from Substituent group B; a $C_{1-6}$ alkoxycarbonyl group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B, Substituent group B:

a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an aryloxycarbonyl group; an aryl $C_{1-6}$ alkoxycarbonyl group; an aryl group; an aryloxy group; a heterocyclic oxy group which may be substituted with one or more substituents selected from a hydroxyl group and a hydroxymethyl group; an aryl $C_{1-6}$ alkoxy group; and an acyloxy group.

10. The method for suppressing adenovirus according to claim 8, wherein $R^3$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or —O—P(O)(OH)—O—$PO_3$H.

11. The method for suppressing adenovirus according to claim 8, wherein $R^3$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, or —O—P(O)(OH)—O—$PO_3$H.

12. The method for suppressing adenovirus according to claim 1, wherein $R^4$ is a $C_{1-20}$ alkoxy group which may be substituted with one or more substituents selected from Substituent group A, a $C_{3-8}$ cycloalkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, a heterocyclic ring group which may be substituted with one or more substituents selected from Substituent group A, a heterocyclic oxy group which may be substituted with one or more substituents selected from Substituent group A, an amino group which may be substituted with one or more substituents selected from Substituent group A, or a hydroxyl group which may be protected, Substituent group A:

a halogen atom; a hydroxyl group which may be protected; a cyano group; a nitro group; a carbamoyl group; an oxo group; a $C_{1-6}$ alkyl group which may be substituted with one or more substituents selected from Substituent group B; a $C_{1-6}$ alkyldisulfanyl group which may be substituted with one or more substituents selected from Substituent group B; a $C_{2-6}$ alkenyl group which may be substituted with one or more substituents selected from Substituent group B; a $C_{2-6}$ alkynyl group which may be substituted with one or more substituents selected from Substituent group B; a $C_{3-8}$ cycloalkyl group which may be substituted with one or more substituents selected from Substituent group B; a $C_{3-8}$ cycloalkyldisulfanyl group which may be substituted with one or more substituents selected from Substituent group B; a $C_{1-6}$ alkoxy group which may be substituted with one or more substituents selected from Substituent group B; an amino group which may be substituted with one or more substituents selected from Substituent group B; a $C_{1-6}$ alkoxycarbonyl group which may be substituted with one or more substituents selected from Substituent group B; a $C_{3-8}$ cycloalkoxycarbonyl group which may be substituted with one or more substituents selected from Substituent group B; an aryl group which may be substituted with one or more substituents selected from Substituent group B; an aryldisulfanyl group which may be substituted with one or more substituents selected from Substituent group B; a heterocyclic ring group which may be substituted with one or more substituents selected from Substituent group B; a heterocyclic oxy group which may be substituted with one or more substituents selected from Substituent group B; an acyloxy group which may be substituted with one or more substituents selected from Substituent group B; an acylthio group which may be substituted with one or more substituents selected from Substituent group B; an aminocarbonyloxy group which may be substituted with one or more substituents selected from Substituent group B; and an aminocarbonylthio group which may be substituted with one or more substituents selected from Substituent group B, Substituent group B:

a halogen atom; a hydroxyl group; a cyano group; a nitro group; a carboxyl group; a carbamoyl group; a hydroxymethyl group; a $C_{1-6}$ alkyl group; a $C_{2-6}$ alkenyl group; a $C_{2-6}$ alkynyl group; a $C_{3-8}$ cycloalkyl group; a $C_{1-6}$ alkoxy group; a $C_{1-6}$ alkoxycarbonyl group; a $C_{3-8}$ cycloalkoxycarbonyl group; an aryloxycarbonyl group; an aryl $C_{1-6}$ alkoxycarbonyl group; an aryl group; an aryloxy group; a heterocyclic oxy group which may be substituted with one or more substituents selected from a hydroxyl group and a hydroxymethyl group; an aryl $C_{1-6}$ alkoxy group; and an acyloxy group.

13. The method for suppressing adenovirus according to claim 12, wherein $R^4$ is a $C_{1-20}$ alkoxy group which may be substituted with one or more substituents selected from Substituent group A, a $C_{1-20}$ alkylthio group which may be substituted with one or more substituents selected from Substituent group A, an aryloxy group which may be substituted with one or more substituents selected from Substituent group A, an amino group which may be substituted with one or more substituents selected from Substituent group A, or a hydroxyl group which may be protected.

14. The method for suppressing adenovirus according to claim 12, wherein $R^4$ is a $C_{1-20}$ alkoxy group which may be substituted with one or more substituents selected from Substituent group A, an amino group which may be substituted with one or more substituents selected from Substituent group A, or a hydroxyl group which may be protected.

15. The method for suppressing adenovirus according to claim 1, wherein a ring formed by combining $R^3$ and $R^4$ together with a phosphorus atom to which $R^3$ and $R^4$ are bonded is a 5- to 10-membered oxygen- and phosphorus-containing heterocyclic ring which may be substituted.

16. A method for suppressing adenovirus, comprising administering, to a subject, a compound selected from isopropyl ((((1S,4R)-4-(2-amino-6-chloro-9H-purin-9-yl)cyclopent-2-en-1-yl)methoxy)(phenoxy)phosphoryl)-L-alaninate, S-(2-(((((1S,4R)-4-(2-amino-6-methoxy-9H-purin-9-yl)cyclopent-2-en-1-yl)methoxy)(phenoxy)phosphoryl)oxy)ethyl) 2,2-dimethylpropanethioate, methyl ((((1S,4R)-4-(2-amino-6-methoxy-9H-purin-9-yl)cyclopent-2-en-1-yl)methoxy)(4-chlorophen oxy)phosphoryl)-L-alaninate, methyl ((((1S,4R)-4-(2-amino-6-methoxy-9H-purin-9-yl)cyclopent-2-en-1-yl)methoxy)(4-bromophenoxy)phosphoryl)-L-alaninate, isopropyl ((((1S,4R)-4-(2-amino-6-methoxy-9H-purin-9-yl)cyclopent-2-en-1-yl)methoxy)(phenoxy)phosphoryl)-L-alaninate, methyl ((((1S,4R)-4-(2-amino-6-chloro-9H-purin-9-yl)cyclopent-2-en-1-yl)methoxy)(4-chlorophenoxy)phosphoryl)-L-alaninate, methyl ((((1S,4R)-4-(2-amino-6-methoxy-9H-purin-9-yl)cyclopent-2-en-1-yl)methoxy)(2-(pivaloylthio)ethoxy)phosphoryl)-L-alaninate, ethyl ((((1S,4R)-4-(2-amino-6-methoxy-9H-purin-9-yl)cyclopent-2-en-1-yl)methoxy)(phenoxy)phosphoryl)-L-alaninate, ((1R,4S)-4-(2-amino-6-methoxy-9H-purin-9-yl)cyclopent-2-en-1-yl)methyl bis(pivaloyloxymethyl)phosphate, cyclopropyl ((((1S,4R)-4-(2-amino-6-methoxy-9H-purin-9-yl)cyclopent-2-en-1-yl)methoxy)(phenoxy)phosphoryl)-L-alaninate, isopropyl ((((1S,4R)-4-(2-amino-6-chloro-9H-purin-9-yl)cyclopent-2-en-1-yl)methoxy)(4-chlorophenoxy)phosphoryl)-L-alaninate, isopropyl ((((1S,4R)-4-(2-amino-6-methoxy-9H-purin-9-yl)cyclopent-2-en-1-yl)methoxy)(4-chlorophen oxy)phosphoryl)-L-alaninate, isopropyl ((((1S,4R)-4-(2-amino-6-chloro-9H-purin-9-yl)cyclopent-2-en-1-yl)methoxy)(2-(pivaloylthio) ethoxy)phosphoryl)-L-alaninate, isopropyl ((((1S,4R)-4-(2-amino-6-methoxy-9H-purin-9-yl)cyclopent-2-en-1-yl)methoxy)(2-(pivaloylthio)ethoxy)phosphoryl)-L-alaninate, isopropyl ((R)-(((1S,4R)-4-(2-amino-6-ethoxy-9H-purin-9-yl)cyclopent-2-en-1-yl)methoxy)(phenoxy)phosphoryl)-L-alaninate, isopropyl ((R)-(((1S,4R)-4-(2-amino-6-isopropoxy-9H-purin-9-yl)cyclopent-2-en-1-yl)methoxy)(phenoxy)phosphoryl)-L-alaninate, isopropyl ((R)-(((1S,4R)-4-(2-amino-6-(2-methoxyethoxy)-9H-purin-9-yl)cyclopent-2-en-1-yl)methoxy) (phenoxy)phosphoryl)-L-alaninate, isopropyl ((R)-(((1S,4R)-4-(2-amino-6-(dimethylamino)-9H-purin-9-yl)cyclopent-2-en-1- yl)methoxy)(p henoxy)phosphoryl)-L-alaninate, isopropyl ((R)-(((1S,4R)-4-(2-amino-6-cyclobutoxy-9H-purin-9-yl) cyclopent-2-en-1-yl)methoxy)(phenoxy)phosphoryl)-L-alaninate, isopropyl ((((1S,4R)-4-(2-amino-6-methoxy-9H-purin-9-yl)cyclopent-2-en-1-yl)methoxy)(3-methoxyphenoxy)phosphoryl)-L-alaninate, isopropyl ((R)-(((1S,4R)-4-(2-amino-6-(azetidin-1-yl)-9H-purin-9-yl) cyclopent-2-en-1-yl)methoxy)(phe noxy)phosphoryl)-L-alaninate, isopropyl 2-(((((1S,4R)-4-(2-amino-6-methoxy-9H-purin-9-yl)cyclopent-2-en-1-yl)methoxy)(phenoxy) phosphoryl)amino)-2-methylpropanoate, isopropyl ((((1S, 4R)-4-(2-amino-6-methoxy-9H-purin-9-yl)cyclopent-2-en-1-yl)methoxy)(phenoxy)phosphoryl)-L-leucinate, isopropyl ((((1S,4R)-4-(2-amino-6-methoxy-9H-purin-9-yl)cyclopent-2-en-1-yl)methoxy)(3-(dimethylamino)phenoxy)phosphoryl)-L-alaninate, isopropyl ((((1S,4R)-4-(2-amino-6-methoxy-9H-purin-9-yl)cyclopent-2-en-1-yl)methoxy)(4-bromophenoxy)phosphoryl)-L-alaninate, isopropyl ((((1S, 4R)-4-(2-amino-6-methoxy-9H-purin-9-yl)cyclopent-2-en-1-yl)methoxy)(3,5-dimethoxyphenoxy)phosphoryl)-L-alaninate, isopropyl ((((1S,4R)-4-(2-amino-6-methoxy-9H-purin-9-yl)cyclopent-2-en-1-yl)methoxy)(3,4-dimethoxyphenoxy)phosphoryl)-L-alaninate, isopropyl ((((1S,4R)-4-(2-amino-6-methoxy-9H-purin-9-yl)cyclopent-2-en-1-yl)methoxy)(benzo[d][1,3]dioxolo-5-yloxy) phosphoryl)-L-alaninate, isopropyl ((((1S,4R)-4-(2-amino-6-methoxy-9H-purin-9-yl)cyclopent-2-en-1-yl)methoxy)(3-(2-methoxy ethoxy)phenoxy)phosphoryl)-L-alaninate, and isopropyl ((((1S,4R)-4-(2-amino-6-methoxy)-9H-purin-9-yl)cyclopent-2-en-1-yl)methoxy)(naphthalen-1-yloxy)phosphoryl)-L-alaninate; or a salt thereof.

17. A compound selected from isopropyl ((((1S,4R)-4-(2-amino-6-chloro-9H-purin-9-yl)cyclopent-2-en-1-yl) methoxy)(phenoxy)phosphoryl)-L-alaninate, S-(2-(((((1S, 4R)-4-(2-amino-6-methoxy-9H-purin-9-yl)cyclopent-2-en-1-yl)methoxy)(phenoxy)phosphoryl)oxy)ethyl) 2,2-dimethylpropanethioate, isopropyl ((((1S,4R)-4-(2-amino-6-methoxy-9H-purin-9-yl)cyclopent-2-en-1-yl)methoxy) (phenoxy)phosphoryl)-L-alaninate, methyl ((((1S,4R)-4-(2-amino-6-methoxy-9H-purin-9-yl)cyclopent-2-en-1-yl) methoxy)(2-(pivaloylthi o)ethoxy)phosphoryl)-L-alaninate, isopropyl ((((1S,4R)-4-(2-amino-6-methoxy-9H-purin-9-yl) cyclopent-2-en-1-yl)methoxy)(4-chlorophen oxy)phosphoryl)-L-alaninate, isopropyl ((((1S,4R)-4-(2-amino-6-methoxy-9H-purin-9-yl)cyclopent-2-en-1-yl)methoxy)(2-(pivaloylthi o)ethoxy)phosphoryl)-L-alaninate, isopropyl ((R)-(((1S,4R)-4-(2-amino-6-ethoxy-9H-purin-9-yl)cyclopent-2-en-1-yl)methoxy)(phenoxy)phosphoryl)-L-alaninate, isopropyl ((R)-(((1S,4R)-4-(2-amino-6-(2-methoxy-ethoxy)-9H-purin-9-yl)cyclopent-2-en-1-yl)methoxy) (phenoxy)phosphoryl)-L-alaninate, isopropyl ((((1S,4R)-4-(2-amino-6-methoxy-9H-purin-9-yl)cyclopent-2-en-1-yl) methoxy)(3-methoxyphenoxy)phosphoryl)-L-alaninate, isopropyl ((((1S,4R)-4-(2-amino-6-methoxy-9H-purin-9-yl) cyclopent-2-en-1-yl)methoxy)(benzo[d][1,3]dioxolo-5-yloxy)phosphoryl)-L-alaninate, and isopropyl ((((1S,4R)-4-(2-amino-6-methoxy-9H-purin-9-yl)cyclopent-2-en-1-yl) methoxy)(3-(2-methoxy ethoxy)phenoxy)phosphoryl)-L-alaninate; or a salt thereof.

18. A compound represented by General Formula [1c]:

[1c]

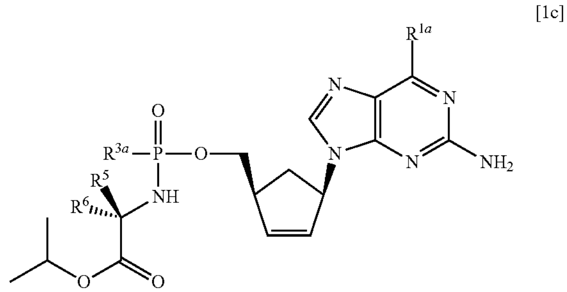

in the formula, $R^{1a}$ represents a halogen atom, a $C_{1-6}$ alkoxy group which may be substituted, or a group represented by General Formula —$NR^7R^8$ where $R^7$ and $R^8$ each represent a $C_{1-6}$ alkyl group which may be identically or differently substituted; or $R^7$ and $R^8$ together with a nitrogen atom to which $R^7$ and $R^8$ are bonded may be combined to form a monocyclic nitrogen-containing heterocyclic ring group which may be substituted;

$R^{3a}$ represents an aryloxy group which may be substituted or a heterocyclic oxy group which may be substituted; and $R^5$ and $R^6$ are the same or different from each other and each represent a hydrogen atom or a $C_{1-6}$ alkyl group which may be substituted; or a salt thereof.

* * * * *

```
                    SEQUENCE LISTING

<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: Synthetic oligonucleotide sequence

<400> SEQUENCE: 1

gtaaaacgac ggccagt                                                17


<210> SEQ ID NO 2
<211> LENGTH: 70
<212> TYPE: DNA
<213> ORGANISM: Artificial Sequence
<220> FEATURE:
<223> OTHER INFORMATION: Synthetic oligonucleotide sequence

<400> SEQUENCE: 2

ccggggatcc tctagagtcg acctgcaggc atgcaagctt ggcactggcc gtcgttttac    60

aacgtcgtga                                                        70
```